(12) United States Patent
Maddon et al.

(10) Patent No.: US 7,850,971 B2
(45) Date of Patent: Dec. 14, 2010

(54) PSMA ANTIBODIES AND PROTEIN MULTIMERS

(75) Inventors: Paul J. Maddon, Scarsdale, NY (US); Gerald P. Donovan, New York, NY (US); William C. Olson, Ossining, NY (US); Norbert Schuelke, Dedham, MA (US); Jason Gardner, Merseyside (GB); Dangshe Ma, Millwood, NY (US)

(73) Assignee: PSMA Development Company, LLC, Tarrytown, NY (US)

( * ) Notice: Subject to any disclaimer, the term of this patent is extended or adjusted under 35 U.S.C. 154(b) by 845 days.

(21) Appl. No.: 10/395,894

(22) Filed: Mar. 21, 2003

(65) Prior Publication Data

US 2004/0033229 A1 Feb. 19, 2004

Related U.S. Application Data

(63) Continuation-in-part of application No. PCT/US02/33944, filed on Oct. 23, 2002.

(60) Provisional application No. 60/335,215, filed on Oct. 23, 2001, provisional application No. 60/362,747, filed on Mar. 7, 2002, provisional application No. 60/412,618, filed on Sep. 20, 2002.

(51) Int. Cl.
*A61K 39/00* (2006.01)
(52) U.S. Cl. .............. 424/185.1; 424/193.1; 424/194.1; 424/277.1; 530/350; 435/183
(58) Field of Classification Search ................ 530/350; 424/185.1, 193.1, 194.1, 277.1; 435/183
See application file for complete search history.

(56) References Cited

U.S. PATENT DOCUMENTS

| | | | |
|---|---|---|---|
| 5,162,504 A | 11/1992 | Horoszewicz | |
| 5,538,866 A | 7/1996 | Israeli et al. | |
| 5,738,867 A | 4/1998 | Spitler | |
| 5,789,245 A | 8/1998 | Dubensky, Jr. et al. | |
| 5,804,602 A | 9/1998 | Slusher et al. | |
| 5,843,723 A | 12/1998 | Dubensky, Jr. et al. | |
| 5,935,818 A | 8/1999 | Israeli et al. | |
| 6,015,694 A | 1/2000 | Dubensky, Jr. et al. | |
| 6,107,090 A | 8/2000 | Bander | |
| 6,136,311 A | 10/2000 | Bander | |
| 6,150,508 A | 11/2000 | Murphy et al. | |
| 6,224,870 B1 | 5/2001 | Segal et al. | |
| 6,242,259 B1 | 6/2001 | Polo et al. | |
| 6,329,201 B1 | 12/2001 | Polo et al. | |
| 6,376,236 B1 | 4/2002 | Dubensky, Jr. et al. | |
| 6,387,888 B1 | 5/2002 | Mincheff et al. | |
| 6,426,196 B1 | 7/2002 | Dubensky, Jr. et al. | |
| 6,569,432 B1 | 5/2003 | Israeli et al. | |
| 6,649,163 B1 | 11/2003 | Bander et al. | |
| 6,770,450 B1 | 8/2004 | Bander et al. | |
| 6,897,062 B1 | 5/2005 | Heston et al. | |
| 6,953,668 B1 | 10/2005 | Israeli et al. | |
| 6,962,981 B1 | 11/2005 | Murphy | |
| 7,037,647 B1 | 5/2006 | Israeli et al. | |
| 7,070,782 B1 | 7/2006 | Israeli et al. | |
| 7,105,159 B1 | 9/2006 | Israeli et al. | |
| 7,112,412 B1 | 9/2006 | Bander et al. | |
| 7,163,680 B2 | 1/2007 | Bander et al. | |
| 7,201,900 B2 | 4/2007 | Murphy et al. | |
| 7,381,407 B1 | 6/2008 | Murphy et al. | |
| 7,399,461 B2 | 7/2008 | Heston et al. | |
| 7,476,513 B2 | 1/2009 | Murphy et al. | |
| 7,514,078 B2 | 4/2009 | Bander et al. | |
| 7,666,425 B1 | 2/2010 | Bander | |
| 2001/0036928 A1 | 11/2001 | Chamberlain et al. | |
| 2002/0015704 A1 | 2/2002 | Bander | |
| 2002/0155093 A1 | 10/2002 | Houghton et al. | |
| 2002/0164318 A1 | 11/2002 | Houghton et al. | |
| 2003/0003101 A1 | 1/2003 | Bander | |
| 2003/0027246 A1 | 2/2003 | Pedyczak et al. | |
| 2003/0031673 A1 | 2/2003 | Bander | |
| 2003/0046714 A1 | 3/2003 | Simard et al. | |
| 2003/0220239 A1 | 11/2003 | Simard et al. | |
| 2004/0001846 A1 | 1/2004 | Israeli et al. | |
| 2004/0024188 A1 | 2/2004 | Murphy et al. | |
| 2004/0037843 A1 | 2/2004 | Fikes et al. | |

(Continued)

FOREIGN PATENT DOCUMENTS

EP    1 917 970 A2    5/2008

(Continued)

OTHER PUBLICATIONS

Troyer et al. (Int. J. Cancer 1995; 62: 552-558).*

(Continued)

*Primary Examiner*—Stephen L Rawlings
(74) *Attorney, Agent, or Firm*—Wolf, Greenfield & Sacks, P.C.

(57) ABSTRACT

The invention includes antibodies or antigen-binding fragments thereof which bind specifically to conformational epitopes on the extracellular domain of PSMA, compositions containing one or a combination of such antibodies or antigen-binding fragments thereof, hybridoma cell lines that produce the antibodies, and methods of using the antibodies or antigen-binding fragments thereof for cancer diagnosis and treatment. The invention also includes oligomeric forms of PSMA proteins, compositions comprising the multimers, and antibodies that selectively bind to the multimers.

27 Claims, 51 Drawing Sheets

U.S. PATENT DOCUMENTS

| | | |
|---|---|---|
| 2004/0105865 A1 | 6/2004 | Bander |
| 2004/0120958 A1 | 6/2004 | Bander et al. |
| 2004/0161776 A1 | 8/2004 | Maddon et al. |
| 2004/0180354 A1 | 9/2004 | Simard et al. |
| 2004/0198657 A1 | 10/2004 | Heston et al. |
| 2004/0253246 A1 | 12/2004 | Israeli et al. |
| 2005/0064504 A1 | 3/2005 | Heston et al. |
| 2005/0142144 A1 | 6/2005 | Simard et al. |
| 2005/0202020 A1 | 9/2005 | Ross et al. |
| 2005/0215472 A1 | 9/2005 | Schulke et al. |
| 2005/0260234 A1 | 11/2005 | Simard et al. |
| 2006/0024316 A1 | 2/2006 | Spitler et al. |
| 2006/0062793 A1 | 3/2006 | Webb et al. |
| 2006/0177450 A1 | 8/2006 | Israeli et al. |
| 2006/0234271 A1 | 10/2006 | Su et al. |
| 2006/0275212 A1 | 12/2006 | Bander et al. |
| 2007/0020278 A1 | 1/2007 | Ross et al. |
| 2007/0036719 A1 | 2/2007 | Cuello et al. |
| 2007/0128671 A1 | 6/2007 | Murphy et al. |
| 2007/0148662 A1 | 6/2007 | Israeli et al. |
| 2007/0160617 A1 | 7/2007 | Ma et al. |
| 2007/0254316 A1 | 11/2007 | Rodriguez et al. |
| 2008/0286284 A1 | 11/2008 | Maddon et al. |
| 2009/0238755 A1 | 9/2009 | Bander |
| 2009/0285843 A1 | 11/2009 | Simard et al. |
| 2009/0311225 A1 | 12/2009 | Koduri |

FOREIGN PATENT DOCUMENTS

| | | |
|---|---|---|
| WO | WO 93/10763 A1 | 6/1993 |
| WO | WO 94/09820 A1 | 5/1994 |
| WO | WO 95/04548 A1 | 2/1995 |
| WO | WO 96/26272 A1 | 8/1996 |
| WO | WO 96/39185 A1 | 12/1996 |
| WO | WO 97/35616 A1 | 10/1997 |
| WO | WO 98/03873 A1 | 1/1998 |
| WO | WO 99/47554 A1 | 9/1999 |
| WO | WO 00/06723 A1 | 2/2000 |
| WO | WO 00/18933 A1 | 4/2000 |
| WO | WO 00/52156 A1 | 9/2000 |
| WO | WO 00/61605 A1 | 10/2000 |
| WO | WO 01/009192 A1 | 2/2001 |
| WO | WO 01/74845 A1 | 10/2001 |
| WO | WO 02/062368 A2 | 8/2002 |
| WO | WO 02/069907 A2 | 9/2002 |
| WO | WO 02/089747 A2 | 11/2002 |
| WO | WO 03/023026 A1 | 3/2003 |
| WO | WO 03/034903 A3 | 5/2003 |
| WO | WO 03/040165 A2 | 5/2003 |
| WO | WO 03/057921 A1 | 7/2003 |
| WO | WO 03/064606 A2 | 8/2003 |
| WO | WO 03/073828 A2 | 9/2003 |
| WO | WO 2006/125481 A1 | 11/2006 |

OTHER PUBLICATIONS

Carter et al. (Proc. Natl. Acad. Sci. USA. Jan. 1996; 93: 749-753).*
Schulke et al. (Proc. Natl. Acad. Sci. USA. Oct. 28, 2003; 100 (22): 12590-12595).*
Mincheff et al. (Eur. Urol. Aug. 2000; 38 (2): 208-217).*
Donovan et al., Antibody and vaccine therapies targeting prostate specific membrane antigen (PSMA). Proceedings of the Annual Meeting of the AACR. New York, NY. Mar. 24, 2001;42:818. Abstract 4389.
Gong et al., Prostate-specific membrane antigen (PSMA)-specific monoclonal antibodies in the treatment of prostate and other cancers. Cancer Metastasis Rev. 1999;18 (4):483-90.
Holmes et al., PSMA specific antibodies and their diagnostic and therapeutic use. Expert Opin Investig Drugs. Mar. 2001;10(3):511-9.
Lapidus et al., Prostate-specific membrane antigen (PSMA) enzyme activity is elevated in prostate cancer cells. Prostate. Dec. 1, 2000;45(4):350-4.
Liu et al., Monoclonal antibodies to the extracellular domain of prostate-specific membrane antigen also react with tumor vascular endothelium. Cancer Res. Sep. 1, 1997;57(17):3629-34.
Smith-Jones et al., In vitro characterization of radiolabeled monoclonal antibodies specific for the extracellular domain of prostate-specific membrane antigen. Cancer Res. Sep. 15, 2000;60(18):5237-43.
Tino et al., Isolation and characterization of monoclonal antibodies specific for protein conformational epitopes present in prostate-specific membrane antigen (PSMA). Hybridoma. Jun. 2000;19(3):249-57.
Barinka et al., Substrate specificity, inhibition and enzymological analysis of recombinant human glutamate carboxypeptidase II. J Neurochem. Feb. 2002;80(3):477-87.
Ma et al., PSMA-targeted toxin- and radio-labelled antibody therapies for prostate cancer. J Urology. Apr. 2003;169(4):211. Poster 817.
Ma et al., Fully human anti-PSMA antibodies for prostate cancer therapy. Proceedings of the American Association for Cancer Research Annual Meeting. Jul. 2003;44:1295. Poster 6471.
Schülke et al., The homodimer of prostate-specific membrane antigen is a functional target for cancer therapy. Proc Natl Acad Sci USA. Oct. 28, 2003;100(22):12590-5.
Schülke et al., Human Prostate Specific Membrane Antigen (PSMA) is expressed as a non-covalent dimer and provides an attractive target for cancer immunotherapy. Eur J Cancer. Nov. 2002;38:S153. Poster 510.
Sokoloff et al., A dual-monoclonal sandwich assay for prostate-specific membrane antigen: levels in tissues, seminal fluid and urine. Prostate. May 1, 2000;43(2):150-7.
Speno et al., Site-directed mutagenesis of predicted active site residues in glutamate carboxypeptidase II. Mol Pharmacol. Jan. 1999;55(1):179-85.
Troyer et al., Detection and characterization of the prostate-specific membrane antigen (PSMA) in tissue extracts and body fluids. Int J Cancer. Sep. 4, 1995;62(5):552-8.
Xiao et al., Generation of a baculovirus recombinant prostate-specific membrane antigen and its use in the development of a novel protein biochip quantitative immunoassay. Protein Expr Purif. Jun. 2000;19(1):12-21.
Ablin "Immunotherapy for prostatic cancer. Previous and Prospective Considerations[1]", *Oncology* (1975) vol. 31, 177-202.
Alvarez et al., Intermolecular disulfide bonds are not required for the expression of the dimeric state and functional activity of the transferrin receptor. EMBO J. Aug. 1989;8(8):2231-40.
Anilkumar et al., Prostate-specific membrane antigen association with filamin a modulates its internalization and NAALADase activity. Cancer Res. May 15, 2003;63(10):2645-8.
Anilkumar et al., Association of prostate-specific membrane antigen with caveolin-1 and its caveolae-dependent internalization in microvascular endothelial cells: implications for targeting to tumor vasculature. Microvasc Res. Jul.-Sep. 2006;72(1-2):54-61. Epub May 19, 2006.
Arlen et al., Therapeutic vaccines for prostate cancer: a review of clinical data. Curr Opin Investig Drugs. Jun. 2005;6(6):592-6. Review.
Bacich et al., Cloning, expression, genomic localization, and enzymatic activities of the mouse homolog of prostate-specific membrane antigen/NAALADase/folate hydrolase. Mamm Genome. Feb. 2001;12(2):117-23.
Barinka et al., Identification of the N-glycosylation sites on glutamate carboxypeptidase II necessary for proteolytic activity. Protein Sci. Jun. 2004;13(6):1627-35.
Barren et al., "Monoclonal antibody 7E11.C5 staining of viable LNCaP cells", *The Prostate* (1997) vol. 30, 65-68.
Bocchia et al., Antitumor vaccination: where we stand. Haematologica. Nov. 2000;85(11):1172-206. Review.
Bodey et al., Failure of cancer vaccines: the significant limitations of this approach to immunotherapy. Anticancer Res. Jul.-Aug. 2000;20(4):2665-76. Review.
Bzdega et al., "Molecular cloning of a peptidase against N-acetylaspartylglutamate from a rack hippocampal cDNA library", *J. Neurochem.* (Dec. 1997) vol. 69, No. 6, 2270-7.

Chandler et al., "Functional specificity of jejunal brush-border pteroylpolyglutamate hydrolase in pig", *Am. J. Physiological Society* (1991) vol. 260, G865-G872.

Chandler et al., "Pteroylpolyglutamate hydrolase from human jejunal brush-borders", *J. of Biol. Chem.* (Jan. 15, 1996) vol. 261, No. 2, 928-933.

Chang et a., "Prostate-specific membrane antigen is produced in tumor-associated neovasculature[1]", *Clinical Cancer Res.* (Oct. 1999) vol. 2674, No. 5, 2674-2681.

Chang et al., "Five different anti-prostate-specific membrane antigen (PSMA) antibodies confirm PSMA expression in tumor-associated neovasculature[1]", *Cancer Res.* (Jul. 1, 1999) vol. 59, 3192-3198.

Chang et al., Monoclonal antibodies: will they become an integral part of the evaluation and treatment of prostate cancer- focus on prostate-specific membrane antigen? Review Article. Curr Opin Urology. 1999;9(5):391-95.

Chang et al., Prostate-Specific Membrane Antigen: Much More Than a Prostate Cancer Marker. Mol Urol. 1999;3(3):313-319.

Chang et al., Metastatic renal cell carcinoma neovasculature expresses prostate-specific membrane antigen. Urology. Apr. 2001;57(4):801-5.

Chen et al., "Cytotoxity of an internalizing 7E11-C5 MAB-SE immunoconjugate against DU145 prostate tumor cells". FASEB J. 1997;11(3):A403. Abstract #2334.

Davis et al., "Crystal structure of prostate-specific membrane antigen, a tumor marker and peptidase" *PNAS* (Apr. 26, 2005) vol. 102, No. 17, 5981-5986.

Devlin et al., "Glutamate carboxypeptidase II: a polymorphism associated with lower levels of serum folate and hyperhomocysteinemia", *Hum. Mol. Genet.* (2000) vol. 9, No. 19, 2937-2844.

Donovan et al., Clinical development of immunotherapies targeting prostate specific membrane antigen. 38th Annual Meeting American Society of Clinical Oncology. Alexandria, VA. May 18-21, 2002. Presentation. PSMA Development Company, LLC. Tarrytown, NY (joint venture between Progenics Pharmaceuticals, Inc. and Cytogen Corporation) and The Cleveland Clinic, Cleveland, OH. Proceedings of ASCO. 2002;21:25b. Abstract #1909.

Ezzell et al., Cancer "Vaccines": An Idea Whose Time Has Come? J of NIH Res. 1995;7:46-49.

Fair et al., "Prostate-specific membrane antigen", *The Prostate* (1997) vol. 32, 140-148.

Feng et al., Purification and Biochemical Characterization of the 7E11-C5 Prostate Carcinoma-Associated Antigen. Proceedings of the 82nd Meeting of the American Association for Cancer. 1991;32:239. Abstract #1418.

Gao et al., Tumor vaccination that enhances antitumor T-cell responses does not inhibit the growth of established tumors even in combination with interleukin-12 treatment: the importance of inducing intratumoral T-cell migration. J Immunother. Nov.-Dec. 2000;23(6):643-53.

Gardner et al., A novel alphavirus replicon vaccine encoding PSMA for immunotherapy of prostate cancer. AACR Meeting. San Francisco, CA. Apr. 6-10, 2002. PSMA Development Company, LLC. Tarrytown, NY (joint venture between Progenics Pharmaceuticals, Inc. and Cytogen Corporation) and The Cleveland Clinic, Cleveland, OH. Proceedings of AACR. 2002;43:609. Abstract #3017.

Gardner et al., Recombinant soluble prostate-specific membrane antigen (rsPSMA) vaccine: preliminary findings of a Phase I safety/immunogenicity trial. J Clin Oncol. ASCO Annual Meeting Proceedings. 2004;22:184S. Abstract #2584.

Gardner et al., Novel prime-boost combinations of PSMA-based vaccines for prostate cancer. PSMA Development Company, LLC (A joint venture between Progenics Pharmaceuticals Inc. and Cytogen Corp.), Tarrytown, NY. AlphaVax, Inc., Research Triangle Park, NC. Presentation. Proceedings of ASCO. 2005:183s. Abstract #2572.

Ghosh et al., Effect of carbohydrate moieties on the folate hydrolysis activity of the prostate specific membrane antigen. The Prostate. 2003;57:140-151.

Goodman et al., Interaction of prostate specific membrane antigen with clathrin and the adaptor protein complex-2. Int J Oncol. Nov. 2007;31(5):1199-203.

Grauer et al., Identification, purification, and subcellular localization of prostate-specific membrane antigen PSM' protein in the LNCaP prostatic carcinoma cell line. Cancer Res. Nov. 1, 1998;58(21):4787-9.

Gregorakis et al., "Prostate-specific membrane antigen: Current and future utility", *Seminars in Urologic Oncology* (Feb. 1998) vol. 16, No. 1, 2-12.

Guinan et al., "Immunotherapy of Prostate Cancer: A Review" *The Prostate* (1984) vol. 5, 221-230.

Halsted et al., "Folypoly-γ-glutamate carboxypeptidase from pig jejunum", *J. of Biol. Chem.* (Aug. 1998) vol. 273, No. 32, 20417-20424.

Heston, "Characterization and glutamyl preferring carboxypeptidase function of prostate specific membrane antigen: A novel folate hydrolase", *Urology* (Supplement to Mar. 1997) vol. 49, No. 3A, 104-112.

Holmes et al., "Analysis of glycosylation of prostate-specific membrane antigen derived from LNCaP cells, prostatic carcinoma tumors, and serum from prostate cancer patients", *The Prostate Supplement* (1996) vol. 7, 25-29.

Horoszewicz et al., Monoclonal antibodies to a new antigenic marker in epithelial prostatic cells and serum of prostatic cancer patients. Anticancer Res. Sep.-Oct. 1987;7(5B):927-35.

Horoszewicz et al., LNCaP model of human prostatic carcinoma. Cancer Res. Apr. 1983;43(4):1809-18.

Israeli et al., "Expression of the prostate-specific membrane antigen[1]", *Cancer Res.* (Apr. 1, 1994) vol. 54, 1807-1811.

Israeli et al., Molecular cloning of a complementary DNA encoding a prostate-specific membrane antigen. Cancer Res. Jan. 15, 1993;53(2):227-30.

Israeli et al., Prostate-specific membrane antigen and other prostatic tumor markers on the horizon. Urol Clin North Am. May 1997;24(2):439-50. Review.

Israeli et al., Purification and Molecular Cloning of a New Prostate-Specific Antigen. Proceedings Am Assoc Cancer Res. 1992;33:356. Abstract #2127.

Jhanwar et al., Current status of therapy of solid tumors. J Nucl Med. Jan. 2005;46 Suppl 1:141S-50S.

Kato et al., Further investigation of the epitope recognized by the new monoclonal antibody 2C9. Int J Urol. Aug. 2003;10(8):439-44.

Keer et al., Elevated transferrin receptor content in human prostate cancer cell lines assessed in vitro and in vivo. J Urol. Feb. 1990;143(2):381-5.

Kinoshita et al., Targeting epitopes in prostate-specific membrane antigen for antibody therapy of prostate cancer. Prostate Cancer Prostatic Dis. 2005;8(4):1-5.

Kuratsukuri et al., "Induction of antibodies against prostate-specific membrane antigen (PSMA) by vaccination with a PSMA DNA vector", *European Urology* (2002) vol. 42, 67-73.

Kuratsukuri et al., Inhibition of prostate-specific membrane antigen (PSMA)-positive tumor growth by vaccination with either full-length or the C-terminal end of PSMA. Int J Cancer. Nov. 20, 2002;102(3):244-9.

Lawrence et al., Crystal structure of the ectodomain of human transferrin receptor. Science. Oct. 22, 1999;286(5440):779-82.

Lee et al., Increased vaccine-specific T cell frequency after peptide-based vaccination correlates with increased susceptibility to in vitro stimulation but does not lead to tumor regression. J Immunol. Dec. 1, 1999;163(11):6292-300.

Leek et al., Prostate-specific membrane antigen: evidence for the existence of a second related human gene. Br J Cancer. Sep. 1995;72(3):583-8.

Liu et al., "Constitutive and antibody-induced internalization of prostate-specific membrane antigen[1]", *Cancer Research* (Sep. 15, 1998) vol. 58, 4055-4060.

Lopes et al., Immunohistochemical and Pharmacokinetic Characterization of the Site-specific Immunoconjugate CYT-356 Derived from Antiprostate Monoclonal Antibody 7E11-C5. Cancer Res. 1991;50:6423-29.

Luthi-Carter et al., Molecular characterization of human brain N-acetylated alpha-linked acidic dipeptidase (NAALADase). J Pharmacol Exp Ther. Aug. 1998;286(2):1020-5.

Luthi-Carter et al., "Hydrolysis of the neuropeptide N-acetylaspartylglutamate (NAAG) by cloned human glutamate carboxypeptidase II[1]", Brain Research (1998) vol. 795, 341-348.

Meighan et al., Recombinant glutamate carboxypeptidase II (prostate specific membrane antigen—PSMA)—cellular localization and bioactivity analyses. J Protein Chem. May 2003;22(4):317-26.

Mlcochová et al., Prostate-specific membrane antigen and its truncated form PSM'. Prostate. Apr. 1, 2009;69(5):471-9.

Murphy et al., Comparison of prostate specific antigen, prostate specific membrane antigen, and LNCaP-based enzyme-linked immunosorbent assays in prostatic cancer patients and patients with benign prostatic enlargement, The Prostate (1995) vol. 26, 164-168.

Muprhy et al., Comparison of prostate specific membrane antigen, and prostate specific antigen levels in prostatic cancer patients. Anticancer Res. (1995) vol. 15, 1473-9.

Murphy et al., Current evaluation of the tissue localization and diagnostic utility of prostate specific membrane antigen. Cancer. Dec. 1, 1998;83(11):2259-69.

Murphy et al., Higher-dose and less frequent dendritic cell infusions with PSMA peptides in hormone-refractory metastatic prostate cancer patients, Prostate (Apr. 1, 2000) vol. 43, No. 1, 59-62. Abstract only.

Murphy et al., "Infusion of dendritic cells pulsed with HLA-A2-specific prostate-specific membrane antigen peptidase: a phase II prostate cancer vaccine trial involving patients with hormone-refractory metastatic disease", Prostate (Jan. 1, 1999) vol. 38, No. 1, 73-8.

Murphy et al., Isolation and Characterization of Monoclonal Antibodies Specific for the Extracellular Domain of Prostate Specific Membrane Antigen. J Urology. 1998;160:2396-401.

Murphy et al., Measurement of prostate-specific membrane antigen in the serum with a new antibody. Prostate. Apr. 1996;28(4):266-71.

Murphy et al., Measurement of serum prostate-specific membrane antigen, a new prognostic marker for prostate cancer. Urology. May 1998;51(5A Suppl):89-97.

Murphy et al., "Phase I clinical trial: T-cell therapy for prostate cancer using autologous dendritic cells pulsed with HLA-A0201-specific peptidase from prostate-specific membrane", Prostate (Dec. 1996) vol. 29, No. 6, 371-80. Abstract only.

Murphy et al., "Use of artifical neural networks in evaluating prognostic factors determining the response to dendritic cells pulsed with PSMA peptides in prostate cancer patients", Prostate (Jan. 2000) vol. 42, No. 1, 67-72. Abstract only.

Olson et al., Clinical trials of cancer therapies targeting prostate-specific membrane antigen. Rev Recent Clin Trials. Sep. 2007;2(3):182-90.

Pinto et al. "Prostate-specific membrane antigen: a novel folate hydrolase in human prostatic carcinoma cells[1]", Clinical Cancer Res. (Sep. 1996) vol. 2, No. 9, 1445-1451.

Rajasekeran et al., A novel cytoplasmic tail MXXXL motif mediates the internalization of prostate-specific membrane antigen. Mol Biol Cell. Dec. 2003;14(12):4835-45. Epub Oct. 3, 2003.

Robinson et al., Hydrolysis of the brain dipeptide N-acetyl-L-aspartyl-L-glutamate. Identification and characterization of a novel N-acetylated alpha-linked acidic dipeptidase activity from rat brain. J Biol Chem. Oct. 25, 1987;262(30):14498-506.

Rochon et al., Western blot assay for prostate-specific membrane antigen in serum of prostate cancer patients. Prostate. Oct. 1994;25(4):219-23.

Rovenská et al., Tissue expression and enzymologic characterization of human prostate specific membrane antigen and its rat and pig orthologs. Prostate. Feb. 1, 2008;68(2):171-82.

Sacha et al., Expression of glutamate carboxypeptidase II in human brain. Neuroscience. Feb. 23, 2007;144(4):1361-72. Epub Dec. 5, 2006.

Salgaller et al., "Report of immune monitoring of prostate cancer patients undergoing T-cell therapy using dendritic cells pulsed with HLA-A2-specific peptides from prostate-specific membrane antigen (PSMA)", Prostate (May 1998) vol. 35, No. 2, 144-51. Abstract only.

Schmittgen et al., Expression of prostate specific membrane antigen and three alternatively spliced variants of PSMA in prostate cancer patients. Int J Cancer. Nov. 1, 2003;107(2):323-9.

Schneider et al., Primary structure of human transferrin receptor deduced from the mRNA sequence. Nature. Oct. 18-24, 1984;311(5987):675-8.

Schülke et al., The native form of PSMA is a non-covalent homodimer: Implications for targeted immunotherapy of prostate and other cancers. Clin Can Res. 2003;9(Suppl):6228s. Abstract #C104.

Silver et al., "Prostate-specific Membrane Antigen Expression in Normal and Malignant Human Tissues[1]," Clin. Cancer Res. (1997) vol. 3, 81-85.

Slovin et al., Phase I vaccine trial of recombinant soluble prostate specific-membrane antigen (rsPSMA) plus Alhydrogel(r) in patients with biochemically relapsed prostate cancer. ASCO Prostate Cancer Symposium. 2005. Abstract Only.

Slusher et al., Rat brain N-acetylated alpha-linked acidic dipeptidase activity. Purification and immunologic characterization. J Biol Chem. Dec. 5, 1990;265(34):21297-301.

Slusher et al., Suramin potently inhibits the enzymatic activity of PSM. Prostate. Jun. 15, 2000;44(1):55-60.

Spitler, Cancer vaccines: the interferon analogy. Cancer Biother. 1995 Spring;10(1):1-3.

Strassburg et al., Baculovirus recombinant expressing a secreted form of a transmembrane carcinoma-associated antigen. Cancer Res. Feb. 15, 1992;52(4):815-21.

Su et al., "Alternatively spliced variants of prostate-specific membrane antigen RNA: Ratio of expression as a potential measurement of progressioni[1]", Cancer Research (Apr. 1, 1995) vol. 55,1441-1443.

Sweat et al., "Prostate-specific membrane antigen expression is greatest in prostate adenocarcinoma and lymph node metastatses", Urology (1998) vol. 52, No. 4, 637-640.

Tiffany et al., Characterization of the enzymatic activity of PSM: comparison with brain NAALADase. Prostate. Apr. 1, 1999;39(1):28-35.

Troyer et al., "Biochemical characterization and mapping of the 7EII-05.3 epitope of the prostate-specific membrane antigen", Urol. Oncol. (1995) vol. 1, 29-37.

Troyer et al., "Location of prostate-specific membrane antigen in the LNCaP prostate carcinoma cell line", The Prostate (1997) vol. 30, 232-242.

Troyer et al., Molecular characterization of the 7E11-C5 prostate tumor-associated antigen. J Urology. 1993;149:333A. Abstract #482.

Troyer et al., Subcellular Localization of the 7E11-C5 Prostate Specific Antigen, Proc. Am. Assoc. Cancer Res., 1994; 35:283. Abstract #1688.

Vodinelich et al., Structure and function of the transferrin receptor—a possible role in the recognition of natural killer cells. Haematol Blood Transfus. 1983;28:472-4.

Wang et al., "Intracellular pteroylpolyglutamate hydrolase from human jejunal mucoas", J. of Biological Chemistry (1986) vol. 241, No. 20, 13551-13555.

Williams et al., Analysis of prostate-specific membrane antigen splice variants in LNCap cells. Oligonucleotides. 2006 Summer;16(2):186-95.

Wright et al., "Expression of prostate-specific membrane antigen in normal, benign and malignant prostate tissues", Urol. Oncol. (1995) vol. 1, 18-28.

Wright et al., "Upregulation of prostate-specific membrane antigen after androgen-deprivation therapy", Urology (1996) vol. 48, No. 2, 326-334.

* cited by examiner

Human IgG1 cloning – into pcDNA

Construction of pcDNA-huCκ and pcDNA-huIgG1

| | | PCR product | Vector |
|---|---|---|---|
| Cκ | Sense | 5' XbaI HindIII BamHI NheI 3' | 5' NheI NotI 3' |
| | Anti-sense | EcoRI NotI | (pcDNA.neo) |
| Cγ1 | Sense | 5' XbaI KpnI HindIII BamHI NheI 3' | 5' NheI/PmeI 3' |
| | Anti-sense | EcoRI XhoI PmeI | (pcDNA Hygro) |

Construction of pcDNA-Ab (V-C cassette)

| | | PCR product | Vector |
|---|---|---|---|
| Vκ | Sense | BglII or BamHI (if necessary)* | 5' BamHI NheI 3' |
| | Anti-sense | NheI | (pcDNA-huCκ) |
| Vγ1 | Sense | BglII or BamHI (if necessary)* | 5' BamHI NheI 3' |
| | Anti-sense | XbaI | (pcDNA-huIgG1) |

* BamHI primer is used if the V region has an internal BglII site

Human IgG cloning – V-C cassette from pcDNA into "production" vector

| | Insert from pcDNA |
|---|---|
| Igκ | 5' HindIII or BamHI (if alternate sense primer used) |
| | 3' EcoRI, NotI, XhoI, XbaI or PmeI |
| IgG1 | 5' KpnI, HindIII or BamHI (if alternate sense primer used) |
| | 3' EcoRI*, XhoI or PmeI |

* 2$^{nd}$ EcoRI site present in hygromycin resistance gene

Primers used for V region amplification

Vκ-sense:
5' GAAGATCTCACC ATG + 20-23 bp leader sequence 3'
     BglII    Kozak Vκ anti-sense (reverse/complementary):
5' AACTA GCT AGC AGT TCC AGA TTT CAA CTG CTC ATC AGA T 3'
          S   A   T   G   S   K   L   Q   E   D   S (aa. 23-13 Cκ)
         NheI Cloning site of NheI codes for A S - therefore no amino acid change due to cloning.

Vγ-sense:
5' GAAGATCTCACC ATG + 17-29bp leader sequence 3'
    BglII    Kozak Vγ anti-sense(reverse/complementary):
5' GC TCT AGA GGG TGC CAG GGG GAA GAC CGA T 3'
   (R) S   P   A   L   P   F   V   S  (aa. 14-7 Cγ1)
     XbaI Cloning into
5' CG GCT AGC
     S  (A)

Cloning site junction of XbaI/NheI (TCT AGC) codes for S S - therefore no amino acid change due to cloning.

Fig. 12

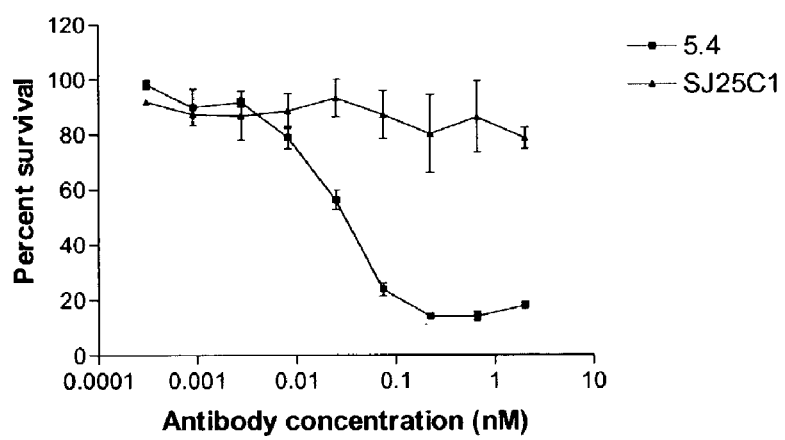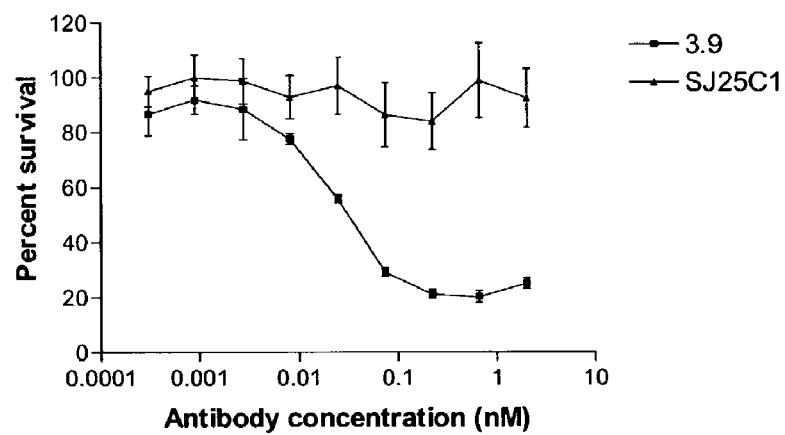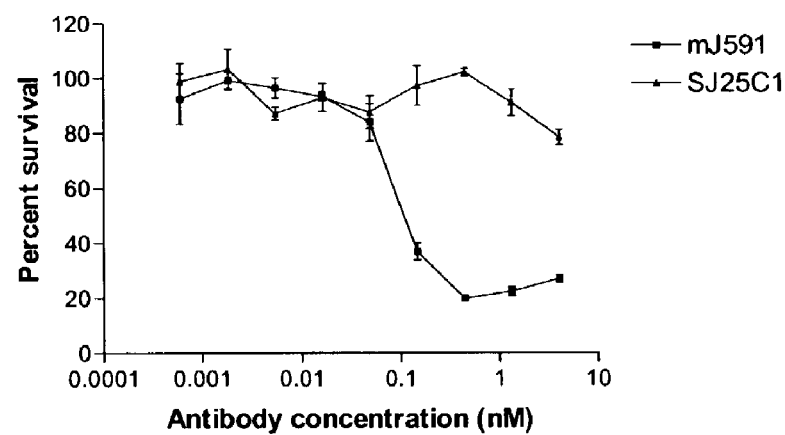
Fig. 28

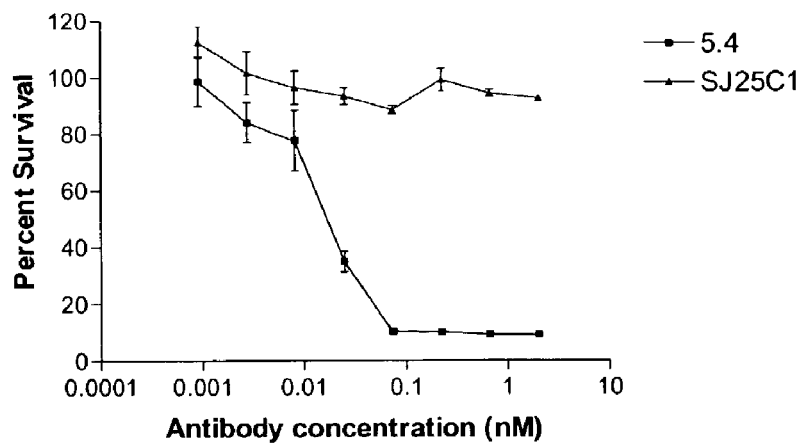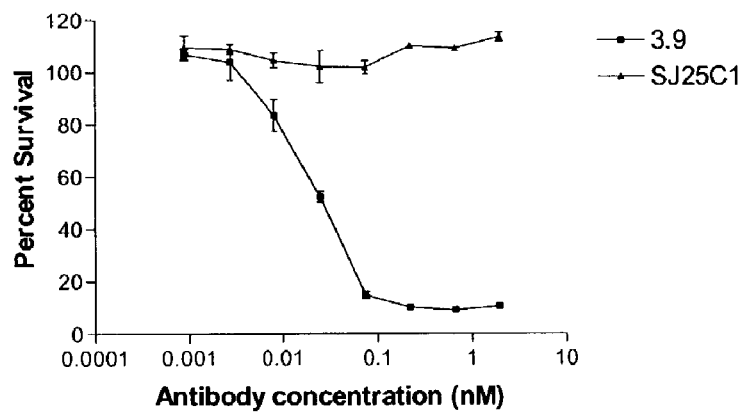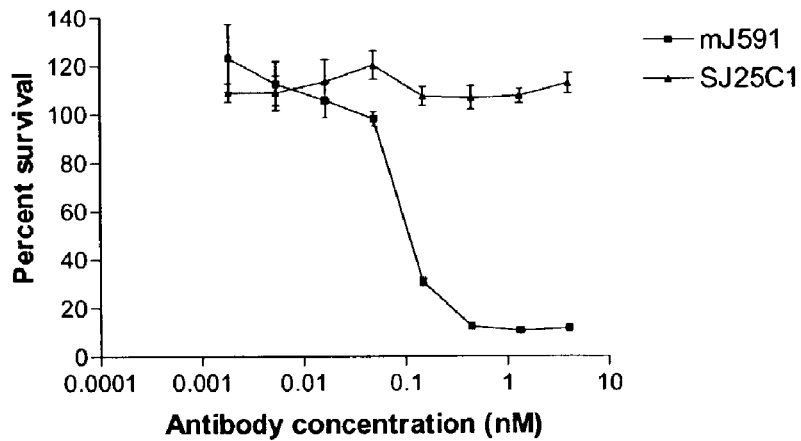
Fig. 29

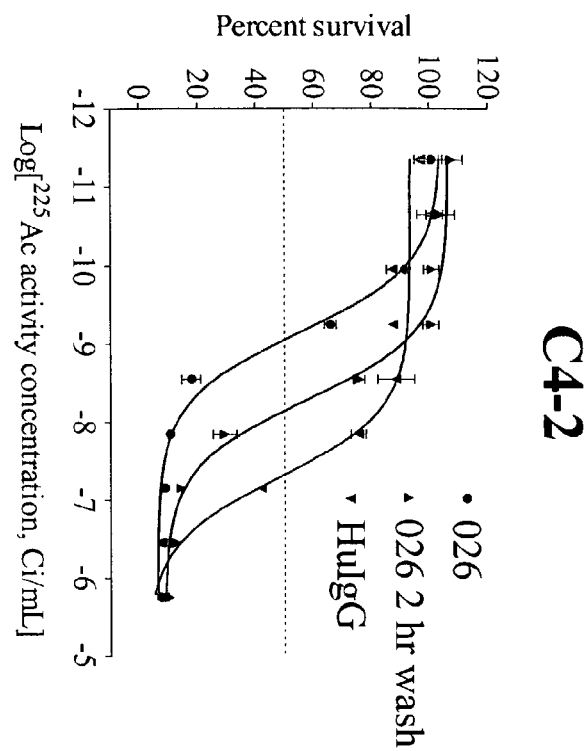
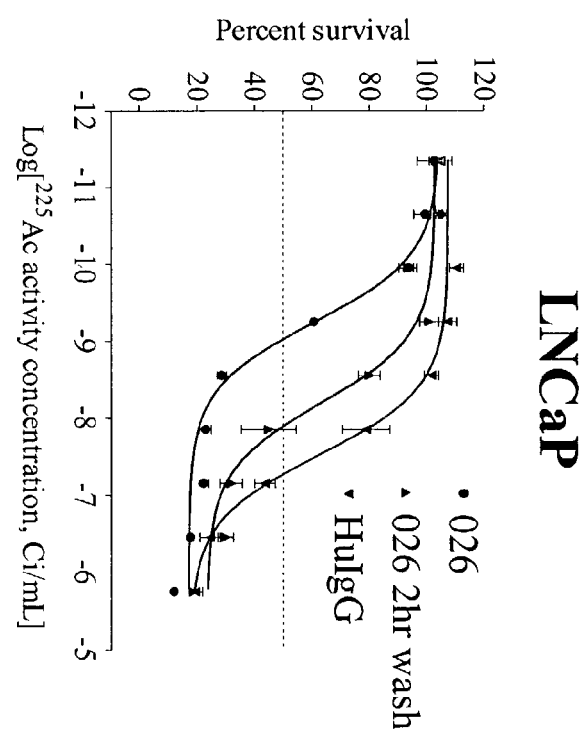
Fig. 38

SEQUENCE LISTING

<160> NUMBER OF SEQ ID NOS: 39

<210> SEQ ID NO 1
<211> LENGTH: 750
<212> TYPE: PRT
<213> ORGANISM: Homo sapiens

<400> SEQUENCE: 1

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

```
Phe Leu Leu Gly Phe Leu Phe Gly Trp Phe Ile Lys Ser Ser Asn Glu
                35                  40                  45

Ala Thr Asn Ile Thr Pro Lys His Asn Met Lys Ala Phe Leu Asp Glu
     50                  55                  60

Leu Lys Ala Glu Asn Ile Lys Lys Phe Leu Tyr Asn Phe Thr Gln Ile
 65                  70                  75                  80

Pro His Leu Ala Gly Thr Glu Gln Asn Phe Gln Leu Ala Lys Gln Ile
                 85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445
```

```
Tyr Ile Asn Ala Asp Ser Ser Ile Glu Gly Asn Tyr Thr Leu Arg Val
        450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
    530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
    610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
        675                 680                 685

His Val Ile Tyr Ala Pro Ser Ser His Asn Lys Tyr Ala Gly Glu Ser
    690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Glu Thr Leu Ser Glu Val Ala
            740                 745                 750

<210> SEQ ID NO 2
<211> LENGTH: 7570
<212> TYPE: DNA
<213> ORGANISM: Artificial Sequence
<220> FEATURE:
<223> OTHER INFORMATION: Synthetic Oligonucleotide

<400> SEQUENCE: 2
gacggatcgg gagatctccc gatccctat ggtcgactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
```

```
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctaga    900
ggtaccaagc ttggatctca ccatggagtt gggactgcgc tggggcttcc tcgttgctct    960
tttaagaggt gtccagtgtc aggtgcaatt ggtggagtct ggggggaggcg tggtccagcc   1020 tgggaggtcc ctgagactct cctgtgcagc gtctggattc gccttcagta gatatggcat   1080
gcactgggtc cgccaggctc caggcaaggg gctggagtgg gtggcagtta tggtatga     1140 tggaagtaat aaatactatg cagactccgt gaagggccga ttcaccatct ccagagacaa   1200
ttccaagaac acgcagtatc tgcaaatgaa cagcctgaga gccgaggaca cggctgtgta   1260
ttactgtgcg agaggcggtg acttcctcta ctactactat tacggtatgg acgtctgggg   1320
ccaagggacc acggtcaccg tctcctcagc ctccaccaag ggcccatcgg tcttccccct   1380
ggcaccctct gcaagagca cctctggggg cacagcggcc ctgggctgcc tggtcaagga   1440
ctacttcccc gaaccggtga cggtgtcgtg gaactcaggc gccctgacca gcggcgtgca   1500
caccttcccg gctgtcctac agtcctcagg actctactcc ctcagcagcg tggtgaccgt   1560
gccctccagc agcttgggca cccagaccta catctgcaac gtgaatcaca agcccagcaa   1620
caccaaggtg gacaagagag ttggtgagag gccagcacag ggagggaggg tgtctgctgg   1680
aagccaggct cagcgctcct gcctggacgc atcccggcta tgcagtccca gtccagggca   1740
gcaaggcagg ccccgtctgc ctcttcaccc ggaggcctct gcccgcccca ctcatgctca   1800
gggagagggt cttctggctt tttccccagg ctctgggcag gcacaggcta ggtgcccta    1860 acccaggccc tgcacacaaa ggggcaggtg ctgggctcag acctgccaag agccatatcc   1920
gggaggaccc tgcccctgac ctaagcccac cccaaaggcc aaactctcca ctccctcagc   1980
tcggacacct tctctcctcc cagattccag taactcccaa tcttctctct gcagagccca   2040
aatcttgtga caaaactcac acatgcccac cgtgcccagg taagccagcc caggcctcgc   2100
cctccagctc aaggcgggac aggtgcccta gagtagcctg catccaggga caggccccag   2160
ccgggtgctg acacgtccac ctccatctct tcctcagcac ctgaactcct ggggggaccg   2220
tcagtcttcc tcttcccccc aaaacccaag gacaccctca tgatctcccg gacccctgag   2280
gtcacatgcg tggtggtgga cgtgagccac gaagaccctg aggtcaagtt caactggtac   2340
gtggacggcg tggaggtgca taatgccaag acaaagccgc gggaggagca gtacaacagc   2400
acgtaccgtg tggtcagcgt cctcaccgtc ctgcaccagg actggctgaa tggcaaggag   2460
tacaagtgca aggtctccaa caaagccctc ccagccccca tcgagaaaac catctccaaa   2520
gccaaaggtg ggacccgtgg ggtgcgaggg ccacatggac agaggccggc tcggcccacc   2580
ctctgccctg agagtgaccg ctgtaccaac ctctgtccct acagggcagc cccgagaacc   2640
acaggtgtac accctgcccc catcccggga ggagatgacc aagaaccagg tcagcctgac   2700
ctgcctggtc aaaggcttct atcccagcga catcgccgtg gagtgggaga gcaatgggca   2760
```

```
gccggagaac aactacaaga ccacgcctcc cgtgctggac tccgacggct ccttcttcct   2820
ctatagcaag ctcaccgtgg acaagagcag gtggcagcag gggaacgtct tctcatgctc   2880
cgtgatgcat gaggctctgc acaaccacta cacgcagaag agcctctccc tgtctccggg   2940
taaatgagaa ttcctcgagt ctagagggcc cgtttaaacc cgctgatcag cctcgactgt   3000
gccttctagt tgccagccat ctgttgtttg cccctccccc gtgccttcct tgaccctgga   3060
aggtgccact cccactgtcc tttcctaata aaatgaggaa attgcatcgc attgtctgag   3120
taggtgtcat tctattctgg ggggtggggt ggggcaggac agcaaggggg aggattggga   3180
agacaatagc aggcatgctg gggatgcggt gggctctatg gcttctgagg cggaaagaac   3240
cagctggggc tctaggggt atccccacgc gccctgtagc ggcgcattaa gcgcggcggg    3300
tgtggtggtt acgcgcagcg tgaccgctac acttgccagc gccctagcgc ccgctccttt   3360
cgctttcttc ccttcctttc tcgccacgtt cgccggcttt cccgtcaag ctctaaatcg    3420 gggcatccct ttagggttcc gatttagtgc tttacggcac ctcgacccca aaaaacttga   3480
ttagggtgat ggttcacgta gtgggccatc gccctgatag acggttttc gccctttgac    3540 gttggagtcc acgttcttta atagtggact cttgttccaa actggaacaa cactcaaccc   3600
tatctcggtc tattcttttg atttataagg gatttgggg atttcggcct attggttaaa    3660
aaatgagctg atttaacaaa aatttaacgc gaattaattc tgtggaatgt gtgtcagtta   3720
gggtgtggaa agtccccagg ctccccaggc aggcagaagt atgcaaagca tgcatctcaa   3780
ttagtcagca accaggtgtg gaaagtcccc aggctcccca gcaggcagaa gtatgcaaag   3840
catgcatctc aattagtcag caaccatagt cccgccccta actccgccca tcccgcccct   3900
aactccgccc agttccgccc attctccgcc ccatggctga ctaatttttt ttatttatgc   3960
agaggccgag gccgcctctg cctctgagct attccagaag tagtgaggag gcttttttgg   4020
aggcctaggc ttttgcaaaa agctcccggg agcttgtata tccattttcg gatctgatca   4080
gcacgtgatg aaaaagcctg aactcaccgc gacgtctgtc gagaagtttc tgatcgaaaa   4140
gttcgacagc gtctccgacc tgatgcagct ctcggagggc gaagaatctc gtgctttcag   4200
cttcgatgta ggagggcgtg gatatgtcct gcgggtaaat agctgcgccg atggtttcta   4260
caaagatcgt tatgtttatc ggcactttgc atcggccgcg ctcccgattc cggaagtgct   4320
tgacattggg gaattcagcg agagcctgac ctattgcatc tcccgccgtg cacagggtgt   4380
cacgttgcaa gacctgcctg aaaccgaact gcccgctgtt ctgcagccgg tcgcggaggc   4440
catggatgcg atcgctgcgg ccgatcttag ccagacgagc gggttcggcc cattcggacc   4500
gcaaggaatc ggtcaataca ctacatggcg tgatttcata tgcgcgattg ctgatcccca   4560
tgtgtatcac tggcaaactg tgatggacga caccgtcagt gcgtccgtcg cgcaggctct   4620
cgatgagctg atgctttggg ccgaggactg ccccgaagtc cggcacctcg tgcacgcgga   4680
tttcggctcc aacaatgtcc tgacggacaa tggccgcata acagcggtca ttgactggag   4740
cgaggcgatg ttcggggatt cccaatacga ggtcgccaac atcttcttct ggaggccgtg   4800
gttggcttgt atggagcagc agacgcgcta cttcgagcgg aggcatccgg agcttgcagg   4860
atcgccgcgg ctccgggcgt atatgctccg cattggtctt gaccaactct atcagagctt   4920
ggttgacggc aatttcgatg atgcagcttg gcgcagggt cgatgcgacg caatcgtccg    4980
atccggagcc gggactgtcg ggcgtacaca atcgcccgc agaagcgcgg ccgtctggac    5040
cgatggctgt gtagaagtac tcgccgatag tggaaaccga cgccccagca ctcgtccgag   5100
```

```
ggcaaaggaa tagcacgtgc tacgagattt cgattccacc gccgccttct atgaaaggtt   5160
gggcttcgga atcgttttcc gggacgccgg ctggatgatc ctccagcgcg gggatctcat   5220
gctggagttc ttcgcccacc ccaacttgtt tattgcagct tataatggtt acaaataaag   5280
caatagcatc acaaatttca caaataaagc attttttca ctgcattcta gttgtggttt   5340
gtccaaactc atcaatgtat cttatcatgt ctgtataccg tcgacctcta gctagagctt   5400
ggcgtaatca tggtcatagc tgtttcctgt gtgaaattgt tatccgctca caattccaca   5460
caacatacga gccggaagca taaagtgtaa agcctggggt gcctaatgag tgagctaact   5520
cacattaatt gcgttgcgct cactgcccgc tttccagtcg ggaaacctgt cgtgccagct   5580
gcattaatga atcggccaac gcgcggggag aggcggtttg cgtattgggc gctcttccgc   5640
ttcctcgctc actgactcgc tgcgctcggt cgttcggctg cggcgagcgg tatcagctca   5700
ctcaaaggcg gtaatacggt tatccacaga atcaggggat aacgcaggaa agaacatgtg   5760
agcaaaaggc cagcaaaagg ccaggaaccg taaaaaggcc gcgttgctgg cgttttccca   5820
taggctccgc cccctgacg agcatcacaa aaatcgacgc tcaagtcaga ggtggcgaaa   5880
cccgacagga ctataaagat accaggcgtt tcccctgga agctcctcg tgcgctctcc   5940 tgttccgacc ctgccgctta ccggatacct gtccgccttt ctcccttcgg gaagcgtggc   6000
gctttctcaa tgctcacgct gtaggtatct cagttcggtg taggtcgttc gctccaagct   6060
gggctgtgtg cacgaacccc cgttcagcc cgaccgctgc gccttatccg gtaactatcg   6120
tcttgagtcc aacccggtaa gacacgactt atcgccactg gcagcagcca ctggtaacag   6180
gattagcaga gcgaggtatg taggcggtgc tacagagttc ttgaagtggt ggcctaacta   6240
cggctacact agaaggacag tatttggtat ctgcgctctg ctgaagccag ttaccttcgg   6300
aaaaagagtt ggtagctctt gatccggcaa acaaaccacc gctggtagcg tggtttttt   6360 tgtttgcaag cagcagatta cgcgcagaaa aaaggatct caagaagatc ctttgatctt   6420
ttctacgggg tctgacgctc agtggaacga aaactcacgt taagggattt tggtcatgag   6480
attatcaaaa aggatcttca cctagatcct tttaaattaa aaatgaagtt ttaaatcaat   6540
ctaaagtata tatgagtaaa cttggtctga cagttaccaa tgcttaatca gtgaggcacc   6600
tatctcagcg atctgtctat ttcgttcatc catagttgcc tgactccccg tcgtgtagat   6660
aactacgata cgggagggct taccatctgg ccccagtgct gcaatgatac cgcgagaccc   6720
acgctcaccg gctccagatt tatcagcaat aaaccagcca gccggaaggg ccgagcgcag   6780
aagtggtcct gcaactttat ccgcctccat ccagtctatt aattgttgcc gggaagctag   6840
agtaagtagt tcgccagtta atagtttgcg caacgttgtt gccattgcta caggcatcgt   6900
ggtgtcacgc tcgtcgtttg gtatggcttc attcagctcc ggttcccaac gatcaaggcg   6960
agttacatga tcccccatgt tgtgcaaaaa agcggttagc tccttcggtc ctccgatcgt   7020
tgtcagaagt aagttggccg cagtgttatc actcatggtt atggcagcac tgcataattc   7080
tcttactgtc atgccatccg taagatgctt ttctgtgact ggtgagtact caaccaagtc   7140
attctgagaa tagtgtatgc ggcgaccgag ttgctcttgc ccggcgtcaa tacgggataa   7200
taccgcgcca catagcagaa ctttaaaagt gctcatcatt ggaaaacgtt cttcggggcg   7260
aaaactctca aggatcttac cgctgttgag atccagttcg atgtaaccca ctcgtgcacc   7320
caactgatct tcagcatctt ttactttcac cagcgtttct gggtgagcaa aaacaggaag   7380
gcaaaatgcc gcaaaaaagg gaataagggc gacacggaaa tgttgaatac tcatactctt   7440 ccttttcaa tattattgaa gcatttatca gggttattgt ctcatgagcg gatacatatt   7500
```
tgaatgtatt tagaaaaata aacaaatagg ggttccgcgc acatttcccc gaaaagtgcc    7560
acctgacgtc                                                            7570

<210> SEQ ID NO 3
<211> LENGTH: 7597
<212> TYPE: DNA
<213> ORGANISM: Artificial Sequence
<220> FEATURE:
<223> OTHER INFORMATION: Synthetic Oligonucleotide

<400> SEQUENCE: 3
gacggatcgg gagatctccc gatccctat ggtcgactct cagtacaatc tgctctgatg      60
ccgcatagtt aagccagtat ctgctccctg cttgtgtgtt ggaggtcgct gagtagtgcg    120
cgagcaaaat ttaagctaca caaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctaga    900
ggtaccaagc ttggatctca ccatgggtc aaccgccatc ctcaccatgg agttgggct    960 gcgctgggtt ctcctcgttg ctcttttaag aggtgtccag tgtcaggtgc agctggtgga   1020
gtctggggga ggcgtggtcc agcctgggag gtccctgaga ctctcctgtg cagcgtctgg   1080
attcaccttc agtaactatg tcatgcactg ggtccgccag gctccaggca aggggctgga   1140
gtgggtggca attatatggt atgatggaag taataaatac tatgcagact ccgtgaaggg   1200
ccgattcacc atctccagag acaattccaa gaacacgctg tatctgcaaa tgaacagcct   1260
gagagccgag gacacggctg tgtattactg tgcgggtgga tataactgga actacgagta   1320
ccactactac ggtatggacg tctggggcca agggaccacg gtcaccgtct cctcagcctc   1380
caccaagggc ccatcggtct tccccctggc accctctagc aagagcacct ctggggcac   1440 agcggccctg ggctgcctgg tcaaggacta cttccccgaa ccggtgacgg tgtcgtggaa   1500
ctcaggcgcc ctgaccagcg gcgtgcacac cttcccggct gtcctacagt cctcaggact   1560
ctactccctc agcagcgtgg tgaccgtgcc ctccagcagc ttgggcaccc agacctacat   1620
ctgcaacgtg aatcacaagc ccagcaacac caaggtggac aagagagttg gtgagaggcc   1680
agcacaggga gggagggtgt ctgctggaag ccaggctcag cgctcctgcc tggacgcatc   1740
ccggctatgc agtcccagtc cagggcagca aggcaggccc cgtctgcctc ttcacccgga   1800
ggcctctgcc cgccccactc atgctcaggg agagggtctt ctggcttttt ccccaggctc   1860
tgggcaggca caggctaggt gcccctaacc caggccctgc acacaaaggg gcaggtgctg   1920

```
ggctcagacc tgccaagagc catatccggg aggaccctgc ccctgaccta agcccacccc    1980
aaaggccaaa ctctccactc cctcagctcg gacaccttct ctcctcccag attccagtaa    2040
ctcccaatct tctctctgca gagcccaaat cttgtgacaa aactcacaca tgccaccgt     2100 gcccaggtaa gccagcccag gcctcgccct ccagctcaag gcgggacagg tgccctagag    2160
tagcctgcat ccagggacag gccccagccg ggtgctgaca cgtccacctc catctcttcc    2220
tcagcacctg aactcctggg gggaccgtca gtcttcctct tcccccaaa acccaaggac     2280 accctcatga tctcccggac ccctgaggtc acatgcgtgg tggtggacgt gagccacgaa    2340
gaccctgagg tcaagttcaa ctggtacgtg gacggcgtgg aggtgcataa tgccaagaca    2400
aagccgcggg aggagcagta caacagcacg taccgtgtgg tcagcgtcct caccgtcctg    2460
caccaggact ggctgaatgg caaggagtac aagtgcaagg tctccaacaa agccctccca    2520
gcccccatcg agaaaaccat ctccaaagcc aaaggtggga cccgtggggt gcgagggcca    2580
catggacaga ggccggctcg gcccaccctc tgccctgaga gtgaccgctg taccaacctc    2640
tgtccctaca gggcagcccc gagaaccaca ggtgtacacc ctgcccccat cccgggagga    2700
gatgaccaag aaccaggtca gcctgacctg cctggtcaaa ggcttctatc ccagcgacat    2760
cgccgtggag tgggagagca atgggcagcc ggagaacaac tacaagacca cgcctcccgt    2820
gctggactcc gacggctcct tcttcctcta tagcaagctc accgtggaca gagcaggtg     2880 gcagcagggg aacgtcttct catgctccgt gatgcatgag gctctgcaca accactacac    2940
gcagaagagc ctctccctgt ctccgggtaa atgagaattc ctcgagtcta gagggcccgt    3000
ttaaacccgc tgatcagcct cgactgtgcc ttctagttgc cagccatctg ttgtttgccc    3060
ctcccccgtg ccttccttga ccctggaagg tgccactccc actgtccttt cctaataaaa    3120
tgaggaaatt gcatcgcatt gtctgagtag gtgtcattct attctggggg gtggggtggg    3180
gcaggacagc aagggggagg attgggaaga caatagcagg catgctgggg atgcggtggg    3240
ctctatggct tctgaggcgg aaagaaccag ctggggctct agggggtatc cccacgcgcc    3300
ctgtagcggc gcattaagcg cggcgggtgt ggtggttacg cgcagcgtga ccgctacact    3360
tgccagcgcc ctagcgcccg ctcctttcgc tttcttccct tcctttctcg ccacgttcgc    3420
cggctttccc cgtcaagctc taaatcgggg catcccttta gggttccgat ttagtgcttt    3480
acggcacctc gaccccaaaa aacttgatta gggtgatggt tcacgtagtg gccatcgcc     3540 ctgatagacg ttttttcgcc ctttgacgtt ggagtccacg ttctttaata gtggactctt    3600
gttccaaact ggaacaacac tcaaccctat ctcggtctat tcttttgatt tataagggat    3660
tttggggatt tcggcctatt ggttaaaaaa tgagctgatt taacaaaaat ttaacgcgaa    3720
ttaattctgt ggaatgtgtg tcagttaggg tgtggaaagt ccccaggctc cccaggcagg    3780
cagaagtatg caaagcatgc atctcaatta gtcagcaacc aggtgtggaa agtccccagg    3840
ctccccagca ggcagaagta tgcaaagcat gcatctcaat tagtcagcaa ccatagtccc    3900
gcccctaact ccgcccatcc cgcccctaac tccgcccagt tccgcccatt ctccgcccca    3960
tggctgacta attttttttta tttatgcaga ggccgaggcc gcctctgcct ctgagctatt    4020
ccagaagtag tgaggaggct ttttggagg cctaggcttt tgcaaaaagc tcccgggagc     4080
ttgtatatcc attttcggat ctgatcagca cgtgatgaaa aagcctgaac tcaccgcgac    4140
gtctgtcgag aagtttctga tcgaaaagtt cgacagcgtc tccgacctga tgcagctctc    4200
ggagggcgaa gaatctcgtg ctttcagctt cgatgtagga gggcgtggat atgtcctgcg    4260
ggtaaatagc tgcgccgatg gtttctacaa agatcgttat gtttatcggc actttgcatc    4320
```

```
ggccgcgctc ccgattccgg aagtgcttga cattggggaa ttcagcgaga gcctgaccta    4380
ttgcatctcc cgccgtgcac agggtgtcac gttgcaagac ctgcctgaaa ccgaactgcc    4440
cgctgttctg cagccggtcg cggaggccat ggatgcgatc gctgcggccg atcttagcca    4500
gacgagcggg ttcggcccat tcggaccgca aggaatcggt caatacacta catggcgtga    4560
tttcatatgc gcgattgctg atccccatgt gtatcactgg caaactgtga tggacgacac    4620
cgtcagtgcg tccgtcgcgc aggctctcga tgagctgatg ctttgggccg aggactgccc    4680
cgaagtccgg cacctcgtgc acgcggattt cggctccaac aatgtcctga cggacaatgg    4740
ccgcataaca gcggtcattg actggagcga ggcgatgttc ggggattccc aatacgaggt    4800
cgccaacatc ttcttctgga ggccgtggtt ggcttgtatg gagcagcaga cgcgctactt    4860
cgagcggagg catccggagc ttgcaggatc gccgcggctc cgggcgtata tgctccgcat    4920
tggtcttgac caactctatc agagcttggt tgacggcaat tcgatgatg cagcttgggc     4980 gcagggtcga tgcgacgcaa tcgtccgatc cggagccggg actgtcgggc gtacacaaat    5040
cgcccgcaga agcgcggccg tctggaccga tggctgtgta gaagtactcg ccgatagtgg    5100
aaaccgacgc cccagcactc gtccgagggc aaaggaatag cacgtgctac gagatttcga    5160
ttccaccgcc gccttctatg aaaggttggg cttcggaatc gttttccggg acgccggctg    5220
gatgatcctc cagcgcgggg atctcatgct ggagttcttc gcccacccca acttgtttat    5280
tgcagcttat aatggttaca aataaagcaa tagcatcaca aatttcacaa ataaagcatt    5340
tttttcactg cattctagtt gtggtttgtc caaactcatc aatgtatctt atcatgtctg    5400
tataccgtcg acctctagct agagcttggc gtaatcatgg tcatagctgt ttcctgtgtg    5460
aaattgttat ccgctcacaa ttccacacaa catacgagcc ggaagcataa agtgtaaagc    5520
ctggggtgcc taatgagtga gctaactcac attaattgcg ttgcgctcac tgcccgcttt    5580
ccagtcggga aacctgtcgt gccagctgca ttaatgaatc ggccaacgcg cggggagagg    5640
cggtttgcgt attgggcgct cttccgcttc ctcgctcact gactcgctgc gctcggtcgt    5700
tcggctgcgg cgagcggtat cagctcactc aaaggcggta atacggttat ccacagaatc    5760
aggggataac gcaggaaaga acatgtgagc aaaaggccag caaaaggcca ggaaccgtaa    5820
aaaggccgcg ttgctggcgt ttttccatag gctccgcccc cctgacgagc atcacaaaaa    5880
tcgacgctca agtcagaggt ggcgaaaccc gacaggacta taaagatacc aggcgtttcc    5940
ccctggaagc tccctcgtgc gctctcctgt tccgaccctg ccgcttaccg gatacctgtc    6000
cgcctttctc ccttcgggaa gcgtggcgct ttctcaatgc tcacgctgta ggtatctcag    6060
ttcggtgtag tcgttcgct ccaagctggg ctgtgtgcac gaaccccccg ttcagcccga    6120
ccgctgcgcc ttatccggta actatcgtct tgagtccaac ccggtaagac acgacttatc    6180
gccactggca gcagccactg gtaacaggat tagcagagcg aggtatgtag gcggtgctac    6240
agagttcttg aagtggtggc ctaactacgg ctacactaga aggacagtat ttggtatctg    6300
cgctctgctg aagccagtta ccttcggaaa aagagttggt agctcttgat ccggcaaaca    6360
aaccaccgct ggtagcggtg gtttttttgt ttgcaagcag cagattacgc gcagaaaaaa    6420
aggatctcaa gaagatcctt tgatcttttc tacgggtct gacgctcagt ggaacgaaaa     6480
ctcacgttaa gggattttgg tcatgagatt atcaaaaagg atcttcacct agatcctttt    6540
aaattaaaaa tgaagtttta atcaatcta agtatatat gagtaaactt ggtctgacag       6600
ttaccaatgc ttaatcagtg aggcacctat ctcagcgatc tgtctatttc gttcatccat    6660
```

-continued

```
agttgcctga ctccccgtcg tgtagataac tacgatacgg gagggcttac catctggccc    6720
cagtgctgca atgataccgc gagacccacg ctcaccggct ccagatttat cagcaataaa    6780
ccagccagcc ggaagggccg agcgcagaag tggtcctgca actttatccg cctccatcca    6840
gtctattaat tgttgccggg aagctagagt aagtagttcg ccagttaata gtttgcgcaa    6900
cgttgttgcc attgctacag gcatcgtggt gtcacgctcg tcgtttggta tggcttcatt    6960
cagctccggt tcccaacgat caaggcgagt tacatgatcc cccatgttgt gcaaaaaagc    7020
ggttagctcc ttcggtcctc cgatcgttgt cagaagtaag ttggccgcag tgttatcact    7080
catggttatg gcagcactgc ataattctct tactgtcatg ccatccgtaa gatgcttttc    7140
tgtgactggt gagtactcaa ccaagtcatt ctgagaatag tgtatgcggc gaccgagttg    7200
ctcttgcccg gcgtcaatac gggataatac cgcgccacat agcagaactt taaaagtgct    7260
catcattgga aaacgttctt cggggcgaaa actctcaagg atcttaccgc tgttgagatc    7320
cagttcgatg taacccactc gtgcacccaa ctgatcttca gcatctttta ctttcaccag    7380
cgtttctggg tgagcaaaaa caggaaggca aaatgccgca aaaaagggaa taagggcgac    7440
acggaaatgt tgaatactca tactcttcct ttttcaatat tattgaagca tttatcaggg    7500
ttattgtctc atgagcggat acatatttga atgtatttag aaaaataaac aataggggt    7560 tccgcgcaca tttccccgaa aagtgccacc tgacgtc                             7597
```

<210> SEQ ID NO 4
<211> LENGTH: 7579
<212> TYPE: DNA
<213> ORGANISM: Artificial Sequence
<220> FEATURE:
<223> OTHER INFORMATION: Synthetic Oligonucleotide

<400> SEQUENCE: 4

```
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta caactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctaga     900
ggtaccaagc ttggatctca ccatggagtt gggacttagc tgggttttcc tcgttgctct     960
tttaagaggt gtccagtgtc aggtccagct ggtggagtct gggggaggcg tggtccagcc    1020
tgggaggtcc ctgagactct cctgtgcagc gtctggattc accttcagta gctatggcat    1080
gcactgggtc cgccaggctc caggcaaggg gctggactgg gtggcaatta tttggcatga    1140
```

```
tggaagtaat aaatactatg cagactccgt gaagggccga ttcaccatct ccagagacaa    1200
ttccaagaag acgctgtacc tgcaaatgaa cagtttgaga gccgaggaca cggctgtgta    1260
ttactgtgcg agagcttggg cctatgacta cggtgactat gaatactact tcggtatgga    1320
cgtctgggc caagggacca cggtcaccgt ctcctcagcc tccaccaagg gcccatcggt    1380
cttcccctg gcaccctcta gcaagagcac ctctggggggc acagcggccc tgggctgcct    1440
ggtcaaggac tacttccccg aaccggtgac ggtgtcgtgg aactcaggcg ccctgaccag    1500
cggcgtgcac accttcccgg ctgtcctaca gtcctcagga ctctactccc tcagcagcgt    1560
ggtgaccgtg ccctccagca gcttgggcac ccagacctac atctgcaacg tgaatcacaa    1620
gcccagcaac accaaggtgg acaagagagt tggtgagagg ccagcacagg gagggagggt    1680
gtctgctgga agccaggctc agcgctcctg cctggacgca tcccggctat gcagtcccag    1740
tccagggcag caaggcaggc cccgtctgcc tcttcacccg gaggcctctg cccgccccac    1800
tcatgctcag ggagagggtc ttctggcttt ttccccaggc tctgggcagg cacaggctag    1860
gtgcccctaa cccaggccct gcacacaaag gggcaggtgc tgggctcaga cctgccaaga    1920
gccatatccg ggaggaccct gcccctgacc taagcccacc ccaaaggcca aactctccac    1980
tccctcagct cggacacctt ctctcctccc agattccagt aactcccaat cttctctctg    2040
cagagcccaa atcttgtgac aaaactcaca catgcccacc gtgcccaggt aagccagccc    2100
aggcctcgcc ctccagctca aggcgggaca ggtgccctag agtagcctgc atccagggac    2160
aggccccagc cgggtgctga cacgtccacc tccatctctt cctcagcacc tgaactcctg    2220
gggggaccgt cagtcttcct cttccccca aacccaagg acaccctcat gatctcccgg    2280
accctgagg tcacatgcgt ggtggtgac gtgagccacg aagaccctga ggtcaagttc    2340
aactggtacg tggacggcgt ggaggtgcat aatgccaaga caaagccgcg ggaggagcag    2400
tacaacagca cgtaccgtgt ggtcagcgtc ctcaccgtcc tgcaccagga ctggctgaat    2460
ggcaaggagt acaagtgcaa ggtctccaac aaagccctcc cagcccccat cgagaaaacc    2520
atctccaaag ccaaaggtgg acccgtgggg gtgcgagggc acatggaca gaggccggct    2580
cggcccaccc tctgccctga gagtgaccgc tgtaccaacc tctgtcccta cagggcagcc    2640
ccgagaacca caggtgtaca ccctgccccc atcccgggag gagatgacca agaaccaggt    2700
cagcctgacc tgcctggtca aaggcttcta tcccagcgac atcgccgtgg agtgggagag    2760
caatgggcag ccggagaaca actacaagac cacgcctccc gtgctggact ccgacggctc    2820
cttcttcctc tatagcaagc tcaccgtgga caagagcagg tggcagcagg ggaacgtctt    2880
ctcatgctcc gtgatgcatg aggctctgca caaccactac acgcagaaga gcctctccct    2940
gtctccgggt aaatgagaat cctcgagtc tagagggccc gtttaaaccc gctgatcagc    3000
ctcgactgtg ccttctagtt gccagccatc tgttgtttgc ccctcccccg tgccttcctt    3060
gaccctggaa ggtgccactc ccactgtcct ttcctaataa aatgaggaaa ttgcatcgca    3120
ttgtctgagt aggtgtcatt ctattctggg ggtggggtg gggcaggaca gcaaggggga    3180
ggattgggaa gacaatagca ggcatgctgg ggatgcggtg ggctctatgg cttctgaggc    3240
ggaaagaacc agctggggct ctaggggta tccccacgcg ccctgtagcg gcgcattaag    3300
cgcggcgggt gtggtggtta cgcgcagcgt gaccgctaca cttgccagcg ccctagcgcc    3360
cgctcctttc gctttcttcc cttcctttct cgccacgttc gccggctttc cccgtcaagc    3420
tctaaatcgg ggcatccctt tagggttccg atttagtgct ttacggcacc tcgaccccaa    3480
```

```
aaaacttgat tagggtgatg gttcacgtag tgggccatcg ccctgataga cggttttcg      3540
cccttgacg ttggagtcca cgttctttaa tagtggactc ttgttccaaa ctggaacaac      3600
actcaaccct atctcggtct attcttttga tttataaggg attttgggga tttcggccta     3660
ttggttaaaa aatgagctga tttaacaaaa atttaacgcg aattaattct gtggaatgtg     3720
tgtcagttag ggtgtggaaa gtccccaggc tccccaggca ggcagaagta tgcaaagcat     3780
gcatctcaat tagtcagcaa ccaggtgtgg aaagtcccca ggctcccag caggcagaag      3840
tatgcaaagc atgcatctca attagtcagc aaccatagtc ccgcccctaa ctccgcccat     3900
cccgcccta actccgccca gttccgccca ttctccgccc catggctgac taatttttt      3960
tatttatgca gaggccgagg ccgcctctgc ctctgagcta ttccagaagt agtgaggagg     4020
ctttttgga ggcctaggct tttgcaaaaa gctcccggga gcttgtatat ccattttcgg      4080
atctgatcag cacgtgatga aaaagcctga actcaccgcg acgtctgtcg agaagtttct    4140
gatcgaaaag ttcgacagcg tctccgacct gatgcagctc tcggagggcg aagaatctcg     4200
tgctttcagc ttcgatgtag gagggcgtgg atatgtcctg cgggtaaata gctgcgccga     4260
tggtttctac aaagatcgtt atgtttatcg gcactttgca tcggccgcgc tcccgattcc     4320
ggaagtgctt gacattgggg aattcagcga gagcctgacc tattgcatct cccgccgtgc     4380
acagggtgtc acgttgcaag acctgcctga aaccgaactg cccgctgttc tgcagccggt     4440
cgcggaggcc atggatgcga tcgctgcggc cgatcttagc cagacgagcg ggttcggccc     4500
attcggaccg caaggaatcg gtcaatacac tacatggcgt gatttcatat gcgcgattgc     4560
tgatccccat gtgtatcact ggcaaactgt gatggacgac accgtcagtg cgtccgtcgc     4620
gcaggctctc gatgagctga tgctttgggc cgaggactgc cccgaagtcc ggcacctcgt     4680
gcacgcggat ttcggctcca caatgtcct gacggacaat ggccgcataa cagcggtcat     4740
tgactggagc gaggcgatgt tcggggattc ccaatacgag gtcgccaaca tcttcttctg     4800
gaggccgtgg ttggcttgta tggagcagca gacgcgctac ttcgagcgga ggcatccgga     4860
gcttgcagga tcgccgcggc tccgggcgta tatgctccgc attggtcttg accaactcta     4920
tcagagcttg gttgacggca atttcgatga tgcagcttgg gcgcagggtc gatgcgacgc     4980
aatcgtccga tccggagccg ggactgtcgg gcgtacacaa atcgcccgca gaagcgcggc     5040
cgtctggacc gatggctgtg tagaagtact cgccgatagt ggaaaccgac gccccagcac     5100
tcgtccgagg gcaaaggaat agcacgtgct acgagatttc gattccaccg ccgccttcta    5160
tgaaaggttg ggcttcggaa tcgttttccg ggacgccggc tggatgatcc tccagcgcgg    5220
ggatctcatg ctggagttct tcgcccaccc caacttgttt attgcagctt ataatggtta     5280
caaataaagc aatagcatca caaatttcac aaataaagca tttttttcac tgcattctag    5340
ttgtggtttg tccaaactca tcaatgtatc ttatcatgtc tgtataccgt cgacctctag    5400
ctagagcttg gcgtaatcat ggtcatagct gtttcctgtg tgaaattgtt atccgctcac    5460
aattccacac aacatacgag ccggaagcat aaagtgtaaa gcctggggtg cctaatgagt     5520
gagctaactc acattaattg cgttgcgctc actgcccgct ttccagtcgg gaaacctgtc     5580
gtgccagctg cattaatgaa tcggccaacg cgcggggaga ggcggtttgc gtattgggcg     5640
ctcttccgct tcctcgctca ctgactcgct gcgctcggtc gttcggctgc ggcgagcggt     5700
atcagctcac tcaaaggcgg taatacggtt atccacagaa tcagggata acgcaggaaa     5760
gaacatgtga gcaaaaggcc agcaaaaggc caggaaccgt aaaaaggccg cgttgctggc    5820
gttttccat aggctccgcc cccctgacga gcatcacaaa aatcgacgct caagtcagag     5880
```

-continued

| | |
|---|---|
| gtggcgaaac ccgacaggac tataaagata ccaggcgttt cccctggaa gctccctcgt | 5940 |
| gcgctctcct gttccgaccc tgccgcttac cggatacctg tccgcctttc tcccttcggg | 6000 |
| aagcgtggcg ctttctcaat gctcacgctg taggtatctc agttcggtgt aggtcgttcg | 6060 |
| ctccaagctg ggctgtgtgc acgaaccccc cgttcagccc gaccgctgcg ccttatccgg | 6120 |
| taactatcgt cttgagtcca acccggtaag acacgactta tcgccactgg cagcagccac | 6180 |
| tggtaacagg attagcagag cgaggtatgt aggcggtgct acagagttct tgaagtggtg | 6240 |
| gcctaactac ggctacacta aaggacagt atttggtatc tgcgctctgc tgaagccagt | 6300 |
| taccttcgga aaagagttg gtagctcttg atccggcaaa caaccaccg ctggtagcgg | 6360 |
| tggtttttt gtttgcaagc agcagattac gcgcagaaaa aaaggatctc aagaagatcc | 6420 |
| tttgatcttt tctacggggt ctgacgctca gtggaacgaa actcacgtt aagggatttt | 6480 |
| ggtcatgaga ttatcaaaaa ggatcttcac ctagatcctt ttaaattaaa aatgaagttt | 6540 |
| taaatcaatc taaagtatat atgagtaaac ttggtctgac agttaccaat gcttaatcag | 6600 |
| tgaggcacct atctcagcga tctgtctatt tcgttcatcc atagttgcct gactccccgt | 6660 |
| cgtgtagata actacgatac gggagggctt accatctggc cccagtgctg caatgatacc | 6720 |
| gcgagaccca cgctcaccgg ctccagattt atcagcaata aaccagccag ccggaagggc | 6780 |
| cgagcgcaga agtggtcctg caactttatc cgcctccatc cagtctatta attgttgccg | 6840 |
| ggaagctaga gtaagtagtt cgccagttaa tagtttgcgc aacgttgttg ccattgctac | 6900 |
| aggcatcgtg gtgtcacgct cgtcgtttgg tatggcttca ttcagctccg gttcccaacg | 6960 |
| atcaaggcga gttacatgat ccccatgtt gtgcaaaaaa gcggttagct ccttcggtcc | 7020 |
| tccgatcgtt gtcagaagta agttggccgc agtgttatca ctcatggtta tggcagcact | 7080 |
| gcataattct cttactgtca tgccatccgt aagatgcttt tctgtgactg gtgagtactc | 7140 |
| aaccaagtca ttctgagaat agtgtatgcg gcgaccgagt tgctcttgcc cggcgtcaat | 7200 |
| acgggataat accgcgccac atagcagaac tttaaaagtg ctcatcattg gaaaacgttc | 7260 |
| ttcggggcga aaactctcaa ggatcttacc gctgttgaga tccagttcga tgtaacccac | 7320 |
| tcgtgcaccc aactgatctt cagcatcttt tactttcacc agcgtttctg ggtgagcaaa | 7380 |
| aacaggaagg caaaatgccg caaaaaaggg aataagggcg acacggaaat gttgaatact | 7440 |
| catactcttc cttttcaat attattgaag catttatcag ggttattgtc tcatgagcgg | 7500 |
| atacatattt gaatgtattt agaaaaataa acaaataggg gttccgcgca catttccccg | 7560 |
| aaaagtgcca cctgacgtc | 7579 |

<210> SEQ ID NO 5
<211> LENGTH: 7558
<212> TYPE: DNA
<213> ORGANISM: Artificial Sequence
<220> FEATURE:
<223> OTHER INFORMATION: Synthetic Oligonucleotide

<400> SEQUENCE: 5

| | |
|---|---|
| gacggatcgg gagatctccc gatcccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |

-continued

```
tggagttccg cgttacataa cttacggtaa atggcccgcc tggctgaccg cccaacgacc      360
cccgcccatt gacgtcaata atgacgtatg ttcccatagt aacgccaata gggactttcc      420
attgacgtca atgggtggac tatttacggt aaactgccca cttggcagta catcaagtgt      480
atcatatgcc aagtacgccc cctattgacg tcaatgacgg taaatggccc gcctggcatt      540
atgcccagta catgacctta tgggactttc ctacttggca gtacatctac gtattagtca      600
tcgctattac catggtgatg cggttttggc agtacatcaa tgggcgtgga tagcggtttg      660
actcacgggg atttccaagt ctccacccca ttgacgtcaa tgggagtttg ttttggcacc      720
aaaatcaacg ggactttcca aaatgtcgta acaactccgc cccattgacg caaatgggcg      780
gtaggcgtgt acggtgggag gtctatataa gcagagctct ctggctaact agagaaccca      840
ctgcttactg gcttatcgaa attaatacga ctcactatag ggagacccaa gctggctaga      900
ggtaccaagc ttggatccca ccatggggtc aaccgtcatc ctcgccctcc tcctggctgt      960
tctccaagga gtctgtgccg aggtgcagct ggtgcagtct ggagcagagg tgaaaaagcc     1020
cggggagtct ctgaagatct cctgtaaggg ttctggatac agctttacca gttactggat     1080
cggctgggtg cgccagatgc ccgggaaagg cctggagtgg atggggatca tctatcctgg     1140
tgactctgat accagataca gcccgtcctt ccaaggccag gtcaccatct cagccgacaa     1200
gtccatcagc accgcctacc tgcagtggag cagcctgaag gcctcggaca ccgccatgta     1260
ttactgtgcg agacggatgg cagcagctgg ccccttttgac tactggggcc agggaaccct     1320
ggtcaccgtc tcctcagcct ccaccaaggg cccatcggtc ttccccctgg cacccctctag     1380 caagagcacc tctgggggca gcggccct gggctgcctg gtcaaggact acttccccga      1440
accggtgacg gtgtcgtgga actcaggcgc cctgaccagc ggcgtgcaca ccttcccggc     1500
tgtcctacag tcctcaggac tctactccct cagcagcgtg gtgaccgtgc cctccagcag     1560
cttgggcacc cagacctaca tctgcaacgt gaatcacaag cccagcaaca ccaaggtgga     1620
caagagagtt ggtgagaggc cagcacaggg agggagggtg tctgctggaa gccaggctca     1680
gcgctcctgc ctggacgcat cccggctatg cagtcccagt ccagggcagc aaggcaggcc     1740
ccgtctgcct cttcacccgg aggcctctgc ccgccccact catgctcagg gagagggtct     1800
tctggctttt tccccaggct ctgggcaggc acaggctagg tgcccctaac ccaggccctg     1860
cacacaaagg ggcaggtgct gggctcagac ctgccaagag ccatatccgg gaggaccctg     1920
cccctgacct aagcccaccc caaaggccaa actctccact ccctcagctc ggacaccttc     1980
tctcctccca gattccagta actcccaatc ttctctctgc agagcccaaa tcttgtgaca     2040
aaactcacac atgcccaccg tgcccaggta gccagccca ggcctcgccc tccagctcaa     2100
ggcgggacag gtgccctaga gtagcctgca tccagggaca ggccccagcc gggtgctgac     2160
acgtccacct ccatctcttc ctcagcacct gaactcctgg ggggaccgtc agtcttcctc     2220
ttccccccaa aacccaagga caccctcatg atctcccgga cccctgaggt cacatgcgtg     2280
gtggtggacg tgagccacga agaccctgag gtcaagttca actggtacgt ggacggcgtg     2340
gaggtgcata atgccaagac aaagccgcgg gaggagcagt acaacagcac gtaccgtgtg     2400
gtcagcgtcc tcaccgtcct gcaccaggac tggctgaatg gcaaggagta caagtgcaag     2460
gtctccaaca aagccctccc agcccccatc gagaaaacca tctccaaagc caaggtgggg     2520
acccgtgggg tgcgagggcc acatggacag aggccggctc ggcccaccct ctgccctgag     2580
agtgaccgct gtaccaacct ctgtccctac agggcagccc cgagaaccac aggtgtacac     2640
cctgccccca tcccgggagg agatgaccaa gaaccaggtc agcctgacct gcctggtcaa     2700
```

```
aggcttctat cccagcgaca tcgccgtgga gtgggagagc aatgggcagc cggagaacaa    2760
ctacaagacc acgcctcccg tgctggactc cgacggctcc ttcttcctct atagcaagct    2820
caccgtggac aagagcaggt ggcagcaggg gaacgtcttc tcatgctccg tgatgcatga    2880
ggctctgcac aaccactaca cgcagaagag cctctccctg tctccgggta aatgagaatt    2940
cctcgagtct agagggcccg tttaaacccg ctgatcagcc tcgactgtgc cttctagttg    3000
ccagccatct gttgtttgcc cctcccccgt gccttccttg accctggaag gtgccactcc    3060
cactgtcctt tcctaataaa atgaggaaat tgcatcgcat tgtctgagta ggtgtcattc    3120
tattctgggg ggtggggtgg ggcaggacag caaggggag gattgggaag acaatagcag    3180
gcatgctggg gatgcggtgg gctctatggc ttctgaggcg gaaagaacca gctgggctc    3240 taggggtat ccccacgcgc cctgtagcgg cgcattaagc gcggcgggtg tggtggttac    3300
gcgcagcgtg accgctacac ttgccagcgc cctagcgccc gctcctttcg ctttcttccc    3360
ttcctttctc gccacgttcg ccggctttcc ccgtcaagct ctaaatcggg gcatcccttt    3420
agggttccga tttagtgctt tacggcacct cgaccccaaa aaacttgatt agggtgatgg    3480
ttcacgtagt gggccatcgc cctgatagac ggttttttcgc cctttgacgt tggagtccac    3540
gttctttaat agtggactct tgttccaaac tggaacaaca ctcaacccta tctcggtcta    3600
ttcttttgat ttataaggga ttttggggat ttcggcctat tggttaaaaa atgagctgat    3660
ttaacaaaaa tttaacgcga attaattctg tggaatgtgt gtcagttagg gtgtggaaag    3720
tccccaggct ccccaggcag gcagaagtat gcaaagcatg catctcaatt agtcagcaac    3780
caggtgtgga aagtccccag gctccccagc aggcagaagt atgcaaagca tgcatctcaa    3840
ttagtcagca accatagtcc cgcccctaac tccgcccatc ccgcccctaa ctccgcccag    3900
ttccgcccat tctccgcccc atggctgact aatttttttt atttatgcag aggccgaggc    3960
cgcctctgcc tctgagctat tccagaagta gtgaggagga tttttttggag cctaggctt    4020 ttgcaaaaag ctcccgggag cttgtatatc cattttcgga tctgatcagc acgtgatgaa    4080
aaagcctgaa ctcaccgcga cgtctgtcga agtttctg atcgaaaagt cgacagcgt    4140 ctccgacctg atgcagctct cggagggcga agaatctcgt gctttcagct tcgatgtagg    4200
agggcgtgga tatgtcctgc gggtaaatag ctgcgccgat ggtttctaca agatcgtta    4260 tgtttatcgg cactttgcat cggccgcgct cccgattccg gaagtgcttg acattgggga    4320
attcagcgag agcctgacct attgcatctc ccgccgtgca cagggtgtca cgttgcaaga    4380
cctgcctgaa accgaactgc ccgctgttct gcagccggtc gcggaggcca tggatgcgat    4440
cgctgcggcc gatcttagcc agacgagcgg gttcggccca ttcggaccgc aaggaatcgg    4500
tcaatacact acatggcgtg atttcatatg cgcgattgct gatccccatg tgtatcactg    4560
gcaaactgtg atggacgaca ccgtcagtgc gtccgtcgcg caggctctcg atgagctgat    4620
gctttgggcc gaggactgcc ccgaagtccg gcacctcgtg cacgcggatt tcggctccaa    4680
caatgtcctg acggacaatg gccgcataac agcggtcatt gactgagcg aggcgatgtt    4740 cggggattcc caatacgagg tcgccaacat cttcttctgg aggccgtggt tggcttgtat    4800
ggagcagcag acgcgctact cgagcggag gcatccggag cttgcaggat cgccgcggct    4860
ccgggcgtat atgctccgca ttggtcttga ccaactctat cagagcttgg ttgacggcaa    4920
tttcgatgat gcagcttggg cgcagggtcg atgcgacgca atcgtccgat ccggagccgg    4980
gactgtcggg cgtacacaaa tcgcccgcag aagcgcggcc gtctggaccg atggctgtgt    5040
```

```
agaagtactc gccgatagtg gaaaccgacg ccccagcact cgtccgaggg caaaggaata    5100
gcacgtgcta cgagatttcg attccaccgc cgccttctat gaaaggttgg gcttcggaat    5160
cgttttccgg gacgccggct ggatgatcct ccagcgcggg gatctcatgc tggagttctt    5220
cgcccacccc aacttgttta ttgcagctta taatggttac aaataaagca atagcatcac    5280
aaatttcaca aataaagcat ttttttcact gcattctagt tgtggtttgt ccaaactcat    5340
caatgtatct tatcatgtct gtataccgtc gacctctagc tagagcttgg cgtaatcatg    5400
gtcatagctg tttcctgtgt gaaattgtta tccgctcaca attccacaca acatacgagc    5460
cggaagcata aagtgtaaag cctggggtgc ctaatgagtg agctaactca cattaattgc    5520
gttgcgctca ctgcccgctt tccagtcggg aaacctgtcg tgccagctgc attaatgaat    5580
cggccaacgc gcggggagag gcggtttgcg tattgggcgc tcttccgctt cctcgctcac    5640
tgactcgctg cgctcggtcg ttcggctgcg gcgagcggta tcagctcact caaaggcggt    5700
aatacggtta tccacagaat caggggataa cgcaggaaag aacatgtgag caaaaggcca    5760
gcaaaaggcc aggaaccgta aaaaggccgc gttgctggcg tttttccata ggctccgccc    5820
ccctgacgag catcacaaaa atcgacgctc aagtcagagg tggcgaaacc cgacaggact    5880
ataaagatac caggcgtttc ccctggaag ctccctcgtg cgctctcctg ttccgaccct    5940
gccgcttacc ggatacctgt ccgcctttct cccttcggga agcgtggcgc tttctcaatg    6000
ctcacgctgt aggtatctca gttcggtgta ggtcgttcgc tccaagctgg gctgtgtgca    6060 cgaaccccc gttcagcccg accgctgcgc cttatccggt aactatcgtc ttgagtccaa    6120
cccggtaaga cacgacttat cgccactggc agcagccact ggtaacagga ttagcagagc    6180
gaggtatgta ggcggtgcta cagagttctt gaagtggtgg cctaactacg gctacactag    6240
aaggacagta tttggtatct gcgctctgct gaagccagtt accttcggaa aaagagttgg    6300
tagctcttga tccggcaaac aaaccaccgc tggtagcggt ggtttttttg tttgcaagca    6360
gcagattacg cgcagaaaaa aaggatctca agaagatcct ttgatctttt ctacggggtc    6420
tgacgctcag tggaacgaaa actcacgtta agggattttg gtcatgagat tatcaaaaag    6480
gatcttcacc tagatccttt taaattaaaa atgaagtttt aaatcaatct aaagtatata    6540
tgagtaaact tggtctgaca gttaccaatg cttaatcagt gaggcaccta tctcagcgat    6600
ctgtctattt cgttcatcca tagttgcctg actccccgtc gtgtagataa ctacgatacg    6660
ggagggctta ccatctggcc ccagtgctgc aatgataccg cgagacccac gctcaccggc    6720
tccagattta tcagcaataa accagccagc cggaagggcc gagcgcagaa gtggtcctgc    6780
aactttatcc gcctccatcc agtctattaa ttgttgccgg gaagctagag taagtagttc    6840
gccagttaat agtttgcgca acgttgttgc cattgctaca ggcatcgtgg tgtcacgctc    6900
gtcgtttggt atggcttcat tcagctccgg ttcccaacga tcaaggcgag ttacatgatc    6960
ccccatgttg tgcaaaaaag cggttagctc cttcggtcct ccgatcgttg tcagaagtaa    7020
gttggccgca gtgttatcac tcatggttat ggcagcactg cataattctc ttactgtcat    7080
gccatccgta agatgctttt ctgtgactgg tgagtactca accaagtcat tctgagaata    7140
gtgtatgcgg cgaccgagtt gctcttgccc ggcgtcaata cgggataata ccgcgccaca    7200
tagcagaact ttaaaagtgc tcatcattgg aaaacgttct cggggcgaa aactctcaag    7260 gatcttaccg ctgttgagat ccagttcgat gtaacccact cgtgcaccca actgatcttc    7320
agcatctttt actttcacca gcgtttctgg gtgagcaaaa acaggaaggc aaaatgccgc    7380
aaaaaaggga ataagggcga cacggaaatg ttgaatactc atactcttcc ttttttcaata    7440
```

| | |
|---|---|
| ttattgaagc atttatcagg gttattgtct catgagcgga tacatatttg aatgtattta | 7500 |
| gaaaaataaa caaatagggg ttccgcgcac atttccccga aaagtgccac ctgacgtc | 7558 |

<210> SEQ ID NO 6
<211> LENGTH: 7576
<212> TYPE: DNA
<213> ORGANISM: Artificial Sequence
<220> FEATURE:
<223> OTHER INFORMATION: Synthetic Oligonucleotide

<400> SEQUENCE: 6

| | |
|---|---|
| gacggatcgg gagatctccc gatcccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggac tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta caactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctaga | 900 |
| ggtaccaagc ttggatctca ccatggagtt tgggctgtgc tggattttcc tcgttgctct | 960 |
| tttaagaggt gtccagtgtc aggtgcagct ggtggagtct gggggaggcg tggtccagcc | 1020 |
| tgggaggtcc ctgagactct cctgtgcagc ctctggattc accttcatta gctatggcat | 1080 |
| gcactgggtc cgccaggctc aggcaagggg ctggagtgg gtggcagtta tatcatatga | 1140 |
| tggaagtaat aaatactatg cagactccgt gaagggccga ttcaccatct ccagagacaa | 1200 |
| ttccaagaac acgctgtatc tgcaaatgaa cagcctgaga gctgaggaca cggctgtgta | 1260 |
| ttactgtgcg agagtattag tgggagcttt atattattat aactactacg gatggacgt | 1320 |
| ctggggccaa gggaccacgg tcaccgtctc ctcagcctcc accaagggcc catcggtctt | 1380 |
| cccccctggca ccctctagca agagcacctc tgggggcaca gcggccctgg gctgcctggt | 1440 |
| caaggactac ttccccgaac cggtgacggt gtcgtggaac tcaggcgccc tgaccagcgg | 1500 |
| cgtgcacacc ttcccggctg tcctacagtc ctcaggactc tactccctca gcagcgtggt | 1560 |
| gaccgtgccc tccagcagct tgggcaccca gacctacatc tgcaacgtga atcacaagcc | 1620 |
| cagcaacacc aaggtggaca agagagttgg tgagaggcca gcacagggag ggagggtgtc | 1680 |
| tgctggaagc caggctcagc gctcctgcct ggacgcatcc cggctatgca gtcccagtcc | 1740 |
| agggcagcaa ggcaggcccc gtctgcctct tcacccggag cctctgcccg ccccactca | 1800 |
| tgctcaggga gagggtcttc tggctttttc cccaggctct gggcaggcac aggctaggtg | 1860 |
| cccctaaccc aggccctgca cacaaagggg caggtgctgg gctcagacct gccaagagcc | 1920 |

-continued

```
atatccggga ggaccctgcc cctgacctaa gcccacccca aaggccaaac tctccactcc   1980
ctcagctcgg acaccttctc tcctcccaga ttccagtaac tcccaatctt ctctctgcag   2040
agcccaaatc ttgtgacaaa actcacacat gcccaccgtg cccaggtaag ccagcccagg   2100
cctcgccctc cagctcaagg cgggacaggt gccctagagt agcctgcatc cagggacagg   2160
ccccagccgg gtgctgacac gtccacctcc atctcttcct cagcacctga actcctgggg   2220
ggaccgtcag tcttcctctt ccccccaaaa cccaaggaca ccctcatgat ctcccggacc   2280
cctgaggtca catgcgtggt ggtggacgtg agccacgaag accctgaggt caagttcaac   2340
tggtacgtga cggcgtgga ggtgcataat gccaagacaa agccgcggga ggagcagtac   2400
aacagcacgt accgtgtggt cagcgtcctc accgtcctgc accaggactg gctgaatggc   2460
aaggagtaca agtgcaaggt ctccaacaaa gccctcccag cccccatcga gaaaaccatc   2520
tccaaagcca aggtgggac ccgtggggtg cgagggccac atggacagag gccggctcgg   2580
cccaccctct gccctgagag tgaccgctgt accaacctct gtcccctacag gcagccccg   2640
agaaccacag gtgtacaccc tgccccatc ccgggaggag atgaccaaga accaggtcag   2700
cctgacctgc ctggtcaaag gcttctatcc cagcgacatc gccgtggagt gggagagcaa   2760
tgggcagccg gagaacaact acaagaccac gcctcccgtg ctggactccg acggctcctt   2820
cttcctctat agcaagctca ccgtggacaa gagcaggtgg cagcagggga acgtcttctc   2880
atgctccgtg atgcatgagg ctctgcacaa ccactacacg cagaagagcc tctccctgtc   2940
tccgggtaaa tgagaattcc tcgagtctag agggcccgtt taaacccgct gatcagcctc   3000
gactgtgcct tctagttgcc agccatctgt tgtttgcccc tcccccgtgc cttccttgac   3060
cctggaaggt gccactccca ctgtcctttc ctaataaaat gaggaaattg catcgcattg   3120
tctgagtagg tgtcattcta ttctgggggg tggggtgggg caggacagca agggggagga   3180
ttgggaagac aatagcaggc atgctgggga tgcggtgggc tctatggctt ctgaggcgga   3240
aagaaccagc tggggctcta gggggtatcc ccacgcgccc tgtagcggcg cattaagcgc   3300
ggcgggtgtg gtggttacgc gcagcgtgac cgctacactt gccagcgccc tagcgcccgc   3360
tcctttcgct ttcttccctt cctttctcgc cacgttcgcc ggctttcccc gtcaagctct   3420
aaatcgggc atccctttag ggttccgatt tagtgcttta cggcacctcg accccaaaaa   3480
acttgattag ggtgatggtt cacgtagtgg gccatcgccc tgatagacgg ttttcgccc   3540
tttgacgttg gagtccacgt tctttaatag tggactcttg ttccaaactg gaacaacact   3600
caaccctatc tcggtctatt cttttgattt ataagggatt ttggggattt cggcctattg   3660
gttaaaaaat gagctgattt aacaaaaatt taacgcgaat taattctgtg aatgtgtgt   3720
cagttagggt gtggaaagtc cccaggctcc ccaggcaggc agaagtatgc aaagcatgca   3780
tctcaattag tcagcaacca ggtgtggaaa gtccccaggc tccccagcag gcagaagtat   3840
gcaaagcatg catctcaatt agtcagcaac catagtcccg cccctaactc cgcccatccc   3900
gcccctaact ccgcccagtt ccgcccattc tccgccccat ggctgactaa tttttttat   3960
ttatgcagag gccgaggccg cctctgcctc tgagctattc cagaagtagt gaggaggctt   4020
ttttggaggc ctaggctttt gcaaaaagct cccgggagct tgtatatcca ttttcggatc   4080
tgatcagcac gtgatgaaaa agcctgaact caccgcgacg tctgtcgaga gtttctgat   4140
cgaaaagttc gacagcgtct ccgacctgat gcagctctcg gagggcgaag aatctcgtgc   4200
tttcagcttc gatgtaggag ggcgtggata tgtcctgcgg gtaaatagct gcgccgatgg   4260
tttctacaaa gatcgttatg tttatcggca ctttgcatcg gccgcgctcc cgattccgga   4320
```

```
agtgcttgac attggggaat tcagcgagag cctgacctat tgcatctccc gccgtgcaca   4380
gggtgtcacg ttgcaagacc tgcctgaaac cgaactgccc gctgttctgc agccggtcgc   4440
ggaggccatg gatgcgatcg ctgcggccga tcttagccag acgagcgggt tcggcccatt   4500
cggaccgcaa ggaatcggtc aatacactac atggcgtgat ttcatatgcg cgattgctga   4560
tccccatgtg tatcactggc aaactgtgat ggacgacacc gtcagtgcgt ccgtcgcgca   4620
ggctctcgat gagctgatgc tttgggccga ggactgcccc gaagtccggc acctcgtgca   4680
cgcggatttc ggctccaaca atgtcctgac ggacaatggc cgcataacag cggtcattga   4740
ctggagcgag gcgatgttcg ggattccca atacgaggtc gccaacatct tcttctggag   4800
gccgtggttg gcttgtatgg agcagcagac gcgctacttc gagcggaggc atccggagct   4860
tgcaggatcg ccgcggctcc gggcgtatat gctccgcatt ggtcttgacc aactctatca   4920
gagcttggtt gacggcaatt tcgatgatgc agcttgggcg cagggtcgat gcgacgcaat   4980
cgtccgatcc ggagccggga ctgtcgggcg tacacaaatc gcccgcagaa gcgcggccgt   5040
ctggaccgat ggctgtgtag aagtactcgc cgatagtgga aaccgacgcc ccagcactcg   5100
tccgagggca aggaatagc acgtgctacg agatttcgat tccaccgccg ccttctatga   5160
aaggttgggc ttcggaatcg ttttccggga cgccggctgg atgatcctcc agcgcgggga   5220
tctcatgctg gagttcttcg cccaccccaa cttgtttatt gcagcttata atggttacaa   5280
ataaagcaat agcatcacaa atttcacaaa taaagcattt ttttcactgc attctagttg   5340
tggtttgtcc aaactcatca atgtatctta tcatgtctgt ataccgtcga cctctagcta   5400
gagcttggcg taatcatggt catagctgtt tcctgtgtga aattgttatc cgctcacaat   5460
tccacacaac atacgagccg gaagcataaa gtgtaaagcc tggggtgcct aatgagtgag   5520
ctaactcaca ttaattgcgt tgcgctcact gcccgctttc cagtcgggaa acctgtcgtg   5580
ccagctgcat taatgaatcg gccaacgcgc ggggagaggc ggtttgcgta ttgggcgctc   5640
ttccgcttcc tcgctcactg actcgctgcg ctcggtcgtt cggctgcggc gagcggtatc   5700
agctcactca aaggcggtaa tacggttatc cacagaatca ggggataacg caggaaagaa   5760
catgtgagca aaaggccagc aaaaggccag gaaccgtaaa aaggccgcgt tgctggcgtt   5820
tttccatagg ctccgccccc ctgacgagca tcacaaaaat cgacgctcaa gtcagaggtg   5880
gcgaaacccg acaggactat aaagatacca ggcgtttccc cctggaagct ccctcgtgcg   5940
ctctcctgtt ccgaccctgc cgcttaccgg atacctgtcc gcctttctcc cttcgggaag   6000
cgtggcgctt tctcaatgct cacgctgtag gtatctcagt tcggtgtagg tcgttcgctc   6060
caagctgggc tgtgtgcacg aacccccgt tcagcccgac cgctgcgcct tatccggtaa   6120
ctatcgtctt gagtccaacc cggtaagaca cgacttatcg ccactggcag cagccactgg   6180
taacaggatt agcagagcga ggtatgtagg cggtgctaca gagttcttga agtggtggcc   6240
taactacggc tacactagaa ggacagtatt tggtatctgc gctctgctga agccagttac   6300
cttcggaaaa agagttggta gctcttgatc cggcaaacaa accaccgctg gtagcggtgg   6360 ttttttgtt tgcaagcagc agattacgcg cagaaaaaa ggatctcaag aagatccttt   6420
gatcttttct acgggtctg acgctcagtg gaacgaaaac tcacgttaag ggattttggt   6480
catgagatta tcaaaaagga tcttcaccta gatccttta aattaaaaat gaagttttaa   6540
atcaatctaa agtatatatg agtaaacttg gtctgacagt taccaatgct taatcagtga   6600
ggcacctatc tcagcgatct gtctatttcg ttcatccata gttgcctgac tccccgtcgt   6660
```

```
gtagataact acgatacggg agggcttacc atctggcccc agtgctgcaa tgataccgcg      6720
agacccacgc tcaccggctc cagatttatc agcaataaac cagccagccg aagggccga       6780 gcgcagaagt ggtcctgcaa ctttatccgc ctccatccag tctattaatt gttgccggga      6840
agctagagta agtagttcgc cagttaatag tttgcgcaac gttgttgcca ttgctacagg      6900
catcgtggtg tcacgctcgt cgtttggtat ggcttcattc agctccggtt cccaacgatc      6960
aaggcgagtt acatgatccc ccatgttgtg caaaaaagcg gttagctcct tcggtcctcc      7020
gatcgttgtc agaagtaagt tggccgcagt gttatcactc atggttatgg cagcactgca      7080
taattctctt actgtcatgc catccgtaag atgcttttct gtgactggtg agtactcaac      7140
caagtcattc tgagaatagt gtatgcggcg accgagttgc tcttgcccgg cgtcaatacg      7200
ggataatacc gcgccacata gcagaacttt aaaagtgctc atcattggaa aacgttcttc     7260
ggggcgaaaa ctctcaagga tcttaccgct gttgagatcc agttcgatgt aacccactcg      7320
tgcacccaac tgatcttcag catcttttac tttcaccagc gtttctgggt gagcaaaaac      7380
aggaaggcaa aatgccgcaa aaaagggaat aagggcgaca cggaaatgtt gaatactcat      7440
actcttcctt tttcaatatt attgaagcat ttatcagggt tattgtctca tgagcggata      7500
catatttgaa tgtatttaga aaaataaaca ataggggtt ccgcgcacat tccccgaaa        7560 agtgccacct gacgtc                                                     7576
```

<210> SEQ ID NO 7
<211> LENGTH: 7561
<212> TYPE: DNA
<213> ORGANISM: Artificial Sequence
<220> FEATURE:
<223> OTHER INFORMATION: Synthetic Oligonucleotide
<400> SEQUENCE: 7

```
gacggatcgg gagatctccc gatccctat ggtcgactct cagtacaatc tgctctgatg        60
ccgcatagtt aagccagtat ctgctccctg cttgtgtgtt ggaggtcgct gagtagtgcg      120
cgagcaaaat ttaagctaca acaaggcaag gcttgaccga caattgcatg aagaatctgc      180
ttagggttag gcgttttgcg ctgcttcgcg atgtacgggc cagatatacg cgttgacatt      240
gattattgac tagttattaa tagtaatcaa ttacggggtc attagttcat agcccatata      300
tggagttccg cgttacataa cttacggtaa atggcccgcc tggctgaccg cccaacgacc      360
cccgcccatt gacgtcaata atgacgtatg ttcccatagt aacgccaata gggactttcc      420
attgacgtca atgggtggac tatttacggt aaactgccca cttggcagta catcaagtgt      480
atcatatgcc aagtacgccc cctattgacg tcaatgacgg taaatggccc gcctggcatt      540
atgcccagta catgacctta tgggactttc ctacttggca gtacatctac gtattagtca      600
tcgctattac catggtgatg cggttttggc agtacatcaa tgggcgtgga tagcggtttg      660
actcacgggg atttccaagt ctccacccca ttgacgtcaa tgggagtttg ttttggcacc      720
aaaatcaacg ggactttcca aaatgtcgta acaactccgc cccattgacg caaatgggcg      780
gtaggcgtgt acggtgggag gtctatataa gcagagctct ctggctaact agagaaccca      840
ctgcttactg gcttatcgaa attaatacga ctcactatag ggagacccaa gctggctaga      900
ggtaccggat ctcaccatgg agttgggct gagctggtt ttcctcgttg ctcttttaag        960
aggtgtccag tgtcaggagc agctggtgga gtctggggga ggcgtggtcc agcctgggag     1020
gtccctgaga ctctcctgtg cagcgtctgg attcaccttc agtacctatg catgcactg      1080 ggtccgccag gctccaggca aggggctgga gtgggtggca gttacatggc atgatggaag     1140
```

```
taataaatac tatgcagact ccgtgaaggg ccgattcacc atctccagag acaactccaa    1200
gaacacgctg tatctgcaaa tgaacagcct gagagccgag gacacggctg tgtattactg    1260
tgcgagagga ggagtgggag caacttacta ctactactac ggtatggacg tctggggcca    1320
agggaccacg gtcaccgtct cctcagcctc caccaagggc ccatcggtct tccccctggc    1380
accctctagc aagagcacct ctggggggcac agcggccctg gctgcctgg tcaaggacta    1440 cttccccgaa ccggtgacgg tgtcgtggaa ctcaggcgcc ctgaccagcg gcgtgcacac    1500
cttcccggct gtcctacagt cctcaggact ctactccctc agcagcgtgg tgaccgtgcc    1560
ctccagcagc ttgggcaccc agacctacat ctgcaacgtg aatcacaagc ccagcaacac    1620
caaggtggac aagagagttg gtgagaggcc agcacaggga gggagggtgt ctgctggaag    1680
ccaggctcag cgctcctgcc tggacgcatc ccggctatgc agtcccagtc cagggcagca    1740
aggcaggccc cgtctgcctc ttcacccgga ggcctctgcc cgcccactc atgctcaggg    1800 agagggtctt ctggcttttt ccccaggctc tgggcaggca caggctaggt gcccctaacc    1860
caggccctgc acacaaaggg gcaggtgctg ggctcagacc tgccaagagc catatccggg    1920
aggaccctgc ccctgaccta agcccacccc aaaggccaaa ctctccactc cctcagctcg    1980
gacaccttct ctcctcccag attccagtaa ctcccaatct tctctctgca gagcccaaat    2040
cttgtgacaa aactcacaca tgcccaccgt gcccaggtaa gccagcccag gcctcgccct    2100
ccagctcaag cgggacaggt gccctagag tagcctgcat ccaggacag gccccagccg    2160 ggtgctgaca cgtccacctc catctcttcc tcagcacctg aactcctggg gggaccgtca    2220
gtcttcctct tccccccaaa acccaaggac accctcatga tctcccggac ccctgaggtc    2280
acatgcgtgg tggtggacgt gagccacgaa gaccctgagg tcaagttcaa ctggtacgtg    2340
gacggcgtgg aggtgcataa tgccaagaca aagccgcggg aggagcagta caacagcacg    2400
taccgtgtgg tcagcgtcct caccgtcctg caccaggact ggctgaatgg caaggagtac    2460
aagtgcaagg tctccaacaa agccctccca gcccccatcg agaaaaccat ctccaaagcc    2520
aaaggtggga cccgtggggt gcgagggcca catggacaga ggccggctcg gcccaccctc    2580
tgccctgaga gtgaccgctg taccaacctc tgtccctaca gggcagcccc gagaaccaca    2640
ggtgtacacc ctgcccccat cccgggagga gatgaccaag aaccaggtca gcctgacctg    2700
cctggtcaaa ggcttctatc ccagcgacat cgccgtggag tgggagagca atgggcagcc    2760
ggagaacaac tacaagacca cgcctcccgt gctggactcc gacggctcct tcttcctcta    2820
tagcaagctc accgtggaca agagcaggtg gcagcagggg aacgtcttct catgctccgt    2880
gatgcatgag gctctgcaca accactacac gcagaagagc ctctccctgt ctccgggtaa    2940
atgactcgag tctagagggc ccgtttaaac ccgctgatca gcctcgactg tgccttctag    3000
ttgccagcca tctgttgttt gcccctcccc cgtgccttcc ttgaccctgg aaggtgccac    3060
tcccactgtc ctttcctaat aaaatgagga aattgcatcg cattgtctga gtaggtgtca    3120
ttctattctg gggggtgggg tggggcagga cagcaagggg gaggattggg aagacaatag    3180
caggcatgct ggggatgcgg tgggctctat ggcttctgag gcggaaagaa ccagctgggg    3240
ctctaggggg tatccccacg cgccctgtag cggcgcatta agcgcggcgg gtgtggtggt    3300
tacgcgcagc gtgaccgcta cacttgccag cgccctagcg cccgctcctt tcgctttctt    3360
cccttccttt ctcgccacgt tcgccggctt tccccgtcaa gctctaaatc ggggcatccc    3420
tttagggttc cgatttagtg ctttacggca cctcgacccc aaaaaacttg attagggtga    3480
```

```
tggttcacgt agtgggccat cgccctgata gacggttttt cgccctttga cgttggagtc    3540
cacgttcttt aatagtggac tcttgttcca aactggaaca acactcaacc ctatctcggt    3600
ctattctttt gatttataag ggattttggg gatttcggcc tattggttaa aaaatgagct    3660
gatttaacaa aaatttaacg cgaattaatt ctgtggaatg tgtgtcagtt agggtgtgga    3720
aagtccccag gctccccagg caggcagaag tatgcaaagc atgcatctca attagtcagc    3780
aaccaggtgt ggaaagtccc caggctcccc agcaggcaga agtatgcaaa gcatgcatct    3840
caattagtca gcaaccatag tcccgcccct aactccgccc atcccgcccc taactccgcc    3900
cagttccgcc cattctccgc cccatggctg actaattttt tttatttatg cagaggccga    3960
ggccgcctct gcctctgagc tattccagaa gtagtgagga ggcttttttg gaggcctagg    4020
cttttgcaaa aagctcccgg gagcttgtat atccattttc ggatctgatc agcacgtgat    4080
gaaaaagcct gaactcaccg cgacgtctgt cgagaagttt ctgatcgaaa agttcgacag    4140
cgtctccgac ctgatgcagc tctcggaggg cgaagaatct cgtgctttca gcttcgatgt    4200
aggagggcgt ggatatgtcc tgcgggtaaa tagctgcgcc gatggttttct acaaagatcg    4260
ttatgtttat cggcactttg catcggccgc gctcccgatt ccggaagtgc ttgacattgg    4320
ggaattcagc gagagcctga cctattgcat ctcccgccgt gcacagggtg tcacgttgca    4380
agacctgcct gaaaccgaac tgcccgctgt tctgcagccg gtcgcggagg ccatggatgc    4440
gatcgctgcg gccgatctta gccagacgag cgggttcggc ccattcggac cgcaaggaat    4500
cggtcaatac actacatggc gtgatttcat atgcgcgatt gctgatcccc atgtgtatca    4560
ctggcaaact gtgatggacg acaccgtcag tgcgtccgtc gcgcaggctc tcgatgagct    4620
gatgctttgg gccgaggact gccccgaagt ccggcacctc gtgcacgcgg atttcggctc    4680
caacaatgtc ctgacggaca atggccgcat aacagcggtc attgactgga gcgaggcgat    4740
gttcggggat tcccaatacg aggtcgccaa catcttcttc tggaggccgt ggttggcttg    4800
tatgagcag cagacgcgct acttcgagcg gaggcatccg gagcttgcag gatcgccgcg    4860
gctccgggcg tatatgctcc gcattggtct tgaccaactc tatcagagct tggttgacgg    4920
caatttcgat gatgcagctt gggcgcaggg tcgatgcgac gcaatcgtcc gatccggagc    4980
cgggactgtc gggcgtacac aaatcgcccg cagaagcgcg gccgtctgga ccgatggctg    5040
tgtagaagta ctcgccgata gtggaaaccg acgccccagc actcgtccga gggcaaagga    5100
atagcacgtg ctacgagatt tcgattccac cgccgccttc tatgaaaggt tgggcttcgg    5160
aatcgttttc cgggacgccg gctggatgat cctccagcgc ggggatctca tgctggagtt    5220
cttcgcccac cccaacttgt ttattgcagc ttataatggt tacaaataaa gcaatagcat    5280
cacaaatttc acaaataaag cattttttc actgcattct agttgtggtt tgtccaaact    5340
catcaatgta tcttatcatg tctgtatacc gtcgacctct agctagagct tggcgtaatc    5400
atggtcatag ctgtttcctg tgtgaaattg ttatccgctc acaattccac acaacatacg    5460
agccggaagc ataaagtgta aagcctgggg tgcctaatga gtgagctaac tcacattaat    5520
tgcgttgcgc tcactgcccg ctttccagtc gggaaacctg tcgtgccagc tgcattaatg    5580
aatcggccaa cgcgcgggga gaggcggttt gcgtattggg cgctcttccg cttcctcgct    5640
cactgactcg ctgcgctcgg tcgttcggct gcggcgagcg gtatcagctc actcaaaggc    5700
ggtaatacgg ttatccacag aatcagggga taacgcagga agaacatgt gagcaaaagg    5760
ccagcaaaag gccaggaacc gtaaaaaggc cgcgttgctg cgttttttcc ataggctccg    5820
ccccctgac gagcatcaca aaaatcgacg ctcaagtcag aggtggcgaa acccgacagg    5880
```

-continued

| | |
|---|---|
| actataaaga taccaggcgt ttcccctgg aagctccctc gtgcgctctc ctgttccgac | 5940 |
| cctgccgctt accggatacc tgtccgcctt tctcccttcg ggaagcgtgg cgctttctca | 6000 |
| atgctcacgc tgtaggtatc tcagttcggt gtaggtcgtt cgctccaagc tgggctgtgt | 6060 |
| gcacgaaccc cccgttcagc ccgaccgctg cgccttatcc ggtaactatc gtcttgagtc | 6120 |
| caacccggta agacacgact tatcgccact ggcagcagcc actggtaaca ggattagcag | 6180 |
| agcgaggtat gtaggcggtg ctacagagtt cttgaagtgg tggcctaact acggctacac | 6240 |
| tagaaggaca gtatttggta tctgcgctct gctgaagcca gttaccttcg gaaaaagagt | 6300 |
| tggtagctct tgatccggca aacaaaccac cgctggtagc ggtggttttt ttgtttgcaa | 6360 |
| gcagcagatt acgcgcagaa aaaaaggatc tcaagaagat cctttgatct tttctacggg | 6420 |
| gtctgacgct cagtggaacg aaaactcacg ttaagggatt ttggtcatga gattatcaaa | 6480 |
| aaggatcttc acctagatcc ttttaaatta aaaatgaagt tttaaatcaa tctaaagtat | 6540 |
| atatgagtaa acttggtctg acagttacca atgcttaatc agtgaggcac ctatctcagc | 6600 |
| gatctgtcta tttcgttcat ccatagttgc ctgactcccc gtcgtgtaga taactacgat | 6660 |
| acgggagggc ttaccatctg gccccagtgc tgcaatgata ccgcgagacc cacgctcacc | 6720 |
| ggctccagat ttatcagcaa taaaccagcc agccggaagg gccgagcgca gaagtggtcc | 6780 |
| tgcaacttta tccgcctcca tccagtctat taattgttgc cgggaagcta gagtaagtag | 6840 |
| ttcgccagtt aatagtttgc gcaacgttgt tgccattgct acaggcatcg tggtgtcacg | 6900 |
| ctcgtcgttt ggtatggctt cattcagctc cggttcccaa cgatcaaggc gagttacatg | 6960 |
| atcccccatg ttgtgcaaaa aagcggttag ctccttcggt cctccgatcg ttgtcagaag | 7020 |
| taagttggcc gcagtgttat cactcatggt tatggcagca ctgcataatt ctcttactgt | 7080 |
| catgccatcc gtaagatgct tttctgtgac tggtgagtac tcaaccaagt cattctgaga | 7140 |
| atagtgtatg cggcgaccga gttgctcttg cccggcgtca atacgggata taccgcgcc | 7200 |
| acatagcaga actttaaaag tgctcatcat tggaaaacgt tcttcgggggc gaaaactctc | 7260 |
| aaggatctta ccgctgttga gatccagttc gatgtaaccc actcgtgcac ccaactgatc | 7320 |
| ttcagcatct tttactttca ccagcgtttc tgggtgagca aaaacaggaa ggcaaaatgc | 7380 |
| cgcaaaaaag ggaataaggg cgacacggaa atgttgaata ctcatactct tcctttttca | 7440 |
| atattattga agcatttatc agggttattg tctcatgagc ggatacatat ttgaatgtat | 7500 |
| ttagaaaaat aaacaaatag gggttccgcg cacatttccc cgaaaagtgc cacctgacgt | 7560 |
| c | 7561 |

<210> SEQ ID NO 8
<211> LENGTH: 6082
<212> TYPE: DNA
<213> ORGANISM: Artificial Sequence
<220> FEATURE:
<223> OTHER INFORMATION: Synthetic Oligonucleotide

<400> SEQUENCE: 8

| | |
|---|---|
| gacggatcgg gagatctccc gatcccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag cttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |

-continued

```
tggagttccg cgttacataa cttacggtaa atggcccgcc tggctgaccg cccaacgacc      360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctaga    900
aagcttggat ctcaccatga gggtccctgc tcagctcctg ggactcctgc tgctctggct    960
cccagatacc agatgtgaca tccagatgac ccagtctcca tcctccctgt ctgcatctgt    1020
aggagacaga gtcaccatca cttgccgggc gagtcagggc attagcaatt atttagcctg    1080
gtatcagcag aaaacaggga aagttcctaa gttcctgatc tatgaagcat ccactttgca    1140
atcaggggtc ccatctcggt tcagtggcgg tggatctggg acagatttca ctctcaccat    1200
cagcagcctg cagcctgaag atgttgcaac ttattactgt caaaattata acagtgcccc    1260
attcactttc ggccctggga ccaaagtgga tatcaaacga actgtggctg cacctctgt    1320 cttcatcttc ccgccatctg atgagcagtt gaaatctgga actgctagcg ttgtgtgcct    1380
gctgaataac ttctatccca gagaggccaa agtacagtgg aaggtggata acgccctcca    1440
atcgggtaac tcccaggaga gtgtcacaga gcaggacagc aaggacagca cctacagcct    1500
cagcagcacc ctgacgctga gcaaagcaga ctacgagaaa cacaaagtct acgcctgcga    1560
agtcacccat cagggcctga gctcgcccgt cacaaagagc ttcaacaggg gagagtgtta    1620
ggaattcgcg gccgctcgag tctagagggc ccgtttaaac ccgctgatca gcctcgactg    1680
tgccttctag ttgccagcca tctgttgttt gccctccccc gtgccttcc ttgaccctgg    1740 aaggtgccac tcccactgtc ctttcctaat aaaatgagga aattgcatcg cattgtctga    1800
gtaggtgtca ttctattctg gggggtgggg tggggcagga cagcaagggg gaggattggg    1860
aagacaatag caggcatgct ggggatgcgg tgggctctat ggcttctgag gcggaaagaa    1920
ccagctgggg ctctagggg tatccccacg cgccctgtag cggcgcatta agcgcggcgg    1980
gtgtggtggt tacgcgcagc gtgaccgcta cacttgccag cgccctagcg cccgctcctt    2040
tcgctttctt cccttccttt ctcgccacgt tcgccggctt tccccgtcaa gctctaaatc    2100
ggggcatccc tttagggttc cgatttagtg ctttacggca cctcgacccc aaaaaacttg    2160
attagggtga tggttcacgt agtgggccat cgccctgata cggttttt cgccctttga    2220 cgttggagtc cacgttcttt aatagtggac tcttgttcca aactggaaca acactcaacc    2280
ctatctcggt ctattctttt gatttataag ggattttggg gatttcggcc tattggttaa    2340
aaaatgagct gatttaacaa aaatttaacg cgaattaatt ctgtggaatg tgtgtcagtt    2400
agggtgtgga aagtccccag gctccccagg caggcagaag tatgcaaagc atgcatctca    2460
attagtcagc aaccaggtgt ggaaagtccc caggctcccc agcaggcaga agtatgcaaa    2520
gcatgcatct caattagtca gcaaccatag tcccgcccct aactccgccc atcccgcccc    2580
taactccgcc cagttccgcc cattctccgc cccatggctg actaatttt tttatttatg    2640 cagaggccga ggccgcctct gcctctgagc tattccagaa gtagtgagga ggcttttttg    2700
```

-continued

```
gaggcctagg cttttgcaaa aagctcccgg gagcttgtat atccattttc ggatctgatc   2760
aagagacagg atgaggatcg tttcgcatga ttgaacaaga tggattgcac gcaggttctc   2820
cggccgcttg ggtggagagg ctattcggct atgactgggc acaacagaca atcggctgct   2880
ctgatgccgc cgtgttccgg ctgtcagcgc agggcgcccc ggttcttttt gtcaagaccg   2940
acctgtccgg tgccctgaat gaactgcagg acgaggcagc gcggctatcg tggctggcca   3000
cgacgggcgt tccttgcgca gctgtgctcg acgttgtcac tgaagcggga agggactggc   3060
tgctattggg cgaagtgccg gggcaggatc tcctgtcatc tcaccttgct cctgccgaga   3120
aagtatccat catggctgat gcaatgcggc ggctgcatac gcttgatccg gctacctgcc   3180
cattcgacca ccaagcgaaa catcgcatcg agcgagcacg tactcggatg aagccggtc    3240 ttgtcgatca ggatgatctg gacgaagagc atcaggggct cgcgccagcc gaactgttcg   3300
ccaggctcaa ggcgcgcatg cccgacggcg aggatctcgt cgtgacccat ggcgatgcct   3360
gcttgccgaa tatcatggtg gaaaatggcc gcttttctgg attcatcgac tgtggccggc   3420
tgggtgtggc ggaccgctat caggacatag cgttggctac ccgtgatatt gctgaagagc   3480
ttggcggcga atgggctgac cgcttcctcg tgctttacgg tatcgccgct cccgattcgc   3540
agcgcatcgc cttctatcgc cttcttgacg agttcttctg agcgggactc tggggttcga   3600
aatgaccgac caagcgacgc ccaacctgcc atcacgagat tcgattccca ccgccgcctt   3660
ctatgaaagg ttgggcttcg gaatcgtttt ccgggacgcc ggctggatga tcctccagcg   3720
cggggatctc atgctggagt tcttcgccca ccccaacttg tttattgcag cttataatgg   3780
ttacaaataa agcaatagca tcacaaattt cacaaataaa gcattttttt cactgcattc   3840
tagttgtggt ttgtccaaac tcatcaatgt atcttatcat gtctgtatac cgtcgacctc   3900
tagctagagc ttggcgtaat catggtcata gctgtttcct gtgtgaaatt gttatccgct   3960
cacaattcca cacaacatac gagccggaag cataaagtgt aaagcctggg gtgcctaatg   4020
agtgagctaa ctcacattaa ttgcgttgcg ctcactgccc gctttccagt cgggaaacct   4080
gtcgtgccag ctgcattaat gaatcggcca acgcgcgggg agaggcggtt tgcgtattgg   4140
gcgctcttcc gcttcctcgc tcactgactc gctgcgctcg gtcgttcggc tgcggcgagc   4200
ggtatcagct cactcaaagg cggtaatacg gttatccaca gaatcagggg ataacgcagg   4260
aaagaacatg tgagcaaaag gccagcaaaa ggccaggaac cgtaaaaagg ccgcgttgct   4320
ggcgtttttc cataggctcc gcccccctga cgagcatcac aaaaatcgac gctcaagtca   4380
gaggtggcga aacccgacag gactataaag ataccaggcg tttccccctg gaagctccct   4440
cgtgcgctct cctgttccga ccctgccgct taccggatac ctgtccgcct ttctcccttc   4500
gggaagcgtg gcgctttctc aatgctcacg ctgtaggtat ctcagttcgg tgtaggtcgt   4560
tcgctccaag ctgggctgtg tgcacgaacc ccccgttcag cccgaccgct gcgccttatc   4620
cggtaactat cgtcttgagt ccaacccggt aagacacgac ttatcgccac tggcagcagc   4680
cactggtaac aggattagca gagcgaggta tgtaggcggt gctacagagt tcttgaagtg   4740
gtggcctaac tacggctaca ctagaaggac agtatttggt atctgcgctc tgctgaagcc   4800
agttaccttc ggaaaaagag ttggtagctc ttgatccggc aaacaaacca ccgctggtag   4860
cggtggtttt tttgtttgca agcagcagat tacgcgcaga aaaaaggat ctcaagaaga   4920 tcctttgatc ttttctacgg ggtctgacgc tcagtggaac gaaaactcac gttaagggat   4980
tttggtcatg agattatcaa aaaggatctt cacctagatc cttttaaatt aaaaatgaag   5040
```

-continued

| | |
|---|---|
| ttttaaatca atctaaagta tatatgagta aacttggtct gacagttacc aatgcttaat | 5100 |
| cagtgaggca cctatctcag cgatctgtct atttcgttca tccatagttg cctgactccc | 5160 |
| cgtcgtgtag ataactacga tacgggaggg cttaccatct ggccccagtg ctgcaatgat | 5220 |
| accgcgagac ccacgctcac cggctccaga tttatcagca ataaaccagc cagccggaag | 5280 |
| ggccgagcgc agaagtggtc ctgcaacttt atccgcctcc atccagtcta ttaattgttg | 5340 |
| ccgggaagct agagtaagta gttcgccagt taatagtttg cgcaacgttg ttgccattgc | 5400 |
| tacaggcatc gtggtgtcac gctcgtcgtt tggtatggct tcattcagct ccggttccca | 5460 |
| acgatcaagg cgagttacat gatccccat gttgtgcaaa aaagcggtta gctccttcgg | 5520 |
| tcctccgatc gttgtcagaa gtaagttggc cgcagtgtta tcactcatgg ttatggcagc | 5580 |
| actgcataat tctcttactg tcatgccatc cgtaagatgc ttttctgtga ctggtgagta | 5640 |
| ctcaaccaag tcattctgag aatagtgtat gcggcgaccg agttgctctt gcccggcgtc | 5700 |
| aatacgggat aataccgcgc cacatagcag aactttaaaa gtgctcatca ttggaaaacg | 5760 |
| ttcttcgggg cgaaaactct caaggatctt accgctgttg agatccagtt cgatgtaacc | 5820 |
| cactcgtgca cccaactgat cttcagcatc ttttactttc accagcgttt ctgggtgagc | 5880 |
| aaaaacagga aggcaaaatg ccgcaaaaaa gggaataagg gcgacacgga aatgttgaat | 5940 |
| actcatactc ttccttttc aatattattg aagcatttat cagggttatt gtctcatgag | 6000 |
| cggatacata tttgaatgta tttagaaaaa taaacaaata ggggttccgc gcacatttcc | 6060 |
| ccgaaaagtg ccacctgacg tc | 6082 |

<210> SEQ ID NO 9
<211> LENGTH: 6082
<212> TYPE: DNA
<213> ORGANISM: Artificial Sequence
<220> FEATURE:
<223> OTHER INFORMATION: Synthetic Oligonucleotide

<400> SEQUENCE: 9

| | |
|---|---|
| gacggatcgg gagatctccc gatccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggac tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctaga | 900 |
| aagcttggat ctcaccatga gggtccccgc tcagctcctg ggctcctgc tgctctgttt | 960 |
| cccaggtgcc agatgtgaca tccagatgac ccagtctcca tcctcactgt ctgcatctgt | 1020 |

```
aggagacaga gtcaccatca cttgtcgggc gagtcagggc attaccaatt atttagcctg   1080
gtttcagcag aaaccaggga agcccctaa gtcccttatc tatgctgcat ccagtttgca    1140
aagtggggtc ccatcaaagt tcagcggcag tggatctggg acagatttca gtctcaccat   1200
cagcagcctg cagcctgaag attttgcaac ttattactgc aacagtata atagttaccc    1260 gatcaccttc ggccaaggga cacgactgga gattaaacga actgtggctg caccatctgt   1320
cttcatcttc ccgccatctg atgagcagtt gaaatctgga actgctagcg ttgtgtgcct   1380
gctgaataac ttctatccca gagaggccaa agtacagtgg aaggtggata cgccctcca    1440 atcgggtaac tcccaggaga gtgtcacaga gcaggacagc aaggacagca cctacagcct   1500
cagcagcacc ctgacgctga gcaaagcaga ctacgagaaa cacaaagtct acgcctgcga   1560
agtcacccat cagggcctga gctcgcccgt cacaaagagc ttcaacaggg gagagtgtta   1620
ggaattcgcg gccgctcgag tctagagggc ccgtttaaac ccgctgatca gcctcgactg   1680
tgccttctag ttgccagcca tctgttgttt gcccctcccc cgtgccttcc ttgaccctgg   1740
aaggtgccac tcccactgtc ctttcctaat aaaatgagga attgcatcg cattgtctga    1800 gtaggtgtca ttctattctg ggggtgggg tgggcagga cagcaagggg gaggattggg     1860
aagacaatag caggcatgct ggggatgcgg tgggctctat ggcttctgag gcggaaagaa   1920
ccagctgggg ctctaggggg tatccccacg cgccctgtag cggcgcatta agcgcggcgg   1980
gtgtggtggt tacgcgcagc gtgaccgcta cacttgccag cgccctagcg cccgctcctt   2040
tcgctttctt cccttccttt ctcgccacgt tcgccggctt tccccgtcaa gctctaaatc   2100
ggggcatccc tttagggttc cgatttagtg ctttacggca cctcgacccc aaaaaacttg   2160
attagggtga tggttcacgt agtgggccat cgccctgata cggttttt cgcccttga     2220 cgttggagtc cacgttcttt aatagtggac tcttgttcca aactggaaca acactcaacc   2280
ctatctcggt ctattctttt gatttataag ggattttggg gatttcggcc tattggttaa   2340
aaaatgagct gatttaacaa aaatttaacg cgaattaatt ctgtggaatg tgtgtcagtt   2400
agggtgtgga aagtccccag gctccccagg caggcagaag tatgcaaagc atgcatctca   2460
attagtcagc aaccaggtgt ggaaagtccc caggctcccc agcaggcaga agtatgcaaa   2520
gcatgcatct caattagtca gcaaccatag tcccgcccct aactccgccc atcccgcccc   2580
taactccgcc cagttccgcc cattctccgc cccatggctg actaatttt tttatttatg   2640 cagaggccga ggccgcctct gcctctgagc tattccagaa gtagtgagga ggcttttttg   2700
gaggcctagg cttttgcaaa aagctcccgg gagcttgtat atccattttc ggatctgatc   2760
aagagacagg atgaggatcg tttcgcatga ttgaacaaga tggattgcac gcaggttctc   2820
cggccgcttg ggtggagagg ctattcggct atgactgggc acaacagaca atcggctgct   2880
ctgatgccgc cgtgttccgg ctgtcagcgc aggggcgccc ggttcttttt gtcaagaccg   2940
acctgtccgg tgccctgaat gaactgcagg acgaggcagc gcggctatcg tggctggcca   3000
cgacgggcgt tccttgcgca gctgtgctcg acgttgtcac tgaagcggga agggactggc   3060
tgctattggg cgaagtgccg gggcaggatc tcctgtcatc tcaccttgct cctgccgaga   3120
aagtatccat catggctgat gcaatgcggc ggctgcatac gcttgatccg gctacctgcc   3180
cattcgacca ccaagcgaaa catcgcatcg agcgagcacg tactcggatg gaagccggtc   3240
ttgtcgatca ggatgatctg gacgaagagc atcaggggct cgcgccagcc gaactgttcg   3300
ccaggctcaa ggcgcgcatg cccgacggcg aggatctcgt cgtgacccat ggcgatgcct   3360
```

```
gcttgccgaa tatcatggtg gaaaatggcc gcttttctgg attcatcgac tgtggccggc    3420
tgggtgtggc ggaccgctat caggacatag cgttggctac ccgtgatatt gctgaagagc    3480
ttggcggcga atgggctgac cgcttcctcg tgctttacgg tatcgccgct cccgattcgc    3540
agcgcatcgc cttctatcgc cttcttgacg agttcttctg agcgggactc tggggttcga    3600
aatgaccgac caagcgacgc ccaacctgcc atcacgagat ttcgattcca ccgccgcctt    3660
ctatgaaagg ttgggcttcg gaatcgtttt ccgggacgcc ggctggatga tcctccagcg    3720
cggggatctc atgctggagt tcttcgccca ccccaacttg tttattgcag cttataatgg    3780
ttacaaataa agcaatagca tcacaaattt cacaaataaa gcattttttt cactgcattc    3840
tagttgtggt ttgtccaaac tcatcaatgt atcttatcat gtctgtatac cgtcgacctc    3900
tagctagagc ttggcgtaat catggtcata gctgtttcct gtgtgaaatt gttatccgct    3960
cacaattcca cacaacatac gagccggaag cataaagtgt aaagcctggg gtgcctaatg    4020
agtgagctaa ctcacattaa ttgcgttgcg ctcactgccc gctttccagt cgggaaacct    4080
gtcgtgccag ctgcattaat gaatcggcca acgcgcgggg agaggcggtt tgcgtattgg    4140
gcgctcttcc gcttcctcgc tcactgactc gctgcgctcg tcgttcggc tgcggcgagc     4200
ggtatcagct cactcaaagg cggtaatacg gttatccaca gaatcagggg ataacgcagg    4260
aaagaacatg tgagcaaaag gccagcaaaa ggccaggaac cgtaaaaagg ccgcgttgct    4320
ggcgtttttc cataggctcc gcccccctga cgagcatcac aaaaatcgac gctcaagtca    4380
gaggtggcga aacccgacag gactataaag ataccaggcg tttccccctg gaagctccct    4440
cgtgcgctct cctgttccga ccctgccgct taccggatac ctgtccgcct ttctcccttc    4500
gggaagcgtg gcgctttctc aatgctcacg ctgtaggtat ctcagttcgg tgtaggtcgt    4560
tcgctccaag ctgggctgtg tgcacgaacc ccccgttcag cccgaccgct gcgccttatc    4620
cggtaactat cgtcttgagt ccaacccggt aagacacgac ttatcgccac tggcagcagc    4680
cactggtaac aggattagca gagcgaggta tgtaggcggt gctacagagt tcttgaagtg    4740
gtggcctaac tacggctaca ctagaaggac agtatttggt atctgcgctc tgctgaagcc    4800
agttaccttc ggaaaaagag ttggtagctc ttgatccggc aaacaaacca ccgctggtag    4860
cggtggtttt tttgtttgca agcagcagat tacgcgcaga aaaaaaggat ctcaagaaga    4920
tcctttgatc ttttctacgg ggtctgacgc tcagtggaac gaaaactcac gttaagggat    4980
tttggtcatg agattatcaa aaaggatctt cacctagatc cttttaaatt aaaaatgaag    5040
ttttaaatca atctaaagta tatatgagta aacttggtct gacagttacc aatgcttaat    5100
cagtgaggca cctatctcag cgatctgtct atttcgttca tccatagttg cctgactccc    5160
cgtcgtgtag ataactacga tacgggaggg cttaccatct ggccccagtg ctgcaatgat    5220
accgcgagac ccacgctcac cggctccaga tttatcagca ataaaccagc cagccggaag    5280
ggccgagcgc agaagtggtc ctgcaacttt atccgcctcc atccagtcta ttaattgttg    5340
ccgggaagct agagtaagta gttcgccagt taatagtttg cgcaacgttg ttgccattgc    5400
tacaggcatc gtggtgtcac gctcgtcgtt tggtatggct tcattcagct ccggttccca    5460
acgatcaagg cgagttacat gatccccat gttgtgcaaa aaagcggtta gctccttcgg    5520
tcctccgatc gttgtcagaa gtaagttggc cgcagtgtta tcactcatgg ttatggcagc    5580
actgcataat tctcttactg tcatgccatc cgtaagatgc ttttctgtga ctggtgagta    5640
ctcaaccaag tcattctgag aatagtgtat gcggcgaccg agttgctctt gcccggcgtc    5700
aatacgggat aataccgcgc cacatagcag aactttaaaa gtgctcatca ttggaaaacg    5760
```

-continued

| | |
|---|---|
| ttcttcgggg cgaaaactct caaggatctt accgctgttg agatccagtt cgatgtaacc | 5820 |
| cactcgtgca cccaactgat cttcagcatc ttttactttc accagcgttt ctgggtgagc | 5880 |
| aaaaacagga aggcaaaatg ccgcaaaaaa gggaataagg gcgacacgga aatgttgaat | 5940 |
| actcatactc ttccttttc aatattattg aagcatttat cagggttatt gtctcatgag | 6000 |
| cggatacata tttgaatgta tttagaaaaa taaacaaata ggggttccgc gcacatttcc | 6060 |
| ccgaaaagtg ccacctgacg tc | 6082 |

<210> SEQ ID NO 10
<211> LENGTH: 6082
<212> TYPE: DNA
<213> ORGANISM: Artificial Sequence
<220> FEATURE:
<223> OTHER INFORMATION: Synthetic Oligonucleotide

<400> SEQUENCE: 10

| | |
|---|---|
| gacggatcgg gagatctccc gatcccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggac tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctaga | 900 |
| aagcttggat ctcaccatga gggtccctgc tcagctcctg gggctcctgc tgctctgttt | 960 |
| cccaggtgcc agatgtgaca tccagatgac ccagtctcca tcctcactgt ctgcatctgt | 1020 |
| aggagacaga gtcaccatca cttgtcgggc gagtcagggc attagccatt atttagcctg | 1080 |
| gtttcagcag aaaccaggga aagcccctaa gtccctgatc tatgctgcat ccagtttgca | 1140 |
| aagtggggtc ccatcaaagt tcagcggcag tggatctggg acagatttca ctctcaccat | 1200 |
| cagcagccta cagcctgaag attttgcaac ttattactgc caacagtata atagtttccc | 1260 |
| gctcactttc ggcggaggga ccaaggtgga gatcaaacga actgtggctg caccatctgt | 1320 |
| cttcatcttc ccgccatctg atgagcagtt gaaatctgga actgctagcg ttgtgtgcct | 1380 |
| gctgaataac ttctatccca gagaggccaa agtacagtgg aaggtggata acgcctcca | 1440 |
| atcgggtaac tcccaggaga gtgtcacaga gcaggacagc aaggacagca cctacagcct | 1500 |
| cagcagcacc ctgacgctga gcaaagcaga ctacgagaaa cacaaagtct acgcctgcga | 1560 |
| agtcacccat cagggcctga gctcgcccgt cacaaagagc ttcaacaggg gagagtgtta | 1620 |
| ggaattcgcg gccgctcgag tctagagggc ccgtttaaac ccgctgatca gcctcgactg | 1680 |

```
tgccttctag ttgccagcca tctgttgttt gcccctcccc cgtgccttcc ttgaccctgg    1740
aaggtgccac tcccactgtc ctttcctaat aaaatgagga aattgcatcg cattgtctga    1800
gtaggtgtca ttctattctg gggggtgggg tggggcagga cagcaagggg gaggattggg    1860
aagacaatag caggcatgct ggggatgcgg tgggctctat ggcttctgag gcggaaagaa    1920
ccagctgggg ctctaggggg tatccccacg cgccctgtag cggcgcatta agcgcggcgg    1980
gtgtggtggt tacgcgcagc gtgaccgcta cacttgccag cgccctagcg cccgctcctt    2040
tcgctttctt cccttccttt ctcgccacgt tcgccggctt tccccgtcaa gctctaaatc    2100
ggggcatccc tttagggttc cgatttagtg ctttacggca cctcgacccc aaaaaacttg    2160
attagggtga tggttcacgt agtgggccat cgccctgata cggttttttc gccctttga    2220 cgttggagtc cacgttcttt aatagtggac tcttgttcca aactggaaca acactcaacc    2280
ctatctcggt ctattctttt gatttataag ggattttggg gatttcggcc tattggttaa    2340
aaaatgagct gatttaacaa aaatttaacg cgaattaatt ctgtggaatg tgtgtcagtt    2400
agggtgtgga aagtccccag gctccccagg caggcagaag tatgcaaagc atgcatctca    2460
attagtcagc aaccaggtgt ggaaagtccc caggctcccc agcaggcaga agtatgcaaa    2520
gcatgcatct caattagtca gcaaccatag tcccgcccct aactccgccc atcccgcccc    2580
taactccgcc cagttccgcc cattctccgc cccatggctg actaattttt tttatttatg    2640
cagaggccga ggccgcctct gcctctgagc tattccagaa gtagtgagga ggcttttttg    2700
gaggcctagg cttttgcaaa aagctcccgg gagcttgtat atccattttc ggatctgatc    2760
aagagacagg atgaggatcg tttcgcatga ttgaacaaga tggattgcac gcaggttctc    2820
cggccgcttg ggtggagagg ctattcggct atgactgggc acaacagaca atcggctgct    2880
ctgatgccgc cgtgttccgg ctgtcagcgc agggggcgcc cggttctttt gtcaagaccg    2940
acctgtccgg tgccctgaat gaactgcagg acgaggcagc gcggctatcg tggctggcca    3000
cgacgggcgt tccttgcgca gctgtgctcg acgttgtcac tgaagcggga agggactggc    3060
tgctattggg cgaagtgccg gggcaggatc tcctgtcatc tcaccttgct cctgccgaga    3120
aagtatccat catggctgat gcaatgcggc ggctgcatac gcttgatccg gctacctgcc    3180
cattcgacca ccaagcgaaa catcgcatcg agcgagcacg tactcggatg aagccggtc    3240 ttgtcgatca ggatgatctg gacgaagagc atcaggggct cgcgccagcc gaactgttcg    3300
ccaggctcaa ggcgcgcatg cccgacggcg aggatctcgt cgtgacccat ggcgatgcct    3360
gcttgccgaa tatcatggtg gaaaatggcc gcttttctgg attcatcgac tgtggccggc    3420
tgggtgtggc ggaccgctat caggacatag cgttggctac ccgtgatatt gctgaagagc    3480
ttggcggcga atgggctgac cgcttcctcg tgctttacgg tatcgccgct cccgattcgc    3540
agcgcatcgc cttctatcgc cttcttgacg agttcttctg agcgggactc tggggttcga    3600
aatgaccgac caagcgacgc ccaacctgcc atcacgagat ttcgattcca ccgccgcctt    3660
ctatgaaagg ttgggcttcg gaatcgtttt ccgggacgcc ggctggatga tcctccagcg    3720
cggggatctc atgctggagt tcttcgccca ccccaacttg tttattgcag cttataatgg    3780
ttacaaataa agcaatagca tcacaaattt cacaaataaa gcatttttt cactgcattc    3840 tagttgtggt ttgtccaaac tcatcaatgt atcttatcat gtctgtatac cgtcgacctc    3900
tagctagagc ttggcgtaat catggtcata gctgtttcct gtgtgaaatt gttatccgct    3960
cacaattcca cacaacatac gagccggaag cataaagtgt aaagcctggg gtgcctaatg    4020
agtgagctaa ctcacattaa ttgcgttgcg ctcactgccc gctttccagt cgggaaacct    4080
```

```
gtcgtgccag ctgcattaat gaatcggcca acgcgcgggg agaggcggtt tgcgtattgg    4140
gcgctcttcc gcttcctcgc tcactgactc gctgcgctcg gtcgttcggc tgcggcgagc    4200
ggtatcagct cactcaaagg cggtaatacg gttatccaca gaatcagggg ataacgcagg    4260
aaagaacatg tgagcaaaag gccagcaaaa ggccaggaac cgtaaaaagg ccgcgttgct    4320 ggcgttttc cataggctcc gcccccctga cgagcatcac aaaaatcgac gctcaagtca    4380
gaggtggcga aacccgacag gactataaag ataccaggcg tttccccctg gaagctccct    4440
cgtgcgctct cctgttccga ccctgccgct taccggatac ctgtccgcct ttctcccttc    4500
gggaagcgtg gcgctttctc aatgctcacg ctgtaggtat ctcagttcgg tgtaggtcgt    4560
tcgctccaag ctgggctgtg tgcacgaacc cccgttcag cccgaccgct gcgccttatc    4620
cggtaactat cgtcttgagt ccaacccggt aagacacgac ttatcgccac tggcagcagc    4680
cactggtaac aggattagca gagcgaggta tgtaggcgt gctacagagt tcttgaagtg    4740
gtggcctaac tacggctaca ctagaaggac agtatttggt atctgcgctc tgctgaagcc    4800
agttaccttc ggaaaaagag ttggtagctc ttgatccggc aaacaaacca ccgctggtag    4860
cggtggtttt tttgtttgca agcagcagat tacgcgcaga aaaaaggat ctcaagaaga    4920 tcctttgatc ttttctacgg ggtctgacgc tcagtggaac gaaaactcac gttaagggat    4980
tttggtcatg agattatcaa aaaggatctt cacctagatc cttttaaatt aaaaatgaag    5040
ttttaaatca atctaaagta tatatgagta aacttggtct gacagttacc aatgcttaat    5100
cagtgaggca cctatctcag cgatctgtct atttcgttca tccatagttg cctgactccc    5160
cgtcgtgtag ataactacga tacgggaggg cttaccatct ggccccagtg ctgcaatgat    5220
accgcgagac ccacgctcac cggctccaga tttatcagca ataaaccagc cagccggaag    5280
ggccgagcgc agaagtggtc ctgcaacttt atccgcctcc atccagtcta ttaattgttg    5340
ccgggaagct agagtaagta gttcgccagt taatagtttg cgcaacgttg ttgccattgc    5400
tacaggcatc gtggtgtcac gctcgtcgtt tggtatggct tcattcagct ccggttccca    5460
acgatcaagg cgagttacat gatcccccat gttgtgcaaa aaagcggtta gctccttcgg    5520
tcctccgatc gttgtcagaa gtaagttggc cgcagtgtta tcactcatgg ttatggcagc    5580
actgcataat tctcttactg tcatgccatc cgtaagatgc ttttctgtga ctggtgagta    5640
ctcaaccaag tcattctgag aatagtgtat gcggcgaccg agttgctctt gcccggcgtc    5700
aatacgggat aataccgcgc cacatagcag aactttaaaa gtgctcatca ttggaaaacg    5760
ttcttcgggg cgaaaactct caaggatctt accgctgttg agatccagtt cgatgtaacc    5820
cactcgtgca cccaactgat cttcagcatc ttttactttc accagcgttt ctgggtgagc    5880
aaaaacagga aggcaaaatg ccgcaaaaaa gggaataagg gcgacacgga aatgttgaat    5940
actcatactc ttcctttttc aatattattg aagcatttat cagggttatt gtctcatgag    6000
cggatacata tttgaatgta tttagaaaaa taaacaaata ggggttccgc gcacatttcc    6060
ccgaaaagtg ccacctgacg tc                                             6082
```

<210> SEQ ID NO 11
<211> LENGTH: 6085
<212> TYPE: DNA
<213> ORGANISM: Artificial Sequence
<220> FEATURE:
<223> OTHER INFORMATION: Synthetic Oligonucleotide

<400> SEQUENCE: 11

```
gacggatcgg gagatctccc gatccctat ggtcgactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttaggggttag gcgttttgcg ctgcttcgcg atgtacgggc cagatatacg cgttgacatt   240
gattattgac tagttattaa tagtaatcaa ttacgggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggac tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctaga   900
aagcttggat ctcaccatga gggtccccgc tcagcttctc ttccttctgc tactctggct   960
cccagatacc actggaggaa tagtgatgac gcagtctcca gccaccctgt ctgtgtctcc  1020
agggggaaaga gccaccctct cctgcaggac cagtcagagt attggctgga acttagcctg  1080
gtaccaacag aaacctggcc aggctcccag gctcctcatc tatggtgcat cttccaggac  1140
cactggtatc ccagccaggt tcagtggcag tgggtctggg acagagttca ctctcaccat  1200
cagcagcctg cagtctgaag attctgcagt ttattactgt cagcattatg ataactggcc  1260
catgtgcagt tttggccagg gaccgagct ggagatcaaa cgaactgtgg ctgcaccatc  1320
tgtcttcatc ttcccgccat ctgatgagca gttgaaatct ggaactgcta gcgttgtgtg  1380
cctgctgaat aacttctatc ccagagaggc caaagtacag tggaaggtgg ataacgccct  1440
ccaatcgggt aactcccagg agagtgtcac agagcaggac agcaaggaca gcacctacag  1500
cctcagcagc accctgacgc tgagcaaagc agactacgag aaacacaaag tctacgcctg  1560
cgaagtcacc catcagggcc tgagctcgcc cgtcacaaag agcttcaaca ggggagagtg  1620
ttaggaattc gcggccgctc gagtctagag ggcccgttta acccgctgat cagcctcga   1680
ctgtgccttc tagttgccag ccatctgttg tttgcccctc ccccgtgcct tccttgaccc  1740
tggaaggtgc cactcccact gtcctttcct aataaaatga ggaaattgca tcgcattgtc  1800
tgagtaggtg tcattctatt ctggggggtg ggtgggggca ggacagcaag ggggaggatt  1860
gggaagacaa tagcaggcat gctggggatg cggtgggctc tatggcttct gaggcggaaa  1920
gaaccagctg gggctctagg gggtatcccc acgcgccctg tagcggcgca ttaagcgcgg  1980
cgggtgtggt ggttacgcgc agcgtgaccg ctacacttgc cagcgcccta gcgcccgctc  2040
ctttcgcttt cttcccttcc tttctcgcca cgttcgccgg ctttccccgt caagctctaa  2100
atcggggcat ccctttaggg ttccgattta gtgctttacg gcacctcgac cccaaaaaac  2160
ttgattaggg tgatggttca cgtagtgggc catcgccctg atagacggtt tttcgccctt  2220
tgacgttgga gtccacgttc tttaatagtg gactcttgtt ccaaactgga acaacactca  2280
accctatctc ggtctattct tttgatttat aagggatttt ggggatttcg gcctattggt  2340
taaaaaatga gctgatttaa caaaaattta acgcgaatta attctgtgga atgtgtgtca  2400
```

```
gttagggtgt ggaaagtccc caggctcccc aggcaggcag aagtatgcaa agcatgcatc    2460
tcaattagtc agcaaccagg tgtggaaagt ccccaggctc cccagcaggc agaagtatgc    2520
aaagcatgca tctcaattag tcagcaacca tagtcccgcc cctaactccg cccatcccgc    2580
ccctaactcc gcccagttcc gcccattctc cgccccatgg ctgactaatt ttttttattt    2640
atgcagaggc cgaggccgcc tctgcctctg agctattcca gaagtagtga ggaggctttt    2700
ttggaggcct aggcttttgc aaaaagctcc cgggagcttg tatatccatt ttcggatctg    2760
atcaagagac aggatgagga tcgtttcgca tgattgaaca agatggattg cacgcaggtt    2820
ctccggccgc ttgggtggag aggctattcg gctatgactg ggcacaacag acaatcggct    2880
gctctgatgc cgccgtgttc cggctgtcag cgcaggggcg cccggttctt tttgtcaaga    2940
ccgacctgtc cggtgccctg aatgaactgc aggacgaggc agcgcggcta tcgtggctgg    3000
ccacgacggg cgttccttgc gcagctgtgc tcgacgttgt cactgaagcg ggaagggact    3060
ggctgctatt gggcgaagtg ccggggcagg atctcctgtc atctcacctt gctcctgccg    3120
agaaagtatc catcatggct gatgcaatgc ggcggctgca tacgcttgat ccggctacct    3180
gcccattcga ccaccaagcg aaacatcgca tcgagcgagc acgtactcgg atggaagccg    3240
gtcttgtcga tcaggatgat ctggacgaag agcatcaggg gctcgcgcca gccgaactgt    3300
tcgccaggct caaggcgcgc atgcccgacg gcgaggatct cgtcgtgacc catggcgatg    3360
cctgcttgcc gaatatcatg gtggaaaatg gccgcttttc tggattcatc gactgtggcc    3420
ggctgggtgt ggcggaccgc tatcaggaca tagcgttggc tacccgtgat attgctgaag    3480
agcttggcgg cgaatgggct gaccgcttcc tcgtgcttta cggtatcgcc gctcccgatt    3540
cgcagcgcat cgccttctat cgccttcttg acgagttctt ctgagcggga ctctggggtt    3600
cgaaatgacc gaccaagcga cgcccaacct gccatcacga gatttcgatt ccaccgccgc    3660
cttctatgaa aggttgggct tcggaatcgt tttccgggac gccggctgga tgatcctcca    3720
gcgcggggat ctcatgctgg agttcttcgc ccaccccaac ttgtttattg cagcttataa    3780
tggttacaaa taaagcaata gcatcacaaa tttcacaaat aaagcatttt ttcactgca    3840 ttctagttgt ggtttgtcca aactcatcaa tgtatcttat catgtctgta taccgtcgac    3900
ctctagctag agcttggcgt aatcatggtc atagctgttt cctgtgtgaa attgttatcc    3960
gctcacaatt ccacacaaca tacgagccgg aagcataaag tgtaaagcct ggggtgccta    4020
atgagtgagc taactcacat taattgcgtt gcgctcactg cccgctttcc agtcgggaaa    4080
cctgtcgtgc cagctgcatt aatgaatcgg ccaacgcgcg gggagaggcg gtttgcgtat    4140
tgggcgctct tccgcttcct cgctcactga ctcgctgcgc tcggtcgttc ggctgcggcg    4200
agcggtatca gctcactcaa aggcggtaat acggttatcc acagaatcag gggataacgc    4260
aggaaagaac atgtgagcaa aaggccagca aaaggccagg aaccgtaaaa aggccgcgtt    4320
gctggcgttt ttccataggc tccgcccccc tgacgagcat cacaaaaatc gacgctcaag    4380
tcagaggtgg cgaaacccga caggactata aagataccag gcgtttcccc ctggaagctc    4440
cctcgtgcgc tctcctgttc cgaccctgcc gcttaccgga tacctgtccg cctttctccc    4500
ttcgggaagc gtggcgcttt ctcaatgctc acgctgtagg tatctcagtt cggtgtaggt    4560
cgttcgctcc aagctgggct gtgtgcacga accccccgtt cagcccgacc gctgcgcctt    4620
atccggtaac tatcgtcttg agtccaaccc ggtaagacac gacttatcgc cactggcagc    4680
agccactggt aacaggatta gcagagcgag gtatgtaggc ggtgctacag agttcttgaa    4740
```

```
gtggtggcct aactacggct acactagaag gacagtattt ggtatctgcg ctctgctgaa    4800
gccagttacc ttcggaaaaa gagttggtag ctcttgatcc ggcaaacaaa ccaccgctgg    4860
tagcggtggt ttttttgttt gcaagcagca gattacgcgc agaaaaaaag gatctcaaga    4920
agatcctttg atcttttcta cggggtctga cgctcagtgg aacgaaaact cacgttaagg    4980
gattttggtc atgagattat caaaaaggat cttcacctag atccttttaa attaaaaatg    5040
aagttttaaa tcaatctaaa gtatatatga gtaaacttgg tctgacagtt accaatgctt    5100
aatcagtgag gcacctatct cagcgatctg tctatttcgt tcatccatag ttgcctgact    5160
ccccgtcgtg tagataacta cgatacggga gggcttacca tctggcccca gtgctgcaat    5220
gataccgcga gacccacgct caccggctcc agatttatca gcaataaacc agccagccgg    5280
aagggccgag cgcagaagtg gtcctgcaac tttatccgcc tccatccagt ctattaattg    5340
ttgccgggaa gctagagtaa gtagttcgcc agttaatagt ttgcgcaacg ttgttgccat    5400
tgctacaggc atcgtggtgt cacgctcgtc gtttggtatg gcttcattca gctccggttc    5460
ccaacgatca aggcgagtta catgatcccc catgttgtgc aaaaaagcgg ttagctcctt    5520
cggtcctccg atcgttgtca gaagtaagtt ggccgcagtg ttatcactca tggttatggc    5580
agcactgcat aattctctta ctgtcatgcc atccgtaaga tgcttttctg tgactggtga    5640
gtactcaacc aagtcattct gagaatagtg tatgcggcga ccgagttgct cttgcccggc    5700
gtcaatacgg gataataccg cgccacatag cagaacttta aaagtgctca tcattggaaa    5760
acgttcttcg gggcgaaaac tctcaaggat cttaccgctg ttgagatcca gttcgatgta    5820
acccactcgt gcacccaact gatcttcagc atcttttact ttcaccagcg tttctgggtg    5880
agcaaaaaca ggaaggcaaa atgccgcaaa aaagggaata agggcgacac ggaaatgttg    5940
aatactcata ctcttccttt ttcaatatta ttgaagcatt tatcagggtt attgtctcat    6000
gagcggatac atatttgaat gtatttagaa aaataaacaa ataggggttc cgcgcacatt    6060
tccccgaaaa gtgccacctg acgtc                                          6085
```

<210> SEQ ID NO 12
<211> LENGTH: 6097
<212> TYPE: DNA
<213> ORGANISM: Artificial Sequence
<220> FEATURE:
<223> OTHER INFORMATION: Synthetic Oligonucleotide

<400> SEQUENCE: 12

```
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag cttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
```

```
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctaga    900
aagcttggat ctcaccatga gggtccctgc tcagctcctg gggctgctaa tgctctggat    960
acctggatcc agtgcagata ttgtgatgac ccagactcca ctctctctgt ccgtcacccc   1020
tggacagccg gcctccatct cctgcaagtc tagtcagagc ctcctgcata gtgatggaaa   1080 gaccttttg tattggtatc tgcagaagcc aggccagcct ccacagctcc tgatctatga   1140
ggtttccaac cggttctctg gagtgccaga taggttcagt ggcagcgggt cagggacaga   1200
tttcacactg aaaatcagcc gggtggaggc tgaggatgtt gggctttatt actgcatgca   1260
aagtatacag cttccgctca ctttcggcgg agggaccaag gtggagatca aacgaactgt   1320
ggctgcacca tctgtcttca tcttcccgcc atctgatgag cagttgaaat ctggaactgc   1380
tagcgttgtg tgcctgctga ataacttcta tcccagagag gccaaagtac agtggaaggt   1440
ggataacgcc ctccaatcgg gtaactccca ggagagtgtc acagagcagg acagcaagga   1500
cagcacctac agcctcagca gcaccctgac gctgagcaaa gcagactacg agaaacacaa   1560
agtctacgcc tgcgaagtca cccatcaggg cctgagctcg cccgtcacaa agagcttcaa   1620
caggggagag tgttaggaat cgcggccgc tcgagtctag agggcccgtt taaacccgct   1680
gatcagcctc gactgtgcct tctagttgcc agccatctgt tgtttgcccc tcccccgtgc   1740
cttccttgac cctggaaggt gccactccca ctgtcctttc ctaataaaat gaggaaattg   1800
catcgcattg tctgagtagg tgtcattcta ttctgggggg tggggtgggg caggacagca   1860 aggggagga ttgggaagac aatagcaggc atgctgggga tgcggtgggc tctatggctt   1920
ctgaggcgga aagaaccagc tggggctcta gggggtatcc ccacgcgccc tgtagcggcg   1980
cattaagcgc ggcgggtgtg gtggttacgc gcagcgtgac cgctacactt gccagcgccc   2040
tagcgcccgc tcctttcgct ttcttccctt cctttctcgc cacgttcgcc ggctttcccc   2100
gtcaagctct aaatcgggc atcccttag ggttccgatt tagtgcttta cggcacctcg   2160
accccaaaaa acttgattag ggtgatggtt cacgtagtgg gccatcgccc tgatagacgg   2220 ttttcgccc tttgacgttg gagtccacgt tctttaatag tggactcttg ttccaaactg   2280
gaacaacact caaccctatc tcggtctatt cttttgattt ataagggatt ttggggattt   2340
cggcctattg gttaaaaaat gagctgattt aacaaaaatt taacgcgaat taattctgtg   2400
gaatgtgtgt cagttagggt gtggaaagtc cccaggctcc ccaggcaggc agaagtatgc   2460
aaagcatgca tctcaattag tcagcaacca ggtgtggaaa gtcccaggc tcccagcag   2520 gcagaagtat gcaaagcatg catctcaatt agtcagcaac catagtcccg cccctaactc   2580
cgcccatccc gcccctaact ccgcccagtt ccgcccattc tccgcccat ggctgactaa   2640 ttttttttat ttatgcagag gccgaggccg cctctgcctc tgagctattc cagaagtagt   2700
gaggaggctt ttttggaggc ctaggctttt gcaaaaagct cccgggagct tgtatatcca   2760
ttttcggatc tgatcaagag acaggatgag gatcgtttcg catgattgaa caagatggat   2820
tgcacgcagg ttctccggcc gcttgggtgg agaggctatt cggctatgac tgggcacaac   2880
agacaatcgg ctgctctgat gccgccgtgt tccggctgtc agcgcagggg cgcccggttc   2940
tttttgtcaa gaccgacctg tccggtgccc tgaatgaact gcaggacgag gcagcgcggc   3000
tatcgtggct ggccacgacg ggcgttcctt gcgcagctgt gctcgacgtt gtcactgaag   3060
```

```
cgggaaggga ctggctgcta ttgggcgaag tgccggggca ggatctcctg tcatctcacc    3120
ttgctcctgc cgagaaagta tccatcatgg ctgatgcaat gcggcggctg catacgcttg    3180
atccggctac ctgcccattc gaccaccaag cgaaacatcg catcgagcga gcacgtactc    3240
ggatggaagc cggtcttgtc gatcaggatg atctggacga agagcatcag gggctcgcgc    3300
cagccgaact gttcgccagg ctcaaggcgc gcatgcccga cggcgaggat ctcgtcgtga    3360
cccatggcga tgcctgcttg ccgaatatca tggtggaaaa tggccgcttt tctggattca    3420
tcgactgtgg ccggctgggt gtggcggacc gctatcagga catacgcttg gctacccgtg    3480
atattgctga gagcttggc ggcgaatggg ctgaccgctt cctcgtgctt tacggtatcg    3540
ccgctcccga ttcgcagcgc atcgccttct atcgccttct tgacgagttc ttctgagcgg    3600
gactctgggg ttcgaaatga ccgaccaagc gacgcccaac ctgccatcac gagatttcga    3660
ttccaccgcc gccttctatg aaaggttggg cttcggaatc gttttccggg acgccggctg    3720
gatgatcctc cagcgcgggg atctcatgct ggagttcttc gcccacccca acttgtttat    3780
tgcagcttat aatggttaca ataaagcaa tagcatcaca aatttcacaa ataaagcatt    3840 ttttcactg cattcagtt gtggtttgtc caaactcatc aatgtatctt atcatgtctg    3900
tataccgtcg acctctagct agagcttggc gtaatcatgg tcatagctgt ttcctgtgtg    3960
aaattgttat ccgctcacaa ttccacacaa catacgagcc ggaagcataa agtgtaaagc    4020
ctggggtgcc taatgagtga gctaactcac attaattgcg ttgcgctcac tgcccgcttt    4080
ccagtcggga aacctgtcgt gccagctgca ttaatgaatc ggccaacgcg cggggagagg    4140
cggtttgcgt attgggcgct cttccgcttc ctcgctcact gactcgctgc gctcggtcgt    4200
tcggctgcgg cgagcggtat cagctcactc aaaggcggta atacggttat ccacagaatc    4260
aggggataac gcaggaaaga acatgtgagc aaaaggccag caaaaggcca ggaaccgtaa    4320
aaaggccgcg ttgctggcgt ttttccatag gctccgcccc cctgacgagc atcacaaaaa    4380
tcgacgctca agtcagaggt ggcgaaaccc gacaggacta taaagatacc aggcgtttcc    4440
ccctggaagc tccctcgtgc gctctcctgt tccgaccctg ccgcttaccg gatacctgtc    4500
cgcctttctc ccttcgggaa gcgtggcgct ttctcaatgc tcacgctgta ggtatctcag    4560
ttcggtgtag gtcgttcgct ccaagctggg ctgtgtgcac gaaccccccg ttcagcccga    4620
ccgctgcgcc ttatccggta actatcgtct tgagtccaac ccggtaagac acgacttatc    4680
gccactggca gcagccactg gtaacaggat tagcagagcg aggtatgtag gcggtgctac    4740
agagttcttg aagtggtggc ctaactacgg ctacactaga aggacagtat ttggtatctg    4800
cgctctgctg aagccagtta ccttcggaaa aagagttggt agctcttgat ccggcaaaca    4860
aaccaccgct ggtagcggtg gtttttttgt ttgcaagcag cagattacgc gcagaaaaaa    4920
aggatctcaa gaagatcctt tgatcttttc tacggggtct gacgctcagt ggaacgaaaa    4980
ctcacgttaa gggattttgg tcatgagatt atcaaaaagg atcttcacct agatcctttt    5040
aaattaaaaa tgaagtttta aatcaatcta agtatatat gagtaaactt ggtctgacag    5100
ttaccaatgc ttaatcagtg aggcacctat ctcagcgatc tgtctatttc gttcatccat    5160
agttgcctga ctccccgtcg tgtagataac tacgatacgg gagggcttac catctggccc    5220
cagtgctgca atgataccgc gagacccacg ctcaccggct ccagatttat cagcaataaa    5280
ccagccagcc ggaagggccg agcgcagaag tggtcctgca actttatccg cctccatcca    5340
gtctattaat tgttgccggg aagctagagt aagtagttcg ccagttaata gtttgcgcaa    5400
cgttgttgcc attgctacag gcatcgtggt gtcacgctcg tcgtttggta tggcttcatt    5460
```

-continued

| | |
|---|---|
| cagctccggt tcccaacgat caaggcgagt tacatgatcc cccatgttgt gcaaaaaagc | 5520 |
| ggttagctcc ttcggtcctc cgatcgttgt cagaagtaag ttggccgcag tgttatcact | 5580 |
| catggttatg gcagcactgc ataattctct tactgtcatg ccatccgtaa gatgcttttc | 5640 |
| tgtgactggt gagtactcaa ccaagtcatt ctgagaatag tgtatgcggc gaccgagttg | 5700 |
| ctcttgcccg cgtcaatac gggataaatac cgcgccacat agcagaactt taaaagtgct | 5760 |
| catcattgga aaacgttctt cggggcgaaa actctcaagg atcttaccgc tgttgagatc | 5820 |
| cagttcgatg taacccactc gtgcacccaa ctgatcttca gcatctttta ctttcaccag | 5880 |
| cgtttctggg tgagcaaaaa caggaaggca aaatgccgca aaaagggaa taagggcgac | 5940 |
| acggaaatgt tgaatactca tactcttcct ttttcaatat tattgaagca tttatcaggg | 6000 |
| ttattgtctc atgagcggat acatatttga atgtatttag aaaaataaac aatagggggt | 6060 |
| tccgcgcaca tttccccgaa aagtgccacc tgacgtc | 6097 |

<210> SEQ ID NO 13
<211> LENGTH: 6094
<212> TYPE: DNA
<213> ORGANISM: Artificial Sequence
<220> FEATURE:
<223> OTHER INFORMATION: Synthetic Oligonucleotide

<400> SEQUENCE: 13

| | |
|---|---|
| gacggatcgg gagatctccc gatcccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggac tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctaga | 900 |
| aagcttggat ctcaccatgg tgttgcagac ccaggtcttc atttctctgt tactctggat | 960 |
| ctctggtgcc tacgggggaca tcgtgatgac ccagtctcca gactccctgg ctgtgtctct | 1020 |
| gggcgagagg gccaccatca actgcaagtc caaccagagt gtcttacaca gctccaacaa | 1080 |
| taagaactat ttagcttggt accagcagaa accaggacag cctcctaaat tgctcattta | 1140 |
| ttgggcattc ctccgggaat ccggggtccc tgaccgcttc agtggcagcg gtctgggac | 1200 |
| agatttcact ctcaccatca gcagcctgca ggctgaagat gtggcagttt attactgtca | 1260 |
| ccaatattat tctactttat atacttttcgg cggagggacc aaggtagaga tcaaacgaac | 1320 |
| ygtggctgca ccatctgtct tcatcttccc gccatctgat gagcagttga aatctggaac | 1380 |

```
tgctagcgtt gtgtgcctgc tgaataactt ctatcccaga gaggccaaag tacagtggaa    1440
ggtggataac gccctccaat cgggtaactc ccaggagagt gtcacagagc aggacagcaa    1500
ggacagcacc tacagcctca gcagcaccct gacgctgagc aaagcagact acgagaaaca    1560
caaagtctac gcctgcgaag tcacccatca gggcctgagc tcgcccgtca caagagctt    1620 caacagggga gagtgttagg cggccgctcg agtctagagg gcccgtttaa acccgctgat    1680
cagcctcgac tgtgccttct agttgccagc catctgttgt ttgcccctcc ccgtgcctt    1740 ccttgaccct ggaaggtgcc actcccactg tcctttccta ataaaatgag gaaattgcat    1800
cgcattgtct gagtaggtgt cattctattc tggggggtgg ggtggggcag gacagcaagg    1860
gggaggattg ggaagacaat agcaggcatg ctggggatgc ggtgggctct atggcttctg    1920
aggcggaaag aaccagctgg ggctctaggg ggtatcccca cgcgccctgt agcggcgcat    1980
taagcgcggc gggtgtggtg gttacgcgca gcgtgaccgc tacacttgcc agcgccctag    2040
cgcccgctcc tttcgctttc ttcccttcct ttctcgccac gttcgccggc tttccccgtc    2100
aagctctaaa tcggggcatc cctttagggt tccgatttag tgctttacgg cacctcgacc    2160
ccaaaaaact tgattagggt gatggttcac gtagtgggcc atcgccctga tagacggttt    2220
ttcgcccttt gacgttggag tccacgttct ttaatagtgg actcttgttc caaactggaa    2280
caacactcaa ccctatctcg gtctattctt ttgatttata aggattttg gggatttcgg    2340 cctattggtt aaaaaatgag ctgatttaac aaaaatttaa cgcgaattaa ttctgtggaa    2400
tgtgtgtcag ttagggtgtg aaagtcccc aggctcccca ggcagcaga agtatgcaaa    2460 gcatgcatct caattagtca gcaaccaggt gtggaaagtc cccaggctcc ccagcaggca    2520
gaagtatgca aagcatgcat ctcaattagt cagcaaccat agtcccgccc ctaactccgc    2580
ccatcccgcc cctaactccg cccagttccg cccattctcc gccccatggc tgactaattt    2640
tttttattta tgcagaggcc gaggccgcct ctgcctctga gctattccag aagtagtgag    2700
gaggcttttt tggaggccta ggcttttgca aaaagctccc gggagcttgt atatccattt    2760
tcggatctga tcaagagaca ggatgaggat cgtttcgcat gattgaacaa gatggattgc    2820
acgcaggttc tccggccgct tgggtggaga ggctattcgg ctatgactgg gcacaacaga    2880
caatcggctg ctctgatgcc gccgtgttcc ggctgtcagc gcaggggcgc ccggttcttt    2940
ttgtcaagac cgacctgtcc ggtgccctga atgaactgca ggacgaggca gcgcggctat    3000
cgtggctggc cacgacgggc gttccttgcg cagctgtgct cgacgttgtc actgaagcgg    3060
gaagggactg gctgctattg ggcgaagtgc cggggcagga tctcctgtca tctcaccttg    3120
ctcctgccga gaaagtatcc atcatggctg atgcaatgcg gcggctgcat acgcttgatc    3180
cggctacctg cccattcgac caccaagcga aacatcgcat cgagcgagca cgtactcgga    3240
tggaagccgg tcttgtcgat caggatgatc tggacgaaga gcatcagggg ctcgcgccag    3300
ccgaactgtt cgccaggctc aaggcgcgca tgcccgacgg cgaggatctc gtcgtgaccc    3360
atggcgatgc ctgcttgccg aatatcatgg tggaaaatgg ccgcttttct ggattcatcg    3420
actgtggccg gctgggtgtg gcggaccgct atcaggacat agcgttggct acccgtgata    3480
ttgctgaaga gcttggcggc gaatgggctg accgcttcct cgtgctttac ggtatcgccg    3540
ctcccgattc gcagcgcatc gccttctatc gccttcttga cgagttcttc tgagcgggac    3600
tctggggttc gaaatgaccg accaagcgac gcccaacctg ccatcacgag atttcgattc    3660
caccgccgcc ttctatgaaa ggttgggctt cggaatcgtt ttccgggacg ccggctggat    3720
gatcctccag cgcggggatc tcatgctgga gttcttcgcc caccccaact tgtttattgc    3780
```

```
agcttataat ggttacaaat aaagcaatag catcacaaat ttcacaaata aagcattttt    3840
ttcactgcat tctagttgtg gtttgtccaa actcatcaat gtatcttatc atgtctgtat    3900
accgtcgacc tctagctaga gcttggcgta atcatggtca tagctgtttc ctgtgtgaaa    3960
ttgttatccg ctcacaattc cacacaacat acgagccgga agcataaagt gtaaagcctg    4020
gggtgcctaa tgagtgagct aactcacatt aattgcgttg cgctcactgc ccgctttcca    4080
gtcgggaaac ctgtcgtgcc agctgcatta atgaatcggc caacgcgcgg ggagaggcgg    4140
tttgcgtatt gggcgctctt ccgcttcctc gctcactgac tcgctgcgct cggtcgttcg    4200
gctgcggcga gcggtatcag ctcactcaaa ggcggtaata cggttatcca cagaatcagg    4260
ggataacgca ggaaagaaca tgtgagcaaa aggccagcaa aaggccagga accgtaaaaa    4320
ggccgcgttg ctggcgtttt tccataggct ccgcccccct gacgagcatc acaaaaatcg    4380
acgctcaagt cagaggtggc gaaacccgac aggactataa agataccagg cgtttccccc    4440
tggaagctcc ctcgtgcgct ctcctgttcc gaccctgccg cttaccggat acctgtccgc    4500
ctttctccct tcgggaagcg tggcgctttc tcaatgctca cgctgtaggt atctcagttc    4560
ggtgtaggtc gttcgctcca agctgggctg tgtgcacgaa ccccccgttc agcccgaccg    4620
ctgcgcctta tccggtaact atcgtcttga gtccaacccg gtaagacacg acttatcgcc    4680
actggcagca gccactggta acaggattag cagagcgagg tatgtaggcg gtgctacaga    4740
gttcttgaag tggtgcccta actacggcta cactagaagg acagtatttg gtatctgcgc    4800
tctgctgaag ccagttacct tcggaaaaag agttggtagc tcttgatccg gcaaacaaac    4860
caccgctggt agcggtggtt tttttgtttg caagcagcag attacgcgca gaaaaaaagg    4920
atctcaagaa gatcctttga tcttttctac ggggtctgac gctcagtgga acgaaaactc    4980
acgttaaggg attttggtca tgagattatc aaaaaggatc ttcacctaga tccttttaaa    5040
ttaaaaatga agttttaaat caatctaaag tatatatgag taaacttggt ctgacagtta    5100
ccaatgctta atcagtgagg cacctatctc agcgatctgt ctatttcgtt catccatagt    5160
tgcctgactc cccgtcgtgt agataactac gatacgggag ggcttaccat ctggccccag    5220
tgctgcaatg ataccgcgag acccacgctc accggctcca gatttatcag caataaacca    5280
gccagccgga agggccgagc gcagaagtgg tcctgcaact ttatccgcct ccatccagtc    5340
tattaattgt tgccgggaag ctagagtaag tagttcgcca gttaatagtt tgcgcaacgt    5400
tgttgccatt gctacaggca tcgtggtgtc acgctcgtcg tttggtatgg cttcattcag    5460
ctccggttcc caacgatcaa ggcgagttac atgatccccc atgttgtgca aaaaagcggt    5520
tagctccttc ggtcctccga tcgttgtcag aagtaagttg gccgcagtgt tatcactcat    5580
ggttatggca gcactgcata attctcttac tgtcatgcca tccgtaagat gcttttctgt    5640
gactggtgag tactcaacca agtcattctg agaatagtgt atgcggcgac cgagttgctc    5700
ttgcccggcg tcaatacggg ataataccgc gccacatagc agaactttaa aagtgctcat    5760
cattggaaaa cgttcttcgg ggcgaaaact ctcaaggatc ttaccgctgt tgagatccag    5820
ttcgatgtaa cccactcgtg cacccaactg atcttcagca tcttttactt tcaccagcgt    5880
ttctgggtga gcaaaacagg aaggcaaaa tgccgcaaaa aagggaataa gggcgacacg    5940
gaaatgttga atactcatac tcttcctttt tcaatattat tgaagcattt atcagggtta    6000
ttgtctcatg agcggataca tatttgaatg tatttagaaa aataaacaaa taggggttcc    6060
gcgcacattt ccccgaaaag tgccacctga cgtc                                6094
```

<210> SEQ ID NO 14
<211> LENGTH: 481
<212> TYPE: DNA
<213> ORGANISM: Artificial Sequence
<220> FEATURE:
<223> OTHER INFORMATION: Synthetic Oligonucleotide

<400> SEQUENCE: 14

```
ggatctcacc atggagttgg gactgcgctg gggcttcctc gttgctcttt taagaggtgt    60
ccagtgtcag gtgcaattgg tggagtctgg gggaggcgtg gtccagcctg ggaggtccct   120
gagactctcc tgtgcagcgt ctggattcgc cttcagtaga tatggcatgc actgggtccg   180
ccaggctcca ggcaaggggc tggagtgggt ggcagttata tggtatgatg gaagtaataa   240
atactatgca gactccgtga agggccgatt caccatctcc agagacaatt ccaagaacac   300
gcagtatctg caaatgaaca gcctgagagc cgaggacacg gctgtgtatt actgtgcgag   360
aggcggtgac ttcctctact actactatta cggtatggac gtctggggcc aagggaccac   420
ggtcaccgtc tcctcagcct ccaccaaggg cccatcggtc ttccccctgg cacccctag   480
c                                                                   481
```

<210> SEQ ID NO 15
<211> LENGTH: 142
<212> TYPE: PRT
<213> ORGANISM: Homo sapiens

<400> SEQUENCE: 15

```
Met Glu Leu Gly Leu Arg Trp Gly Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Ala Phe
        35                  40                  45

Ser Arg Tyr Gly Met His Trp Val Arg Gln Ala Pro Gly Lys Gly Leu
    50                  55                  60

Glu Trp Val Ala Val Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Gln Tyr Leu Gln Met Asn Ser Leu Arg Ala Glu Asp Thr Ala Val
            100                 105                 110

Tyr Tyr Cys Ala Arg Gly Gly Asp Phe Leu Tyr Tyr Tyr Tyr Tyr Gly
        115                 120                 125

Met Asp Val Trp Gly Gln Gly Thr Thr Val Thr Val Ser Ser
    130                 135                 140
```

<210> SEQ ID NO 16
<211> LENGTH: 463
<212> TYPE: DNA
<213> ORGANISM: Artificial Sequence
<220> FEATURE:
<223> OTHER INFORMATION: Synthetic Oligonucleotide

<400> SEQUENCE: 16

```
ggatctcacc atgagggtcc ctgctcagct cctggggactc ctgctgctct ggctcccaga    60
taccagatgt gacatccaga tgacccagtc tccatcctcc ctgtctgcat ctgtaggaga   120
cagagtcacc atcacttgcc gggcgagtca gggcattagc aattatttag cctggtatca   180
```

```
gcagaaaaca gggaaagttc ctaagttcct gatctatgaa gcatccactt tgcaatcagg    240
ggtcccatct cggttcagtg gcggtggatc tgggacagat ttcactctca ccatcagcag    300
cctgcagcct gaagatgttg caacttatta ctgtcaaaat tataacagtg ccccattcac    360
tttcggccct gggaccaaag tggatatcaa acgaactgtg gctgcaccct ctgtcttcat    420
cttcccgcca tctgatgagc agttgaaatc tggaactgct agc                     463
```

<210> SEQ ID NO 17
<211> LENGTH: 127
<212> TYPE: PRT
<213> ORGANISM: Homo sapiens

<400> SEQUENCE: 17

```
Met Arg Val Pro Ala Gln Leu Leu Gly Leu Leu Leu Leu Trp Leu Pro
1               5                   10                  15
Asp Thr Arg Cys Asp Ile Gln Met Thr Gln Ser Pro Ser Ser Leu Ser
            20                  25                  30
Ala Ser Val Gly Asp Arg Val Thr Ile Thr Cys Arg Ala Ser Gln Gly
        35                  40                  45
Ile Ser Asn Tyr Leu Ala Trp Tyr Gln Gln Lys Thr Gly Lys Val Pro
    50                  55                  60
Lys Phe Leu Ile Tyr Glu Ala Ser Thr Leu Gln Ser Gly Val Pro Ser
65                  70                  75                  80
Arg Phe Ser Gly Gly Gly Ser Gly Thr Asp Phe Thr Leu Thr Ile Ser
                85                  90                  95
Ser Leu Gln Pro Glu Asp Val Ala Thr Tyr Tyr Cys Gln Asn Tyr Asn
            100                 105                 110
Ser Ala Pro Phe Thr Phe Gly Pro Gly Thr Lys Val Asp Ile Lys
        115                 120                 125
```

<210> SEQ ID NO 18
<211> LENGTH: 508
<212> TYPE: DNA
<213> ORGANISM: Artificial Sequence
<220> FEATURE:
<223> OTHER INFORMATION: Synthetic Oligonucleotide

<400> SEQUENCE: 18

```
ggatctcacc atggggtcaa ccgccatcct caccatggag ttggggctgc gctgggttct     60
cctcgttgct cttttaagag gtgtccagtg tcaggtgcag ctggtggagt ctggggagg    120 cgtggtccag cctgggaggt ccctgagact ctcctgtgca gcgtctggat tcaccttcag    180
taactatgtc atgcactggg tccgccaggc tccaggcaag gggctggagt gggtggcaat    240
tatatggtat gatggaagta ataaatacta tgcagactcc gtgaagggcc gattcaccat    300
ctccagagac aattccaaga acacgctgta tctgcaaatg aacagcctga gccgagga    360 cacggctgtg tattactgtg cgggtggata taactggaac tacgagtacc actactacgg    420
tatggacgtc tggggccaag ggaccacggt caccgtctcc tcagcctcca ccaagggccc    480
atcggtcttc cccctggcac cctctagc                                       508
```

<210> SEQ ID NO 19
<211> LENGTH: 143
<212> TYPE: PRT
<213> ORGANISM: Homo sapiens

<400> SEQUENCE: 19

```
Met Glu Leu Gly Leu Arg Trp Val Leu Leu Val Ala Leu Leu Arg Gly
```

```
                1               5                  10                 15
Val Gln Cys Gln Val Gln Leu Val Glu Ser Gly Gly Gly Val Gln
                    20                  25                 30

Pro Gly Arg Ser Leu Arg Leu Ser Cys Ala Ala Ser Gly Phe Thr Phe
            35                  40                  45

Ser Asn Tyr Val Met His Trp Val Arg Gln Ala Pro Gly Lys Gly Leu
        50                  55                  60

Glu Trp Val Ala Ile Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Gly Gly Tyr Asn Trp Asn Tyr Glu Tyr His Tyr Tyr
        115                 120                 125

Gly Met Asp Val Trp Gly Gln Gly Thr Thr Val Thr Val Ser Ser
    130                 135                 140
```

```
<210> SEQ ID NO 20
<211> LENGTH: 463
<212> TYPE: DNA
<213> ORGANISM: Artificial Sequence
<220> FEATURE:
<223> OTHER INFORMATION: Synthetic Oligonucleotide

<400> SEQUENCE: 20
ggatctcacc atgagggtcc ccgctcagct cctggggctc ctgctgctct gtttcccagg    60
tgccagatgt gacatccaga tgacccagtc tccatcctca ctgtctgcat ctgtaggaga   120
cagagtcacc atcacttgtc gggcgagtca gggcattacc aattatttag cctggtttca   180
gcagaaacca gggaaagccc ctaagtccct tatctatgct gcatccagtt tgcaaagtgg   240
ggtcccatca agttcagcg gcagtggatc tgggacagat ttcagtctca ccatcagcag   300
cctgcagcct gaagattttg caacttatta ctgccaacag tataatagtt acccgatcac   360
cttcggccaa gggacacgac tggagattaa acgaactgtg gctgcaccat ctgtcttcat   420
cttcccgcca tctgatgagc agttgaaatc tggaactgct agc                    463
```

```
<210> SEQ ID NO 21
<211> LENGTH: 127
<212> TYPE: PRT
<213> ORGANISM: Homo sapiens

<400> SEQUENCE: 21

Met Arg Val Pro Ala Gln Leu Leu Gly Leu Leu Leu Leu Cys Phe Pro
1               5                   10                  15

Gly Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Gly
        35                  40                  45

Ile Thr Asn Tyr Leu Ala Trp Phe Gln Gln Lys Pro Gly Lys Ala Pro
    50                  55                  60

Lys Ser Leu Ile Tyr Ala Ala Ser Ser Leu Gln Ser Gly Val Pro Ser
65                  70                  75                  80

Lys Phe Ser Gly Ser Gly Ser Gly Thr Asp Phe Ser Leu Thr Ile Ser
                85                  90                  95

Ser Leu Gln Pro Glu Asp Phe Ala Thr Tyr Tyr Cys Gln Gln Tyr Asn
```

-continued

```
                            100                 105                 110
Ser Tyr Pro Ile Thr Phe Gly Gln Gly Thr Arg Leu Glu Ile Lys
        115                 120                 125

<210> SEQ ID NO 22
<211> LENGTH: 490
<212> TYPE: DNA
<213> ORGANISM: Artificial Sequence
<220> FEATURE:
<223> OTHER INFORMATION: Synthetic Oligonucleotide

<400> SEQUENCE: 22
ggatctcacc atggagttgg gacttagctg ggttttcctc gttgctcttt taagaggtgt      60
ccagtgtcag gtccagctgg tggagtctgg gggaggcgtg gtccagcctg ggaggtccct     120
gagactctcc tgtgcagcgt ctggattcac cttcagtagc tatggcatgc actgggtccg     180
ccaggctcca ggcaagggc tggactgggt ggcaattatt tggcatgatg gaagtaataa     240
atactatgca gactccgtga agggccgatt caccatctcc agagacaatt ccaagaagac     300
gctgtacctg caaatgaaca gtttgagagc cgaggacacg gctgtgtatt actgtgcgag     360
agcttgggcc tatgactacg gtgactatga atactacttc ggtatggacg tctggggcca     420
agggaccacg gtcaccgtct cctcagcctc caccaagggc ccatcggtct tccccctggc     480
accctctagc                                                            490

<210> SEQ ID NO 23
<211> LENGTH: 145
<212> TYPE: PRT
<213> ORGANISM: Homo sapiens

<400> SEQUENCE: 23

Met Glu Leu Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Asp Trp Val Ala Ile Ile Trp His Asp Gly Ser Asn Lys Tyr Tyr Ala
65                  70                  75                  80

Asp Ser Val Lys Gly Arg Phe Thr Ile Ser Arg Asp Asn Ser Lys Lys
                85                  90                  95

Thr Leu Tyr Leu Gln Met Asn Ser Leu Arg Ala Glu Asp Thr Ala Val
            100                 105                 110

Tyr Tyr Cys Ala Arg Ala Trp Ala Tyr Asp Tyr Gly Asp Tyr Glu Tyr
        115                 120                 125

Tyr Phe Gly Met Asp Val Trp Gly Gln Gly Thr Thr Val Thr Val Ser
    130                 135                 140

Ser
145

<210> SEQ ID NO 24
<211> LENGTH: 463
<212> TYPE: DNA
<213> ORGANISM: Artificial Sequence
<220> FEATURE:
<223> OTHER INFORMATION: Synthetic Oligonucleotide
```

<400> SEQUENCE: 24

```
ggatctcacc atgagggtcc ctgctcagct cctggggctc ctgctgctct gtttcccagg      60
tgccagatgt gacatccaga tgacccagtc tccatcctca ctgtctgcat ctgtaggaga     120
cagagtcacc atcacttgtc gggcgagtca gggcattagc cattatttag cctggtttca     180
gcagaaacca gggaaagccc ctaagtccct gatctatgct gcatccagtt tgcaaagtgg     240
ggtcccatca aagttcagcg gcagtggatc tgggacagat ttcactctca ccatcagcag     300
cctacagcct gaagattttg caacttatta ctgccaacag tataatagtt cccgctcac      360
tttcggcgga gggaccaagg tggagatcaa acgaactgtg gctgcaccat ctgtcttcat     420
cttcccgcca tctgatgagc agttgaaatc tggaactgct agc                       463
```

<210> SEQ ID NO 25
<211> LENGTH: 127
<212> TYPE: PRT
<213> ORGANISM: Homo sapiens

<400> SEQUENCE: 25

```
Met Arg Val Pro Ala Gln Leu Leu Gly Leu Leu Leu Leu Cys Phe Pro
  1               5                  10                  15
Gly Ala Arg Cys Asp Ile Gln Met Thr Gln Ser Pro Ser Ser Leu Ser
                 20                  25                  30
Ala Ser Val Gly Asp Arg Val Thr Ile Thr Cys Arg Ala Ser Gln Gly
             35                  40                  45
Ile Ser His Tyr Leu Ala Trp Phe Gln Gln Lys Pro Gly Lys Ala Pro
         50                  55                  60
Lys Ser Leu Ile Tyr Ala Ala Ser Ser Leu Gln Ser Gly Val Pro Ser
 65                  70                  75                  80
Lys Phe Ser Gly Ser Gly Ser Gly Thr Asp Phe Thr Leu Thr Ile Ser
                 85                  90                  95
Ser Leu Gln Pro Glu Asp Phe Ala Thr Tyr Tyr Cys Gln Gln Tyr Asn
                100                 105                 110
Ser Phe Pro Leu Thr Phe Gly Gly Gly Thr Lys Val Glu Ile Lys
            115                 120                 125
```

<210> SEQ ID NO 26
<211> LENGTH: 469
<212> TYPE: DNA
<213> ORGANISM: Artificial Sequence
<220> FEATURE:
<223> OTHER INFORMATION: Synthetic Oligonucleotide

<400> SEQUENCE: 26

```
ggatcccacc atggggtcaa ccgtcatcct cgccctcctc ctggctgttc tccaaggagt      60
ctgtgccgag gtgcagctgg tgcagtctgg agcagaggtg aaaaagcccg ggagtctct      120
gaagatctcc tgtaagggtt ctggatacag ctttaccagt tactgatcg gctgggtgcg      180
ccagatgccc gggaaaggcc tggagtggat gggggatcatc tatcctggtg actctgatac     240
cagatacagc ccgtccttcc aaggccaggt caccatctca gccgacaagt ccatcagcac     300
cgcctacctg cagtggagca gcctgaaggc ctcggacacc gccatgtatt actgtgcgag     360
acggatggca gcagctggcc cctttgacta ctggggccag ggaaccctgg tcaccgtctc     420
ctcagcctcc accaagggcc catcggtctt ccccctggca ccctctagc                 469
```

<210> SEQ ID NO 27
<211> LENGTH: 138

```
<212> TYPE: PRT
<213> ORGANISM: Homo sapiens

<400> SEQUENCE: 27

Met Gly Ser Thr Val Ile Leu Ala Leu Leu Ala Val Leu Gln Gly
1               5                   10                  15

Val Cys Ala Glu Val Gln Leu Val Gln Ser Gly Ala Glu Val Lys Lys
            20                  25                  30

Pro Gly Glu Ser Leu Lys Ile Ser Cys Lys Gly Ser Gly Tyr Ser Phe
        35                  40                  45

Thr Ser Tyr Trp Ile Gly Trp Val Arg Gln Met Pro Gly Lys Gly Leu
    50                  55                  60

Glu Trp Met Gly Ile Ile Tyr Pro Gly Asp Ser Asp Thr Arg Tyr Ser
65                  70                  75                  80

Pro Ser Phe Gln Gly Gln Val Thr Ile Ser Ala Asp Lys Ser Ile Ser
                85                  90                  95

Thr Ala Tyr Leu Gln Trp Ser Ser Leu Lys Ala Ser Asp Thr Ala Met
            100                 105                 110

Tyr Tyr Cys Ala Arg Arg Met Ala Ala Ala Gly Pro Phe Asp Tyr Trp
        115                 120                 125

Gly Gln Gly Thr Leu Val Thr Val Ser Ser
    130                 135

<210> SEQ ID NO 28
<211> LENGTH: 466
<212> TYPE: DNA
<213> ORGANISM: Artificial Sequence
<220> FEATURE:
<223> OTHER INFORMATION: Synthetic Oligonucleotide

<400> SEQUENCE: 28
ggatctcacc atgagggtcc ccgctcagct tctcttcctt ctgctactct ggctcccaga     60
taccactgga ggaatagtga tgacgcagtc tccagccacc ctgtctgtgt ctccagggga    120
aagagccacc ctctcctgca ggaccagtca gagtattggc tggaacttag cctggtacca    180
acagaaacct ggccaggctc ccaggctcct catctatggt gcatcttcca ggaccactgg    240
tatcccagcc aggttcagtg gcagtgggtc tgggacagag ttcactctca ccatcagcag    300
cctgcagtct gaagattctg cagtttatta ctgtcagcat tatgataact ggcccatgtg    360
cagttttggc caggggaccg agctggagat caaacgaact gtggctgcac catctgtctt    420
catcttcccg ccatctgatg agcagttgaa atctggaact gctagc                  466

<210> SEQ ID NO 29
<211> LENGTH: 128
<212> TYPE: PRT
<213> ORGANISM: Homo sapiens

<400> SEQUENCE: 29

Met Arg Val Pro Ala Gln Leu Leu Phe Leu Leu Leu Trp Leu Pro
1               5                   10                  15

Asp Thr Thr Gly Gly Ile Val Met Thr Gln Ser Pro Ala Thr Leu Ser
            20                  25                  30

Val Ser Pro Gly Glu Arg Ala Thr Leu Ser Cys Arg Thr Ser Gln Ser
        35                  40                  45

Ile Gly Trp Asn Leu Ala Trp Tyr Gln Gln Lys Pro Gly Gln Ala Pro
    50                  55                  60

Arg Leu Leu Ile Tyr Gly Ala Ser Ser Arg Thr Thr Gly Ile Pro Ala
```

```
                65                  70                  75                  80
Arg Phe Ser Gly Ser Gly Ser Gly Thr Glu Phe Thr Leu Thr Ile Ser
                    85                  90                  95
Ser Leu Gln Ser Glu Asp Ser Ala Val Tyr Tyr Cys Gln His Tyr Asp
                    100                 105                 110
Asn Trp Pro Met Cys Ser Phe Gly Gln Gly Thr Glu Leu Glu Ile Lys
            115                 120                 125

<210> SEQ ID NO 30
<211> LENGTH: 487
<212> TYPE: DNA
<213> ORGANISM: Artificial Sequence
<220> FEATURE:
<223> OTHER INFORMATION: Synthetic Oligonucleotide

<400> SEQUENCE: 30
ggatctcacc atggagtttg ggctgtgctg gattttcctc gttgctcttt taagaggtgt        60
ccagtgtcag gtgcagctgg tggagtctgg gggaggcgtg gtccagcctg gaggtccct       120 gagactctcc tgtgcagcct ctggattcac cttcattagc tatggcatgc actgggtccg       180
ccaggctcca ggcaaggggc tggagtgggt ggcagttata tcatatgatg gaagtaataa       240
atactatgca gactccgtga agggccgatt caccatctcc agagacaatt ccaagaacac       300
gctgtatctg caaatgaaca gcctgagagc tgaggacacg gctgtgtatt actgtgcgag       360
agtattagtg ggagctttat attattataa ctactacggg atggacgtct ggggccaagg       420
gaccacggtc accgtctcct cagcctccac caagggccca tcggtcttcc ccctggcacc       480
ctctagc                                                                487

<210> SEQ ID NO 31
<211> LENGTH: 144
<212> TYPE: PRT
<213> ORGANISM: Homo sapiens

<400> SEQUENCE: 31

Met Glu Phe Gly Leu Cys Trp Ile Phe Leu Val Ala Leu Leu Arg Gly
1               5                   10                  15
Val Gln Cys Gln Val Gln Leu Val Glu Ser Gly Gly Gly Val Val Gln
                20                  25                  30
Pro Gly Arg Ser Leu Arg Leu Ser Cys Ala Ala Ser Gly Phe Thr Phe
            35                  40                  45
Ile Ser Tyr Gly Met His Trp Val Arg Gln Ala Pro Gly Lys Gly Leu
    50                  55                  60
Glu Trp Val Ala Val Ile Ser Tyr Asp Gly Ser Asn Lys Tyr Tyr Ala
65                  70                  75                  80
Asp Ser Val Lys Gly Arg Phe Thr Ile Ser Arg Asp Asn Ser Lys Asn
                85                  90                  95
Thr Leu Tyr Leu Gln Met Asn Ser Leu Arg Ala Glu Asp Thr Ala Val
            100                 105                 110
Tyr Tyr Cys Ala Arg Val Leu Val Gly Ala Leu Tyr Tyr Tyr Asn Tyr
        115                 120                 125
Tyr Gly Met Asp Val Trp Gly Gln Gly Thr Thr Val Thr Val Ser Ser
    130                 135                 140

<210> SEQ ID NO 32
<211> LENGTH: 478
<212> TYPE: DNA
<213> ORGANISM: Artificial Sequence
```

<220> FEATURE:
<223> OTHER INFORMATION: Synthetic Oligonucleotide

<400> SEQUENCE: 32

| | | | | | |
|---|---|---|---|---|---|
| ggatctcacc | atgagggtcc | ctgctcagct | cctggggctg | ctaatgctct | ggatacctgg | 60 |
| atccagtgca | gatattgtga | tgacccagac | tccactctct | ctgtccgtca | ccctggaca | 120 |
| gccggcctcc | atctcctgca | agtctagtca | gagcctcctg | catagtgatg | gaaagacctt | 180 |
| tttgtattgg | tatctgcaga | agccaggcca | gcctccacag | ctcctgatct | atgaggtttc | 240 |
| caaccggttc | tctggagtgc | cagataggtt | cagtggcagc | gggtcaggga | cagatttcac | 300 |
| actgaaaatc | agccgggtgg | aggctgagga | tgttgggctt | tattactgca | tgcaaagtat | 360 |
| acagcttccg | ctcactttcg | gcggagggac | caaggtggag | atcaaacgaa | ctgtggctgc | 420 |
| accatctgtc | ttcatcttcc | cgccatctga | tgagcagttg | aaatctggaa | ctgctagc | 478 |

<210> SEQ ID NO 33
<211> LENGTH: 132
<212> TYPE: PRT
<213> ORGANISM: Homo sapiens

<400> SEQUENCE: 33

Met Arg Val Pro Ala Gln Leu Leu Gly Leu Leu Met Leu Trp Ile Pro
1               5                   10                  15

Gly Ser Ser Ala Asp Ile Val Met Thr Gln Thr Pro Leu Ser Leu Ser
            20                  25                  30

Val Thr Pro Gly Gln Pro Ala Ser Ile Ser Cys Lys Ser Ser Gln Ser
        35                  40                  45

Leu Leu His Ser Asp Gly Lys Thr Phe Leu Tyr Trp Tyr Leu Gln Lys
    50                  55                  60

Pro Gly Gln Pro Pro Gln Leu Leu Ile Tyr Glu Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Leu Tyr Tyr
            100                 105                 110

Cys Met Gln Ser Ile Gln Leu Pro Leu Thr Phe Gly Gly Gly Thr Lys
        115                 120                 125

Val Glu Ile Lys
    130

<210> SEQ ID NO 34
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 34
gaagatctca ccatg                                                      15

<210> SEQ ID NO 35
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 35
aactagctag cagttccaga tttcaactgc tcatcagat                             39

```
<210> SEQ ID NO 36
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 36
gaagatctca ccatg                                                          15

<210> SEQ ID NO 37
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 37
gctctagagg gtgccagggg gaagaccgat                                          30

<210> SEQ ID NO 38
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 38

Ser Ala Thr Gly Ser Lys Leu Gln Glu Asp Ser
1               5                   10

<210> SEQ ID NO 39
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 39

Arg Ser Pro Ala Leu Pro Phe Val Ser
1               5
```

PSMA ANTIBODIES AND PROTEIN MULTIMERS

RELATED APPLICATIONS

This application is a continuation-in-part of International application PCT/US02/33944 designating the United States, filed on Oct. 23, 2002, which claims the benefit under 35 U.S.C. §119 of U.S. provisional application 60/335,215, filed Oct. 23, 2001, U.S. provisional application 60/362,747, filed Mar. 7, 2002, and U.S. provisional application 60/412,618, filed Sep. 20, 2002, each of which is incorporated herein by reference.

FIELD OF THE INVENTION

This invention relates generally to the field of cancer associated polypeptides and antibodies that recognize native epitopes on the polypeptides. In particular, the invention relates in part to antibodies or antigen-binding fragments thereof which bind specifically to conformational epitopes on the extracellular domain of PSMA, multimeric forms of PSMA proteins, antibodies that selectively bind to the multimers, and compositions containing such antibodies or multimers.

BACKGROUND OF THE INVENTION

Prostate cancer is the most prevalent type of cancer and the second leading cause of death from cancer in American men, with an estimated 179,000 cases and 37,000 deaths in 1999, (Landis, S. H. et al. *C A Cancer J. Clin.* 48:6-29 (1998)). The number of men diagnosed with prostate cancer is steadily increasing as a result of the increasing population of older men as well as a greater awareness of the disease leading to its earlier diagnosis (Parker et al., 1997, *C A Cancer J. Clin.* 47:5-280). The life time risk for men developing prostate cancer is about 1 in 5 for Caucasians, 1 in 6 for African Americans. High risk groups are represented by those with a positive family history of prostate cancer or African Americans.

Over a lifetime, more than ⅔ of the men diagnosed with prostate cancer die of the disease (Wingo et al., 1996, *C A Cancer J. Clin.* 46:113-25). Moreover, many patients who do not succumb to prostate cancer require continuous treatment to ameliorate symptoms such as pain, bleeding and urinary obstruction. Thus, prostate cancer also represents a major cause of suffering and increased health care expenditures.

Where prostate cancer is localized and the patient's life expectancy is 10 years or more, radical prostatectomy offers the best chance for eradication of the disease. Historically, the drawback of this procedure is that most cancers had spread beyond the bounds of the operation by the time they were detected. Patients with bulky, high-grade tumors are less likely to be successfully treated by radical prostatectomy.

Radiation therapy has also been widely used as an alternative to radical prostatectomy. Patients generally treated by radiation therapy are those who are older and less healthy and those with higher-grade, more clinically advanced tumors. Particularly preferred procedures are external-beam therapy which involves three dimensional, confocal radiation therapy where the field of radiation is designed to conform to the volume of tissue treated; interstitial-radiation therapy where seeds of radioactive compounds are implanted using ultrasound guidance; and a combination of external-beam therapy and interstitial-radiation therapy.

For treatment of patients with locally advanced disease, hormonal therapy before or following radical prostatectomy or radiation therapy has been utilized. Hormonal therapy is the main form of treating men with disseminated prostate cancer. Orchiectomy reduces serum testosterone concentrations, while estrogen treatment is similarly beneficial. Diethylstilbestrol from estrogen is another useful hormonal therapy which has a disadvantage of causing cardiovascular toxicity. When gonadotropin-releasing hormone agonists are administered testosterone concentrations are ultimately reduced. Flutamide and other nonsteroidal, anti-androgen agents block binding of testosterone to its intracellular receptors. As a result, it blocks the effect of testosterone, increasing serum testosterone concentrations and allows patients to remain potent—a significant problem after radical prostatectomy and radiation treatments.

Cytotoxic chemotherapy is largely ineffective in treating prostate cancer. Its toxicity makes such therapy unsuitable for elderly patients. In addition, prostate cancer is relatively resistant to cytotoxic agents.

Relapsed or more advanced disease is also treated with anti-androgen therapy. Unfortunately, almost all tumors become hormone-resistant and progress rapidly in the absence of any effective therapy.

Accordingly, there is a need for effective therapeutics for prostate cancer which are not overwhelmingly toxic to normal tissues of a patient, and which are effective in selectively eliminating prostate cancer cells.

SUMMARY OF THE INVENTION

The present invention relates to antibodies or antigen-binding fragments thereof which specifically bind the extracellular domain of prostate specific membrane antigen (PSMA), compositions containing one or a combination of such antibodies or antigen-binding fragments thereof, hybridoma cell lines that produce the antibodies, and methods of using the antibodies or antigen-binding fragments thereof for cancer diagnosis and treatment.

According to one aspect of the invention, isolated antibodies or an antigen-binding fragments thereof are provided. The antibodies or fragments thereof specifically bind to an extracellular domain of prostate specific membrane antigen (PSMA), and competitively inhibit the specific binding of a second antibody to its target epitope on PSMA. In a second aspect of the invention, isolated antibodies or antigen-binding fragments thereof are provided which specifically bind to an epitope on prostate specific membrane antigen (PSMA) defined by a second antibody. In each of the forgoing aspects of the invention, the second antibody is selected from the group consisting of PSMA 3.7, PSMA 3.8, PSMA 3.9, PSMA 3.11, PSMA 5.4, PSMA 7.1, PSMA 7.3, PSMA 10.3, PSMA 1.8.3, PSMA A3.1.3, PSMA A3.3.1, Abgenix 4.248.2, Abgenix 4.360.3, Abgenix 4.7.1, Abgenix 4.4.1, Abgenix 4.177.3, Abgenix 4.16.1, Abgenix 4.22.3, Abgenix 4.28.3, Abgenix 4.40.2, Abgenix 4.48.3, Abgenix 4.49.1, Abgenix 4.209.3, Abgenix 4.219.3, Abgenix 4.288.1, Abgenix 4.333.1, Abgenix 4.54.1, Abgenix 4.153.1, Abgenix 4.232.3, Abgenix 4.292.3, Abgenix 4.304.1, Abgenix 4.78.1, Abgenix 4.152.1, and antibodies comprising (a) a heavy chain encoded by a nucleic acid molecule comprising the coding region or regions of a nucleotide sequence selected from the group consisting of nucleotide sequences set forth as SEQ ID NOs: 2-7, and (b) a light chain encoded by a nucleic acid molecule comprising the coding region or regions of a nucleotide sequence selected from the group consisting of nucleotide sequences set forth as SEQ ID NOs: 8-13.

In certain embodiments, the antibody or antigen-binding fragment thereof is selected from the group consisting of PSMA 3.7, PSMA 3.8, PSMA 3.9, PSMA 3.11 PSMA 5.4, PSMA 7.3, PSMA 10.3, PSMA 1.8.3, PSMA A3.1.3, PSMA A3.3.1, Abgenix 4.248.2, Abgenix 4.360.3, Abgenix 4.7.1, Abgenix 4.4.1, Abgenix 4.177.3, Abgenix 4.16.1, Abgenix 4.22.3, Abgenix 4.28.3, Abgenix 4.40.2, Abgenix 4.48.3, Abgenix 4.49.1, Abgenix 4.209.3, Abgenix 4.219.3, Abgenix 4.288.1, Abgenix 4.333.1, Abgenix 4.54.1, Abgenix 4.153.1, Abgenix 4.232.3, Abgenix 4.292.3, Abgenix 4.304.1, Abgenix 4.78.1, and Abgenix 4.152.1. In other embodiments, the antibody or antigen-binding fragment thereof is selected from the group consisting of antibodies comprising (a) a heavy chain encoded by a nucleic acid molecule comprising the coding region or regions of a nucleotide sequence selected from the group consisting of nucleotide sequences set forth as SEQ ID NOs: 2-7, and (b) a light chain encoded by a nucleic acid molecule comprising the coding region or regions of a nucleotide sequence selected from the group consisting of nucleotide sequences set forth as SEQ ID NOs: 8-13, and antigen-binding fragments thereof.

In further embodiments, the antibody or antigen-binding fragments thereof is encoded by a nucleic acid molecule comprising a nucleotide sequence that is at least about 90% identical to the nucleotide sequence encoding the foregoing antibodies, preferably at least about 95% identical, more preferably at least about 97% identical, still more preferably at least about 98% identical, and most preferably is at least about 99% identical.

In some embodiments of the foregoing aspects, antigen-binding fragments of the isolated antibodies are provided. The antigen-binding fragments include (a) a heavy chain variable region encoded by a nucleic acid molecule comprising the coding regions or regions of a nucleotide sequence selected from the group consisting of nucleotide sequences set forth as: SEQ ID NOs: 14, 18, 22, 26 and 30, and (b) a light chain variable region encoded by a nucleic acid molecule comprising the coding region or region of a nucleotide sequence selected from the group consisting of nucleotide sequences set forth as: SEQ ID NOs: 16, 20, 24, 28 and 32. In other embodiments, the antigen-binding fragment includes (a) a heavy chain variable region comprising an amino acid sequence selected from the group consisting of amino acid sequences set forth as: SEQ ID NOs: 15, 19, 23, 27 and 31, and (b) a light chain variable region comprising an amino acid sequence selected from the group consisting of nucleotide sequences set forth as: SEQ ID NOs: 17, 21, 25, 29 and 33.

In a further embodiments of the invention, isolated antigen-binding fragments of antibodies, which include a CDR of the foregoing antigen-binding fragments are provided. Preferably the CDR is CDR3.

According another aspect of the invention, expression vectors including an isolated nucleic acid molecule encoding the foregoing isolated antibodies or antigen-binding fragments is provided. Host cells transformed or transfected by these expression vectors also are provided.

In certain embodiments, the antibody or antigen-binding fragment thereof is selected for its ability to bind live cells, such as a tumor cell or a prostate cell, preferably LNCaP cells. In other embodiments, the antibody or antigen-binding fragment thereof mediates cytolysis of cells expressing PSMA. Preferably cytolysis of cells expressing PSMA is mediated by effector cells or is complement mediated in the presence of effector cells.

In other embodiments, the antibody or antigen-binding fragment thereof inhibits the growth of cells expressing PSMA. Preferably the antibody or antigen-binding fragment thereof does not require cell lysis to bind to the extracellular domain of PSMA.

In further embodiments, the antibody or antigen-binding fragment thereof is selected from the group consisting of IgG1, IgG2, IgG3, IgG4, IgM, IgA1, IgA2, IgAsec, IgD, IgE or has immunoglobulin constant and/or variable domain of IgG1, IgG2, IgG3, IgG4, IgM, IgA1, IgA2, IgAsec, IgD or IgE. In other embodiments, the antibody is a bispecific or multispecific antibody.

In still other embodiments, the antibody is a recombinant antibody, a polyclonal antibody, a monoclonal antibody, a humanized antibody or a chimeric antibody, or a mixture of these. In particularly preferred embodiments, the antibody is a human antibody, e.g., a monoclonal antibody, polyclonal antibody or a mixture of monoclonal and polyclonal antibodies. In still other embodiments, the antibody is a bispecific or multispecific antibody.

Preferred antigen-binding fragments include a Fab fragment, a F(ab')$_2$ fragment, and a Fv fragment CDR3.

In further embodiments, the isolated antibody or antigen-binding fragment is a monoclonal antibody produced by a hybridoma cell line selected from the group consisting of PSMA 3.7 (PTA-3257), PSMA 3.8, PSMA 3.9 (PTA-3258), PSMA 3.11 (PTA-3269), PSMA 5.4 (PTA-3268), PSMA 7.1 (PTA-3292), PSMA 7.3 (PTA-3293), PSMA 10.3 (PTA-3247), PSMA 1.8.3 (PTA-3906), PSMA A3.1.3 (PTA-3904), PSMA A3.3.1 (PTA-3905), Abgenix 4.248.2 (PTA-4427), Abgenix 4.360.3 (PTA-4428), Abgenix 4.7.1 (PTA-4429), Abgenix 4.4.1 (PTA-4556), Abgenix 4.177.3 (PTA-4557), Abgenix 4.16.1 (PTA-4357), Abgenix 4.22.3 (PTA-4358), Abgenix 4.28.3 (PTA-4359), Abgenix 4.40.2 (PTA-4360), Abgenix 4.48.3 (PTA-4361), Abgenix 4.49.1 (PTA-4362), Abgenix 4.209.3 (PTA-4365), Abgenix 4.219.3 (PTA-4366), Abgenix 4.288.1 (PTA-4367), Abgenix 4.333.1 (PTA-4368), Abgenix 4.54.1 (PTA-4363), Abgenix 4.153.1 (PTA-4388), Abgenix 4.232.3 (PTA-4389), Abgenix 4.292.3 (PTA-4390), Abgenix 4.304.1 (PTA-4391), Abgenix 4.78.1 (PTA-4652), and Abgenix 4.152.1 (PTA-4653).

In certain other embodiments, the antibody or antigen-binding fragment thereof binds to a conformational epitope and/or is internalized into a cell along with the prostate specific membrane antigen. In other embodiments, the isolated antibody or antigen-binding fragment thereof is bound to a label, preferably one selected from the group consisting of a fluorescent label, an enzyme label, a radioactive label, a nuclear magnetic resonance active label, a luminescent label, and a chromophore label.

In still other embodiments, the isolated antibody or antigen-binding fragment thereof is bound to at least one therapeutic moiety, such as a drug, preferably a cytotoxic drug, a replication-selective virus, a toxin or a fragment thereof, or an enzyme or a fragment thereof. Preferred cytotoxic drug include: calicheamicin, esperamicin, methotrexate, doxorubicin, melphalan, chlorambucil, ARA-C, vindesine, mitomycin C, cis-platinum, etoposide, bleomycin, 5-fluorouracil, estramustine, vincristine, etoposide, doxorubicin, paclitaxel, docetaxel, dolastatin 10, auristatin E and auristatin PHE. In other embodiments, the therapeutic moiety is an immunostimulatory or immunomodulating agent, preferably one selected from the group consisting of: a cytokine, chemokine and adjuvant.

In some embodiments, the antibodies or antigen-binding fragments of the invention specifically bind cell-surface PSMA and/or rsPSMA with a binding affinity of about $1 \times 10^{-9}$ M or less. Preferably, the binding affinity is about $1 \times 10^{-10}$ M or less, more preferably the binding affinity is about $1\times10^{-11}$M or less. In other embodiments the binding affinity is less than about $5\times10^{-10}$M.

In additional embodiments, the antibodies or antigen-binding fragments of the invention mediate specific cell killing of PSMA-expressing cells with an $IC_{50}$s of less than about $1\times10^{-10}$M. Preferably the $IC_{50}$s is less than about $1\times10^{-11}$M. More preferably the $IC_{50}$s is less than about $1\times10^{-12}$M. In other embodiments the $IC_{50}$s is less than about $1.5\times10^{-11}$M.

In yet other embodiments, the isolated antibody or antigen-binding fragment thereof is bound to a radioisotope. The radioisotope can emit α radiations, β radiations, or γ radiations. Preferably the radioisotope is selected from the group consisting of $^{225}$Ac, $^{211}$At, $^{212}$Bi, $^{213}$Bi, $^{186}$Rh, $^{188}$Rh, $^{177}$Lu, $^{90}$Y, $^{131}$I, $^{67}$Cu, $^{125}$I, $^{123}$I, $^{77}$Br, $^{153}$Sm, $^{166}$Ho, $^{64}$Cu, $^{212}$Pb, $^{224}$Ra and $^{223}$Ra.

According to another aspect of the invention, hybridoma cell lines are provided that produce an antibody selected from the group consisting of PSMA 3.7, PSMA 3.8, PSMA 3.9, PSMA 3.11, PSMA 5.4, PSMA 7.1, PSMA 7.3, PSMA 10.3, PSMA 1.8.3, PSMA A3.1.3, PSMA A3.3.1, Abgenix 4.248.2, Abgenix 4.360.3, Abgenix 4.7.1, Abgenix 4.4.1, Abgenix 4.177.3, Abgenix 4.16.1, Abgenix 4.22.3, Abgenix 4.28.3, Abgenix 4.40.2, Abgenix 4.48.3, Abgenix 4.49.1, Abgenix 4.209.3, Abgenix 4.219.3, Abgenix 4.288.1, Abgenix 4.333.1, Abgenix 4.54.1, Abgenix 4.153.1, Abgenix 4.232.3, Abgenix 4.292.3, Abgenix 4.304.1, Abgenix 4.78.1 and Abgenix 4.152.1. In some embodiments, the hybridoma cell line is selected from the group consisting of PSMA 3.7 (PTA-3257), PSMA 3.8, PSMA 3.9 (PTA-3258), PSMA 3.11 (PTA-3269), PSMA 5.4 (PTA-3268), PSMA 7.1 (PTA-3292), PSMA 7.3 (PTA-3293), PSMA 10.3 (PTA-3247), PSMA 1.8.3 (PTA-3906), PSMA A3.1.3 (PTA-3904), PSMA A3.3.1 (PTA-3905), Abgenix 4.248.2 (PTA-4427), Abgenix 4.360.3 (PTA-4428), Abgenix 4.7.1 (PTA-4429), Abgenix 4.4.1 (PTA-4556), Abgenix 4.177.3 (PTA-4557), Abgenix 4.16.1 (PTA-4357), Abgenix 4.22.3 (PTA-4358), Abgenix 4.28.3 (PTA-4359), Abgenix 4.40.2 (PTA-4360), Abgenix 4.48.3 (PTA-4361), Abgenix 4.49.1 (PTA-4362), Abgenix 4.209.3 (PTA-4365), Abgenix 4.219.3 (PTA-4366), Abgenix 4.288.1 (PTA-4367), Abgenix 4.333.1 (PTA-4368), Abgenix 4.54.1 (PTA-4363), Abgenix 4.153.1 (PTA-4388), Abgenix 4.232.3 (PTA-4389), Abgenix 4.292.3 (PTA-4390), Abgenix 4.304.1 (PTA-4391), Abgenix 4.78.1 (PTA-4652), and Abgenix 4.152.1 (PTA-4653).

According to a further aspect of the invention, compositions are provided that include the foregoing antibodies or antigen-binding fragments thereof and a pharmaceutically acceptable carrier, excipient, or stabilizer. Other compositions include a combination of two or more of the foregoing antibodies or antigen-binding fragments thereof and a pharmaceutically acceptable carrier, excipient, or stabilizer. In some embodiments, the compositions also include an antitumor agent, an immunostimulatory agent, an immunomodulator, or a combination thereof. Preferred antitumor agents include a cytotoxic agent, an agent that acts on tumor neovasculature, or a combination thereof. Preferred immunomodulators include α-interferon, γ-interferon, tumor necrosis factor-α or a combination thereof. Preferred immunostimulatory agents include interleukin-2, immunostimulatory oligonucleotides, or a combination thereof.

According to another aspect of the invention, kits for detecting prostate cancer for diagnosis, prognosis or monitoring are provided. The kits include the foregoing isolated labeled antibody or antigen-binding fragment thereof, and one or more compounds for detecting the label. Preferably the label is selected from the group consisting of a fluorescent label, an enzyme label, a radioactive label, a nuclear magnetic resonance active label, a luminescent label, and a chromophore label.

The invention in another aspect provides one or more of the foregoing isolated antibodies or antigen-binding fragments thereof packaged in lyophilized form, or packaged in an aqueous medium.

In another aspect of the invention, methods for detecting the presence of PSMA, or a cell expressing PSMA, in a sample are provided. The methods include contacting the sample with any of the foregoing antibodies or antigen-binding fragments thereof which specifically bind to an extracellular domain of PSMA, for a time sufficient to allow the formation of a complex between the antibody or antigen-binding fragment thereof and PSMA, and detecting the PSMA-antibody complex or PSMA-antigen-binding fragment complex. The presence of a complex in the sample is indicative of the presence in the sample of PSMA or a cell expressing PSMA.

In another aspect, the invention provides other methods for diagnosing a PSMA-mediated disease in a subject. The methods include administering to a subject suspected of having or previously diagnosed with PSMA-mediated disease an amount of any of the foregoing antibodies or antigen-binding fragments thereof which specifically bind to an extracellular domain of prostate specific membrane antigen. The method also includes allowing the formation of a complex between the antibody or antigen-binding fragment thereof and PSMA, and detecting the formation of the PSMA-antibody complex or PSMA-antigen-binding fragment antibody complex to the target epitope. The presence of a complex in the subject suspected of having or previously diagnosed with prostate cancer is indicative of the presence of a PSMA-mediated disease.

In certain embodiments of the methods, the PSMA-mediated disease is prostate cancer. In other embodiments, the PSMA-mediated disease is a non-prostate cancer, such as those selected from the group consisting of bladder cancer including transitional cell carcinoma; pancreatic cancer including pancreatic duct carcinoma; lung cancer including non-small cell lung carcinoma; kidney cancer including conventional renal cell carcinoma; sarcoma including soft tissue sarcoma; breast cancer including breast carcinoma; brain cancer including glioblastoma multiforme; neuroendocrine carcinoma; colon cancer including colonic carcinoma; testicular cancer including testicular embryonal carcinoma; and melanoma including malignant melanoma.

In preferred embodiments of the foregoing methods, the antibody or antigen-binding fragment thereof is labeled. In other embodiments of the foregoing methods, a second antibody is administered to detect the first antibody or antigen-binding fragment thereof.

In a further aspect of the invention, methods for assessing the prognosis of a subject with a PSMA-mediated disease are provided. The methods include administering to a subject suspected of having or previously diagnosed with PSMA-mediated disease an effective amount of an antibody or antigen-binding fragment thereof according to claim A1 or B1, allowing the formation of a complex between the antibody or antigen-binding fragment thereof and PSMA, and detecting the formation of the complex to the target epitope. The amount of the complex in the subject suspected of having or previously diagnosed with PSMA-mediated disease is indicative of the prognosis.

In another aspect of the invention, methods for assessing the effectiveness of a treatment of a subject with a PSMA-mediated disease are provided. The methods include administering to a subject suspected treated for a PSMA-mediated disease an effective amount of the foregoing antibodies or antigen-binding fragments thereof, allowing the formation of a complex between the antibody or antigen-binding fragment thereof and PSMA, and detecting the formation of the complex to the target epitope. The amount of the complex in the subject suspected of having or previously diagnosed with PSMA-mediated disease is indicative of the effectiveness of the treatment.

In certain embodiments of these two aspects of the invention, the PSMA-mediated disease is prostate cancer. In other embodiments, the PSMA-mediated disease is a non-prostate cancer. In those embodiments, the non-prostate cancer preferably is selected from the group consisting of bladder cancer including transitional cell carcinoma; pancreatic cancer including pancreatic duct carcinoma; lung cancer including non-small cell lung carcinoma; kidney cancer including conventional renal cell carcinoma; sarcoma including soft tissue sarcoma; breast cancer including breast carcinoma; brain cancer including glioblastoma multiforme; neuroendocrine carcinoma; colon cancer including colonic carcinoma; testicular cancer including testicular embryonal carcinoma; and melanoma including malignant melanoma. In still other embodiments, the antibody or antigen-binding fragment thereof is labeled. In further embodiments, a second antibody is administered to detect the first antibody or antigen-binding fragment thereof.

According to yet another aspect of the invention, methods for inhibiting the growth of a cell expressing PSMA are provided. The methods include contacting a cell expressing PSMA with an amount of at least one of the foregoing antibodies or antigen-binding fragments thereof which specifically binds to an extracellular domain of PSMA effective to inhibit the growth of the cell expressing PSMA.

According to another aspect of the invention, methods for inducing cytolysis of a cell expressing PSMA are provided. The methods include contacting a cell expressing PSMA with an amount of at least one of the foregoing antibodies or antigen-binding fragments thereof which specifically binds to an extracellular domain of PSMA effective to induce cytolysis of the cell expressing PSMA. In certain embodiments, the cytolysis occurs in the presence of an effector cell. In other embodiments, the cytolysis is complement mediated.

According to still another aspect of the invention, methods for treating or preventing a PSMA-mediated disease are provided. The methods include administering to a subject having a PSMA-mediated disease an effective amount of at least one of the forgoing antibodies or antigen-binding fragments thereof to treat or prevent the PSMA-mediated disease. In some embodiments, the PSMA-mediated disease is a cancer, such as prostate cancer or a non-prostate cancer (including the nonprostate cancers described elsewhere herein).

In yet a further aspect of the invention, methods for treating or preventing a PSMA-mediated disease are provided. The methods include administering to a subject having a PSMA-mediated disease or at risk of having a PSMA-mediated disease an amount of at least one of the foregoing antibodies or antigen-binding fragments thereof effective to treat or prevent the PSMA-mediated disease.

In some embodiments, the PSMA-mediated disease is a cancer, such as prostate cancer or a non-prostate cancer (including the nonprostate cancers described elsewhere herein).

In other embodiments, the method also includes administering another therapeutic agent to treat or prevent the PSMA-mediated disease at any time before, during or after the administration of the antibody or antigen-binding fragment thereof. In some of these embodiments, the therapeutic agent is a vaccine, and preferably the vaccine immunizes the subject against PSMA.

In still other embodiments, the antibody or antigen-binding fragment thereof is bound to at least one therapeutic moiety, preferably a cytotoxic drug, a drug which acts on the tumor neovasculature and combinations thereof. Preferred cytotoxic drugs are selected from the group consisting of: calicheamicin, esperamicin, methotrexate, doxorubicin, melphalan, chlorambucil, ARA-C, vindesine, mitomycin C, cisplatinum, etoposide, bleomycin, 5-fluorouracil, estramustine, vincristine, etoposide, doxorubicin, paclitaxel, docetaxel, dolastatin 10, auristatin E and auristatin PHE.

In other embodiments, the antibody or antigen-binding fragment thereof is bound to a radioisotope and the radiations emitted by the radioisotope is selected from the group consisting of $\alpha$, $\beta$ and $\gamma$ radiations. Preferably, the radioisotope is selected from the group consisting $^{225}$Ac, $^{211}$At, $^{212}$Bi, $^{213}$Bi, $^{186}$Rh, $^{188}$Rh, $^{177}$Lu, $^{90}$Y, $^{131}$I, $^{67}$Cu, $^{125}$I, $^{123}$I, $^{77}$Br, $^{153}$Sm, $^{166}$Ho, $^{64}$Cu, $^{212}$Pb, $^{224}$Ra and $^{223}$Ra.

The present invention provides methods for modulating at least one enzymatic activity of PSMA. As used in preferred embodiments of the methods, "modulating" an enzymatic activity of PSMA means enhancing or inhibiting the enzymatic activity. Thus in certain aspects of the invention, methods for inhibiting an enzymatic activity of PSMA are provided, and in other aspects of the invention, methods for enhancing an enzymatic activity of PSMA are provided. The terms "enhancing" and "inhibiting" in this context indicate that the enzymatic activity of PSMA is enhanced or inhibited in the presence of an antibody that specifically binds PSMA, or antigen-binding fragment thereof, relative to the level of activity in the absence of such an antibody or antigen-binding fragment thereof. Enzymatic activities of PSMA include folate hydrolase activity, N-acetylated $\alpha$-linked acidic dipeptidase (NAALADase) activity, dipeptidyl dipeptidase IV activity and $\gamma$-glutamyl hydrolase activity.

Thus the invention in another aspect provides methods for modulating folate hydrolase activity. In certain embodiments of these methods, the activity is inhibited and in other embodiments, the activity is enhanced. The methods include contacting a folate hydrolase polypeptide with an amount of the foregoing isolated antibody or antigen-binding fragment thereof, under conditions wherein the isolated antibody or antigen-binding fragment thereof modulates the folate hydrolase activity. The folate hydrolase polypeptide can be isolated, contained in a sample such as a cell, a cell homogenate, a tissue, or a tissue homogenate, or contained in an organism. The organism preferably is an animal, particularly preferably a mammal.

In another aspect of the invention, methods for modulating N-acetylated $\alpha$-linked acidic dipeptidase (NAALADase) activity are provided. In certain embodiments of these methods, the activity is inhibited and in other embodiments, the activity is enhanced. The methods include contacting a NAALADase polypeptide with an amount of the foregoing isolated antibody or antigen-binding fragment thereof under conditions wherein the isolated antibody or antigen-binding fragment thereof modulates NAALADase activity. The NAALADase polypeptide can be isolated, contained in a sample such as a cell, a cell homogenate, a tissue, or a tissue homogenate, or contained in an organism. The organism preferably is an animal, particularly preferably a mammal.

In yet another aspect of the invention, methods for modulating dipeptidyl dipeptidase IV activity are provided. In certain embodiments of these methods, the activity is inhibited and in other embodiments, the activity is enhanced. The methods include contacting a dipeptidyl dipeptidase IV polypeptide with an amount of the foregoing isolated antibody or antigen-binding fragment thereof under conditions wherein the isolated antibody or antigen-binding fragment thereof modulates dipeptidyl dipeptidase IV activity. The dipeptidyl dipeptidase IV polypeptide can be isolated, contained in a sample such as a cell, a cell homogenate, a tissue, or a tissue homogenate, or contained in an organism. The organism preferably is an animal, particularly preferably a mammal.

In yet another aspect of the invention, methods for modulating γ-glutamyl hydrolase activity are provided. In certain embodiments of these methods, the activity is inhibited and in other embodiments, the activity is enhanced. The methods include contacting a γ-glutamyl hydrolase polypeptide with an amount of the foregoing isolated antibody or antigen-binding fragment thereof under conditions wherein the isolated antibody or antigen-binding fragment thereof modulates γ-glutamyl hydrolase activity. The γ-glutamyl hydrolase polypeptide can be isolated, contained in a sample such as a cell, a cell homogenate, a tissue, or a tissue homogenate, or contained in an organism. The organism preferably is an animal, particularly preferably a mammal.

Methods of specific delivery of at least one therapeutic agent to PSMA-expressing cells are provided according to another aspect of the invention. The methods include administering an effective amount of at least one of the foregoing antibodies or antigen-binding fragments thereof conjugated to the at least one therapeutic agent. In some embodiments, the therapeutic agent is a nucleic acid molecule, an antitumor drug, a toxin or a fragment thereof, an enzyme or a fragment thereof, a replication-selective virus, or an immunostimulatory or immunomodulating agent. Preferred antitumor drugs include cytotoxic drugs, drugs which act on the tumor neovasculature and combinations thereof. Preferred cytotoxic drugs include calicheamicin, esperamicin, methotrexate, doxorubicin, melphalan, chlorambucil, ARA-C, vindesine, mitomycin C, cis-platinum, etoposide, bleomycin, 5-fluorouracil, estramustine, vincristine, etoposide, doxorubicin, paclitaxel, docetaxel, dolastatin 10, auristatin E and auristatin PHE. Preferred immunostimulatory or immunomodulating agent included cytokines, chemokines and adjuvants.

In still another aspect of the invention, isolated antibodies that selectively bind a PSMA protein multimer are provided. In preferred embodiments, the PSMA protein multimer is a dimer, and preferably at least one of the PSMA proteins forming the multimer is a recombinant, soluble PSMA (rsPSMA) polypeptide. Preferably the rsPSMA polypeptide consists essentially of amino acids 44-750 of SEQ ID NO: 1.

In a further aspect of the invention, isolated antibodies are provided that selectively bind a PSMA protein multimer and modulate one or more enzymatic activities of the PSMA protein multimer. As used in preferred embodiments of this aspect of the invention, "modulating" an enzymatic activity of a PSMA multimer means enhancing or inhibiting the enzymatic activity. Thus in certain aspects of the invention, antibodies that inhibit an enzymatic activity of PSMA multimers are provided, and in other aspects of the invention, antibodies that inhibit an enzymatic activity of PSMA multimers are provided. The terms "enhancing" and "inhibiting" in this context indicate that the enzymatic activity of a PSMA multimer is enhanced or inhibited in the presence of an antibody that specifically binds the PSMA multimers, or antigen-binding fragment thereof, relative to the level of activity in the absence of such an antibody or antigen-binding fragment thereof. In some embodiments, the enzymatic activity is selected from the group consisting of folate hydrolase activity, NAALADase activity, dipeptidyl dipeptidase IV activity and γ-glutamyl hydrolase activity. In other embodiments, the enzymatic activity is in the extracellular domain of the PSMA molecule. In still other embodiments, the antibody or antigen-binding fragment thereof specifically binds to an extracellular domain of PSMA.

In a further aspect, an isolated antibody or antigen-binding fragment thereof is provided that selectively binds a PSMA protein multimer. In this aspect, the isolated antibody is raised by immunizing an animal with a preparation comprising a PSMA protein multimer. Preferred preparations used in raising the antibody include those having at least about 10%, 20%, 30%, 40%, 50%, 75%, 90%, or 95% PSMA protein multimer. Preferably the PSMA protein multimer is a dimer.

In yet another aspect of the invention, compositions are provided that include one or more of the foregoing isolated antibodies, and an immunostimulatory molecule, such as an adjuvant and/or and a cytokine. Preferably the immunostimulatory molecule is IL-2 or an immunostimulatory oligonucleotide. In certain embodiments, the foregoing compositions also include a pharmaceutically-acceptable carrier.

The invention also includes methods for inducing an immune response, including administering to a subject in need of such treatment an effective amount of the foregoing isolated antibodies or compositions.

The invention provides, in another aspect, isolated antibodies or antigen-binding fragments thereof that selectively bind a PSMA protein multimer and modulate at least one enzymatic activity of PSMA. As used in preferred embodiments of this aspect of the invention, "modulating" an enzymatic activity of a PSMA means enhancing or inhibiting the enzymatic activity. Thus in certain aspects of the invention, antibodies that inhibit an enzymatic activity of PSMA are provided, and in other aspects of the invention, antibodies that inhibit an enzymatic activity of PSMA are provided. The terms "enhancing' and "inhibiting" in this context indicate that the enzymatic activity of PSMA is enhanced or inhibited in the presence of an antibody that specifically binds PSMA, or antigen-binding fragment thereof, relative to the level of activity in the absence of such an antibody or antigen-binding fragment thereof. The enzyme, in certain embodiments, is selected from the group consisting of hydrolases and peptidases. Preferred hydrolases include folate hydrolase and γ-glutamyl hydrolase. In a particularly preferred embodiment of PSMA inhibition, the hydrolase is folate hydrolase and the antibody is mAb 5.4 or mAb 3.9. Preferred peptidases include NAALADase and dipeptidyl dipeptidase IV. In some embodiments, the enzyme is active in cancer cells and has lesser activity in normal cells than in cancer cells or, preferably, no activity in normal cells. In preferred embodiments, the cancer cells in which the enzyme is active are prostate cancer cells. Compositions including the foregoing isolated antibodies or antigen-binding fragments thereof, and a pharmaceutically acceptable carrier, also are provided by the invention.

In another aspect of the invention, compositions are provided that include an isolated PSMA protein multimer. Preferably the PSMA protein multimer is a dimer. In certain embodiments, the compositions include at least about 10%, 20%, 30%, 40%, 50%, 75%, 90%, or 95% PSMA protein multimer. In other embodiments, the PSMA protein multimer comprises noncovalently associated PSMA proteins. The PSMA proteins preferably are noncovalently associated under nondenaturing conditions.

In certain embodiments of the foregoing compositions, at least one of the PSMA proteins forming the multimer is a recombinant, soluble PSMA (rsPSMA) polypeptide. In other embodiments, the PSMA protein multimer is reactive with a conformation-specific antibody that specifically recognizes PSMA. Preferably, the PSMA protein multimer comprises PSMA proteins in a native conformation and/or the PSMA multimer is enzymatically active. In preferred embodiments, the enzymatic activity is folate hydrolase activity, NAALADase activity, dipeptidyl dipeptidase IV activity and/or γ-glutamyl hydrolase activity.

In still other embodiments, the foregoing compositions also include an adjuvant and/or a cytokine or other immunostimulatory molecule. Preferred cytokines include IL-2, IL-12, IL-18 and GM-CSF. In further embodiments, the foregoing compositions also include a pharmaceutically acceptable carrier.

According to yet another aspect of the invention, methods for inducing an immune response are provided. The methods include administering to a subject in need of such treatment an effective amount of one or more of the foregoing compositions.

In a further aspect, the invention includes isolated recombinant soluble PSMA (rsPSMA) protein multimers, and isolated rsPSMA protein dimers. In some embodiments, the dimer includes noncovalently associated rsPSMA proteins, and preferably the rsPSMA proteins are noncovalently associated under nondenaturing conditions. In other embodiments, the isolated rsPSMA dimer is reactive with a conformation-specific antibody that specifically recognizes PSMA.

In a certain preferred embodiment, the isolated rsPSMA dimer is enzymatically active, with the enzymatic activity selected from the group consisting of folate hydrolase activity, NAALADase activity, dipeptidyl dipeptidase IV activity and γ-glutamyl hydrolase activity.

In still another aspect of the invention, methods of screening for a candidate agent that modulates at least one enzymatic activity of a PSMA enzyme are provided. As used in preferred embodiments of the methods, "modulating" an enzymatic activity of PSMA means enhancing or inhibiting the enzymatic activity. Thus in certain aspects of the invention, methods for screening for a candidate agent that inhibits an enzymatic activity of PSMA are provided, and in other aspects of the invention, methods for screening for a candidate agent that enhances an enzymatic activity of PSMA are provided. The terms "enhancing" and "inhibiting" in this context indicate that the enzymatic activity of PSMA is enhanced or inhibited in the presence of a candidate agent relative to the level of activity in the absence of such an agent. The methods include mixing the candidate agent with an isolated PSMA protein multimer to form a reaction mixture, followed by adding a substrate for the PSMA enzyme to the reaction mixture, and determining the amount of a product formed from the substrate by the PSMA enzyme. A change in the amount of product formed in comparison to a control is indicative of an agent capable of modulating at least one enzymatic activity of the PSMA enzyme. A decrease in the amount of product formed in comparison to a control is indicative of an agent capable of inhibiting at least one enzymatic activity of the PSMA enzyme. An increase in the amount of product formed in comparison to a control is indicative of an agent capable of enhancing at least one enzymatic activity of the PSMA enzyme. In some embodiments the PSMA enzyme is selected from the group consisting of NAALADase, folate hydrolase, dipeptidyl dipeptidase IV and γ-glutamyl hydrolase. In other embodiments the PSMA multimer comprises recombinant, soluble PSMA. In yet other embodiments the candidate agent is selected from the group consisting of an antibody, a small organic compound, or a peptide.

In another aspect of the invention, candidate agents that modulate at least one enzymatic activity of PSMA are provided. The candidate agents are identified according to the foregoing methods. Thus in certain aspects of the invention, candidate agents that inhibit an enzymatic activity of PSMA are provided, and in other aspects of the invention, candidate agents that enhance an enzymatic activity of PSMA are provided. In certain embodiments, the agent is selected from a combinatorial antibody library, a combinatorial protein library, or a small organic molecule library.

The invention also provides methods for identifying compounds that promote dissociation of PSMA dimers. The methods include contacting a PSMA dimer with a compound under conditions that do not promote dissociation of the PSMA dimer in the absence of the compound, measuring the amount of PSMA monomer and/or dimer; and comparing the amount of PSMA monomer and/or dimer measured in the presence of the compound with that observed in the absence of the compound. An increase in the amount of PSMA monomer measured in the presence of the compound indicates that the compound is capable of promoting dissociation of the PSMA dimer. A decrease in the amount of PSMA dimer measured in the presence of the compound indicates that the compound is capable of promoting dissociation of the PSMA dimer. When the amounts of PSMA monomer and PSMA dimer are measured, the methods can include calculating a ratio of PSMA monomer to PSMA dimer and comparing the ratio obtained in the presence of the compound with that obtained in the absence of the compound. In such methods, an increase in the ratio measured in the presence of the compound indicates that the compound is capable of promoting dissociation of the PSMA dimer.

The use of the foregoing compositions, molecules and agents in the preparation of medicaments also is provided. In preferred embodiments, the medicaments are useful in the treatment of conditions related to hyperproliferative diseases including cancer, and diseases of inappropriate NAALADase activity, folate hydrolase activity, dipeptidyl dipeptidase IV activity and/or γ-glutamyl hydrolase activity.

These and other aspects of the invention will be described in further detail in connection with the detailed description of the invention.

BRIEF DESCRIPTION OF THE DRAWINGS

FIG. 12 depicts the cloning protocol for IgG1 antibody cloning into pcDNA. The first four primers shown are set forth as SEQ ID NOs: 34-37, respectively, and the first two amino acid sequences shown are set forth as SEQ ID NOs: 38 and 39, respectively.

FIG. 27 illustrates the binding of the anti-PSMA Abs.

FIG. 28 illustrates the immunotoxin cytotoxicity of murine anti-PSMA antibodies on C4-2 prostate cancer cells. SJ25C-1 as a control antibody is a murine anti-CD19 IgG. The LD 50s (M) for 5.4, 3.9, and mJ591 antibodies were $2.27 \times 10^{-11}$, $2.29 \times 10^{-11}$ and $8.82 \times 10^{-11}$, respectively.

FIG. 29 illustrates the immunotoxin cytotoxicity of murine anti-PSMA antibodies on PSMA-3T3 cells. SJ25C-1 as a control antibody is a murine anti-CD19 IgG. The LD 50s (M) for 5.4, 3.9, and mJ591 antibodies were $1.64 \times 10^{-11}$, $1.9 \times 10^{-11}$ and $8.90 \times 10^{-11}$, respectively.

FIG. 38 shows the in vitro cytotoxicity of $^{225}$Ac labeled mAb 026 on human prostate cancer cell lines (C4-2 and LNCaP).

DETAILED DESCRIPTION OF THE INVENTION

Figure 1:
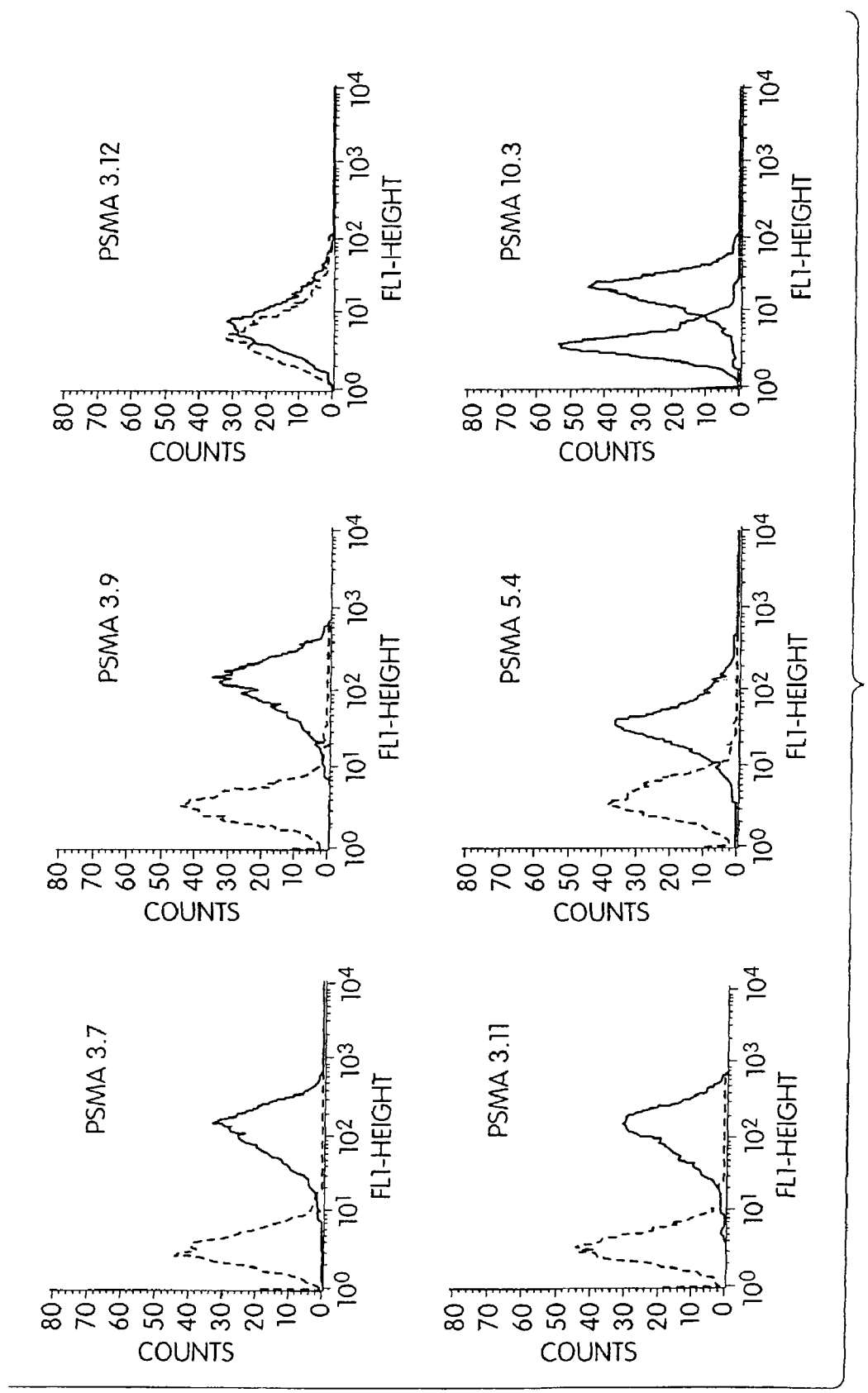
FIG. 1 depicts PSMA reactivity of mAbs as determined by flow cytometry. Anti-PSMA mAbs (3.7, 3.9, 3.11, 3.12, 5.4, and 10.3) incubated with either parental 3T3 cells (denoted by black lines) or 3T3 cells engineered to express cell-surface PSMA (3T3-PSMA; gray lines).

The present invention provides antibodies or antigen-binding fragments thereof which bind specifically to conformational epitopes on the extracellular domain of PSMA, compositions containing one or a combination of such antibodies or antigen-binding fragments thereof, hybridoma cell lines that produce the antibodies, and methods of using the antibodies or antigen-binding fragments thereof for cancer diagnosis and treatment.

Prostate specific membrane antigen (PSMA) is a 100 kD Type II membrane glycoprotein expressed in prostate tissues and was originally identified by reactivity with a monoclonal antibody designated 7E11-C5 (Horoszewicz et al., 1987, *Anticancer Res.* 7:927-935; U.S. Pat. No. 5,162,504). PSMA was obtained in purified form (Wright et al., 1990, Antibody Immunoconjugates and Radio Pharmaceuticals 3:Abstract 193) and characterized as a type II transmembrane protein having sequence identity with the transferrin receptor (Israeli et al., 1994, *Cancer Res.* 54:1807-1811) and with NAALA-Dase activity (Carter et al., 1996, *Proc. Natl. Acad. Sci. U.S.A.* 93:749-753). More importantly, PSMA is expressed in increased amounts in prostate cancer, and elevated levels of PSMA are also detectable in the sera of these patients (Horoszewicz et al., 1987; Rochon et al., 1994, *Prostate* 25:219-223; Murphy et al., 1995, *Prostate* 26:164-168; and Murphy et al., 1995, *Anticancer Res.* 15:1473-1479). PSMA expression increases with disease progression, becoming highest in metastatic, hormone-refractory disease for which there is no present therapy. Provocative recent data indicates that PSMA is also abundantly expressed on the neovasculature of a variety of other important tumors, including bladder, pancreas, sarcoma, melanoma, lung, and kidney tumor cells, but not on normal vasculature.

One aspect of the invention provides an isolated antibody or an antigen-binding fragment thereof which specifically binds to an extracellular domain of PSMA wherein the antibody or the antigen-binding fragment thereof competitively inhibits the specific binding of a second antibody to its target epitope on PSMA, and wherein the second antibody is selected from the group consisting of PSMA 3.7, PSMA 3.8, PSMA 3.9, PSMA 3.11, PSMA 5.4, PSMA 7.1, PSMA 7.3, PSMA 10.3, PSMA 1.8.3, PSMA A3.1.3, PSMA A3.3.1, 4.248.2, 4.360.3, 4.7.1, 4.4.1, 4.177.3, 4.16.1, 4.22.3, 4.28.3, 4.40.2, 4.48.3, 4.49.1, 4.209.3, 4.219.3, 4.288.1, 4.333.1, 4.54.1, 4.153.1, 4.232.3, 4.292.3, 4.304.1, 4.78.1, and 4.152.1.

Another aspect of the invention provides an isolated antibody or an antigen-binding fragment thereof that specifically binds to an epitope on PSMA defined by an antibody selected from the group consisting of PSMA 3.7, PSMA 3.8, PSMA 3.9, PSMA 3.11, PSMA 5.4, PSMA 7.1, PSMA 7.3, PSMA 10.3, PSMA 1.8.3, PSMA A3.1.3, PSMA A3.3.1, 4.248.2, 4.360.3, 4.7.1, 4.4.1, 4.177.3, 4.16.1, 4.22.3, 4.28.3, 4.40.2, 4.48.3, 4.49.1, 4.209.3, 4.219.3, 4.288.1, 4.333.1, 4.54.1, 4.153.1, 4.232.3, 4.292.3, 4.304.1, 4.78.1, and 4.152.1.

In particular embodiments, these antibodies are produced by hybridomas referred to herein as PSMA 3.7, PSMA 3.8, PSMA 3.9, PSMA 3.11, PSMA 5.4, PSMA 7.1, PSMA 7.3, PSMA 10.3, PSMA 1.8.3, PSMA A3.1.3, PSMA A3.3.1, Abgenix 4.248.2, Abgenix 4.360.3, Abgenix 4.7.1, Abgenix 4.4.1, Abgenix 4.177.3, Abgenix 4.16.1, Abgenix 4.22.3, Abgenix 4.28.3, Abgenix 4.40.2, Abgenix 4.48.3, Abgenix 4.49.1, Abgenix 4.209.3, Abgenix 4.219.3, Abgenix 4.288.1, Abgenix 4.333.1, Abgenix 4.54.1, Abgenix 4.153.1, Abgenix 4.232.3, Abgenix 4.292.3, Abgenix 4.304.1, Abgenix 4.78.1, and Abgenix 4.152.1, respectively. These hybridomas were deposited with ATCC as an International Depository Authority and given the following Patent Deposit Designations (Table 1):

TABLE 1

| Antibody | Hybridoma/Plasmid | Patent Deposit Designation | Date of Deposit |
| --- | --- | --- | --- |
| PSMA 3.7 | PSMA 3.7 | PTA-3257 | Apr. 5, 2001 |
| PSMA 3.9 | PSMA 3.9 | PTA-3258 | Apr. 5, 2001 |
| PSMA 3.11 | PSMA 3.11 | PTA-3269 | Apr. 10, 2001 |
| PSMA 5.4 | PSMA 5.4 | PTA-3268 | Apr. 10, 2001 |
| PSMA 7.1 | PSMA 7.1 | PTA-3292 | Apr. 18, 2001 |
| PSMA 7.3 | PSMA 7.3 | PTA-3293 | Apr. 18, 2001 |
| PSMA 10.3 | PSMA 10.3 | PTA-3347 | May 1, 2001 |
|  | PSMA 10.3 HC in pcDNA (SEQ ID NO: 7) | PTA-4413 | May 29, 2002 |
|  | PSMA 10.3 Kappa in pcDNA (SEQ ID NO: 13) | PTA-4414 | May 29, 2002 |
| PSMA 1.8.3 | PSMA 1.8.3 | PTA-3906 | Dec. 5, 2001 |
| PSMA A3.1.3 | PSMA A3.1.3 | PTA-3904 | Dec. 5, 2001 |
| PSMA A3.3.1 | PSMA A3.3.1 | PTA-3905 | Dec. 5, 2001 |
| Abgenix 4.248.2 | Abgenix 4.248.2 | PTA-4427 | Jun. 4, 2002 |
| Abgenix 4.360.3 | Abgenix 4.360.3 | PTA-4428 | Jun. 4, 2002 |
| Abgenix 4.7.1 | Abgenix 4.7.1 | PTA-4429 | Jun. 4, 2002 |
| Abgenix 4.4.1 | Abgenix 4.4.1 | PTA-4556 | Jul. 18, 2002 |
| Abgenix 4.177.3 | Abgenix 4.177.3 | PTA-4557 | Jul. 18, 2002 |
| Abgenix 4.16.1 | Abgenix 4.16.1 | PTA-4357 | May 16, 2002 |
| Abgenix 4.22.3 | Abgenix 4.22.3 | PTA-4358 | May 16, 2002 |
| Abgenix 4.28.3 | Abgenix 4.28.3 | PTA-4359 | May 16, 2002 |
| Abgenix 4.40.2 | Abgenix 4.40.2 | PTA-4360 | May 16, 2002 |
| Abgenix 4.48.3 | Abgenix 4.48.3 | PTA-4361 | May 16, 2002 |
| Abgenix 4.49.1 | Abgenix 4.49.1 | PTA-4362 | May 16, 2002 |
| Abgenix 4.209.3 | Abgenix 4.209.3 | PTA-4365 | May 16, 2002 |
| Abgenix 4.219.3 | Abgenix 4.219.3 | PTA-4366 | May 16, 2002 |
| Abgenix 4.288.1 | Abgenix 4.288.1 | PTA-4367 | May 16, 2002 |
| Abgenix 4.333.1 | Abgenix 4.333.1 | PTA-4368 | May 16, 2002 |
| Abgenix 4.54.1 | Abgenix 4.54.1 | PTA-4363 | May 16, 2002 |

TABLE 1-continued

| Antibody | Hybridoma/Plasmid | Patent Deposit Designation | Date of Deposit |
|---|---|---|---|
| Abgenix 4.153.1 | Abgenix 4.153.1 | PTA-4388 | May 23, 2002 |
| Abgenix 4.232.3 | Abgenix 4.232.3 | PTA-4389 | May 23, 2002 |
| Abgenix 4.292.3 | Abgenix 4.292.3 | PTA-4390 | May 23, 2002 |
| Abgenix 4.304.1 | Abgenix 4.304.1 | PTA-4391 | May 23, 2002 |
| AB-PG1-XG1-006 | AB-PG1-XG1-006 Heavy Chain (SEQ ID NO: 2) | PTA-4403 | May 29, 2002 |
| | AB-PG1-XG1-006 Light Chain (SEQ ID NO: 8) | PTA-4404 | |
| AB-PG1-XG1-026 | AB-PG1-XG1-026 Heavy Chain (SEQ ID NO: 3) | PTA-4405 | May 29, 2002 |
| | AB-PG1-XG1-026 Light Chain (SEQ ID NO: 9) | PTA-4406 | |
| AB-PGI-XG1-051 | AB-PG1-XG1-051 Heavy Chain (SEQ ID NO: 4) | PTA-4407 | May 29, 2002 |
| | AB-PG1-XG1-051 Light Chain (SEQ ID NO: 10) | PTA-4408 | |
| AB-PG1-XG1-069 | AB-PG1-XG1-069 Heavy Chain (SEQ ID NO: 5) | PTA-4409 | May 29, 2002 |
| | AB-PG1-XG1-069 Light Chain (SEQ ID NO: 11) | PTA-4410 | |
| AB-PG1-XG1-077 | AB-PG1-XG1-077 Heavy Chain (SEQ ID NO: 6) | PTA-4411 | May 29, 2002 |
| | AB-PG1-XG1-077 Light Chain (SEQ ID NO: 12) | PTA-4412 | |

In another aspect of the invention, antibodies having particular sequences are provided. Specifically, the antibodies are selected from the group consisting of antibodies comprising: a heavy chain encoded by a nucleic acid molecule comprising the heavy chain coding region or regions of a nucleotide sequence selected from the group consisting of nucleotide sequences set forth as SEQ ID NOs: 2-7, and a light chain encoded by a nucleic acid molecule comprising the light chain coding region or regions of a nucleotide sequence selected from the group consisting of nucleotide sequences set forth as SEQ ID NOs: 8-13. Also provided are antigen-binding fragments of the foregoing antibodies.

The plasmids encoding the heavy and light chains of antibodies PSMA 10.3, AB-PG1-XG1-006, AB-PG1-XG1-026, AB-PG1-XG1-051, AB-PG1-XG1-069, AB-PG1-XG1-077 were also deposited with ATCC and are shown in Table 1 above. As used herein, the names of the deposited hybridomas or plasmids may be used interchangeably with the names of the antibodies. It would be clear to one of skill in the art when the name is intended to refer to the antibody or when it refers to the plasmids or hybridomas that encode or produce the antibodies, respectively. Additionally, the antibody names may be an abbreviated form of the name shown in Table 1. For instance antibody AB-PG1-XG1-006 may be referred to as AB-PG1-XG1-006, PG1-XG1-006, XG1-006, 006, etc. In another example, the antibody name PSMA 4.232.3 may be referred to as PSMA 4.232.1, 4.232.3, 4.232.1, 4.232, etc. It is intended that all of the variations in the name of the antibody refer to the same antibody and not a different one.

Antibodies are also provided that are encoded by particular sets of heavy and light chain sequences. In one embodiment an antibody (AB-PG1-XG1-006) encoded by a nucleic acid molecule which comprises the coding region or regions of the nucleic acid sequences set forth as :SEQ ID NOs: 2 and 8 is provided. In another embodiment the antibody (AB-PG1-XG1-026) is encoded by the nucleic acid molecules comprising the coding region or regions of nucleotide sequences set forth as: SEQ ID NOs: 3 and 9. In still another embodiment the antibody (AB-PG1-XG1-051) is encoded by the nucleic acid molecules comprising the coding region or regions of nucleotide sequences set forth as: SEQ ID NOs: 4 and 10. In yet another embodiment the antibody (AB-PG1-XG1-069) is encoded by the nucleic acid molecules comprising the coding region or regions of nucleotide sequences set forth as: SEQ ID NOs: 5 and 11. In another embodiment the antibody (AB-PG1-XG1-077) is encoded by the nucleic acid molecules comprising the coding region or regions of nucleotide sequences set forth as: SEQ ID NOs: 6 and 12. In yet another embodiment the antibody (PSMA 10.3) is encoded by the nucleic acid molecules comprising the coding region or regions of nucleotide sequences set forth as: SEQ ID NOs: 7 and 13.

In particularly preferred embodiments, the antibodies include a heavy chain variable region encoded by a nucleic acid molecule comprising the coding regions or regions of a nucleotide sequence selected from the group consisting of nucleotide sequences set forth as: SEQ ID NOs: 14, 18, 22, 26 and 30, and a light chain variable region encoded by a nucleic acid molecule comprising the coding region or region of a nucleotide sequence selected from the group consisting of nucleotide sequences set forth as: SEQ ID NOs: 16, 20, 24, 28 and 32. As used herein, a "coding region" refers to a region of a nucleotide sequence that encodes a polypeptide sequence; the coding region can include a region coding for a portion of a protein that is later cleaved off, such as a signal peptide.

Those of skill in the art will appreciate that the invention includes nucleic acids and polypeptides that include nucleotide and amino acid sequences presented herein. In some instances, the nucleotide and amino acid sequences may include sequences that encode or that are signal peptides. The invention embraces each of these sequences with, or without, the portion of the sequence that encodes or is a signal peptide.

Antibodies also are provided that include particular sets of heavy and light chain variable sequences. In one embodiment an antibody (AB-PG1-XG1-006) includes an immunoglobulin variable sequence encoded by nucleic acid molecules which included the coding region or regions of the nucleic acid sequences set forth as :SEQ ID NOs: 14 and 16 is provided. Likewise the antibody may include an immunoglobulin variable sequence which comprises the amino acid sequences set forth as SEQ ID NOs: 15 and 17. In another embodiment the antibody (AB-PG1-XG1-026) includes an immunoglobulin variable sequence encoded by nucleic acid molecules comprising the coding region or regions of nucleotide sequences set forth as: SEQ ID NOs: 18 and 20 or includes an immunoglobulin variable sequence which comprises the amino acid sequences set forth as SEQ ID NOs: 19 and 21. In still another embodiment the antibody (AB-PG1-XG1-051) includes an immunoglobulin variable sequence encoded by the nucleic acid molecules comprising the coding region or regions of nucleotide sequences set forth as: SEQ ID NOs: 22 and 24 or includes an immunoglobulin variable sequence which comprises the amino acid sequences set forth as SEQ ID NOs: 23 and 25. In yet another embodiment the antibody (AB-PG1-XG1-069) includes an immunoglobulin variable sequence encoded by the nucleic acid molecules comprising the coding region or regions of nucleotide sequences set forth as: SEQ ID NOs: 26 and 28 or includes an immunoglobulin variable sequence which comprises the amino acid sequences set forth as SEQ ID NOs: 27 and 29. In another embodiment the antibody (AB-PG1-XG1-077) includes an immunoglobulin variable sequence encoded by the nucleic acid molecules comprising the coding region or regions of nucleotide sequences set forth as: SEQ ID NOs: 30 and 32 or includes an immunoglobulin variable sequence which comprises the amino acid sequences set forth as SEQ ID NOs: 31 and 33.

In certain embodiments, the antibody is encoded by a nucleic acid molecule that is highly homologous to the foregoing nucleic acid molecules. Preferably the homologous nucleic acid molecule comprises a nucleotide sequence that is at least about 90% identical to the nucleotide sequence provided herein. More preferably, the nucleotide sequence is at least about 95% identical, at least about 97% identical, at least about 98% identical, or at least about 99% identical to the nucleotide sequence provided herein. The homology can be calculated using various, publicly available software tools well known to one of ordinary skill in the art. Exemplary tools include the BLAST system available from the website of the National Center for Biotechnology Information (NCBI) at the National Institutes of Health.

One method of identifying highly homologous nucleotide sequences is via nucleic acid hybridization. Thus the invention also includes antibodies having the PSMA-binding properties and other functional properties described herein, which are encoded by nucleic acid molecules that hybridize under high stringency conditions to the foregoing nucleic acid molecules. Identification of related sequences can also be achieved using polymerase chain reaction (PCR) and other amplification techniques suitable for cloning related nucleic acid sequences. Preferably, PCR primers are selected to amplify portions of a nucleic acid sequence of interest, such as a CDR.

The term "high stringency conditions" as used herein refers to parameters with which the art is familiar. Nucleic acid hybridization parameters may be found in references that compile such methods, e.g. *Molecular Cloning: A Laboratory Manual*, J. Sambrook, et al., eds., Second Edition, Cold Spring Harbor Laboratory Press, Cold Spring Harbor, N.Y. 1989, or *Current Protocols in Molecular Biology*, F. M. Ausubel, et al., eds., John Wiley &. Sons, Inc., New York. One example of high-stringency conditions is hybridization at 65° C. in hybridization buffer (3.5X SSC, 0.02% FICOLL, 0.02% polyvinyl pyrrolidone, 0.02% Bovine Serum Albumin, 2.5 mM $NaH_2PO_4$(pH7), 0.5% SDS, 2 mM EDTA). SSC is 0.15 M sodium chloride/0.015 M sodium citrate, pH7; SDS is sodium dodecyl sulphate; and EDTA is ethylenediaminetetracetic acid. After hybridization, a membrane upon which the nucleic acid is transferred is washed, for example, in 2X SSC at room temperature and then at 0.1-0.5X SSC/0.1X SDS at temperatures up to 68° C.

In other preferred embodiments, the antibodies include a heavy chain variable region comprising an amino acid sequence selected from the group consisting of amino acid sequences set forth as: SEQ ID NOs: 15, 19, 23, 27 and 31, and a light chain variable region comprising an amino acid sequence selected from the group consisting of nucleotide sequences set forth as: SEQ ID NOs: 17, 21, 25, 29 and 33.

Antigen-binding fragments of the foregoing also are provided, as described elsewhere herein.

As used herein, the term "antibody" refers to a glycoprotein comprising at least two heavy (H) chains and two light (L) chains inter-connected by disulfide bonds. Each heavy chain is comprised of a heavy chain variable region (abbreviated herein as HCVR or $V_H$) and a heavy chain constant region. The heavy chain constant region is comprised of three domains, $C_H1$, $C_H2$ and $C_H3$. Each light chain is comprised of a light chain variable region (abbreviated herein as LCVR or $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding fragment" of an antibody as used herein, refers to one or more portions of an antibody that retain the ability to specifically bind to an antigen (e.g., PSMA). It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) *Nature* 341:544-546) which consists of a $V_H$ domain; and (vi) an isolated complementarity determining region (CDR). Furthermore, although the two domains of the Fv fragment, V and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional procedures, such as proteolytic fragmentation procedures, as described in J. Goding, Monoclonal Antibodies: Principles and Practice, pp 98-118 (N.Y. Academic Press 1983), which is hereby incorporated by reference as well as by other techniques known to those with skill in the art. The fragments are screened for utility in the same manner as are intact antibodies.

An "isolated antibody", as used herein, is intended to refer to an antibody which is substantially free of other antibodies having different antigenic specificities (e.g., an isolated antibody that specifically binds to PSMA is substantially free of antibodies that specifically bind antigens other than PSMA). An isolated antibody that specifically binds to an epitope, isoform or variant of PSMA may, however, have cross-reactivity to other related antigens, e.g., from other species (e.g., PSMA species homologs). Moreover, an isolated antibody may be substantially free of other cellular material and/or chemicals. As used herein, "specific binding" refers to antibody binding to a predetermined antigen. Typically, the antibody binds with an affinity that is at least two-fold greater than its affinity for binding to a non-specific antigen (e.g., BSA, casein) other than the predetermined antigen or a closely-related antigen.

The isolated antibodies of the invention encompass various antibody isotypes, such as IgG1, IgG2, IgG3, IgG4, IgM, IgA1, IgA2, IgAsec, IgD, IgE. As used herein, "isotype" refers to the antibody class (e.g. IgM or IgG1) that is encoded by heavy chain constant region genes. The antibodies can be full length or can include only an antigen-binding fragment such as the antibody constant and/or variable domain of IgG1, IgG2, IgG3, IgG4, IgM, IgA1, IgA2, IgAsec, IgD or IgE or could consist of a Fab fragment, a F(ab')$_2$ fragment, and a Fv fragment.

The antibodies of the present invention can be polyclonal, monoclonal, or a mixture of polyclonal and monoclonal antibodies. The antibodies can be produced by a variety of techniques well known in the art. Procedures for raising polyclonal antibodies are well known. For example anti-PSMA polyclonal antibodies are raised by administering PSMA protein subcutaneously to New Zealand white rabbits which have first been bled to obtain pre-immune serum. The PSMA can be injected at a total volume of 100 µl per site at six different sites, typically with one or more adjustments. The rabbits are then bled two weeks after the first injection and periodically boosted with the same antigen three times every six weeks. A sample of serum is collected 10 days after each boost. Polyclonal antibodies are recovered from the serum, preferably by affinity chromatography using PSMA to capture the antibody. This and other procedures for raising polyclonal antibodies are disclosed in E. Harlow, et. al., editors, Antibodies: A Laboratory Manual (1988), which is hereby incorporated by reference.

Monoclonal antibody production may be effected by techniques which are also well known in the art. The term "monoclonal antibody," as used herein, refers to a preparation of antibody molecules of single molecular composition. A monoclonal antibody displays a single binding specificity and affinity for a particular epitope. The process of monoclonal antibody production involves obtaining immune somatic cells with the potential for producing antibody, in particular B lymphocytes, which have been previously immunized with the antigen of interest either in vivo or in vitro and that are suitable for fusion with a B-cell myeloma line.

Mammalian lymphocytes typically are immunized by in vivo immunization of the animal (e.g., a mouse) with the desired protein or polypeptide, e.g., with PSMA in the present invention. Such immunizations are repeated as necessary at intervals of up to several weeks to obtain a sufficient titer of antibodies. Once immunized, animals can be used as a source of antibody-producing lymphocytes. Following the last antigen boost, the animals are sacrificed and spleen cells removed. Mouse lymphocytes give a higher percentage of stable fusions with the mouse myeloma lines described herein. Of these, the BALB/c mouse is preferred. However, other mouse strains, rabbit, hamster, sheep and frog may also be used as hosts for preparing antibody -producing cells. See; Goding (in Monoclonal Antibodies: Principles and Practice, 2d ed., pp. 60-61, Orlando, Fla., Academic Press, 1986). In particular, mouse strains that have human immunoglobulin genes inserted in the genome (and which cannot produce mouse immunoglobulins) are preferred. Examples include the HUMAB-MOUSE strains produced by Medarex/GenPharm International, and the XENOMOUSE strains produced by Abgenix. Such mice produce fully human immunoglobulin molecules in response to immunization.

Those antibody-producing cells that are in the dividing plasmablast stage fuse preferentially. Somatic cells may be obtained from the lymph nodes, spleens and peripheral blood of antigen-primed animals, and the lymphatic cells of choice depend to a large extent on their empirical usefulness in the particular fusion system. The antibody-secreting lymphocytes are then fused with (mouse) B cell myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, Nature 256:495 (1975), which is hereby incorporated by reference.

Alternatively, human somatic cells capable of producing antibody, specifically B lymphocytes, are suitable for fusion with myeloma cell lines. While B lymphocytes from biopsied spleens, tonsils or lymph nodes of an individual may be used, the more easily accessible peripheral blood B lymphocytes are preferred. The lymphocytes may be derived from patients with diagnosed prostate carcinomas or another PSMA-expressing cancer. In addition, human B cells may be directly immortalized by the Epstein-Barr virus (Cole et al., 1995, Monoclonal Antibodies and Cancer Therapy, Alan R. Liss, Inc., pp. 77-96). Although somatic cell hybridization procedures are preferred, in principle, other techniques for producing monoclonal antibodies can be employed such as viral or oncogenic transformation of B lymphocytes.

Myeloma cell lines suited for use in hybridoma-producing fusion procedures preferably are non-antibody-producing, have high fusion efficiency, and enzyme deficiencies that render them incapable of growing in certain selective media which support the growth of the desired hybridomas. Examples of such myeloma cell lines that may be used for the production of fused cell lines include P3-X63/Ag8, X63-Ag8.653, NS1/1.Ag 4.1, Sp2/0-Ag14, FO, NSO/U, MPC-11, MPC11-X45-GTG 1.7, S194/5XX0 Bul, all derived from mice; R210.RCY3, Y3-Ag 1.2.3, IR983F and 4B210 derived from rats and U-266, GM1500-GRG2, LICR-LON-HMy2, UC729-6, all derived from humans (Goding, in Monoclonal Antibodies: Principles and Practice, 2d ed., pp. 65-66, Orlando, Fla., Academic Press, 1986; Campbell, in Monoclonal Antibody Technology, Laboratory Techniques in Biochemistry and Molecular Biology Vol. 13, Burden and Von Knippenberg, eds. pp. 75-83, Amsterdam, Elseview, 1984).

Fusion with mammalian myeloma cells or other fusion partners capable of replicating indefinitely in cell culture is effected by standard and well-known techniques, for example, by using polyethylene glycol ("PEG") or other fusing agents (See Milstein and Kohler, Eur. J. Immunol. 6:511 (1976), which is hereby incorporated by reference).

In other embodiments, the antibodies can be recombinant antibodies. The term "recombinant antibody", as used herein, is intended to include antibodies that are prepared, expressed, created or isolated by recombinant means, such as antibodies isolated from an animal (e.g., a mouse) that is transgenic for another species' immunoglobulin genes, antibodies expressed using a recombinant expression vector transfected into a host cell, antibodies isolated from a recombinant, combinatorial antibody library, or antibodies prepared, expressed, created or isolated by any other means that involves splicing of immunoglobulin gene sequences to other DNA sequences.

In yet other embodiments, the antibodies can be chimeric or humanized antibodies. As used herein, the term "chimeric antibody" refers to an antibody, that combines the murine variable or hypervariable regions with the human constant region or constant and variable framework regions. As used herein, the term "humanized antibody" refers to an antibody that retains only the antigen-binding CDRs from the parent antibody in association with human framework regions (see, Waldmann, 1991, *Science* 252:1657). Such chimeric or humanized antibodies retaining binding specificity of the murine antibody are expected to have reduced immunogenicity when administered in vivo for diagnostic, prophylactic or therapeutic applications according to the invention.

According to an alternative embodiment, the monoclonal antibodies of the present invention can be modified to be in the form of a bispecific antibody, or a multispecific antibody. The term "bispecific antibody" is intended to include any agent, e.g., a protein, peptide, or protein or peptide complex, which has two different binding specificities which bind to, or interact with (a) a cell surface antigen and (b) an Fc receptor on the surface of an effector cell. The term "multispecific antibody" is intended to include any agent, e.g., a protein, peptide, or protein or peptide complex, which has more than two different binding specificities which bind to, or interact with (a) a cell surface antigen, (b) an Fe receptor on the surface of an effector cell, and (c) at least one other component. Accordingly, the invention includes, but is not limited to, bispecific, trispecific, tetraspecific, and other multispecific antibodies which are directed to cell surface antigens, such as PSMA, and to Fe receptors on effector cells. The term "bispecific antibodies" further includes diabodies. Diabodies are bivalent, bispecific antibodies in which the $V_H$ and $V_L$ domains are expressed on a single polypeptide chain, but using a linker that is too short to allow for pairing between the two domains on the same chain, thereby forcing the domains to pair with complementary domains of another chain and creating two antigen-binding sites (see e.g., Holliger, P., et al. (1993) *Proc. Natl. Acad. Sci. USA* 90:6444-6448; Poijak, R. J., et al. (1994) *Structure* 2:1121-1123).

A bispecific antibody can be formed of an antigen-binding region specific for the extracellular domain of PSMA and an antigen-binding region specific for an effector cell which has tumoricidal or tumor inhibitory activity. The two antigen-binding regions of the bispecific antibody are either chemically linked or can be expressed by a cell genetically engineered to produce the bispecific antibody. (See generally, Fanger et al., 1995 *Drug News & Perspec.* 8(3):133-137). Suitable effector cells having tumoricidal activity include but are not limited to cytotoxic T-cells (primarily CD8$^+$ cells), natural killer cells, etc. An effective amount of a bispecific antibody according to the invention is administered to a prostrate cancer patient and the bispecific antibody kills and/or inhibits proliferation of the malignant cells after localization at sites of primary or metastatic tumors bearing PSMA.

In certain embodiments, the antibodies are human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse have been grafted onto human framework sequences (referred to herein as "humanized antibodies"). Human antibodies directed against PSMA are generated using transgenic mice carrying parts of the human immune system rather than the mouse system.

Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals results in the production of fully human antibodies to the antigen of interest. Following immunization of these mice (e.g., XENOMOUSE (Abgenix), HUMAB mice (Medarex/GenPharm)), monoclonal antibodies are prepared according to standard hybridoma technology. These monoclonal antibodies have human immunoglobulin amino acid sequences and therefore will not provoke human anti-mouse antibody (HAMA) responses when administered to humans.

Preferably, the mice are 6-16 weeks of age upon the first immunization. For example, a purified or enriched preparation of PSMA antigen (e.g., recombinant PSMA or PSMA-expressing cells) is used to immunize the mice intraperitoneally (IP), although other routes of immunization known to one of ordinary skill in the art are also possible. PSMA antigen is injected in combination with an adjuvant, such as complete Freund's adjuvant, and preferably the initial injection is followed by booster immunizations with antigen in an adjuvant, such as incomplete Freund's adjuvant. The immune response is monitored over the course of the immunization protocol with plasma samples obtained by, for example, retroorbital bleeds. The plasma is screened by ELISA (as described below), and mice with sufficient titers of anti-PSMA human immunoglobulin are used for fusions. Mice are boosted intravenously with antigen 3 days before sacrifice and removal of the spleen.

In particular embodiments, the antibodies are produced by hybridomas referred to herein as PSMA 3.7 (PTA-3257), PSMA 3.8, PSMA 3.9 (PTA-3258), PSMA 3.11 (PTA-3269), PSMA 5.4 (PTA-3268), PSMA 7.1 (PTA-3292), PSMA 7.3 (PTA-3293), PSMA 10.3 (PTA-3347), PSMA 1.8.3 (PTA-3906), PSMA A3.1.3 (PTA-3904), PSMA A3.3.1 (PTA-3905), Abgenix 4.248.2 (PTA-4427), Abgenix 4.360.3 (PTA-4428), Abgenix 4.7.1 (PTA-4429), Abgenix 4.4.1 (PTA-4556), Abgenix 4.177.3 (PTA-4557), Abgenix 4.16.1 (PTA-4357), Abgenix 4.22.3 (PTA-4358), Abgenix 4.28.3 (PTA-4359), Abgenix 4.40.2 (PTA-4360), Abgenix 4.48.3 (PTA-4361), Abgenix 4.49.1 (PTA-4362), Abgenix 4.209.3 (PTA-4365), Abgenix 4.219.3 (PTA-4366), Abgenix 4.288.1 (PTA-4367), Abgenix 4.333.1 (PTA-4368), Abgenix 4.54.1 (PTA-4363), Abgenix 4.153.1 (PTA-4388), Abgenix 4.232.3 (PTA-4389), Abgenix 4.292.3 (PTA-4390), Abgenix 4.304.1 (PTA-4391), Abgenix 4.78.1 (PTA-4652), and Abgenix 4.152.1 (PTA-4653). These hybridomas were deposited pursuant to, and in satisfaction of, the requirements of the Budapest Treaty on the International Recognition of the Deposit of Microorganisms for the Purposes of Patent Procedure with the American Type Culture Collection ("ATCC"), having the address 10801 University Boulevard, Manassas, VA 20110-2209, as an International Depository Authority and given the Patent Deposit Designations shown above and in Table 1.

The present invention further provides nucleic acid molecules encoding anti-PSMA antibodies and vectors comprising the nucleic acid molecules as described herein. The vectors provided can be used to transform or transfect host cells for producing anti-PSMA antibodies with the specificity of antibodies described herein. In a preferred embodiment the antibodies produced will have the specificity of the antibodies AB-PG1-XG1-006, AB-PG1-XG1-026, AB-PG1-XG1-051, AB-PG1, XG1-069, AB-PG1-XG1-077 and PSMA 10.3. In one embodiment the vectors can comprise an isolated nucleic acid molecule encoding the heavy chain of the antibodies listed above encoded by a nucleic acid molecules comprising the coding region or regions of the nucleic acid sequences set forth as SEQ ID NO: 2-7. In another embodiment, the vectors can comprise the nucleic acid sequences encoding the light chain of the antibodies set forth as SEQ ID NOs: 8-13. In a further embodiment the vectors of the invention may comprise a heavy chain and a light chain sequence. In a further embodiment, plasmids are given which produce the antibodies or antigen binding fragments described herein. Plasmids of the invention include plasmids selected from the group consisting of: AB-PG1-XG1-006 Heavy Chain (SEQ ID NO: 2), AB-PG1-XG1-006 Light Chain (SEQ ID NO: 8), AB-PG1-XG1-026 Heavy Chain (SEQ ID NO: 3), AB-PG1-XG1-026 Light Chain (SEQ ID NO: 9), AB-PG1-XG1-051 Heavy Chain (SEQ ID NO: 4), AB-PG1-XG1-051 Light Chain (SEQ ID NO: 10), AB-PG1-XG1-069 Heavy Chain (SEQ ID NO: 5), AB-PG1-XG1-069 Light Chain (SEQ ID NO: 11), AB-PG1-XG1-077 Heavy Chain (SEQ ID NO: 6), AB-PG1-XG1-077 Light Chain (SEQ ID NO: 12), PSMA 10.3 Heavy Chain (SEQ ID NO: 7), and PSMA 10.3 Kappa (SEQ ID NO: 13).

The isolated antibody or antigen-binding fragment thereof preferably is selected for its ability to bind live cells expressing PSMA. In order to demonstrate binding of monoclonal antibodies to live cells expressing the PSMA, flow cytometry can be used. For example, cell lines expressing PSMA (grown under standard growth conditions) or prostate cancer cells that express PSMA are mixed with various concentrations of monoclonal antibodies in PBS containing 0.1% TWEEN 80 and 20% mouse serum, and incubated at 37° C. for 1 hour. After washing, the cells are reacted with fluorescein-labeled anti-human IgG secondary antibody (if human anti-PSMA antibodies were used) under the same conditions as the primary antibody staining. The samples can be analyzed by a fluorescence activated cell sorter (FACS) instrument using light and side scatter properties to gate on single cells. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Binding of the antibody or antigen-binding fragment thereof to live cells expressing PSMA can inhibit the growth of the cells or mediate cytolysis of the cells. Cytolysis can be complement mediated or can be mediated by effector cells. In a preferred embodiment, the cytolysis is carried out in a living organism, preferably a mammal, and the live cell is a tumor cell. Examples of tumors which can be targeted by the antibodies of the invention include, any tumor that expresses PSMA, such as, prostate, bladder, pancreas, lung, colon, kidney, melanomas and sarcomas. In a preferred embodiment the tumor cell is a prostate cancer cell.

The testing of antibody cytolytic activity in vitro by chromium release assay can provide an initial screening prior to testing in vivo models. This testing can be carried out using standard chromium release assays. Briefly, polymorphonuclear cells (PMN), or other effector cells, from healthy donors can be purified by FICOLL Hypaque density centrifugation, followed by lysis of contaminating erythrocytes. Washed PMNs can be suspended in RPMI supplemented with 10% heat-inactivated fetal calf serum and mixed with $^{51}$Cr labeled cells expressing PSMA, at various ratios of effector cells to tumor cells (effector cells:tumor cells). Purified anti-PSMA IgGs can then be added at various concentrations. Irrelevant IgG can be used as negative control. Assays can be carried out for 0-120 minutes at 37° C. Samples can be assayed for cytolysis by measuring $^{51}$Cr release into the culture supernatant. Anti-PSMA monoclonal antibodies can also be tested in combinations with each other to determine whether cytolysis is enhanced with multiple monoclonal antibodies.

Antibodies which bind to PSMA also can be tested in an in vivo model (e.g., in mice) to determine their efficacy in mediating cytolysis and killing of cells expressing PSMA, e.g., tumor cells. These antibodies can be selected, for example, based on the following criteria, which are not intended to be exclusive:

1) binding to live cells expressing PSMA;
2) high affinity of binding to PSMA;
3) binding to a unique epitope on PSMA (to eliminate the possibility that antibodies with complimentary activities when used in combination would compete for binding to the same epitope);
4) opsonization of cells expressing PSMA;
5) mediation of growth inhibition, phagocytosis and/or killing of cells expressing PSMA in the presence of effector cells;
6) modulation (inhibition or enhancement) of NAALADase, folate hydrolase, dipeptidyl peptidase IV and/or γ-glutamyl hydrolase activities;
7) growth inhibition, cell cycle arrest and/or cytotoxicity in the absence of effector cells;
8) internalization of PSMA;
9) binding to a conformational epitope on PSMA;
10) minimal cross-reactivity with cells or tissues that do not express PSMA; and
11) preferential binding to dimeric forms of PSMA rather than monomeric forms of PSMA.

Preferred antibodies of the invention meet one or more, and preferably all, of these criteria. In a particular embodiment, the antibodies are used in combination, e.g., as a pharmaceutical composition comprising two or more different anti-PSMA antibodies or binding fragments thereof. For example, anti-PSMA antibodies having different, but complementary activities can be combined in a single therapy to achieve a desired therapeutic or diagnostic effect. An illustration of this would be a composition containing an anti-PSMA antibody that mediates highly effective killing of target cells in the presence of effector cells, combined with another anti-PSMA antibody that inhibits the growth of cells expressing PSMA.

In a preferred aspect of the invention, the antibody or antigen-binding fragment thereof binds to a conformational epitope within the extracellular domain of the PSMA molecule. To determine if the selected human anti-PSMA antibodies bind to conformational epitopes, each antibody can be tested in assays using native protein (e.g., non-denaturing immunoprecipitation, flow cytometric analysis of cell surface binding) and denatured protein (e.g., Western blot, immunoprecipitation of denatured proteins). A comparison of the results will indicate whether the antibodies bind conformational epitopes. Antibodies that bind to native protein but not denatured protein are those antibodies that bind conformational epitopes, and are preferred antibodies.

In another preferred aspect of the invention, the antibody or antigen-binding fragment thereof binds to a dimer-specific epitope on PSMA. Generally, antibodies or antigen-binding fragments thereof which bind to a dimer-specific epitope preferentially bind the PSMA dimer rather than the PSMA monomer. To determine if the selected human anti-PSMA antibodies bind preferentially (i.e., selectively and/or specifically) to a PSMA dimer, each antibody can be tested in assays (e.g., immunoprecipitation followed by Western blotting) using native dimeric PSMA protein and dissociated monomeric PSMA protein. A comparison of the results will indicate whether the antibodies bind preferentially to the dimer or to the monomer. Antibodies that bind to the PSMA dimer but not to the monomeric PSMA protein are preferred antibodies.

Preferred antibodies include antibodies that competitively inhibit the specific binding of a second antibody to its target epitope on PSMA. To determine competitive inhibition, a variety of assays known to one of ordinary skill in the art can be employed. For example, the cross-competition assays set forth in Examples 4 and 21 can be used to determine if an antibody competitively inhibits binding to PSMA by another antibody. These examples provide cell-based methods employing flow cytometry or solid phase binding analysis. Other assays that evaluate the ability of antibodies to cross-compete for PSMA molecules that are not expressed on the surface of cells, in solid phase or in solution phase, also can be used. These assays preferably use the PSMA multimers described herein.

Certain preferred antibodies competitively inhibit the specific binding of a second antibody to its target epitope on PSMA by at least about 10%, 20%, 30%, 40%, 50%, 60%, 70%, 80%, 90%, 95%, or 99%. Inhibition can be assessed at various molar ratios or mass ratios; for example competitive binding experiments can be conducted with a 2-fold, 3-fold, 4-fold, 5-fold, 7-fold, 10-fold or more molar excess of the first antibody over the second antibody.

Other preferred antibodies include antibodies that specifically (i.e., selectively) bind to an epitope on PSMA defined by a second antibody. To determine the epitope, one can use standard epitope mapping methods known in the art. For example, fragments (peptides) of PSMA antigen (preferably synthetic peptides) that bind the second antibody can be used to determine whether a candidate antibody binds the same epitope. For linear epitopes, overlapping peptides of a defined length (e.g., 8 or more amino acids) are synthesized. The peptides preferably are offset by 1 amino acid, such that a series of peptides covering every 8 amino acid fragment of the PSMA protein sequence are prepared. Fewer peptides can be prepared by using larger offsets, e.g., 2 or 3 amino acids. In addition, longer peptides (e.g., 9-, 10- or 11-mers) can be synthesized. Binding of peptides to antibodies can be determined using standard methodologies including surface plasmon resonance (BIACORE™; see Example 22) and ELISA assays. For examination of conformational epitopes, larger PSMA fragments can be used. Other methods that use mass spectrometry to define conformational epitopes have been described and can be used (see, e.g., Baerga-Ortiz et al., *Protein Science* 11:1300-1308, 2002 and references cited therein). Still other methods for epitope determination are provided in standard laboratory reference works, such as Unit 6.8 ("Phage Display Selection and Analysis of B-cell Epitopes") and Unit 9.8 ("Identification of Antigenic Determinants Using Synthetic Peptide Combinatorial Libraries") of *Current Protocols in Immunology*, Coligan et al., eds., John Wiley & Sons.

Epitopes can be confirmed by introducing point mutations or deletions into a known epitope, and then testing binding with one or more antibodies to determine which mutations reduce binding of the antibodies.

In one embodiment of the invention the antibody or antigen-binding fragment thereof binds to and is internalized with PSMA expressed on cells. The mechanism by which the antibody or antigen-binding fragment thereof is internalized with the prostate specific membrane antigen is not critical to the practice of the present invention. For example, the antibody or antigen-binding fragment thereof can induce internalization of PSMA. Alternatively, internalization of the antibody or antigen-binding fragment thereof can be the result of routine internalization of PSMA. The antibody or antigen-binding fragment thereof can be used in an unmodified form, alone or in combination with other compositions. Alternatively, the antibody or antigen-binding fragment thereof can be bound to a substance effective to kill the cells upon binding of the antibody or antigen-binding fragment thereof to prostate specific membrane antigen and upon internalization of the biological agent with the prostate specific membrane antigen.

The human PSMA antibodies of the present invention specifically bind cell-surface PSMA and/or rsPSMA with sub-nanomolar affinity. The human PSMA antibodies of the present invention have binding affinities of about $1\times10^{-9}$M or less, preferably about $1\times10^{-10}$M or less, more preferably $1\times10^{-11}$M or less. In a particular embodiment the binding affinity is less than about $5\times10^{-10}$M.

An antibody can be linked to a detectable marker, an antitumor agent or an immunomodulator. Antitumor agents can include cytotoxic agents and agents that act on tumor neovasculature. Detectable markers include, for example, radioactive or fluorescent markers. Cytotoxic agents include cytotoxic radionuclides, chemical toxins and protein toxins.

The cytotoxic radionuclide or radiotherapeutic isotope preferably is an alpha-emitting isotope such as $^{225}$Ac, $^{211}$At, $^{212}$Bi, 213Bi, $^{212}$Pb, $^{224}$Ra or $^{223}$Ra. Alternatively, the cytotoxic radionuclide may a beta-emitting isotope such as $^{186}$Rh, $^{188}$Rh, $^{177}$Lu, $^{90}$Y, $^{131}$I, $^{67}$CU, $^{64}$Cu, $^{153}$Sm or $^{166}$Ho. Further, the cytotoxic radionuclide may emit Auger and low energy electrons and include the isotopes $^{125}$I, $^{123}$I or $^{77}$Br.

Suitable chemical toxins or chemotherapeutic agents include members of the enediyne family of molecules, such as calicheamicin and esperamicin. Chemical toxins can also be taken from the group consisting of methotrexate, doxorubicin, melphalan, chlorambucil, ARA-C, vindesine, mitomycin C, cis-platinum, etoposide, bleomycin and 5-fluorouracil. Other antineoplastic agents that may be conjugated to the anti-PSMA antibodies of the present invention include dolastatins (U.S. Pat. Nos. 6,034,065 and 6,239,104) and derivatives thereof. Of particular interest is dolastatin 10 (dolavaline-valine-dolaisoleuine-dolaproine-dolaphenine) and the derivatives auristatin PHE (dolavaline-valine-dolaisoleuine-dolaproine-phenylalanine-methyl ester) (Pettit, G. R. et al., *Anticancer Drug Des.* 13(4):243-277, 1998; Woyke, T. et al., *Antimicrob. Agents Chemother.* 45(12):3580-3584, 2001), and aurastatin E and the like. Toxins that are less preferred in the compositions and methods of the invention include poisonous lectins, plant toxins such as ricin, abrin, modeccin, botulina and diphtheria toxins. Of course, combinations of the various toxins could also be coupled to one antibody molecule thereby accommodating variable cytotoxicity. Other chemotherapeutic agents are known to those skilled in the art.

Toxin-conjugated forms of the PSMA antibodies of the present invention mediate specific cell killing of PSMA-expressing cells at picomolar concentrations. The toxin-conjugated PSMA antibodies of the present invention exhibit $IC_{50}$s at concentrations of less than about $1\times10^{-10}$M, preferably less than about $1\times10^{-11}$M, more preferably less than about $1\times10^{-12}$M. In a particular embodiment an $IC_{50}$ is achieved at a concentration of less than about $1.5\times10^{-11}$M.

Agents that act on the tumor vasculature can include tubulin-binding agents such as combrestatin A4 (Griggs et al., Lancet Oncol. 2:82, 2001), angiostatin and endostatin (reviewed in Rosen, Oncologist 5:20, 2000, incorporated by reference herein) and interferon inducible protein 10 (U.S. Pat. No. 5,994,292). A number of antiangiogenic agents currently in clinical trials are also contemplated. Agents currently in clinical trials include: 2ME2, Angiostatin, ANGIOZYME, Anti-VEGF RhuMAb, Apra (CT-2584), AVICINE, Benefin, BMS275291, Carboxyamidotriazole, CC4047, CC5013, CC7085, CDC801, CGP-41251 (PKC 412), CM101, Combretastatin A-4 Prodrug, EMD 121974, Endostatin, Flavopiridol, Genistein (GCP), Green Tea Extract, IM-862, ImmTher, Interferon alpha, Interleukin-12, IRESSA (ZD1839), Marimastat, METASTAT(Col-3), NEOVASTAT, Octreotide, Paclitaxel, Penicillamine, PHOTOFRIN, PHOTOPOINT, PI-88, Prinomastat (AG-3340), PTK787 (ZK22584), RO317453, Solimastat, Squalamine, SU 101, SU 5416, SU-6668, Suradista (FCE 26644), Suramin (Metaret), Tetrathiomolybdate, Thalidomide, TNP-470 and VITAXIN. Additional antiangiogenic agents are described by Kerbel, J. Clin. Oncol. 19(18s):45s-51s, 2001, which is incorporated by reference herein. Immunomodulators suitable for conjugation to anti-PSMA antibodies include α-interferon, γ-interferon, and tumor necrosis factor alpha (TNFα).

The coupling of one or more toxin molecules to the anti-PSMA antibody is envisioned to include many chemical mechanisms, for instance covalent binding, affinity binding, intercalation, coordinate binding, and complexation. The toxic compounds used to prepare the anti-PSMA immunotoxins are attached to the antibodies or PSMA-binding fragments thereof by standard protocols known in the art.

The covalent binding can be achieved either by direct condensation of existing side chains or by the incorporation of external bridging molecules. Many bivalent or polyvalent agents are useful in coupling protein molecules to other proteins, peptides or amine functions, etc. For example, the literature is replete with coupling agents such as carbodiimides, diisocyanates, glutaraldehyde, diazobenzenes, and hexamethylene diamines. This list is not intended to be exhaustive of the various coupling agents known in the art but, rather, is exemplary of the more common coupling agents.

In preferred embodiments, it is contemplated that one may wish to first derivatize the antibody, and then attach the toxin component to the derivatized product. Suitable cross-linking agents for use in this manner include, for example, SPDP (N-succinimidyl-3-(2-pyridyldithio)propionate), and SMPT, 4-succinimidyl-oxycarbonyl-methyl-(2-pyridyldithio)toluene.

In addition, protein toxins can be fused to the anti-PSMA antibody or PSMA binding fragment by genetic methods to form a hybrid immunotoxin fusion protein. To make a fusion immunotoxin protein in accordance with the invention, a nucleic acid molecule is generated that encodes an anti-PSMA antibody, a fragment of an anti-PSMA antibody, a single chain anti-PSMA antibody, or a subunit of an anti-PSMA antibody linked to a protein toxin. Such fusion proteins contain at least a targeting agent (e.g., anti-PSMA antibody subunit) and a toxin of the invention, operatively attached. The fusion proteins may also include additional peptide sequences, such as peptide spacers which operatively attach the targeting agent and toxin compound, as long as such additional sequences do not appreciably affect the targeting or toxin activities of the fusion protein. The two proteins can be attached by a peptide linker or spacer, such as a glycine-serine spacer peptide, or a peptide hinge, as is well known in the art. Thus, for example, the C-terminus of an anti-PSMA antibody or fragment thereof can be fused to the N-terminus of the protein toxin molecule to form an immunotoxin that retains the binding properties of the anti-PSMA antibody. Other fusion arrangements will be known to one of ordinary skill in the art.

To express the fusion immunotoxin, the nucleic acid encoding the fusion protein is inserted into an expression vector in accordance with standard methods, for stable expression of the fusion protein, preferably in mammalian cells, such as CHO cells. The fusion protein can be isolated and purified from the cells or culture supernatant using standard methodology, such as a PSMA affinity column.

Radionuclides typically are coupled to an antibody by chelation. For example, in the case of metallic radionuclides, a bifunctional chelator is commonly used to link the isotope to the antibody or other protein of interest. Typically, the chelator is first attached to the antibody, and the chelator-antibody conjugate is contacted with the metallic radioisotope. A number of bifunctional chelators have been developed for this purpose, including the diethylenetriamine pentaacetic acid (DTPA) series of amino acids described in U.S. Pat. Nos. 5,124,471, 5,286,850 and 5,434,287, which are incorporated herein by reference. As another example, hydroxamic acid-based bifunctional chelating agents are described in U.S. Pat. No. 5,756,825, the contents of which are incorporated herein. Another example is the chelating agent termed p-SCN-Bz-HEHA (1,4,7,10,13,16-hexaazacyclo-octadecane-N,N',N'',N''',N'''',N'''''-hexaacetic acid) (Deal et al., J. Med. Chem. 42:2988, 1999), which is an effective chelator of radiometals such as $^{225}$Ac. Yet another example is DOTA (1,4,7,10-tetraazacyclododecane N,N',N'',N'''-tetraacetic acid), which is a bifunctional chelating agent (see McDevitt et al., Science 294:1537-1540, 2001) that can be used in a two-step method for labeling followed by conjugation.

In another aspect, the invention provides compositions comprising an isolated antibody, an antibody derivatized or linked to other functional moieties, or an antigen-binding fragment thereof or a combination of one or more of the aforementioned antibodies or antigen-binding fragments thereof. The compositions include a physiologically or pharmaceutically acceptable carrier, excipient, or stabilizer mixed with the isolated antibody or antigen-binding fragment thereof. In a preferred embodiment, the compositions include a combination of multiple (e.g., two or more) isolated antibodies or antigen-binding portions thereof of the invention. Preferably, each of the antibodies or antigen-binding portions thereof of the composition binds to a distinct conformational epitope of PSMA. In one embodiment, anti-PSMA antibodies having complementary activities are used in combination, e.g., as a pharmaceutical composition, comprising two or more anti-PSMA antibodies. For example, an antibody that mediates highly effective cytolysis of target cells in the presence of effector cells can be combined with another antibody that inhibits the growth of cells expressing PSMA. As used herein, "target cell" shall mean any undesirable cell in a subject (e.g., a human or animal) that can be targeted by a composition of the invention. In preferred embodiments, the target cell is a cell expressing or overexpressing PSMA. Cells expressing PSMA typically include tumor cells, such as prostate, bladder, pancreas, lung, kidney, colon tumor cells, melanomas, and sarcomas.

Pharmaceutical compositions of the invention also can be administered in combination therapy, i.e., combined with other agents. For example, the combination therapy can include a composition of the present invention with at least one anti-tumor agent, immunomodulator, immunostimulatory agent, or other conventional therapy. The agent may be bound or conjugated to or formed as a recombinant fusion molecule with the PSMA antibodies of the present invention for directed targeting of the agent to PSMA-expressing cells.

The PSMA antibodies of the present invention may be used as a targeting moiety for delivery of replication-selective virus to PSMA-expressing cells for tumor therapy. Replication-competent virus such as the p53 pathway targeting adenovirus mutant dl1520, ONYX-015, kill tumor cells selectively (Biederer, C. et al., J. Mol. Med. 80(3):163-175, 2002).

As used herein, "pharmaceutically acceptable carrier" or "physiologically acceptable carrier" includes any and all salts, solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody may be coated in a material to protect the compound from the action of acids and other natural conditions that may inactivate the compound.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents, such as supplementary immune potentiating agents including adjuvants, chemokines and cytokines. When used in medicine, the salts should be pharmaceutically acceptable, but non-pharmaceutically acceptable salts may conveniently be used to prepare pharmaceutically-acceptable salts thereof and are not excluded from the scope of the invention.

A salt retains the desired biological activity of the parent compound and does not impart any undesired toxicological effects (see e.g., Berge, S. M., et al. (1977) *J. Pharm. Sci.* 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

An anti-PSMA antibody composition may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for parenteral administration conveniently comprise a sterile aqueous or non-aqueous preparation of anti-PSMA antibodies, which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-or di-glycerides. In addition, fatty acids such as oleic acid may be used in the preparation of injectables. Carrier formulations suitable for oral, subcutaneous, intravenous, intramuscular, etc. administration can be found in *Remington's Pharmaceutical Sciences*, Mack Publishing Co., Easton, Pa.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

The therapeutics of the invention can be administered by any conventional route, including injection or by gradual infusion over time. The administration may, for example, be oral, intravenous, intraperitoneal, intramuscular, intracavity, intratumor, or transdermal. When antibodies are used therapeutically, preferred routes of administration include intravenous and by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences,* 18th edition, 1990, pp. 1694-1712; incorporated by reference). Those of skill in the art can readily determine the various parameters and conditions for producing antibody aerosols without resorting to undue experimentation.

The compositions of the invention are administered in effective amounts. An "effective amount" is that amount of an anti-PSMA antibody composition that alone, or together with further doses, produces the desired response, e.g. treats a malignancy in a subject. This may involve only slowing the progression of the disease temporarily, although more preferably, it involves halting the progression of the disease permanently. This can be monitored by routine methods. The desired response to treatment of the disease or condition also can be delaying the onset or even preventing the onset of the disease or condition.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The pharmaceutical compositions used in the foregoing methods preferably are sterile and contain an effective amount of anti-PSMA antibodies for producing the desired response in a unit of weight or volume suitable for administration to a patient. The response can, for example, be measured by determining the physiological effects of the anti-PSMA antibody composition, such as regression of a tumor or decrease of disease symptoms. Other assays will be known to one of ordinary skill in the art and can be employed for measuring the level of the response.

The doses of anti-PSMA antibodies administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

In general, doses can range from about 10 μg/kg to about 100,000 μg/kg. Based upon the composition, the dose can be delivered continuously, such as by continuous pump, or at periodic intervals. Desired time intervals of multiple doses of a particular composition can be determined without undue experimentation by one skilled in the art. Other protocols for the administration of anti-PSMA antibody compositions will be known to one of ordinary skill in the art, in which the dose amount, schedule of administration, sites of administration, mode of administration and the like vary from the foregoing.

In general, doses of radionuclide delivered by the anti-PSMA antibodies of the invention can range from about 0.01 mCi/Kg to about 10 mCi/kg. Preferably the dose of radionuclide ranges from about 0.1 mCi/Kg to about 1.0 mCi/kg. The optimal dose of a given isotope can be determined empirically by simple routine titration experiments well known to one of ordinary skill in the art.

Administration of anti-PSMA antibody compositions to mammals other than humans, e.g. for testing purposes or veterinary therapeutic purposes, is carried out under substantially the same conditions as described above.

The compositions (antibodies to PSMA and derivatives/conjugates thereof) of the present invention have in vitro and in vivo diagnostic and therapeutic utilities. For example, these molecules can be administered to cells in culture, e.g. in vitro or ex vivo, or in a subject, e.g., in vivo, to treat, prevent or diagnose a variety of disorders. As used herein, the term "subject" is intended to include humans and non-human animals. Preferred subjects include a human patient having a disorder characterized by expression, typically aberrant expression (e.g., overexpression) of PSMA.

One aspect of the present invention relates to a method of detecting cancerous cells or portions thereof in a biological sample (e.g., histological or cytological specimens, biopsies and the like), and, in particular, to distinguish malignant tumors from normal tissues and non-malignant tumors. This method involves providing an antibody or an antigen-binding binding fragment thereof, probe, or ligand, which binds to an extracellular domain of PSMA of such cells, e.g., an anti-PSMA antibody. The anti-PSMA antibody is bound to a label that permits the detection of the cells or portions thereof (e.g., PSMA or fragments thereof liberated from such cancerous cells) upon binding of the anti-PSMA antibody to the cells or portions thereof. The biological sample is contacted with the labeled anti-PSMA antibody under conditions effective to permit binding of the anti-PSMA antibody to the extracellular domain of PSMA of any of the cells or portions thereof in the biological sample. The presence of any cells or portions thereof in the biological sample is detected by detection of the label. In one preferred form, the contact between the anti-PSMA antibody and the biological sample is carried out in a living mammal and involves administering the anti-PSMA antibody to the mammal under conditions that permit binding of the anti-PSMA antibody to PSMA of any of the cells or portions thereof in the biological sample. Again, such administration can be carried out by any suitable method known to one of ordinary skill in the art.

In addition, the anti-PSMA antibodies of the present invention can be used in immunofluorescence techniques to examine human tissue, cell and bodily fluid specimens. In a typical protocol, slides containing cryostat sections of frozen, unfixed tissue biopsy samples or cytological smears are air dried, formalin or acetone fixed, and incubated with the monoclonal antibody preparation in a humidified chamber at room temperature. The slides are then washed and further incubated with a preparation of a secondary antibody directed against the monoclonal antibody, usually some type of anti-mouse immunoglobulin if the monoclonal antibodies used are derived from the fusion of a mouse spleen lymphocyte and a mouse myeloma cell line. This secondary antibody is tagged with a compound, for instance rhodamine or fluorescein isothiocyanate, that fluoresces at a particular wavelength. The staining pattern and intensities within the sample are then determined by fluorescent light microscopy and optionally photographically recorded.

As yet another alternative, computer enhanced fluorescence image analysis or flow cytometry can be used to examine tissue specimens or exfoliated cells, i.e., single cell preparations from aspiration biopsies of tumors using the anti-PSMA antibodies of this invention. The anti-PSMA antibodies of the invention are particularly useful in quantitation of live tumor cells, i.e., single cell preparations from aspiration biopsies of prostate tumors by computer enhanced fluorescence image analyzer or with a flow cytometer. The antibodies of the invention are particularly useful in such assays to differentiate benign from malignant prostate tumors since the PSMA protein to which the anti-PSMA antibodies bind is expressed in increased amounts by malignant tumors as compared to benign prostate tumors. The percent PSMA positive cell population, alone or in conjunction with determination of other attributes of the cells (e.g., DNA ploidy of these cells), may, additionally, provide very useful prognostic information by providing an early indicator of disease progression.

In yet another alternative embodiment, the antibodies of the present invention can be used in combination with other known antibodies to provide additional information regarding the malignant phenotype of a cancer.

The method of the present invention can be used to screen patients for diseases associated with the presence of cancerous cells or portions thereof. Alternatively, it can be used to identify the recurrence of such diseases, particularly when the disease is localized in a particular biological material of the patient. For example, recurrence of prostatic disease in the prostatic fossa may be encountered following radical prostatectomy. Using the method of the present invention, this recurrence can be detected by administering a short range radiolabeled antibody to the mammal and then detecting the label rectally, such as with a transrectal detector probe.

Alternatively, the contacting step can be carried out in a sample of serum or urine or other body fluids, including but not limited to seminal fluid, prostatic fluid, ejaculate, and the like, such as to detect the presence of PSMA in the body fluid. When the contacting is carried out in a serum or urine sample, it is preferred that the biological agent recognize substantially no antigens circulating in the blood other than PSMA. Since intact cells do not excrete or secrete PSMA into the extracellular environment, detecting PSMA in serum, urine, or other body fluids generally indicates that cells are being lysed or shed. Thus, the biological agents and methods of the present invention can be used to determine the effectiveness of a cancer treatment protocol by monitoring the level of PSMA in serum, urine or other body fluids.

In a particularly preferred embodiment of the method of detecting cancerous cells in accordance with the present invention, the anti-PSMA antibodies or an antigen-binding fragment thereof, binds to and is internalized with the prostate specific membrane antigen of such cells. Again, the biological agent is bound to a label effective to permit detection of the cells or portions thereof upon binding of the biological agent to and internalization of the biological agent with the prostate specific membrane antigen.

Biological agents suitable for detecting cancerous cells include anti-PSMA antibodies, such as monoclonal or polyclonal antibodies. In addition, antibody fragments, half-antibodies, hybrid derivatives, probes, and other molecular constructs may be utilized. These biological agents, such as antibodies, antigen-binding fragments thereof, probes, or ligands, bind to extracellular domains of prostate specific membrane antigens or portions thereof in cancerous cells. As a result, the biological agents bind not only to cells which are fixed or cells whose intracellular antigenic domains are otherwise exposed to the extracellular environment. Consequently, binding of the biological agents is concentrated in areas where there are prostate cells, irrespective of whether these cells are fixed or unfixed, viable or necrotic. Additionally or alternatively, these biological agents bind to and are internalized with prostate specific membrane antigens or portions thereof in normal, benign hyperplastic, and to a greater degree in cancerous cells.

The antibodies or antigen-binding fragments thereof can also be utilized in in vivo therapy of cancer. The antibodies can be used alone or covalently attached, either directly or via linker, to a compound which kills and/or inhibits proliferation of the malignant cells or tissues following administration and localization of the conjugates. When the antibody is used by itself, it may mediate tumor destruction by complement fixation or antibody-dependent cellular cytotoxicity. Alternatively, the antibody may be administered in combination with a chemotherapeutic drug to result in synergistic therapeutic effects (Baslya and Mendelsohn, 1994 *Breast Cancer Res. and Treatment* 29:127-138). A variety of different types of substances can be directly conjugated to the antibody for therapeutic uses, including radioactive metal and non-metal isotopes, chemotherapeutic drugs, toxins, etc. as described above and known in the art (see, e.g., Vitetta and Uhr, 1985, *Annu. Rev. Immunol.* 3:197).

The antibodies or antigen-binding fragments thereof of the invention can also be administered together with complement. Accordingly, within the scope of the invention are compositions comprising antibodies or antigen-binding fragments thereof and serum or complement. These compositions are advantageous in that the complement is located in close proximity to the human antibodies or antigen-binding fragments thereof. Alternatively, the antibodies or antigen-binding fragments thereof of the invention and the complement or serum can be administered separately.

The antibodies can be administered with one or more immunostimulatory agents to induce or enhance an immune response, such as IL-2 and immunostimulatory oligonucleotides (e.g., those containing CpG motifs). Preferred immunostimulatory agents stimulate specific arms of the immune system, such as natural killer (NK) cells that mediate antibody-dependent cell cytotoxicity (ADCC).

Antigens, such as the PSMA dimers described herein, can be administered with one or more adjuvants to induce or enhance an immune response. An adjuvant is a substance which potentiates the immune response. Adjuvants of many kinds are well known in the art. Specific examples of adjuvants include monophosphoryl lipid A (MPL, SmithKline Beecham); saponins including QS21 (SmithKline Beecham); immunostimulatory oligonucleotides (e.g., CpG oligonucleotides described by Kreig et al., *Nature* 374:546-9, 1995); incomplete Freund's adjuvant; complete Freund's adjuvant; MONTANIDE; vitamin E and various water-in-oil emulsions prepared from biodegradable oils such as squalene and/or tocopherol, Quil A, Ribi Detox, CRL-1005, L-121, and combinations thereof.

Other agents which stimulate the immune response of the subject to PSMA multimer antigens can also be administered to the subject. For example, cytokines are also useful in vaccination protocols as a result of their lymphocyte regulatory properties. Many cytokines useful for such purposes will be known to one of ordinary skill in the art, including interleukin-2 (IL-2); IL-4; IL-5; IL-12, which has been shown to enhance the protective effects of vaccines (see, e.g., *Science* 268: 1432-1434, 1995); GM-CSF; IL-15; IL-18; combinations thereof, and the like. Thus cytokines can be administered in conjunction with antibodies, antigens, chemokines and/or adjuvants to increase an immune response.

Chemokines useful in increasing immune responses include but are not limited to SLC, ELC, MIP3α, MIP3β, IP-10, MIG, and combinations thereof.

The antibodies or antigen-binding fragments thereof of the present invention can be used in conjunction with other therapeutic treatment modalities. Such other treatments include surgery, radiation, cryosurgery, thermotherapy, hormone treatment, chemotherapy, vaccines, and other immunotherapies.

Also encompassed by the present invention is a method which involves using the antibodies or antigen-binding fragments thereof for prophylaxis. For example, these materials can be used to prevent or delay development or progression of cancer.

Use of the cancer therapy of the present invention has a number of benefits. Since the anti-PSMA antibodies or antigen-binding fragments thereof according to the present invention preferentially target prostate cancer cells, other tissue is spared. As a result, treatment with such biological agents is safer, particularly for elderly patients. Treatment according to the present invention is expected to be particularly effective, because it directs high levels of anti-PSMA antibodies or antigen-binding fragments thereof to the bone marrow and lymph nodes where prostate cancer metastases predominate. Moreover, tumor sites for prostate cancer tend to be small in size and, therefore, easily destroyed by cytotoxic agents. Treatment in accordance with the present invention can be effectively monitored with clinical parameters such as serum prostate specific antigen and/or pathological features of a patient's cancer, including stage, Gleason score, extracapsular, seminal, vesicle or perineural invasion, positive margins, involved lymph nodes, etc. Alternatively, these parameters can be used to indicate when such treatment should be employed.

Because the antibodies or antigen-binding fragments thereof of the present invention bind to living cells, therapeutic methods using these biological agents are much more effective than those which target lysed cells. For the same reasons, diagnostic and imaging methods which determine the location of living normal, benign hyperplastic, or cancerous cells are much improved by employing the antibodies or antigen-binding fragments thereof of the present invention. In addition, the ability to differentiate between living and dead cells can be advantageous, especially to monitor the effectiveness of a particular treatment regimen.

Also within the scope of the invention are kits comprising the compositions of the invention and instructions for use. The kits can further contain at least one additional reagent, such as complement, or one or more additional antibodies of the invention (e.g., an antibody having a complementary activity which binds to an epitope in PSMA antigen distinct from the first antibody). Other kits can include the PSMA multimers described hereinbelow.

Kits containing the antibodies or antigen-binding fragments thereof of the invention can be prepared for in vitro diagnosis, prognosis and/or monitoring cancer by the immunohistological, immunocytological and immunoserological methods described above. The components of the kits can be packaged either in aqueous medium or in lyophilized form. When the antibodies or antigen-binding fragments thereof are used in the kits in the form of conjugates in which a label moiety is attached, such as an enzyme or a radioactive metal ion, the components of such conjugates can be supplied either in fully conjugated form, in the form of intermediates or as separate moieties to be conjugated by the user or the kit.

A kit may comprise a carrier being compartmentalized to receive in close confinement therein one or more container means or series of container means such as test tubes, vials, flasks, bottles, syringes, or the like. A first of said container means or series of container means may contain one or more anti-PSMA antibodies or antigen-binding fragments thereof or PSMA. A second container means or series of container means may contain a label or linker-label intermediate capable of binding to the primary anti-PSMA antibodies (or fragment thereof).

Kits for use in in vivo tumor localization and therapy method containing the anti-PSMA antibodies or antigen-binding fragments thereof conjugated to other compounds or substances can be prepared. The components of the kits can be packaged either in aqueous medium or in lyophilized form. When the antibodies or antigen-binding fragments thereof are used in the kits in the form of conjugates in which a label or a therapeutic moiety is attached, such as a radioactive metal ion or a therapeutic drug moiety, the components of such conjugates can be supplied either in fully conjugated form, in the form of intermediates or as separate moieties to be conjugated by the user of the kit.

In one aspect of the invention, a method for modulating at least one enzymatic activity of PSMA, the activity selected from the group consisting of N-acetylated α-linked acidic dipeptidase (NAALADase), folate hydrolase, dipeptidyl dipeptidase IV and γ-glutamyl hydrolase activity or combination thereof in vitro or in vivo. The modulation may be enhancement or inhibition of at least one enzymatic activity of PSMA.

In a preferred embodiment, the invention provides methods for inhibiting at least one enzymatic activity of PSMA, the activity selected from the group consisting of N-acetylated α-linked acidic dipeptidase (NAALADase), folate hydrolase, dipeptidyl dipeptidase IV and γ-glutamyl hydrolase activity or combination thereof in vitro or in vivo. The method comprises contacting a NAALADase, a folate hydrolase, a dipeptidyl dipeptidase IV and/or a γ-glutamyl hydrolase with an amount of an isolated antibody or antigen-binding fragment thereof of the invention under conditions wherein the isolated monoclonal antibody or antigen-binding fragment thereof inhibits NAALADase, folate hydrolase, dipeptidyl dipeptidase IV or γ-glutamyl hydrolase activity.

Tissue levels of NAALADase can be determined by detergent solubilizing homogenizing tissues, pelleting the insoluble material by centrifugation and measuring the NAALADase activity in the remaining supernatant. Likewise, the NAALADase activity in bodily fluids can also be measured by first pelleting the cellular material by centrifugation and performing a typical enzyme assay for NAALADase activity on the supernatant. NAALADase enzyme assays have been described by Frieden, 1959, *J. Biol, Chem.*, 234:2891. In this assay, the reaction product of the NAALADase enzyme is glutamic acid. This is derived from the enzyme catalyzed cleavage of N-acetylaspartylglutamate to yield N-acetylaspartic acid and glutamic acid. Glutamic acid, in a $NAD(P)^+$ requiring step, yields 2-oxoglutarate plus NAD(P)H in a reaction catalyzed by glutamate dehydrogenase. Progress of the reaction can easily and conveniently be measured by the change in absorbance at 340 nm due to the conversion of $NAD(P)^+$ to NAD(P)H.

Folate hydrolase activity of PSMA can be measured by performing enzyme assays as described by Heston and others (e.g., *Clin. Cancer Res.* 2(9):1445-51, 1996; *Urology* 49(3A Suppl): 104-12,1997). Folate hydrolases such as PSMA remove the gamma-linked glutamates from polyglutamated folates. Folate hydrolase activity can be measured using substrates such as methotrexate tri-gamma glutamate (MTX-Glu3), methotrexate di-gamma glutamate (MTXGlu2) and pteroylpentaglutamate (PteGlu5), for example using capillary electrophoresis (see *Clin. Cancer Res.* 2(9):1445-51, 1996). Timed incubations of PSMA with polyglutamated substrates is followed by separation and detection of hydrolysis products.

The invention also includes isolated antibodies and binding fragments thereof that selectively bind PSMA multimers. As used herein, particularly with respect to the binding of PSMA multimers by the anti-PSMA antibodies and binding fragments, "selectively binds" means that an antibody preferentially binds to a PSMA protein multimer (e.g., with greater avidity, greater binding affinity) rather than to a PSMA protein monomer. In preferred embodiments, the antibodies of the invention bind to a PSMA protein multimer with an avidity and/or binding affinity that is 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 7-fold, 10-fold, 20-fold, 30-fold, 40-fold, 50-fold, 70-fold, 100-fold, 200-fold, 300-fold, 500-fold, 1000-fold or more than that exhibited by the antibody for a PSMA protein monomer. Preferably, the antibody selectively binds a PSMA protein multimer, and not a PSMA protein monomer, i.e., substantially exclusively binds to a PSMA protein multimer. Most preferably, the antibody selectively binds a PSMA protein dimer.

The isolated antibody or binding fragment that selectively binds a PSMA protein multimer can, in some embodiments, modulate enzymatic activity of the PSMA protein multimer. In one such embodiment, the antibody inhibits at least one enzymatic activity such as NAALADase activity, folate hydrolase activity, dipeptidyl dipeptidase IV activity, γ-glutamyl hydrolase activity, or combinations thereof. In another embodiment, the antibody enhances at least one enzymatic activity such as NAALADase activity, folate hydrolase activity, dipeptidyl dipeptidase IV activity, γ-glutamyl hydrolase activity, or combinations thereof.

A PSMA protein multimer, as used herein, is a protein complex of at least two PSMA proteins or fragments thereof. The PSMA protein multimers can be composed of various combinations of full-length PSMA proteins (e.g., SEQ ID NO: 1), recombinant soluble PSMA (rsPSMA, e.g., amino acids 44-750 of SEQ ID NO: 1) and fragments of the foregoing that form multimers (i.e., that retain the protein domain required for forming dimers and/or higher order multimers of PSMA). In preferred embodiments, at least one of the PSMA proteins forming the multimer is a recombinant, soluble PSMA (rsPSMA) polypeptide. Preferred PSMA protein multimers are dimers, particularly those formed from recombinant soluble PSMA protein. A particularly preferred embodiment is a rsPSMA homodimer.

The PSMA protein multimers referred to herein are believed to assume a native conformation and preferably have such a conformation. The PSMA proteins in certain embodiments are noncovalently bound together to form the PSMA protein multimer. For example, it has been discovered that PSMA protein noncovalently associates to form dimers under non-denaturing conditions, as described in the Examples below.

The PSMA protein multimers can, and preferably do, retain the activities of PSMA. The PSMA activity may be an enzymatic activity, such as folate hydrolase activity, NAALADase activity, dipeptidyl peptidase IV activity and γ-glutamyl hydrolase activity. Methods for testing the PSMA activity of multimers are well known in the art (reviewed by O'Keefe et al. in: *Prostate Cancer: Biology, Genetics, and the New Therapeutics*, L. W. K. Chung, W. B. Isaacs and J. W. Simons (eds.) Humana Press, Totowa, N.J., 2000, pp. 307-326), some of which are described in the Examples herein below.

In certain aspects, the invention also includes compositions including one or more of the isolated PSMA protein multimers described herein, such as the PSMA protein dimer. In preferred embodiments, a PSMA protein multimer composition contains at least about 10% PSMA protein multimer. In other embodiments, the PSMA protein multimer composition contains at least about 20%, 30%, 40%, 50%, 60%, 70%, 75%, 80%, 85%, 90%, 95%, 99% or 99.5% PSMA protein multimer. In a preferred embodiment, the PSMA protein multimer composition contains substantially pure PSMA protein multimer, with substantially no PSMA protein monomer. It is understood that the list of specific percentages includes by inference all of the unnamed percentages between the recited percentages.

As used herein with respect to polypeptides, proteins or fragments thereof, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may be, but need not be, substantially pure. The term "substantially pure" means that the proteins or polypeptides are essentially free of other substances with which they may be found in nature or in vivo systems to an extent practical and appropriate for their intended use. Substantially pure polypeptides may be produced by techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from the substances with which it may be associated in living systems, i.e. isolated from other proteins.

Fragments of a PSMA protein preferably are those fragments which retain a distinct functional capability of the PSMA protein. Functional capabilities which can be retained in a fragment include binding of other PSMA molecules to form dimers and higher order multimers, interaction with antibodies, interaction with other polypeptides or fragments thereof, and enzymatic activity. Other PSMA protein fragments, e.g., other recombinant soluble fragments of SEQ ID NO: 1, can be selected according to their functional properties. For example, one of ordinary skill in the art can prepare PSMA fragments recombinantly and test those fragments according to the methods exemplified below.

Modifications to a PSMA polypeptide are typically made to the nucleic acid which encodes the PSMA polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the PSMA amino acid sequence.

In general, modified PSMA polypeptides include polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a PSMA polypeptide by eliminating proteolysis by proteases in an expression system (e.g., dibasic amino acid residues in yeast expression systems in which KEX2 protease activity is present).

Modifications conveniently are prepared by altering a nucleic acid molecule that encodes the PSMA polypeptide. Mutations of a nucleic acid which encode a PSMA polypeptide preferably preserve the amino acid reading frame of the coding sequence, and preferably do not create regions in the nucleic acid which are likely to hybridize to form secondary structures, such a hairpins or loops, which can be deleterious to expression of the modified polypeptide.

Modifications can be made by selecting an amino acid substitution, or by random mutagenesis of a selected site in a nucleic acid which encodes the PSMA polypeptide. Modified PSMA polypeptides then can be expressed and tested for one or more activities (e.g., antibody binding, enzymatic activity, multimeric stability) to determine which mutation provides a modified polypeptide with the desired properties. Further mutations can be made to modified PSMA polypeptides (or to non-modified PSMA polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a PSMA coding sequence or cDNA clone to enhance expression of the polypeptide. The activity of modified PSMA polypeptides can be tested by cloning the gene encoding the modified PSMA polypeptide into a bacterial or mammalian expression vector, introducing the vector into an appropriate host cell, expressing the modified PSMA polypeptide, and testing for a functional capability of the PSMA polypeptides as disclosed herein. The foregoing procedures are well known to one of ordinary skill in the art.

The skilled artisan will also realize that conservative amino acid substitutions may be made in PSMA polypeptides to provide functionally equivalent PSMA polypeptides, i.e., modified PSMA polypeptides that retain the functional capabilities of PSMA polypeptides. As used herein, a "conservative amino acid substitution" refers to an amino acid substitution which does not alter the relative charge or size characteristics of the protein in which the amino acid substitution is made. Modified PSMA polypeptides can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent PSMA polypeptides include conservative amino acid substitutions of SEQ ID NO: 1, or fragments thereof, such as the recombinant soluble PSMA polypeptide (amino acids 44-750 of SEQ ID NO: 1). Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Conservative amino-acid substitutions in PSMA polypeptides typically are made by alteration of a nucleic acid encoding a PSMA polypeptide. Such substitutions can be made by a variety of methods known to one of ordinary skill in the art. For example, amino acid substitutions may be made by PCR-directed mutation, site-directed mutagenesis, or by chemical synthesis of a gene encoding a PSMA polypeptide. Where amino acid substitutions are made to a small fragment of a PSMA polypeptide, the substitutions can be made by directly synthesizing the peptide. The activity of functionally equivalent fragments of PSMA polypeptides can be tested by cloning the gene encoding the altered PSMA polypeptide into a bacterial or mammalian expression vector, introducing the vector into an appropriate host cell, expressing the altered PSMA polypeptide, and testing for a functional capability of the PSMA polypeptides as disclosed herein.

The PSMA protein multimers as described herein have a number of uses, some of which are described elsewhere herein. The multimers are useful for testing of compounds that modulate PSMA enzymatic activity or PSMA multimerization. The multimers can be used to isolate antibodies that selectively bind PSMA, including those selective for conformational epitopes, those selective for binding PSMA multimers and not PSMA monomers, and those that selectively modulate an enzymatic activity of PSMA. The multimers, particularly dimeric PSMA, also can be used to induce or increase immune responses to PSMA, as vaccine compositions.

Agents that selectively modulate an enzymatic activity of PSMA include agents that inhibit or enhance at least one enzymatic activity of PSMA, such as NAALADase activity, folate hydrolase activity, dipeptidyl dipeptidase IV activity, γ-glutamyl hydrolase activity, or combinations thereof.

Thus methods of screening for candidate agents that modulate at least one enzymatic activity of a PSMA enzyme are provided in accordance with the invention. The methods can include mixing the candidate agent with an isolated PSMA protein multimer to form a reaction mixture, thereby contacting the PSMA enzyme with the candidate agent. The methods also include adding a substrate for the PSMA enzyme to the reaction mixture, and determining the amount of a product formed from the substrate by the PSMA enzyme. Such methods are adaptable to automated, high-throughput screening of compounds. A decrease in the amount of product formed in comparison to a control is indicative of an agent capable of inhibiting at least one enzymatic activity of the PSMA enzyme. An increase in the amount of product formed in comparison to a control is indicative of an agent capable of enhancing at least one enzymatic activity of the PSMA enzyme. The PSMA enzyme can be NAALADase, folate hydrolase, dipeptidyl dipeptidase IV and/or γ-glutamyl hydrolase. The PSMA enzyme preferably is a PSMA multimer that includes recombinant soluble PSMA, most preferably a noncovalently associated dimer of PSMA in a native conformation.

The reaction mixture comprises a candidate agent. The candidate agent is preferably an antibody, a small organic compound, or a peptide, and accordingly can be selected from combinatorial antibody libraries, combinatorial protein libraries, or small organic molecule libraries. Typically, a plurality of reaction mixtures are run in parallel with different agent concentrations to obtain a different response to the various concentrations. Typically, one of these concentrations serves as a negative control, i.e., at zero concentration of agent or at a concentration of agent below the limits of assay detection.

Candidate agents encompass numerous chemical classes, although typically they are organic compounds, proteins or antibodies (and fragments thereof that bind antigen). In some preferred embodiments, the candidate agents are small organic compounds, i.e., those having a molecular weight of more than 50 yet less than about 2500, preferably less than about 1000 and, more preferably, less than about 500. Candidate agents comprise functional chemical groups necessary for structural interactions with polypeptides and/or nucleic acids, and typically include at least an amine, carbonyl, hydroxyl, or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random or non-random peptides, combinatorial libraries of proteins or antibodies, and the like. Alternatively, libraries of natural compounds in the form of bacterial, fungal, plant, and animal extracts are available or readily produced. Additionally, natural and synthetically produced libraries and compounds can be readily be modified through conventional chemical, physical, and biochemical means. Further, known agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc. which may be used to facilitate optimal protein-protein and/or protein-agent binding. Such a reagent may also reduce non-specific or background interactions of the reaction components. Other reagents that improve the efficiency of the assay such as protease inhibitors, nuclease inhibitors, antimicrobial agents, and the like may also be used.

The mixture of the foregoing reaction materials is incubated under conditions whereby, the candidate agent interacts with the PSMA enzyme. The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours.

After incubation, the presence or absence of PSMA enzyme activity is detected by any convenient method available to the user. For example, the reaction mixture can contain a substrate for the PSMA enzyme. Preferably the substrate and/or the product formed by the action of the PSMA enzyme are detectable. The substrate usually comprises, or is coupled to, a detectable label. A wide variety of labels can be used, such as those that provide direct detection (e.g., radioactivity, luminescence, optical, or electron density, etc) or indirect detection (e.g., epitope tag such as the FLAG epitope, enzyme tag such as horseradish peroxidase, etc.). The label may be bound to the substrate, or incorporated into the structure of the substrate.

A variety of methods may be used to detect the label, depending on the nature of the label and other assay components. For example, the label may be detected while bound to the substrate or subsequent to separation from the substrate. Labels may be directly detected through optical or electron density, radioactive emissions, nonradiative energy transfers, etc. or indirectly detected with antibody conjugates, streptavidin-biotin conjugates, etc. Methods for detecting a variety of labels are well known in the art.

EXAMPLES

Materials and Methods

DNA Constructs. All secreted PSMA constructs were derived from the original human PSMA clone P55A provided by Dr. W. D. W. Heston (Israeli et al., *Cancer Res.* 53: 227-230, 1993). The constructs were subcloned into expression vector PPI4 (Trkola et al., *Nature* 384: 184-187, 1996) for high-level expression and secretion in mammalian cells. Recombinant soluble PSMA (rsPSMA) corresponds to the entire extracellular domain of PSMA (amino acids 44-750 of SEQ ID NO:1 (GENBANK Protein Accession number AAA60209)).

pcDNA Plasmid Constructs: Nucleic acid molecules encoding the anti-PSMA antibodies 10.3, 006, 026, 051, 069 and 077 were cloned into plasmid pcDNA. The cloning protocol is given in FIG. 12. Primers (SEQ ID NOs: 33-36, sense and anti-sense) used for the variable region amplifications are also shown. The plasmids constructed for anti-PSMA antibodies 006, 026, 051, 069, 077 and 10.3 contain nucleotide sequences encoding the heavy chain of the antibodies (SEQ ID NOs: 2-7; PTA-4403, PTA-4405, PTA-4407, PTA-4409, PTA-4411, PTA-4413, respectively) or contain nucleotide sequences encoding light chain of the antibodies (SEQ ID NOs: 8-13; PTA-4404, PTA-4406, PTA-4408, PTA-4410, PTA-4412 and PTA-4414, respectively). Plasmid maps are given in FIGS. 13-24.

Western Blots. Cells were lysed in PBS containing 1 mM EDTA, 1% NP-40, 1% TRITON X-100, and 5 mg/ml aprotinin and cell debris was removed by centrifugation at 3000 g for 30 min at 4° C. Lysates were separated on a 5-20% gradient gel before transfer to nitrocellulose membranes. The resulting blots were blocked in PBS containing 5% milk, 0.02% SDS and 0.1% TRITON X-100 before incubation with MAB544 primary antibody (Maine Biotechnologies) at a concentration of 2 mg/ml. After three washes, blots were incubated with a goat anti-mouse HRP-conjugated secondary antibody at a concentration of 0.2 mg/ml. Blots are visualized using the Renaissance chemiluminescence system (Perkin-Elmer Life Sciences, Boston, Mass.).

ELISA. Cells were lysed in PBS containing 1 mM EDTA, 1% NP-40, 1% TRITON X-100, and 5 mg/ml aprotinin. The resulting cell membranes were plated onto 96-well plates and dried in a sterile hood overnight. The plates were then blocked with PBS containing casein and TWEEN 20 before addition of mouse sera or hybridoma supernatants, using purified MAB544 (Maine Biotechnologies) or 7E11 (Cytogen) as a standard. After washing in PBS, an alkaline phosphatase conjugated secondary antibody (subclass specific) was incubated and subsequently washed in PBS. The pNPP substrate was then added for colorimetric detection at a wavelength of 405 nm.

Flow Cytometry. Wild-type 3T3 or PSMA-expressing 3T3 cells ($10^6$ cells per condition) were washed in PBS containing 0.1% $NaN_3$. Antibodies or sera were then added (1:100 dilution in PBS) and incubated on ice for 30 minutes. After washing in PBS+0.1% $NaN_3$, the cells were incubated with anti-mouse IgG+IgM (Calbiotech) for 30 minutes on ice. Cells were washed again in PBS+0.1% $NaN_3$ and analyzed by flow cytometry.

Example 1

Generation of a Panel of Monoclonal Antibodies (mAbs) to Conformational Epitopes on PSMA A panel of anti-PSMA mAbs that represent promising candidates for therapy was created. Briefly, the mAbs were generated as follows: BALB/c mice were immunized subcutaneously with recombinant PSMA at approximately three-week intervals. After a total of 4 injections, mice were sacrificed and their splenocytes fused with a myeloma cell line using standard techniques in order to create hybridomas. Individual hybridoma supernatants were screened by ELISA for reactivity with PSMA derived from either LNCaP human prostate tumor cells or from 3T3 cells engineered to express full-length human PSMA (3T3-PSMA cells). Positive clones were secondarily screened by flow cytometry for specific reactivity with intact 3T3-PSMA and LNCaP cells so as to select antibodies that recognize native, cell-surface PSMA and thus have the greatest therapeutic potential.

Mice having the ability to produce human antibodies (XenoMouse™, Abgenix; Mendez et al., Nature Genetics 15:146, 1997) were immunized subcutaneously once or twice weekly with $5 \times 10^6$ LNCaP cells adjuvanted with alum or Titermax™ Gold (Sigma Chemical Co., St. Louis, Mo.). Animals were boosted twice with 10 µg of recombinant PSMA protein immunoaffinity captured onto protein G magnetic microbeads (Miltenyi Biotec, Auburn, Calif.). PSMA mAb 3.11 was used for capture. Splenocytes were fused with NSO myeloma cells and the hybridomas that resulted were screened as above by flow cytometry to detect clones producing antibodies reactive with the extracellular portion of PSMA. One clone, 10.3 (PTA-3347), produced such antibodies.

Figure 2:
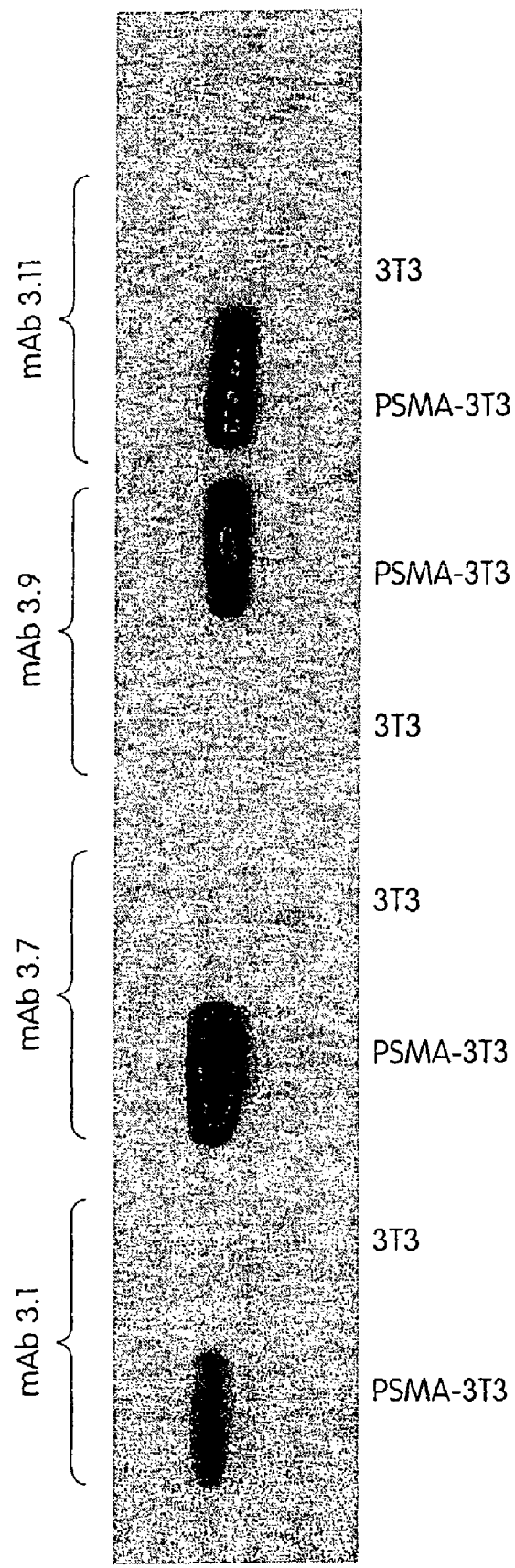
FIG. 2 shows a digitized image of immunoprecipitation of PSMA by mAbs. Lysates from 3T3-PSMA cells or parental 3T3 cells were incubated with each mAb and then precipitated using Protein A/G agarose beads. After washing, proteins were resolved on a polyacrylamide gel, blotted onto nitrocellulose membranes and visualized using the MAB544 anti-PSMA mAb.
Figure 3:
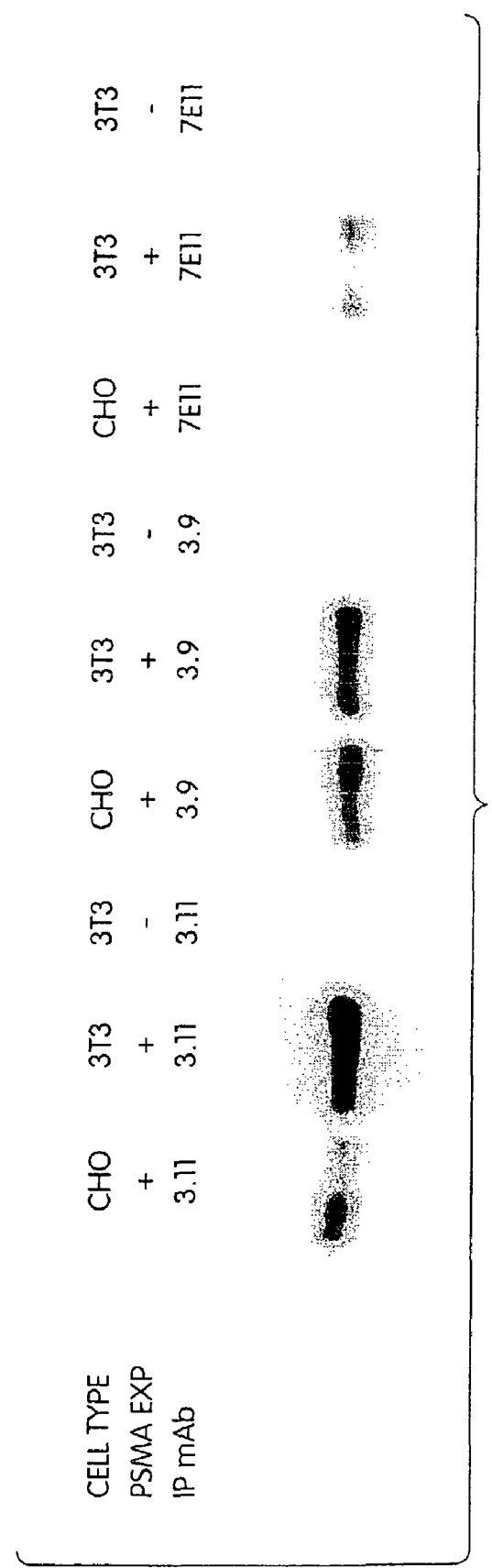
FIG. 3 shows the recognition of non-denatured PSMA by several PSMA antibodies that recognize PSMA conformation.

These methods have yielded a high proportion of mAbs that react exclusively with conformation-specific epitopes on cell-surface PSMA. As shown in FIG. 1, several (mAbs 3.7, 3.9, 3.11, 5.4, and 10.3) but not all (mAb 3.12) mAbs specifically bind viable PSMA-expressing cells. Using recombinant soluble PSMA proteins expressed in Chinese hamster ovary (CHO) cell lines, it further was demonstrated that the mAbs bind epitopes in the extracellular region of PSMA. The mAbs were also tested for their ability to immunoprecipitate native PSMA from 3T3-PSMA cell lysates. The mAbs positive in flow cytometry (FIG. 1) were also effective in immunoprecipitation (FIG. 2), whereas mAb 3.12 was unreactive. FIG. 3 shows the recognition of non-denatured full-length PSMA and recombinant soluble PSMA by several PSMA antibodies that recognize PSMA conformation. This further confirms that these methods yield a preponderance of mAbs that efficiently recognize native PSMA.

Figure 4:
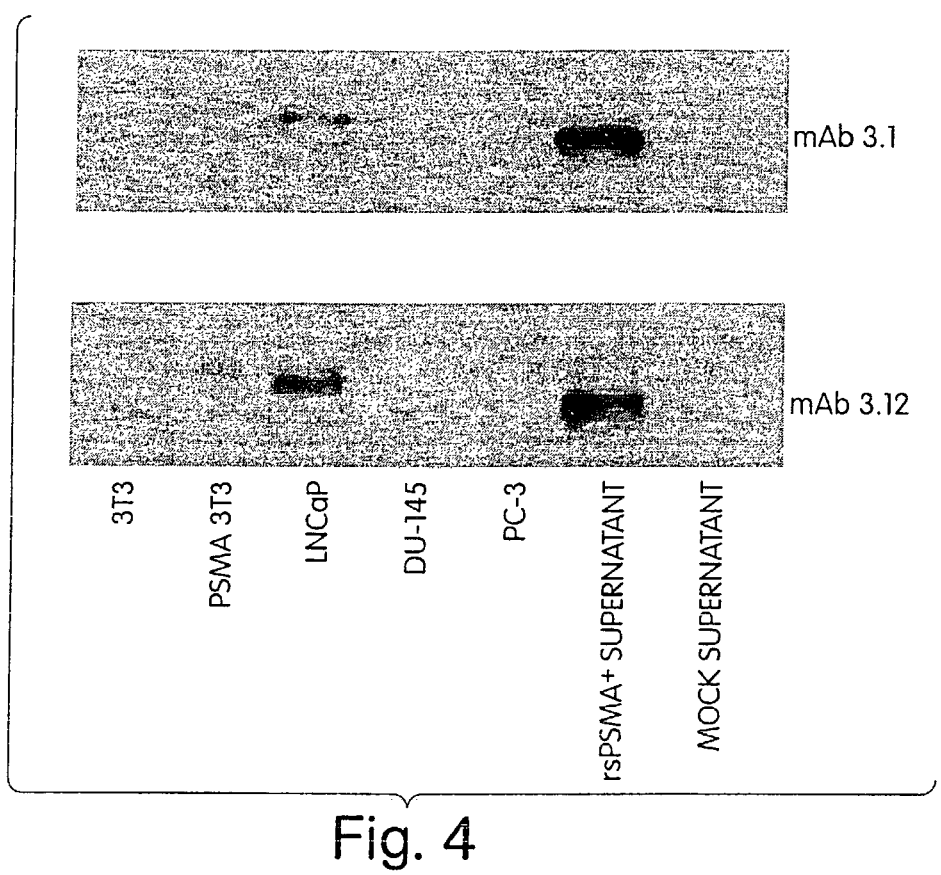
FIG. 4 is a digitized image of a Western blot that shows the recognition of denatured PSMA by two PSMA antibodies and shows that antibodies that recognize PSMA conformation do not recognize denatured PSMA.

The mAbs were tested for reactivity with denatured PSMA by Western blot analysis (FIG. 4). Lysates from the indicated cells and samples (controls: 3T3 cells, PSMA-negative human prostate cell lines PC-3 and DU145, mock supernatant; PSMA-positive samples: PSMA-expressing 3T3 cells, PSMA-positive human prostate cell line LNCaP, rsPSMA-positive supernatant) were resolved by SDS-PAGE, electroblotted, and probed with anti-PSMA mAbs 3.1 and 3.12 (ATCC Patent Deposit Designations PTA-3639 and PTA-3640, respectively). Four mAbs tested in parallel (3.7, 3.8, 3.9, 3.11) showed no reactivity to either full-length or secreted rsPSMA proteins. 7E11 mAb immunoprecipitated full-length but not secreted rsPSMA.

The mAbs reactive in flow cytometry and immunoprecipitation (mAbs 3.7, 3.9, 3.11, 5.4, and 10.3) were all unreactive in Western blot analysis, indicating that the mAbs do not recognize linear epitopes. Taken together, the data strongly suggest that these 5 mAbs recognize conformation-specific epitopes located in the extracellular domain of PSMA. Since mAbs to conformational epitopes typically possess the greatest affinity and specificity for antigen, they represent preferred candidates for therapy.

The reactivities of certain anti-PSMA antibodies are described in Table 2:

TABLE 2

Anti-PSMA Antibody Properties

| mAb | Reactivity | | | | Epitope |
|-----|-------|----------------|----|---------|---------|
|     | ELISA | Flow Cytometry | IP | Western |         |
| 3.1 | + | + | + | + | Linear, Extracellular, exposed on native PSMA |
| 3.7 | + | + | + | − | Conformational, extracellular |
| 3.8 | + | + | + | − | Conformational, extracellular |
| 3.9 | + | + | + | − | Conformational, extracellular |
| 3.11 | + | + | + | − | Conformational, extracellular |
| 3.12 | + | − | − | + | Linear, Extracellular, not exposed on native PSMA |
| 5.4 | + | + | + | − | Conformational, extracellular |
| 7.1 | + | − | − | + | Linear, Extracellular, not exposed on native PSMA |
| 7.3 | + | + | + | − | Conformational, extracellular |
| 10.3 | + | + | + | − | Conformational, extracellular |
| 1.8.3 | + | + | | − | Extracellular |
| A3.1.3 | + | + | | − | Extracellular |
| A3.3.1 | + | + | | − | Extracellular |

The mAbs were determined by ELISA to be primarily of the mouse IgG2a, mouse IgG2b and human IgG1 isotypes, which mediate potent effector functions. Although a number of anti-PSMA mAbs have been described over the years and evaluated for therapeutic potential (see, e.g., Liu, H. et al. Cancer Res. 57: 3629-3634, 1997; Chang, S. S. et al. Cancer Res. 59: 3192-3198, 1999; Murphy, G. P. et al. J Urology 160: 2396-2401, 1998), none inhibit the enzymatic activity of PSMA and few recognize conformational determinants on PSMA.

Example 2

Production of Anti-PSMA mAbs

To accurately and quantitatively assess the therapeutic potential of these mAbs, the mAbs are produced in a quantity and quality suitable for extensive in vitro and in vivo characterization. Briefly, the mAb-secreting hybridomas are cultured in roller bottles in DMEM/F12 medium supplemented with 10% FBS that has been depleted of bovine IgG (Life Technologies). During the production phase of the culture, cells are maintained at ~$5 \times 10^6$ cells/mL via twice-weekly exchanges of media. Collected media are clarified by filtration through a 0.22 micron filter and stored at −95° C. prior to purification. Given an average antibody expression levels of ~25 mg/L, approximately 3L of roller bottle supernatants are required for each antibody to allow for losses in purification.

Culture supernatants from a given hybridoma are pooled and loaded onto a Protein A SEPHAROSE affinity column. Mouse IgG2a, mouse IgG2b and human IgG1 antibodies are loaded directly, but supernatants containing mouse IgG1 antibodies are adjusted to pH 8.5 and 1M NaCl prior to loading in order to promote binding. After washing the column, the mAb is eluted with low pH buffer into fractions using 1M Tris, pH 8.0. Elution peak fractions are pooled, dialyzed against PBS buffer, concentrated to 5 mg/mL and stored in sterile aliquots at −95° C. All purification procedures are carried out using endotoxin-free buffers and sanitized chromatography columns. Purified mAbs are tested for purity by reducing and nonreducing SDS-PAGE, for PSMA binding affinity by ELISA, and for endotoxin levels by the limulus amebocyte lysate assay. These procedures routinely yield "animal-grade" antibody at >95% purity and <0.5 endotoxin units per milligram of protein.

Example 3

Evaluation of the Therapeutic Potential of the Unlabeled mAbs In Vitro

Purified mAbs are tested in a battery of assays for therapeutically relevant properties, including affinity, specificity, enzyme inhibitory activity and effector functions. The ideal product candidate binds and inhibits PSMA activity at sub-nanomolar concentrations and mediates potent cell-killing through Fc-related effector functions.

First, the mAbs' affinity for cell-surface and secreted forms of PSMA is measured by flow cytometry and ELISA, respectively. In the flow cytometry assay, varying amounts of mAbs are incubated with $5 \times 10^5$ 3T3-PSMA cells in FACS buffer (PBS containing 1% FBS and 0.1% $NaN_3$) for 2 hr to allow for saturation binding. Cells are washed and incubated with a phycoerythrin-coupled goat antibody to mouse IgG (ICN/Cappel) for detection of bound mAb by flow cytometry. Specific binding is calculated by subtracting the fluorescence intensity observed with parental 3T3 cells.

For ELISA, CHO cell-derived recombinant soluble PSMA protein (rsPSMA, Progenics, Tarrytown, N.Y.) is diluted to 1 µg/ml in 50 mM carbonate buffer, pH 9.4, and coated overnight at 4° C. onto 96-well IMMULON II microtiter plates at 100 µl well. The plates are then blocked for 2 hr with PBS buffer containing 5% BSA. mAbs are added in a range of concentrations in ELISA buffer (PBS buffer containing 2% BSA, 1% FBS and 0.5% TWEEN 20) for 2 hours at room temperature. The plates are washed, and horseradish peroxidase conjugated goat antibody to mouse IgG is added for 1 hr at room temperature. The plates are washed again and 3,3',5,5'-tetramethylbenzidine dihydrochloride (TMB) substrate (Pierce, Rockford, Ill.) is added for colorimetric readout at 450 nm using an ELISA plate reader (Molecular Devices, Sunnyvale, Calif.).

Example 4 mAb Cross-Competition Binding Assay

To identify whether a given group of mAbs recognize distinct or overlapping epitopes on PSMA, cross-competition binding assays are performed (Liu, H. et al. Cancer Res 57: 3629-3634, 1997). In this flow cytometry assay, a biotinylated test mAb is incubated with 3T3-PSMA cells in the presence or absence of varying concentrations of unlabeled competitor mAbs as described above. Following washing, phycoerythrin-conjugated streptavidin is added to determine the amount of bound biotinylated mAb. The percent inhibition is defined relative to that observed in the presence of an isotype-matched mAb of irrelevant specificity (0% inhibition) and to that observed using excess unlabeled test mAb (100% inhibition).

Example 5

Effects of mAbs on PSMA Enzymatic Activity

PSMA has been shown to possess both folate hydrolase (pteroyl-glutamyl carboxypeptidase) and N-acetylated α-linked acidic dipeptidase (NAALADase) enzymatic activities, which may influence the proliferation and malignancies of the tumor cell (Heston, W. D. W. Prostate. Basic and Clinical Aspects (R. K. Naz, ed.). CRC Press, New York: 219-243, 1997). A first set of mAbs described above (mAb 3.9, mAb 5.4 and mAb 7.3) and mAb J591 (ATCC #HB-12126) were tested for folate hydrolase modulating activity using previously described assays for measuring PSMA enzymatic activity (Pinto, J. T. et al. Clinical Cancer Res 2: 1445-1451, 1996).

Briefly, folate hydrolase activity was measured as follows. Fifty µM methotrexate di-gamma glutamate and 10 µg/ml rsPSMA (premixed with anti-PSMA or irrelevant mAb) was incubated in pH 4.5 acetate buffer in a volume of 100 µl for 2 hr at 37° C. Reactions were terminated by boiling for 5 minutes prior to separation of free, mono- and di-gamma glutamate forms of methotrexate by capillary electrophoresis on a Spectra Phoresis 1000 (Thermo Separation, San Jose, Calif.). The various methotrexate derivatives were quantified based on their retention times and absorbance at 300 nm.

Figure 7:
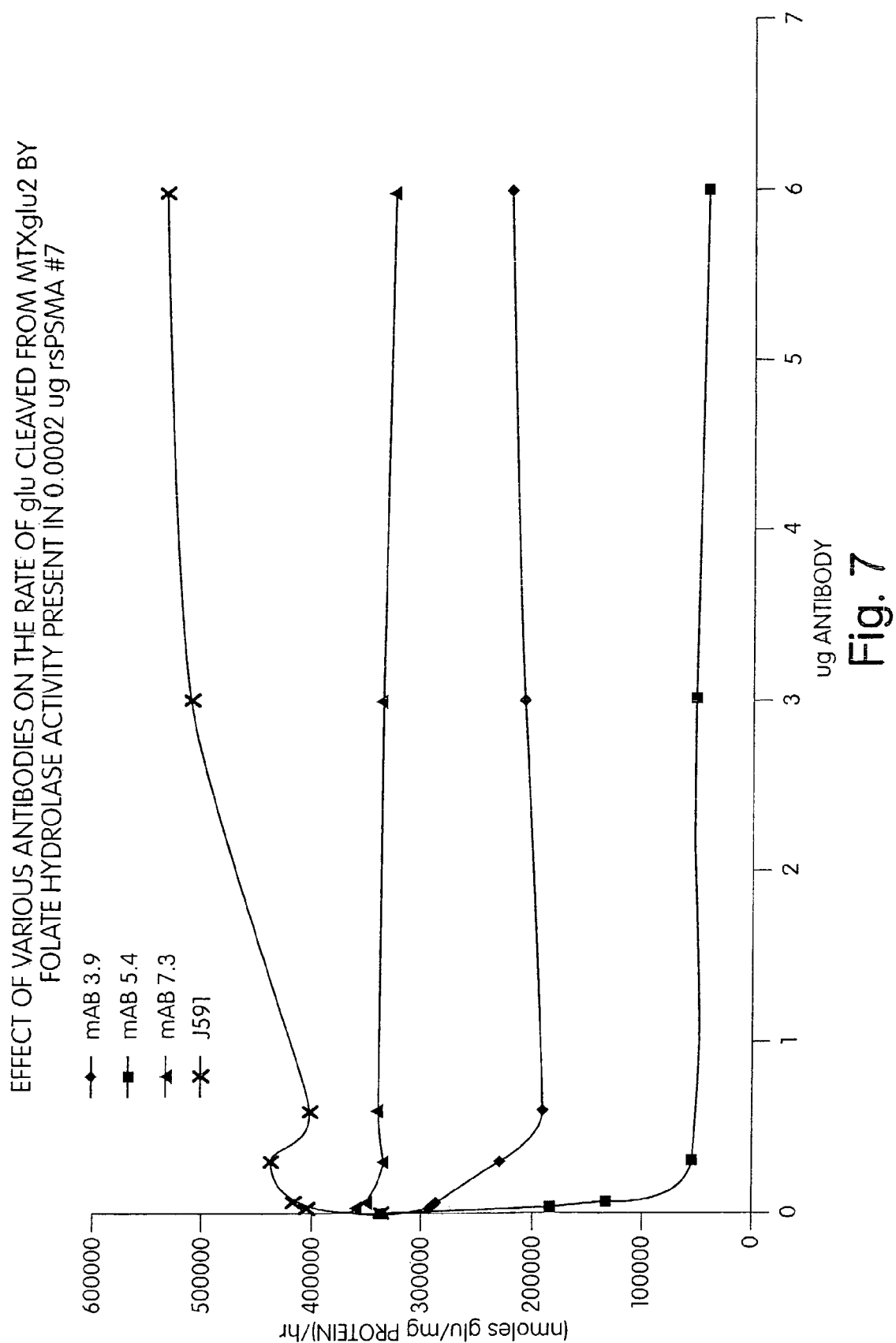
FIG. 7 shows the effect of four antibodies (mAb 3.9, mAb 5.4, mAb 7.3 and mAb J591) on the enzymatic activity of folate hydrolase through measuring the rate of cleavage of glutamate from methotrexate di-gamma glutamate by folate hydrolase present in 0.0002 µg rsPSMA #7.
Figure 8:
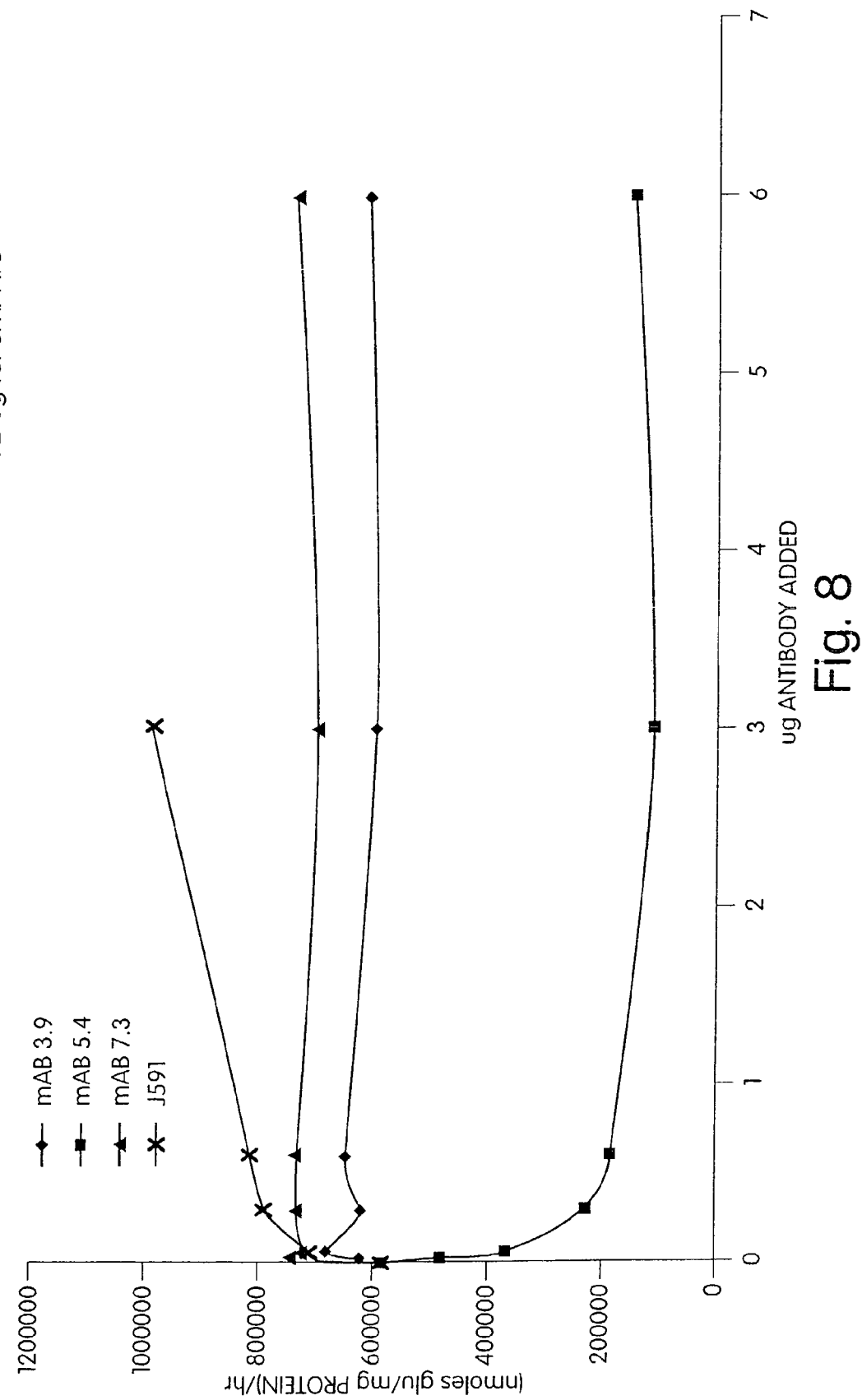
FIG. 8 shows the effect of four antibodies (mAb 3.9, mAb 5.4, mAb 7.3 and mAb J591) on the enzymatic activity of folate hydrolase through measuring the rate of cleavage of glutamate from methotrexate di-gamma glutamate by folate hydrolase present in 0.0002 µg rsPSMA #8.
Figure 9:
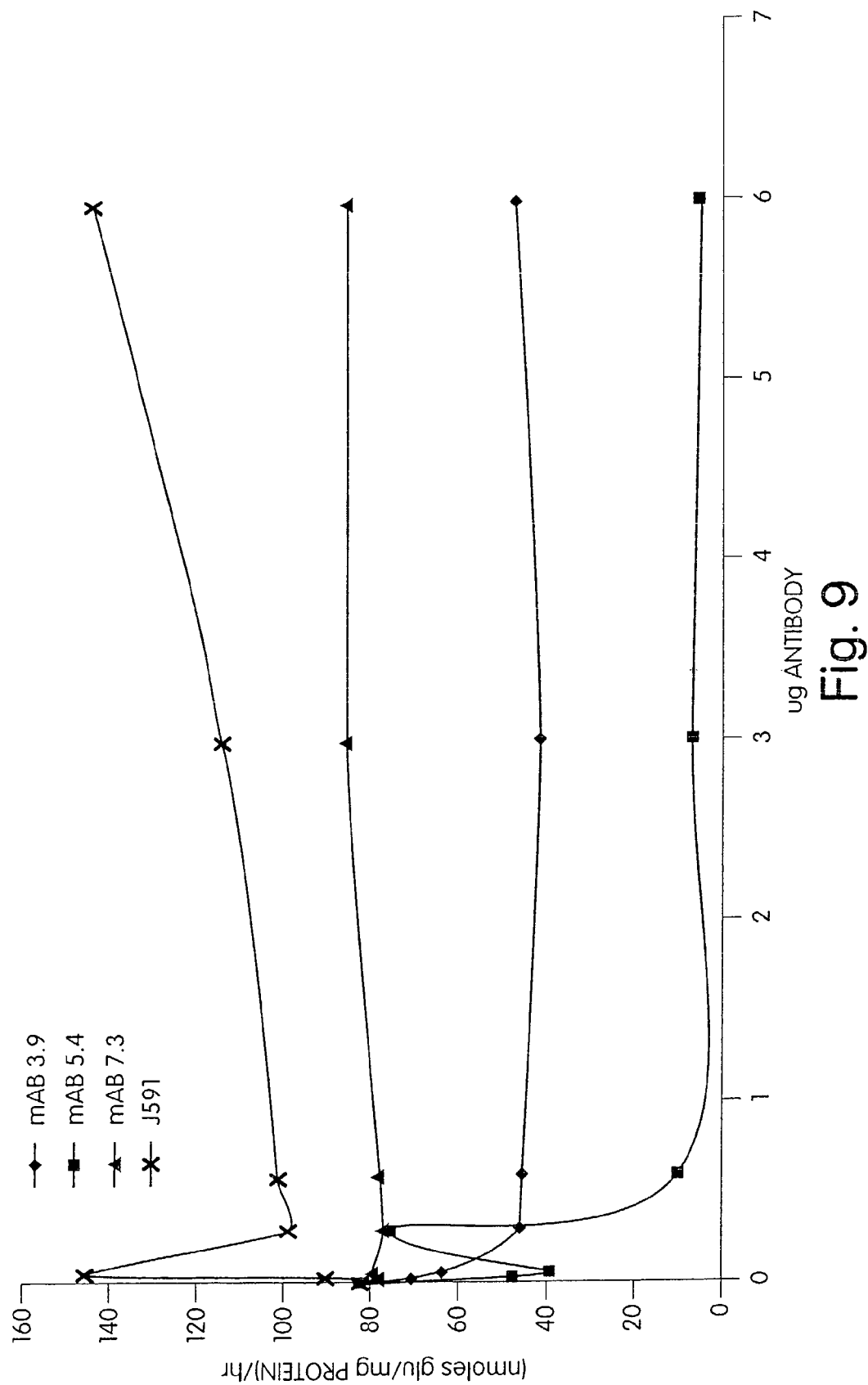
FIG. 9 shows the effect of four antibodies (mAb 3.9, mAb 5.4, mAb 7.3 and mAb J591) on the enzymatic activity of folate hydrolase through measuring the rate of cleavage of glutamate from methotrexate di-gamma glutamate by folate hydrolase present in lysates of C4-2 cells.

The data show that mAb 5.4 potently blocks the enzymatic activity of purified rsPSMA protein and in lysates of C4-2 cells. C4-2 is an androgen independent derivative of the LNaCP cell line (human prostate cancer line) which expresses endogenous PSMA. More details regarding the C4-2 cell line may be found in O'Keefe D. S. et al. Prostate 45: 149-157, 2000). FIGS. 7 and 8 provide the results for two production lots of rsPSMA (rsPSMA #7 and rsPSMA #8). The results for the C4-2 cell lysates are shown in FIG. 9. The figures illustrate the effect of four antibodies (mAb 3.9, mAb 5.4, mAb 7.3 and mAb J591) on the enzymatic activity of folate hydrolase by way of the rate of cleavage of glutamate from methotrexate di-gamma glutamate (MTXGlu2) by folate hydrolase present in the two production lots of rsPSMA and in the C4-2 cell lysates. In addition to the inhibitory effects of mAb 5.4, mAb 3.9 was also found to inhibit folate hydrolase activity.

Figure 10:
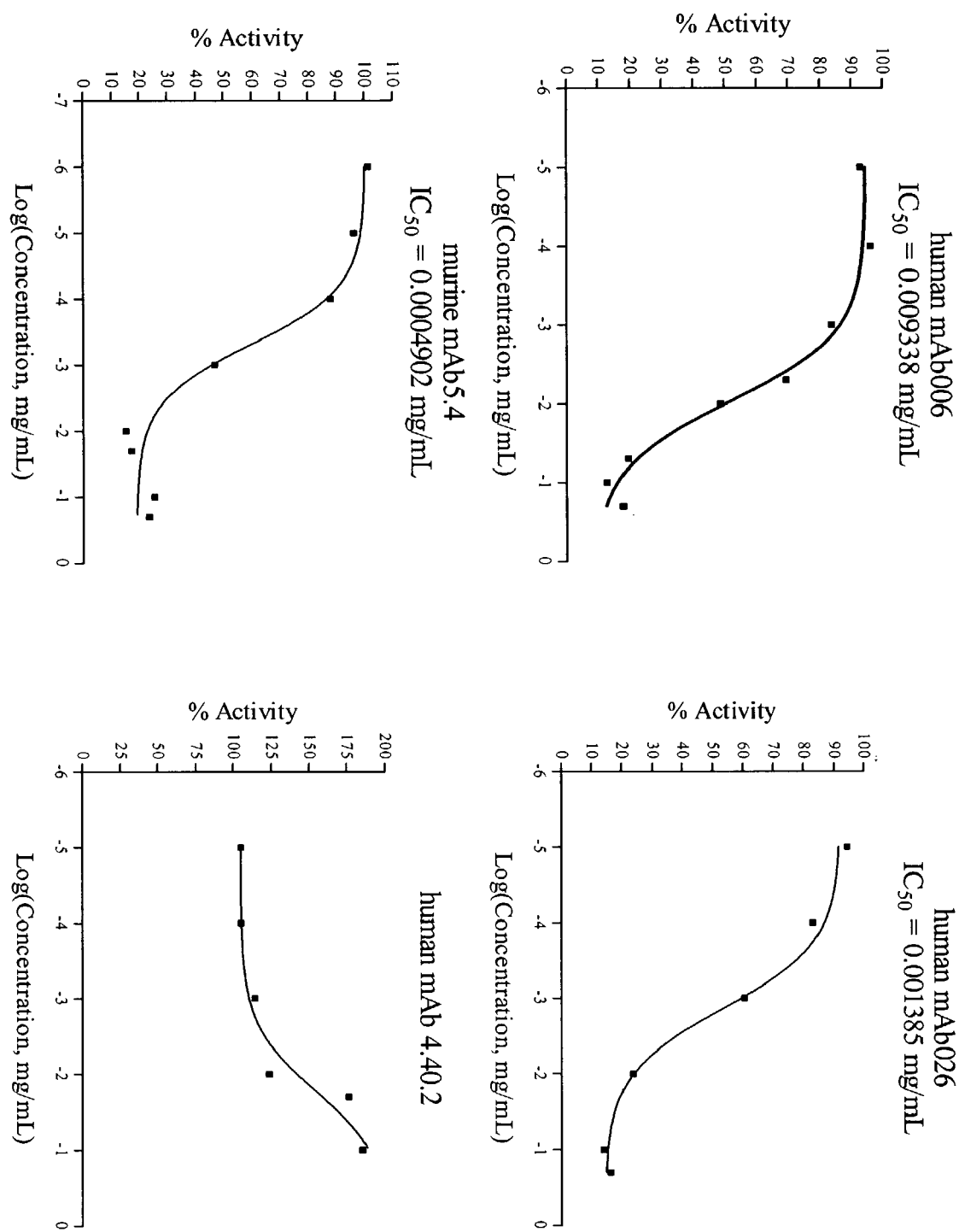
FIG. 10 shows the impact of four antibodies (human mAbs 006, 026 and 4.40.2 as well as murine mAb 5.4) on PSMA folate hydrolase activity.

Another set of mAbs (mAb 4.40.2, mAb 006, mAb 026 and mAb 5.4) was also tested for folate hydrolase modulating activity. The data confirm that mAb 5.4 potently blocks folate hydrolase activity of PSMA (FIG. 10). The concentration of mAb 5.4 which inhibited PSMA enzymatic activity by 50% (IC50, also referred to as EC50 or "effective concentration") was determined to be $4.902 \times 10^{-4}$ mg/mL. The data further show that mAb 006 and mAb 026 also block PSMA folate hydrolase activity, while mAb 4.40.2 did not (FIG. 10). The IC50 values for mAb 006 and mAb 026 were $9.338 \times 10^{-3}$ mg/mL and $1.385 \times 10^{-3}$ mg/mL, respectively.

For NAALADase activity assays, rsPSMA protein is incubated with varying amounts of anti-PSMA or control mAbs in 50 mM Tris pH 7.4, mM $CoCl_2$ for 10 minutes at 37° C. before adding 50 µl of 0.6 µM N-acetylaspartyl-[$^3$H]glutamate. After 15 minutes, the reaction is stopped by adding 1 ml of 100 mM $NaPO_4$. Cleaved glutamate is separated from the substrate by ion exchange chromatography and detected by scintillation counting. Each measurement is performed in triplicate.

Example 6

Reactivity with Normal and Malignant Human Tissues by Immunohistochemistry

Anti-PSMA mAbs are tested by immunohistochemistry for reactivity with both normal and malignant human tissues using an avidin-biotin peroxidase method (Silver, D. A. et al. Clin Cancer Res 3: 81-85,1997). Frozen or paraffin-embedded tissues can be used. Paraffin-embedded tissue sections are deparaffinized and endogenous peroxidase activity is blocked by incubation with 1% $H_2O_2$ for 15 minutes. Sections are blocked in a 1:10 dilution of horse serum in 2% PBS-BSA (Sigma Chemical, St Louis, Mo.) for 30 minutes before overnight incubation with 2 µg/ml anti-PSMA mAb in 2% PBS-BSA. After washing, sections are incubated with biotinylated secondary antibody, washed, and incubated with avidin:biotin peroxidase complexes (Vector Laboratories, Burlingame, Calif.) diluted 1:25 in PBS for 30 minutes. After washing, sections are visualized by immersion in PBS containing 0.05% diaminobenzidine tetrachloride, 0.01% $H_2O_2$, and 0.5% TRITON X-100. Negative control sections are incubated with isotype-matched mAbs of irrelevant specificity. As a positive control, 7E11 (Cytogen, Princeton, N.J.), a well-characterized anti-PSMA mAb, is used.

Example 7

Antibody-Dependent Cellular Cytotoxicity (ADCC)

In the ADCC assay, mAbs are serially diluted and combined with $^{51}$Cr-labeled 3T3-PSMA cells or human prostate PC-3 cells that have been engineered to express human PSMA (PC-3-PSMA cells). NK effector cells are purified from lymph nodes or spleens using anti-NK microbeads (Miltenyi Biotec). Sera, NK effector cells, and $^{51}$Cr-loaded target cells are co-incubated at effector:target cell ratios of 10:1, 20:1, and 40:1, with each condition performed in triplicate. Cells are incubated 4-5 hours at 37° C. before supernatants are collected for measurement of $^{51}$Cr release by gamma counting. The percent specific lysis is determined relative to that observed in the presence of isotype-matched non-specific mAb (0% lysis) to that obtained using 10% sodium dodecyl sulfate (100% lysis).

Example 8

Complement-Mediated Lysis (CML)

For CML, $^{51}$Cr-loaded 3T3-PSMA or PC-3-PSMA cells serve as target cells. Serial dilutions of mAbs are co-incubated with rabbit complement and target cells for 4-5 hours at 37° C., with each condition being performed in triplicate. Supernatants are then collected and counted with a gamma counter. Specific lysis is computed as previously done with the ADCC assay data.

Example 9

Anti-Proliferative Effects

To test anti-proliferative effects of these antibodies, anti-PSMA mAbs are serially diluted and incubated with LNCaP, PC-3-PSMA and parental PC-3 cells in log-phase growth. At 4 hr, 24 hr, and 72 hr intervals, cells are removed and analyzed for density and viability by trypan blue staining and WST-1 assay (Roche Biochemicals).

Example 10

Optimization of Chelation and Radiolabeling Procedures

The most promising mAbs identified using the procedures described in the foregoing examples will be optimized for biochemical and biological stability and activity after labeling prior to evaluation in animals. Success in in vitro experiments is defined as identification of a radiolabeled mAb that specifically kills PSMA-expressing tumor cells at >10-fold lower concentrations than unlabeled or similarly labeled isotype control mAb.

Because the preferred α- and β-emitting isotopes are all radiometals, each of the mAbs is first conjugated with an appropriate metal chelating agent. Based on the favorable in vivo stability data and its proven use in human clinical trials, the bifunctional chelating agent C-functionalized trans cyclohexyldiethylenetriaminepentaacetic acid (p-SCN-CHX-A"-DTPA) is the preferred agent for attaching either $^{90}$Y or $^{213}$Bi to the antibody (Brechbiel, M. W. et al. *J. Chem. Soc. Chem. Commun.* 1169-1170, 1991). A form of this chelate has previously been tested in more than 70 doses in humans in ongoing trials at Memorial-Sloan Kettering Cancer Center (McDevitt, M. R. et al. *J. Nucl. Med.* 40:1722-1727, 1999). For $^{225}$Ac, our initial studies will examine a novel bifunctional chelating agent termed p-SCN-Bz-HEHA (1,4,7,10,13,16-hexaazacyclooctadecane-N,N',N",N'",N"",N""'-hexaacetic acid) (Deal, K. A. et al. *J. Med. Chem.* 42:2988-2992, 1999). The objective is to optimize the antibody conjugation and chelation ratios to maximize labeling yield and activity while maintaining suitable stability for in vivo utilization. Additional chelating agents also are used as they become available from the N.I.H. and other sources.

Initially, the antibody is rendered metal-free by incubation with a large molar excess of EDTA at pH=5. The EDTA and any metals scavenged from the antibody preparation are removed via continuous buffer exchange/dialysis so as to replace the pH=5 buffer with the conjugation buffer (Nikula, T. K. et al. *Nucl. Med. Biol.* 22:387-390, 1995). Conditions that yield optimal chelator to antibody ratio but still remain immunoreactive are identified by systematically varying the chelator:antibody ratio, reaction time, temperature, and/or buffer systems about initial conditions that employ a 40-fold molar excess of chelator to antibody in HEPES buffer, pH 8.5. The number of chelates bound per antibody is determined using an established spectrophotometric method (Pippin, C. G. et al. *Bioconjugate Chemistry* 3: 342-345, 1992).

For $^{90}$Y and $^{225}$Ac constructs, labeling efficiency is measured directly. For $^{213}$Bi, initial antibody constructs are tested for chelation efficiency using $^{111}$In, which has similar chelation chemistry as $^{213}$Bi but possesses the advantages of a longer half life ($t_{1/2}$=3 days), ready availability, and traceable γ-emission. Once optimized using $^{111}$In, labeling efficiency is determined for $^{213}$Bi.

Radiolabeled mAb is purified over a BioRad 10DG desalting column using 1% HSA as the mobile phase and evaluated by instant thin layer liquid chromatography (ITLC) and/or high performance liquid chromatography (HPLC) to determine the percent incorporation of radionuclide (Zamora, P. O. et al. *Biotechniques* 16: 306-311, 1994). ITLC and HPLC provide a means of establishing purity and identifying the percent of low molecular weight radiochemical impurities (i.e., metal chelates, colloids, and free metal). Duplicate ITLC strips for each mobile phase are developed, dried, and cut at the $R_f$ of 0.5 mark and counted in a gamma counter. The HPLC system is equipped with both an online UV absorption detector and radioactivity detector. The HPLC elution profile directly correlates radioactivity with protein and low molecular weight species as a function of the elution time. A TSK SW3000$_{XL}$ column (TosoHaas, Montgomeryville, Pa.) is used and calibrated using a range of protein molecular weight standards.

Example 11

Affinity and Immunoreactivity of Radiolabeled mAbs

Once radiolabeled constructs are obtained, purified, and assessed for biochemical and radiochemical purity, biological activity is determined. Binding activity of the radioconstruct is performed by Scatchard analysis of binding data obtained using whole LNCaP and 3T3-PSMA cells and/or membrane fractions as previously described (Scheinberg, D. A. et al. *Leukemia* 3: 440-445 (1991).

The immunoreactivity of the synthetic constructs is evaluated in order to correlate the chelate:antibody molar ratio with the biological activity. Briefly, 2 ng of labeled mAb is incubated with a ~25-fold excess of PSMA as expressed on 3T3-PSMA cells. After a 30 min incubation at 0° C., the cells are collected by centrifugation and the supernatant containing unbound mAb is added to fresh 3T3-PSMA cells for an additional 30 min at 0° C. Both sets of cells are centrifuged and washed twice with cold PBS. The cell pellets, supernatant and wash fractions are counted for radioactivity. Immunoreactivity is defined as the amount of radioactivity in the cell pellets divided by the total radioactivity in the cell pellets, supernatant and wash fractions.

Example 12 mAb Internalization

Figure 11:
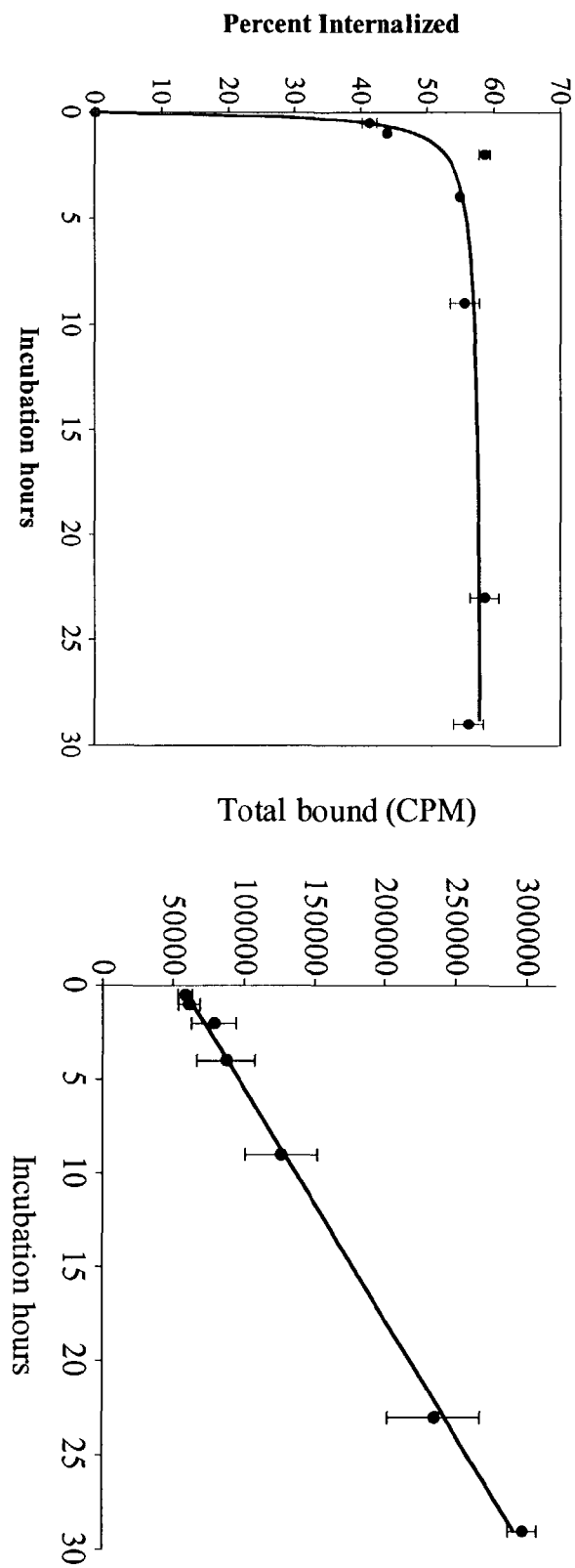
FIG. 11 illustrates the rapid and efficient internalization of $^{111}$In labeled mAb 026 incubated with C4-2 cells.
Figure 13:
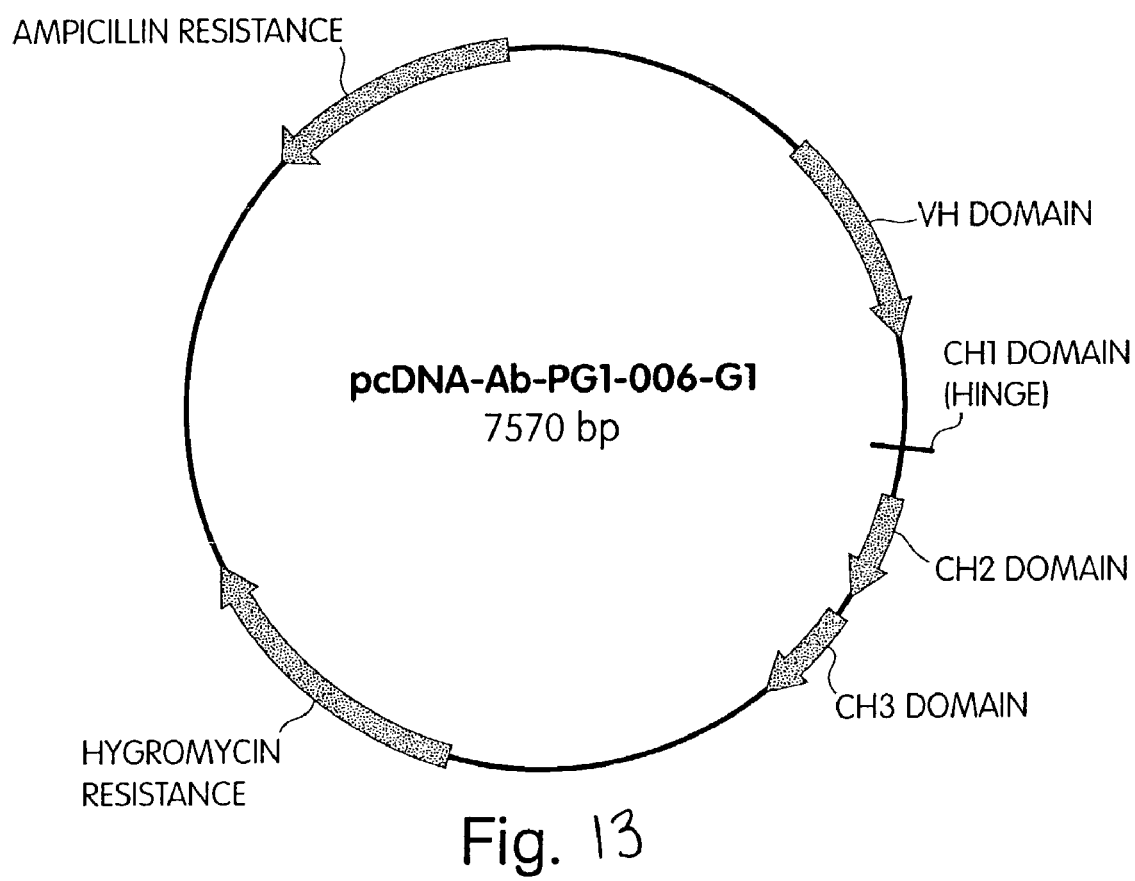
FIG. 13 provides the plasmid map of a nucleic acid molecule encoding the heavy chain of antibody AB-PG1-XG1-006.
Figure 14:
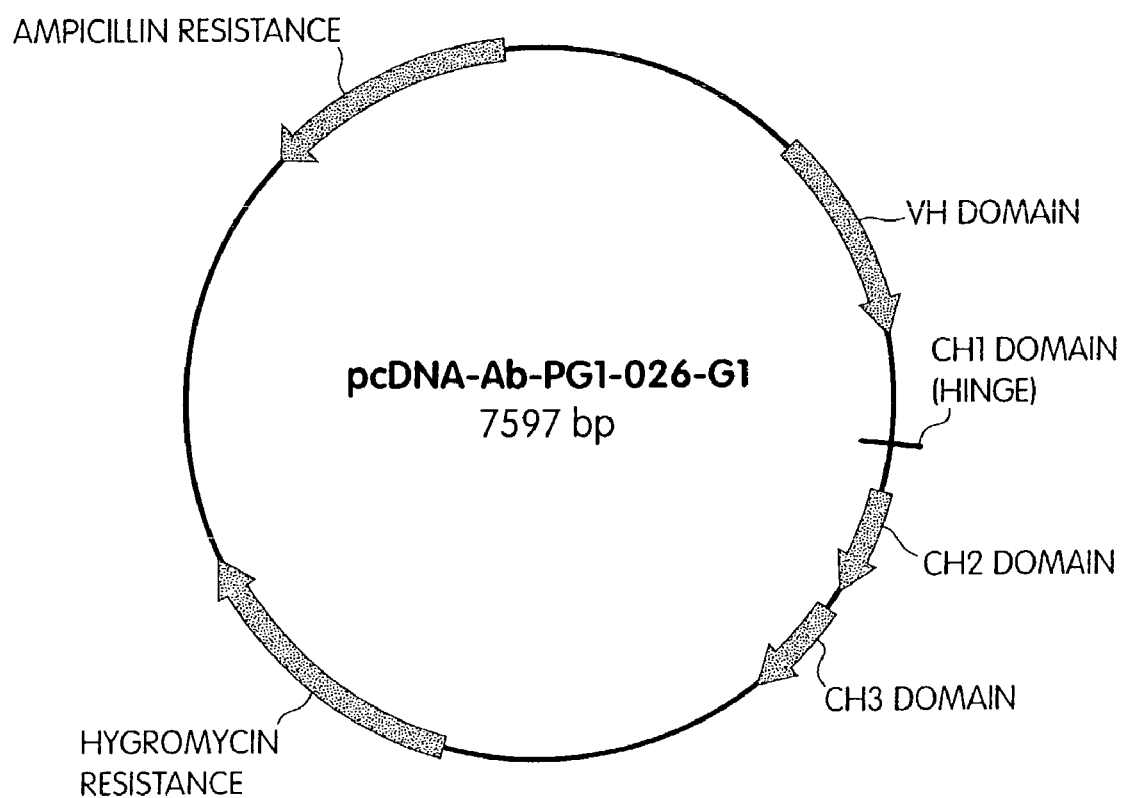
FIG. 14 provides the plasmid map of a nucleic acid molecule encoding the heavy chain of antibody AB-PG1-XG1-026.
Figure 15:
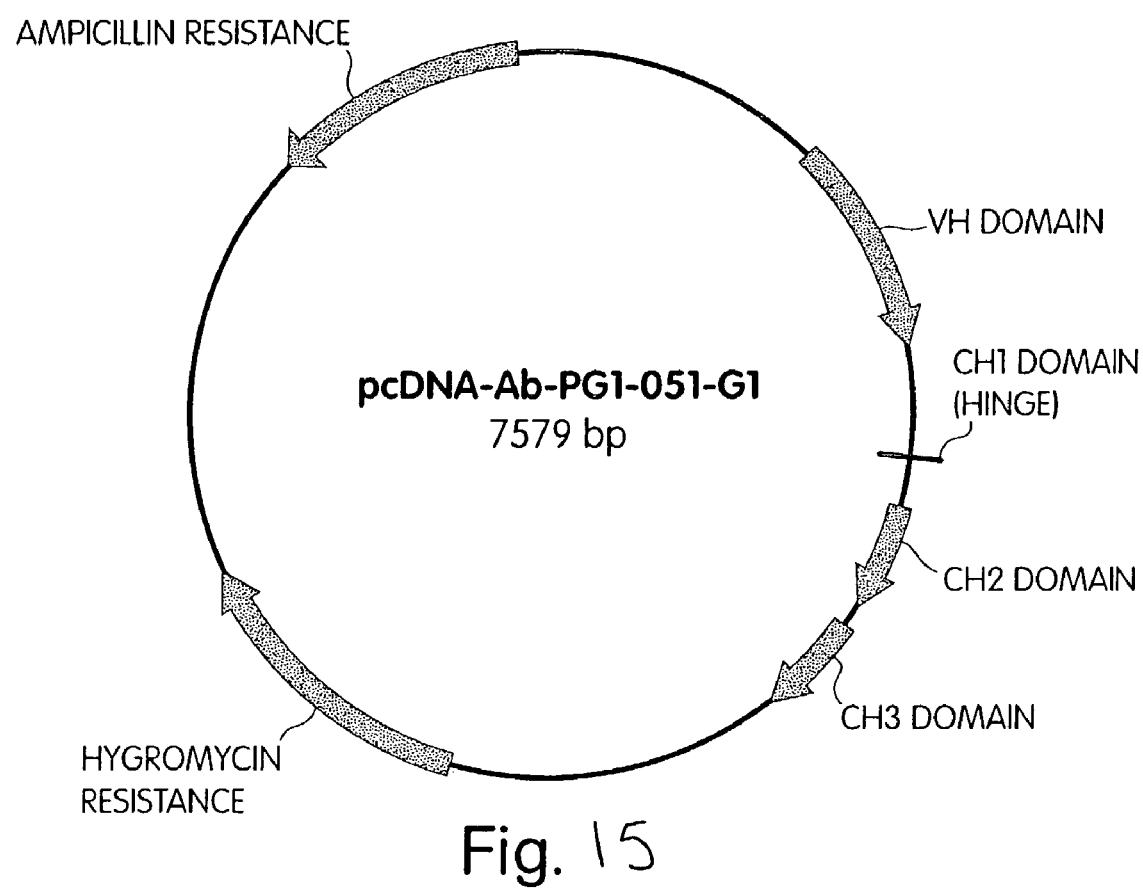
FIG. 15 provides the plasmid map of a nucleic acid molecule encoding the heavy chain of antibody AB-PG1-XG1-051.
Figure 16:
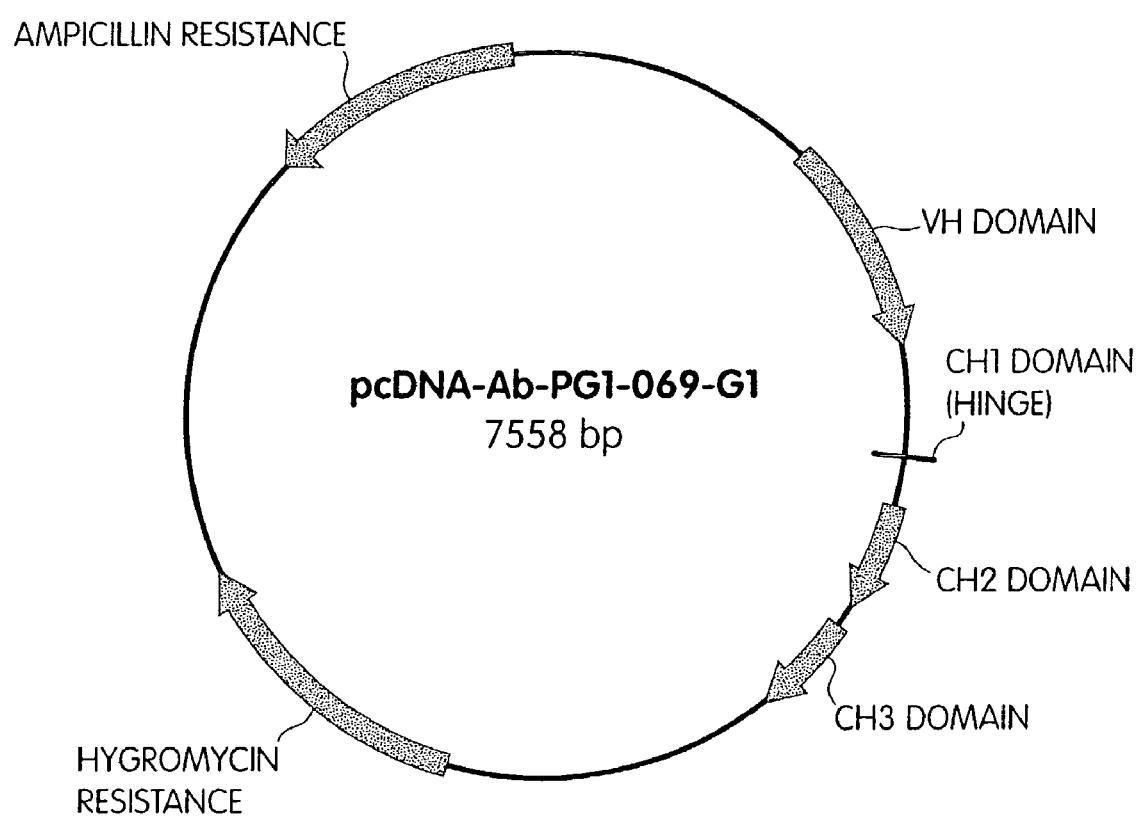
FIG. 16 provides the plasmid map of a nucleic acid molecule encoding the heavy chain of antibody AB-PG1-XG1-069.
Figure 17:
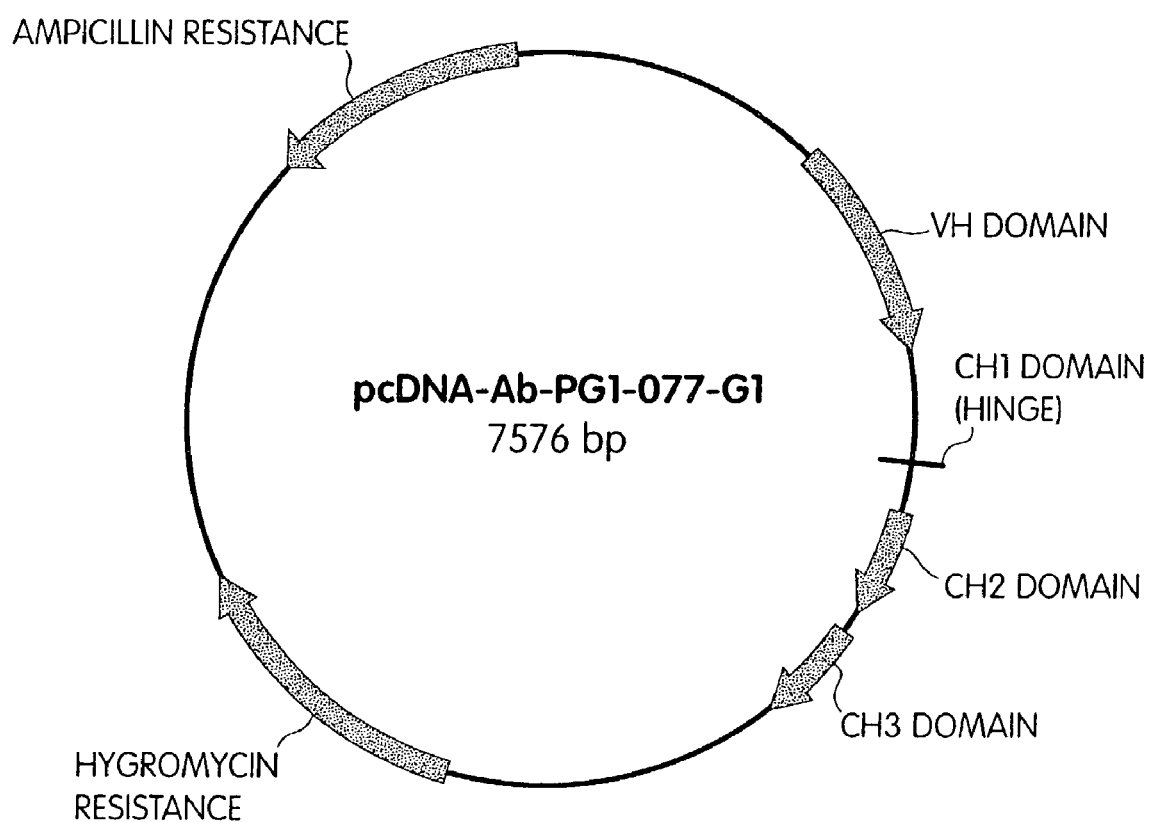
FIG. 17 provides the plasmid map of a nucleic acid molecule encoding the heavy chain of antibody AB-PG1-XG1-077.
Figure 18:
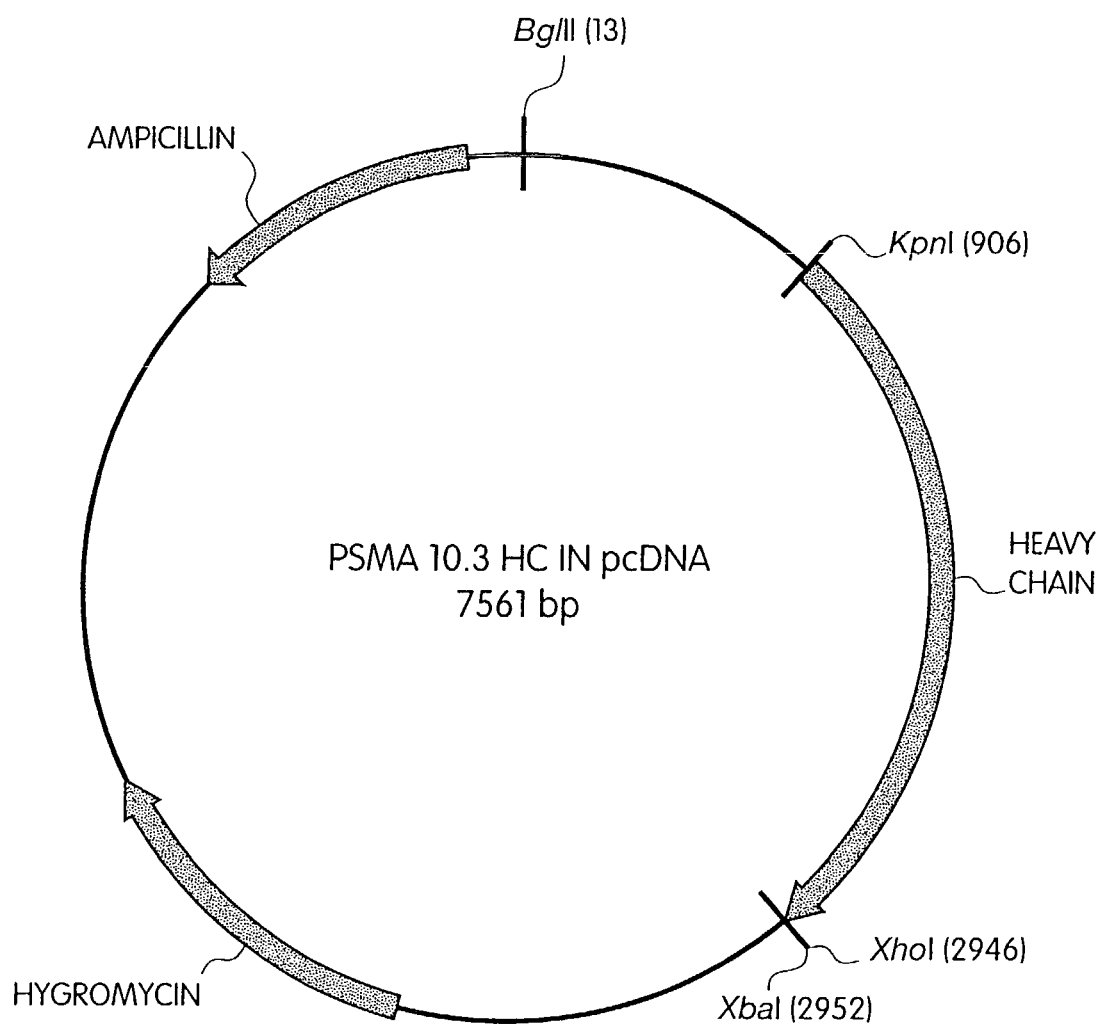
FIG. 18 provides the plasmid map of a nucleic acid molecule encoding the heavy chain of antibody PSMA 10.3.
Figure 19:
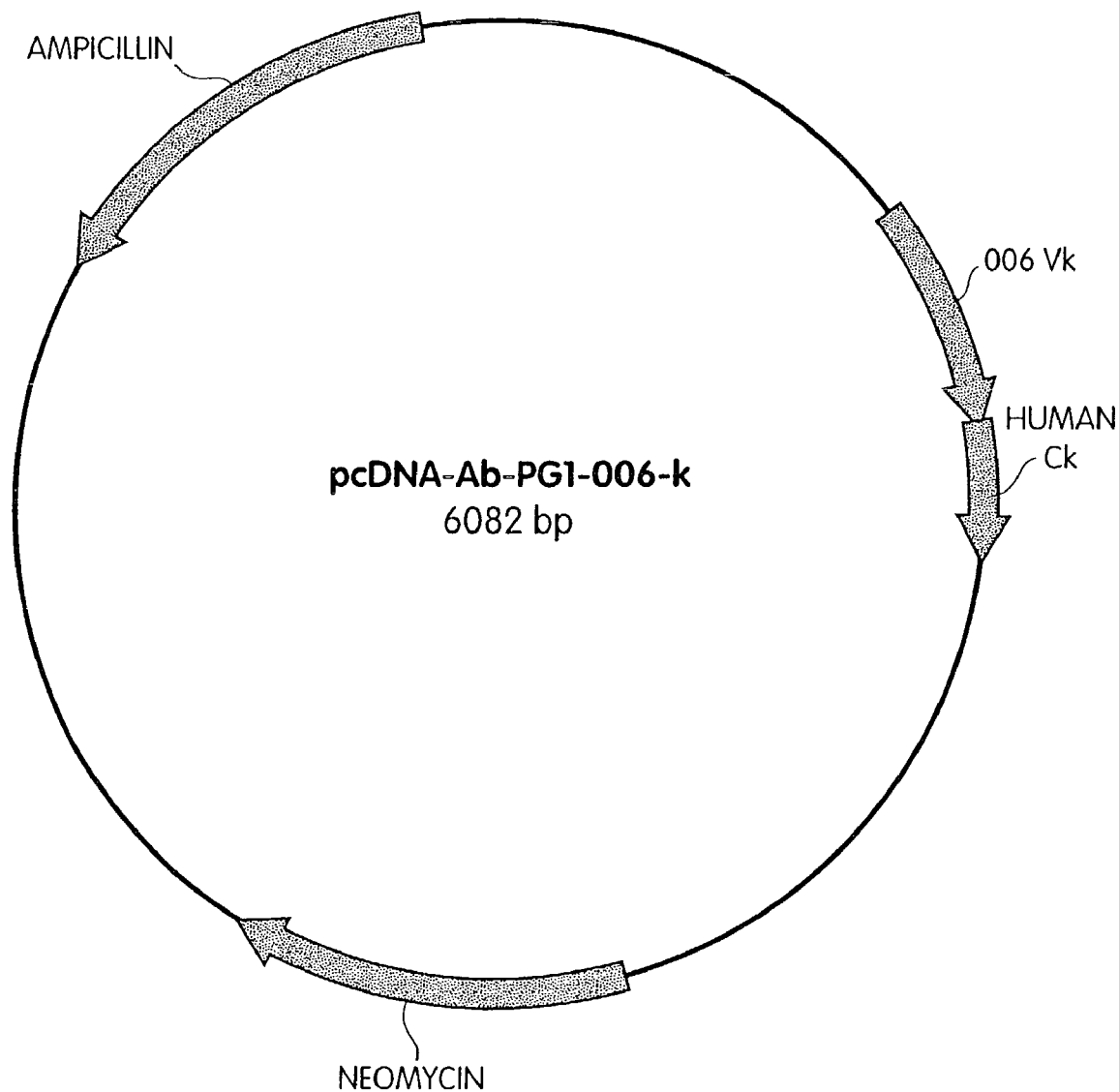
FIG. 19 provides the plasmid map of a nucleic acid molecule encoding the light chain of antibody AB-PG1-XG1-006.
Figure 20:
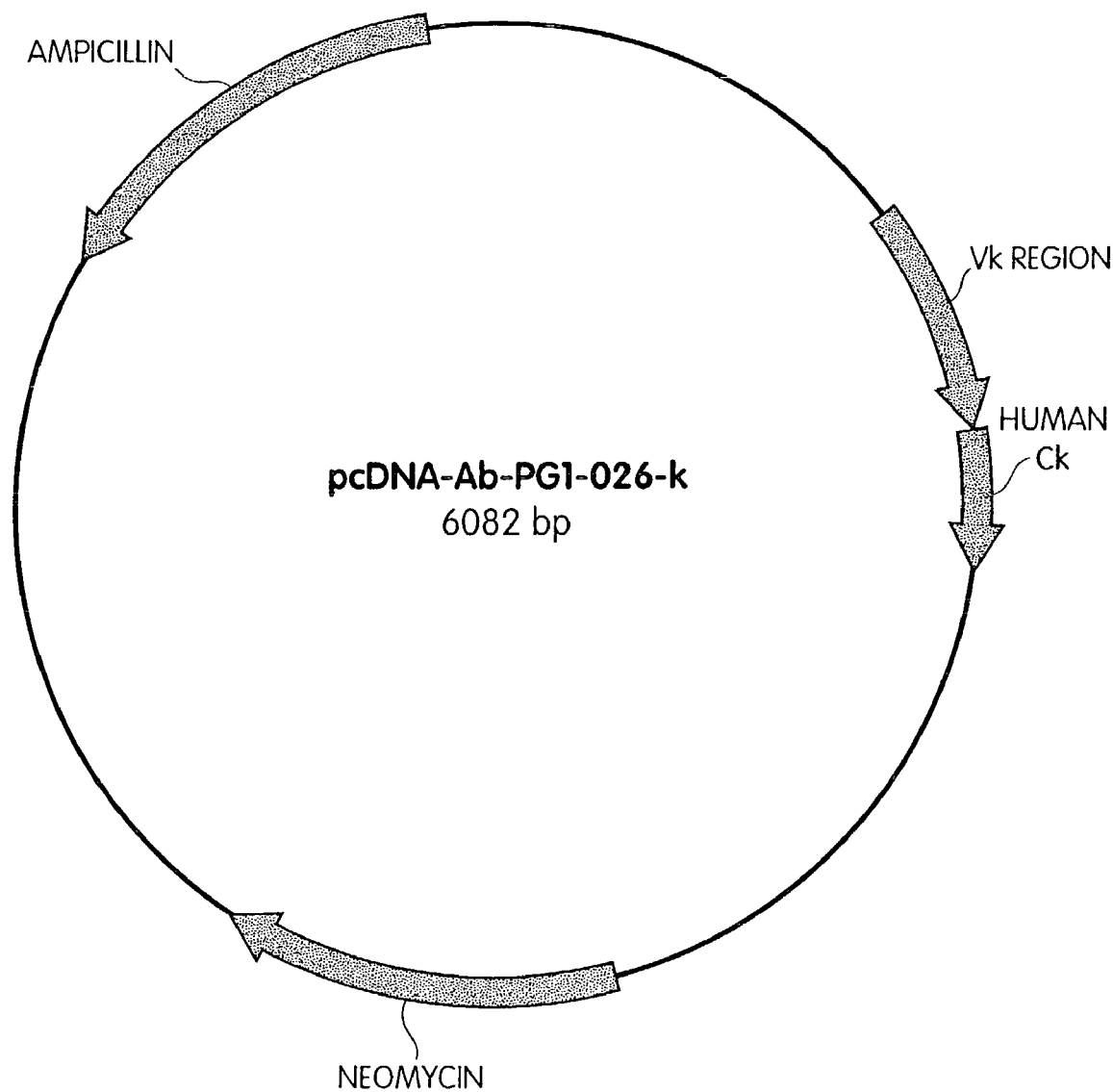
FIG. 20 provides the plasmid map of a nucleic acid molecule encoding the light chain of antibody AB-PG1-XG1-026.
Figure 21:
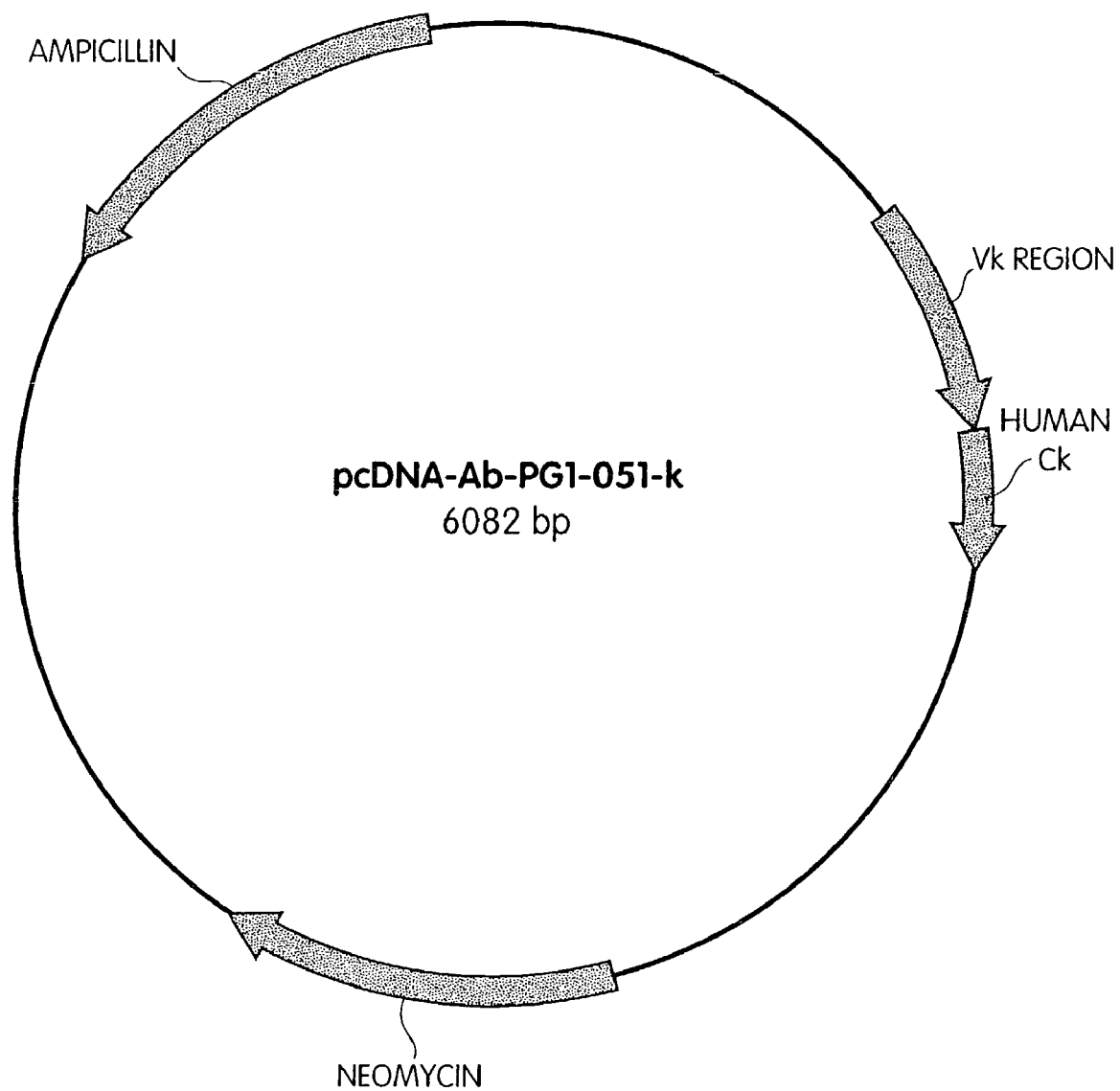
FIG. 21 provides the plasmid map of a nucleic acid molecule encoding the light chain of antibody AB-PG1-XG1-051.
Figure 22:
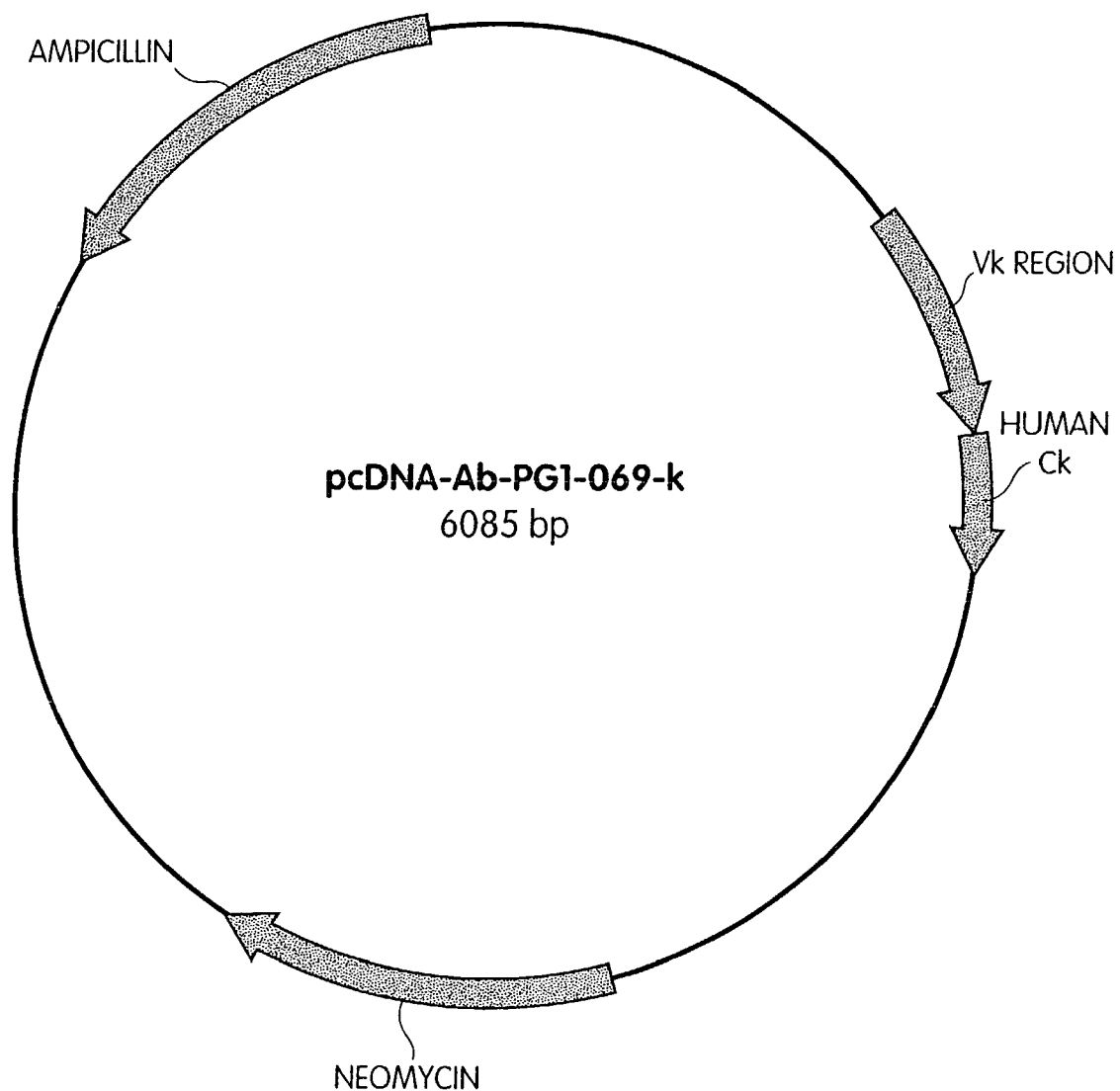
FIG. 22 provides the plasmid map of a nucleic acid molecule encoding the light chain of antibody AB-PG1-XG1-069.
Figure 23:
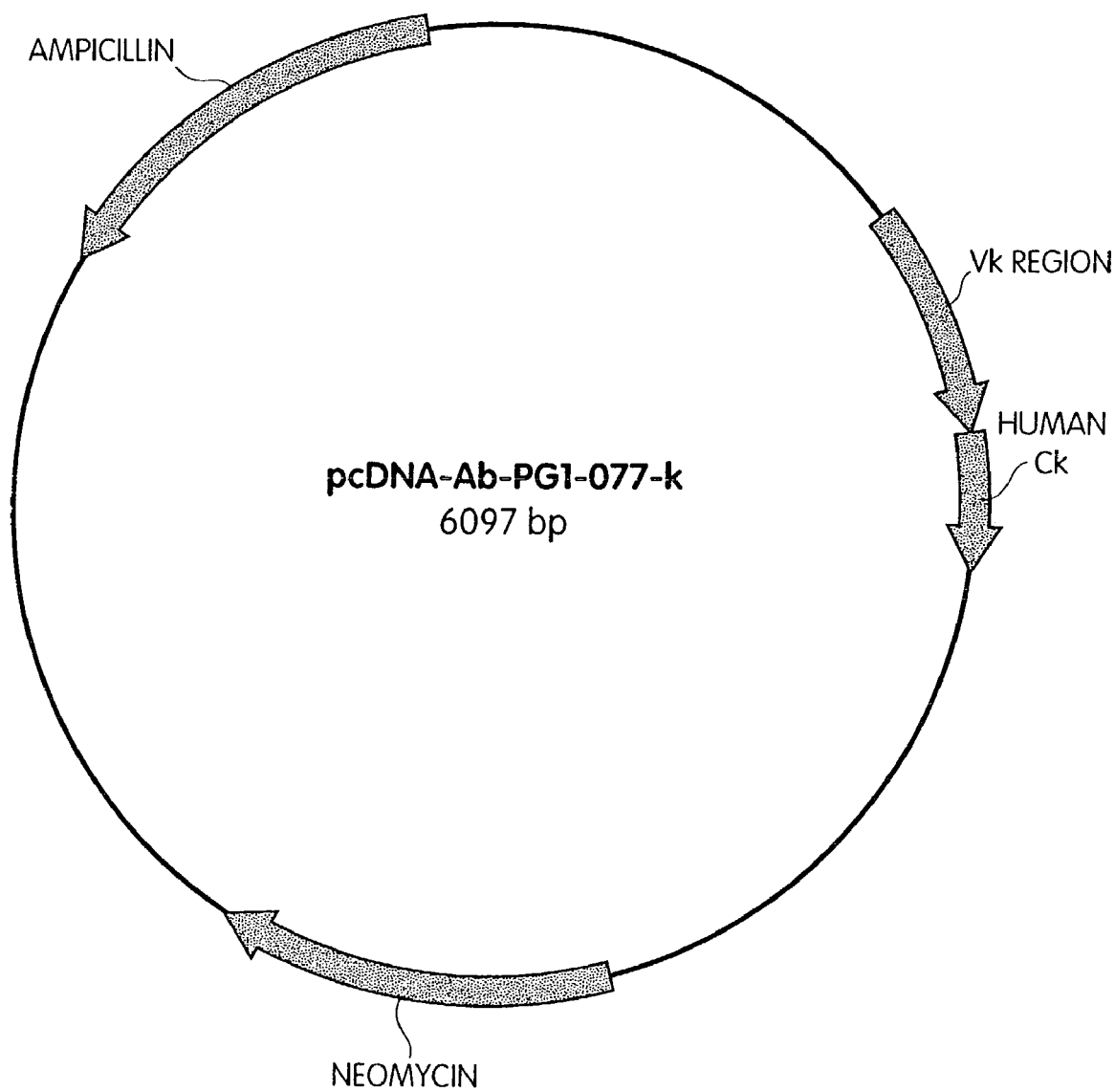
FIG. 23 provides the plasmid map of a nucleic acid molecule encoding the light chain of antibody AB-PG1-XG1-077.
Figure 24:
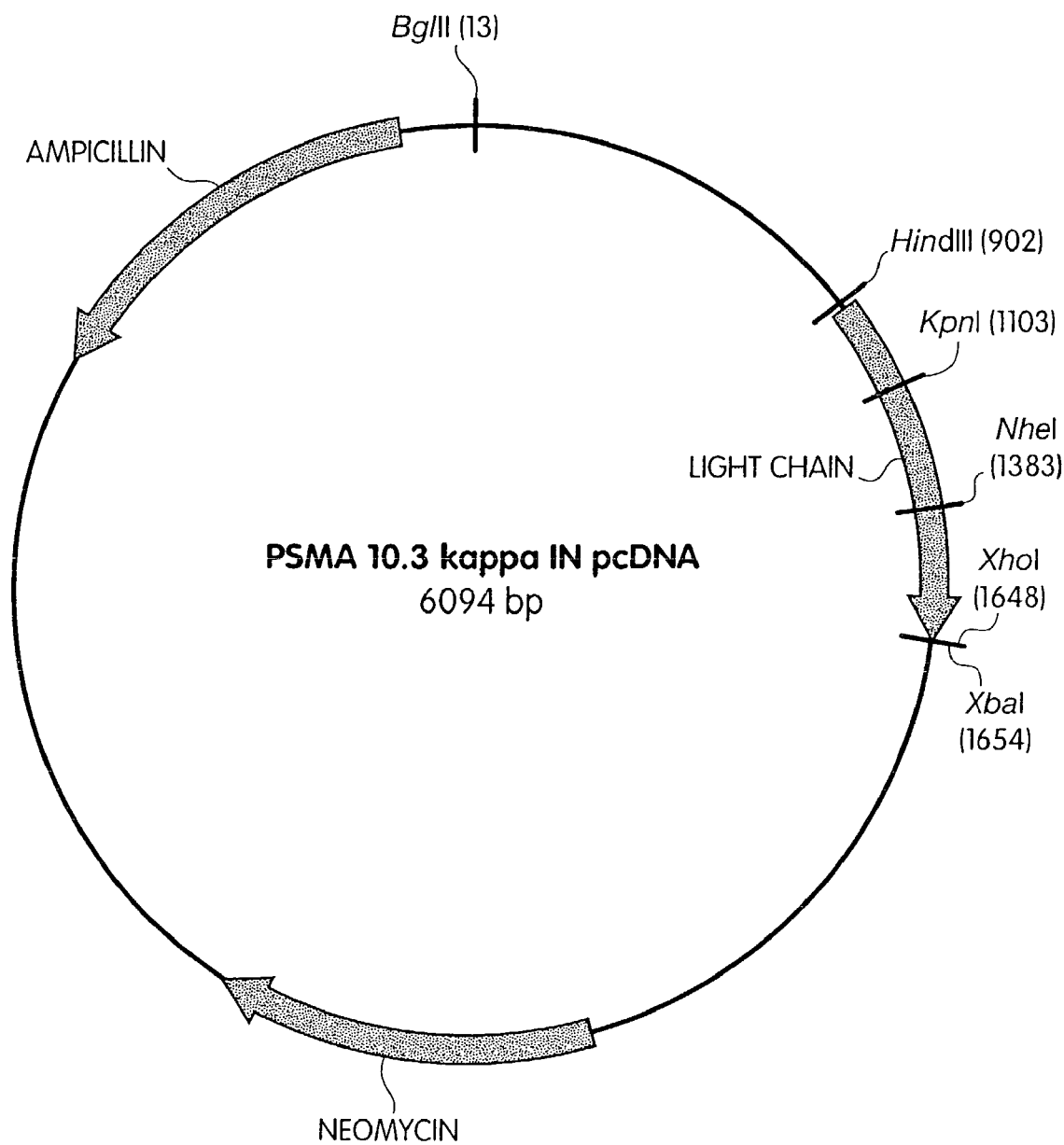
FIG. 24 provides the plasmid map of a nucleic acid molecule encoding the light chain of antibody PSMA 10.3.

The activity of radiolabeled mAbs can be significantly modulated by their internalization rates. Based upon previous results by other groups (Smith-Jones P. M. et al. *Cancer Res* 60: 5237-5243, 2000), significant internalization of PSMA after binding with one or more of the mAb constructs was expected. Internalization of the cell surface antibody-antigen complex was measured using $^{111}$In radiolabeled antibody (mAb 026) constructs (Caron, P. C. et al. *Cancer Res* 52: 6761-6767, 1992). Briefly, 5×10$^5$ C4-2 cells were incubated at 37° C. in 5% CO$_2$ with $^{111}$In radiolabeled antibody. At different times, cells were washed with PBS and cell-surface bound radiolabeled constructs were stripped with 1ml of 50 mM glycine/150 mM NaCl, pH=2.8. Total cell-associated radioactivity and acid-resistant (internalized) radioactivity were determined by γ-counting. Percent internalization and total binding were calculated. $^{111}$In labeled mAb 026 was found to be rapidly and efficiently internalized. FIG. 11 shows the percent internalization and total binding of $^{111}$In labeled mAb 026 as a function of incubation time. Cells (such as parental 3T3 cells) that do not express PSMA can be used as a control to determine non-specific binding.

Example 13

In Vitro Cytotoxicity Studies

Assessment of in vitro cytotoxicity of α-labeled mAbs was undertaken once the immunoreactivity of the radioimmunoconjugate was established. Approximately 50,000 target cells (either LNCaP or 3T3-PSMA cells) were treated in 96 well plates and analyzed 24-96 hours later. Quantification of cell death due to $^{225}$Ac-labeled constructs (or $^{213}$Bi) was accomplished by determining the uptake of $^3$H-thymidine by surviving cells (Nikula, T. K. et al. *J. Nucl. Med.* 40: 166-176, 1999). Specificity was determined by use of control cells (PSMA-negative human prostate cell lines PC-3 and DU-145, as well as control 3T3 cells), blocking with excess unlabeled antibody, and control radioconjugates.

The cytotoxic effects of antibody conjugate concentration, specific activity, and time of exposure were then assessed. Cytotoxicity was expressed relative to that seen with 1M HCl (100% cell death) and media (background cell death). LD$_{50}$ values were calculated by plotting cell viability as a function of the number of $^{225}$Ac atoms bound on the cells (McDevitt, M. R. et al. (1998) *Eur. J. Nucl. Med.* 25: 1341-1351 (1998).

Figure 25:
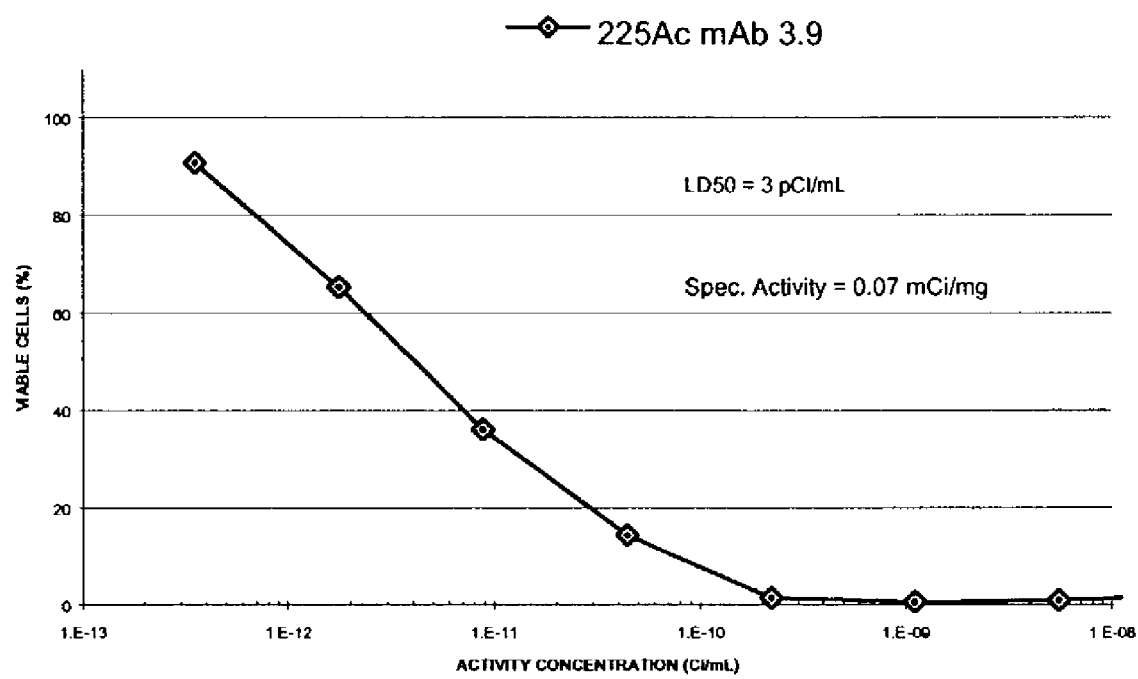
FIG. 25 depicts the cytotoxicity of $^{225}$Ac-3.9 on LNCaP target cells.

Multicellular spheroids of LNCaP-FGC cells had been established and were used to investigate the potential of radioimmunotherapy (RIT) to eradicate minimal disease in vitro. These three-dimensional spheroids mimic tissue structures more accurately than monolayer cultures and thus provide a more relevant model of solid tumors (O'Connor, K. C. *Pharm. Res.* 16: 486-493, 1999). LNCaP-FGC is a fast growing clone of the original LNCaP cell line, and the cells were grown using a liquid overlay technique to a size of 200-600 μm (Ballangrud, A. M. et al. *Clin. Cancer Res.* 5: 3171 s-3176s, 1999). In larger spheroids, the inner mass of cells becomes necrotic, while the outer rim consists of proliferating tumor cells. Antibody penetration was measured by confocal microscopy, and prior results suggested that an anti-PSMA antibody should penetrate to a depth of 40-50 μm (Ballangrud, A. M. et al. 7th Conference on Radioimmunodetection and Radioimmunotherapy of Cancer, Princeton N.J., 1998). The in vitro cytotoxicity of $^{225}$Ac-3.9 on LNCaP target cells is shown in FIG. 25. The percentage of viable PSMA$^+$ LNCaP cells was plotted as a function of activity of the radioconjugate. Addition of a 100-fold excess of unlabeled antibody was used as a control for specificity.

Example 14

Evaluation of the In Vivo Efficacy of Unlabeled and Radiolabeled mAbs in Mouse Xenograft Models of Human Prostate Cancer Antibodies that are successful in the foregoing assays demonstrate significant specificity and functional properties that suggest they will be useful for therapeutic use. The most promising of these radiolabeled and "naked" mAb constructs are evaluated in the best available mouse models of prostate cancer. The studies employ an established xenograft model in which the LNCaP human prostate tumor cell line is injected into immunocompromised nude mice and allowed to form solid tumors (Ellis, W. J. et al. *Clin Cancer Res* 2: 1039-1048 (1996), which then are treated with both radiolabeled and unlabeled anti-PSMA mAb constructs. Follow-on studies also utilize a mouse xenograft model, CWR22, which reproduces many of the key biological features of human prostate cancer.

Lncap Tumor Cell Xenograft Model

A construct showing high affinity and high specificity is taken into the LNCaP tumor cell xenograft in vivo model for biodistribution and pharmacokinetic analysis. $^{111}$In-labeled anti-PSMA antibody is used for these studies due to its favorable chelation chemistry, radioactive half-life and traceable gamma emission. Timepoints are evaluated as appropriate for the half-lives of $^{213}$Bi, $^{225}$Ac, $^{177}$Lu and $^{90}$Y, which are the nuclides of therapeutic interest. Labeled radioconstructs (1-5 μg) are injected i.v. into nude mice (normal and tumor bearing) and the mice are sacrificed at 5 min, 15 min, 30 min, 60 min, 2 hrs, 4 hrs, 18 hrs, and 24 hrs post-injection. Blood and major organs are taken from animals, weighed, and the percent radioactivity injected per gram of tissue is determined (Nikula, T. K. et al. *J. Nucl. Med.* 40: 166-176, 1999). Specificity is addressed by pre-injection with excess unlabeled construct. Macroscopic tumor volume and animal survival rates is recorded throughout the experiments.

A dose-ranging study is also conducted to determine the toxicity of the constructs when administered via i.v. or i.p. injection to normal and tumor-bearing mice. These animals are routinely examined for toxic side effects during the course of the studies by blood chemistry and physical examination. Animals are sacrificed during and at the conclusion of the study in order to collect blood and body tissues for further evaluation. Previous data has demonstrated an approximate maximum tolerated dose of 250 µCi/mouse, so total doses are kept below that level.

Once i.v. biodistribution and toxicity is documented, radiotherapy of tumors is assessed. Groups of five mice are injected with <1 µg radiolabeled anti-PSMA mAb construct both pre- and post-tumor challenge to assess anti-tumor activity. Antigen negative (RAJI or RAMOS) xenografted tumors are also used as a control. Other controls include (1) treatment with unlabeled anti-PSMA mAb only and (2) excess unlabeled anti-PSMA mAb pretreatment before $^{213}$Bi, $^{225}$Ac, $^{177}$Lu and/or $^{90}$Y-labeled anti-PSMA to block specific targeting.

Groups of tumor bearing mice are injected with unlabeled anti-PSMA mAbs (at equimolar concentrations) and several dose levels of radiolabeled anti-PSMA or a similarly labeled isotype control antibody. The effect on tumor growth is assessed over time. Statistical differences between therapy groups is determined using an analysis of variance (ANOVA) method and animal survival is illustrated using Kaplan-Meier plots. The efficacy of $^{213}$Bi, $^{225}$Ac, $^{177}$Lu and/or $^{90}$Y-labeled anti-PSMA constructs is correlated to the data obtained in vitro. Success in these experiments is defined as the ability to significantly (p <0.05) increase life-span and/or decrease tumor volume as compared to a radiolabeled isotype control mAb.

Furthermore, the tumor models are used to test whether predosing with unlabeled antibody prior to injection of radiolabeled antibody improves delivery of the radiolabeled antibody to the tumor. The tumor-bearing mice are injected with <1 µg radiolabeled anti-PSMA antibody with or without a prior single injection of 5-100 µg of unlabeled antibody. After several days, animals are sacrificed for evaluation of the distribution of radioactivity in the tumor, normal tissue, and blood. If predosing with unlabeled antibody improves delivery and targeting of radiolabeled antibody to the tumors, this approach is applied and optimized in toxicity and therapeutic studies.

In addition to overall survival, the role of timing of the injection after tumor transplantation (Day 1 vs 3 vs 7), the role of dosage (dose-response curves using 3-4 dose levels), the role of schedule (single vs multiple divided daily injections) and the specificity of the treatment (pre-treatment with unlabeled anti-PSMA to block targeting) is examined.

These in vivo studies are designed to address the maximum tolerated dose of radiolabeled antibody, the activity of the antibody, the optimal dosing schedule (single or multiple injections), and the effect on tumor size. Successful completion of this work enables determination of the feasibility of PSMA-targeted alpha particle radioimmunotherapy (RIT) of prostate cancer and identifies the optimal $^{213}$Bi and/or $^{225}$Ac-labeled constructs to enter into clinical development.

CWR22 Mouse Xenograft Model

The most promising anti-PSMA mAbs in unlabeled, toxin-labeled and/or radiolabeled form are tested in the CWR22 human prostate cancer xenograft mouse model, (Wainstein, M. A. et al. *Cancer Res* 54:6049-6052 (1994); Nagabhushan, M. et al. *Cancer Res* 56:3042-3046 (1996); Pretlow, T. G. et al. *J. Natl Cancer Inst* 85:394-398 (1993)). This model has many features of the human condition including a dependence on androgens, a correlation between measured levels of PSA in serum and tumor size, and high-level expression of PSMA. Following androgen withdrawal, PSA levels decrease to nearly undetectable levels and tumor volume decreases. Later, the tumor regrows as an androgen-independent neoplasm, manifest initially by a rise in PSA and later, measurable tumor growth. After androgen withdrawal, tumors regrow at variable time periods.

Four to six week old nude athymic BALB/c male mice are obtained from the National Cancer Institute-Frederick Cancer Center and maintained in pressurized ventilated caging. While immunodeficient in many respects, these mice mediate wild-type levels of ADCC and CML. The CWR22 tumor line is propagated in the animals by the injection of minced tumor tissue from an established tumor into the subcutaneous tissue of the flanks of athymic nude mice together with reconstituted basement membrane (MATRIGEL, Collaborative Research, Bedford, Mass.). To maintain serum androgen levels, the mice are administered 12.5-mg sustained-release testosterone pellets (Innovative Research of America, Sarasota, FL) subcutaneously before receiving tumors. Three to four weeks after inoculation, tumors of approximately 1.5 ×1.0 ×1.0 cm are measured. Androgens are withdrawn by surgical castration under pentobarbital anesthesia and removal of the sustained-release testosterone pellets. Tumor size is determined by caliper measurements of height, width and depth. PSA values are performed on the serum of the mice after tail bleeding using a Tandem-R PSA immuno-radiometric assay (Hybritech, San Diego, Calif.).

Groups of five mice are injected with anti-PSMA mAb or a similar isotype control mAb at dosages from 5-100 µg to assess anti-tumor activity. The effect of scheduling single doses vs. multiple divided daily injections is also examined. Macroscopic tumor volume and animal survival rates are recorded throughout the experiments. Statistical differences between therapy groups are determined using an analysis of variance (ANOVA) method and animal survival are illustrated using Kaplan-Meier plots, with success defined as a difference of p<0.05. Similarly, the efficacy of "naked" mAbs is compared to that seen with $^{90}$Y, $^{177}$Lu, $^{213}$Bi and/or $^{225}$Ac-labeled anti-PSMA constructs.

These in vivo studies are designed to address the maximum tolerated dose of mAb, the activity of the antibody, the optimal dosage and dosing schedule (single or multiple divided injections), and the effect of treatment on tumor size. Successful completion of this work will enable determination of the feasibility of PSMA-targeted immunotherapy of prostate cancer and identification of the optimal constructs to enter into clinical development.

Example 15

Investigation of Native PSMA Protein Conformation

Extraction of PSMA from the Cell Surface of LNCaP and 3T3 Cells

LNCaP or 3T3 cells were grown to confluency in a T150 cell culture flask, detached using cell dissociation solution (Mediatech, Herndon, Va.) and transferred to a 15 ml conical tube. The cells were washed twice with PBS and resuspended with 2 ml of M-Per™ Mammalian Protein Extraction Reagent (Pierce, Rockford, Ill.). Following incubation for 10 min at 4° C., cell debris and insoluble aggregates were removed by centrifugation at 15,000 rpm for 30 min at 4° C. The supernatant was transferred to a cryogenic vial and stored at −80° C. until further use.

Production and Purification of Recombinant, Soluble PSMA (rsPSMA)

The extracellular domain of PSMA (amino acids 44-750 of the full-length protein, SEQ ID NO:1) was obtained as a secreted protein from a DXB11 Chinese hamster ovary (CHO) cell line, stably transfected with an rsPSMA expression vector. The cells were grown in a Celligen Plus 2.2L Packed Bed Bioreactor (New Brunswick Scientific, Edison, N.J.) in protein-free media. The Bioreactor was operated in perfusion mode, and supernatant was collected aseptically into collection bags maintained at 4° C. The protease inhibitor aprotinin was added to the harvest supernatant, which was concentrated 25-fold prior to storage at −90° C. For purification, the concentrate was thawed and purified using subsequent steps of Concanavalin A lectin affinity chromatography and Butyl-SEPHAROSE hydrophobic interaction chromatography. The purified protein was dialyzed against 10 mM potassium phosphate, pH 7.0. The purified rsPSMA protein is dimeric, and possesses folate hydrolase enzymatic activity when tested according to published procedures (Pinto et al., *Clinical Cancer Research* 2:1445, 1996) and reacts with each of a panel of conformation-specific monoclonal antibodies, indicating that rsPSMA adopts a native conformation.

Polyacrylamide Gel Electrophoresis (PAGE) and Western Blotting of the Different PSMA Proteins For each individual PAGE analysis, 15 μl of each cell lysate and 5 μl of the purified rsPSMA were used.

SDS-PAGE was performed using standard procedures. Samples were prepared by boiling for 5 minutes in the presence of Laemmli sample buffer (with or without the reducing agent dithiothreitol [DTT]). Samples were then applied on a 4-15% Tris-Glycine gel (BioRad, Hercules, Calif.). After electrophoresis for 1 h at 200V, the proteins were transferred onto nitrocellulose (BioRad) and analyzed by Western blotting.

The oligomeric nature of the different PSMA proteins was analyzed using Blue Native PAGE (BN-PAGE). Each sample was diluted with an equal volume of 2×BN-PAGE sample buffer (0.1M MOPS/0.1M Tris/40% glycerol/0.1% Coomassie G-250) prior to loading onto the gel. BN-PAGE was performed using 4-12% BisTris gels (Invitrogen, Carlsbad, Calif.) and 50 mM MOPS/50 mM Tris, pH 7.7 as running buffer. Coomassie Blue was omitted from the cathode buffer to avoid interference with protein binding during the transfer of the proteins onto nitrocellulose. Following electrophoresis for 2.5 hrs at 125V, the proteins were transferred onto a nitrocellulose membrane (BioRad) and analyzed by Western blotting.

Western blotting was performed as follows: Subsequent to transfer, the nitrocellulose membrane was blocked with 5% milk in PBS / 0.1% TRITON X-100/0.02% SDS, which was also used for the subsequent wash and antibody incubation steps. PSMA proteins were detected using the anti-PSMA mAbs 3.1 or 3.9 (Progenics Pharmaceuticals) as primary antibody and HRP-labeled anti-mouse IgG as secondary antibody and 1h incubation at room temperature. The membranes were colorimetrically developed using chemiluminescence (NEN Plus, Perkin Elmer Life Sciences, Boston, Mass.).

Results

Figure 5:
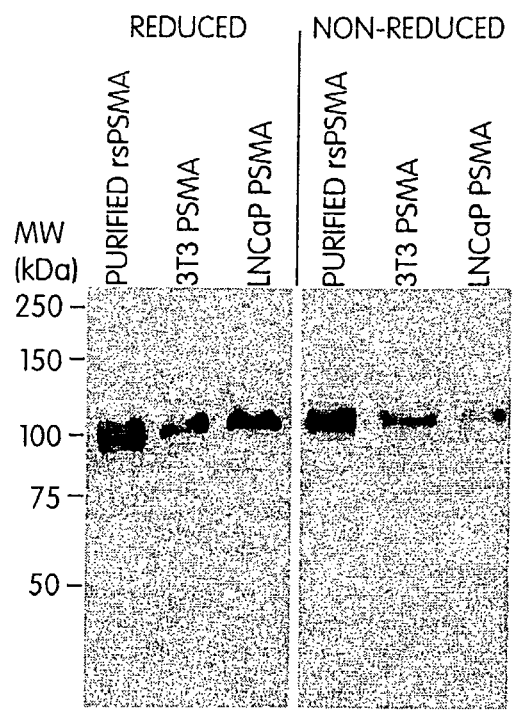
FIG. 5 is a digitized image of a polyacrylamide gel that shows an analysis of purified recombinant, soluble PSMA (rsPSMA) and of full-length PSMA from 3T3 cells (3T3 PSMA) or LNCaP cells (LNCaP PSMA) by reduced and non-reduced SDS-PAGE.

Both full-length PSMA and recombinant, soluble PSMA (rsPSMA) migrate on reducing and non-reducing SDS-PAGE with a molecular weight of ~100 kDa (FIG. 5). The result for full-length PSMA is in accordance with prior observations (Israeli et al., U.S. Pat. No. 5,538,866; Murphy et al., U.S. Pat. No. 6,158,508; Israeli, et al., *Cancer Research* 54:1807, 1994; Troyer et al. *Int. J. Cancer* 62:552, 1995; Troyer et al., *The Prostate* 30:233, 1997; Grauer et al., *Cancer Research* 58:4787, 1998). In each of these reports, full-length PSMA migrated as a major band of 100-120 kDa, with a minor (typically <5% of the total PSMA protein) 180-200 kDa band observed in a subset of reports (U.S. Pat. No. 6,158,508; Troyer et al., 1995; Troyer et al., 1997). Troyer et al. (1995) describe the 180-200 kDa species as being a noncovalently associated PSMA dimer that can be disrupted with increasing concentrations of SDS detergent.

rsPSMA contains 94% (707 of 750) of the amino acids present in full-length PSMA, and the two proteins are not clearly resolved in this analysis, as expected.

SDS-PAGE allows the analysis of denatured proteins only. In order to examine native proteins in their native state, other techniques have to be employed, such as Blue Native PAGE (BN-PAGE). BN-PAGE is used to determine the native molecular weight of proteins and their noncovalent complexes (Schägger & v. Jagow, *Anal. Biochem.* 199:223-231, 1991; Schagger et al., *Anal. Biochem.* 217:220-230, 1994). The dye Coomassie Blue G-250 binds to the hydrophobic domains on the surface of most proteins, enhances solubility, and introduces a charge shift on the native proteins resulting in migration towards the anode at pH 7.5 irrespective of the isoelectric point of the protein. Although the migration velocity of proteins in BN-PAGE varies somewhat, the molecular mass of proteins can be determined by their respective end points of migration due to the decreasing pore size of the acrylamide gradient present in the gels.

Figure 6:
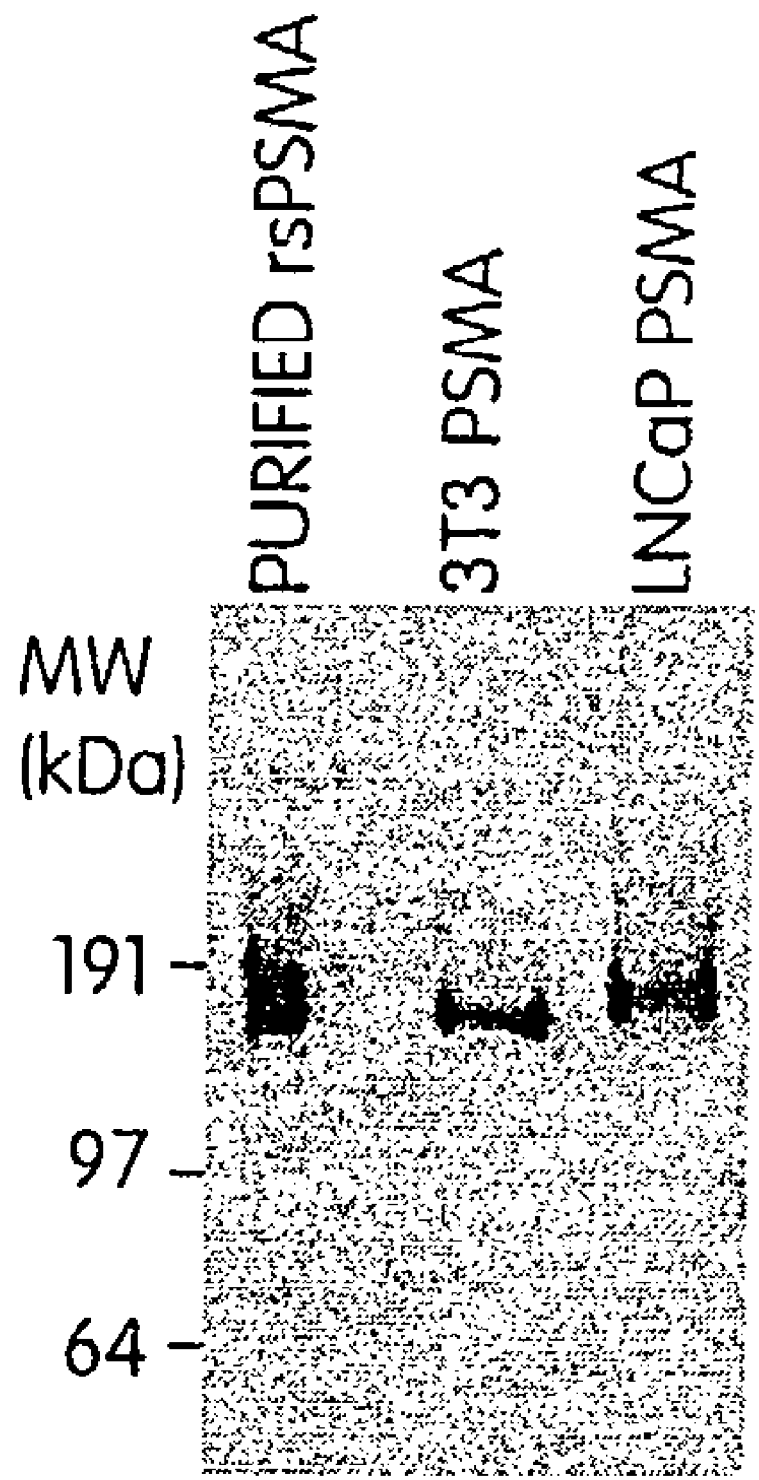
FIG. 6 is a digitized image of a polyacrylamide gel that depicts a Blue Native PAGE analysis of purified recombinant, soluble PSMA (Purified rsPSMA) and of full-length PSMA extracted from 3T3 cells (3T3 PSMA) or LNCaP cells (LNCaP PSMA).

When analyzed by BN-PAGE, full-length PSMA (extracted from LNCaP or 3T3 cells) as well as purified rsPSMA migrate with a molecular weight of ~190 kDa (FIG. 6). This surprising observation for full-length PSMA indicates that the predominant form of cell-surface PSMA is a noncovalently associated dimer. This unexpected result can be contrasted with that of previous reports (U.S. Pat. No. 6,158,508; Troyer et al. 1995; Troyer et al., 1997), where the PSMA dimer represents a minor species in SDS-PAGE analyses. Presumably, the noncovalent PSMA dimer is largely dissociated by boiling in the presence of the denaturing detergent SDS.

Moreover, the result for the purified rsPSMA protein indicates that the dimer is stabilized via interactions between extracellular amino acids in addition to or exclusive of amino acids in the transmembrane or intracellular segments, which are not present in rsPSMA.

Example 16

Dissociation of PSMA Multimers

PSMA is a putative zinc metalloprotease, and site-directed mutagenesis of amino acids implicated in zinc binding results in a profound loss of enzymatic activity (Speno et al., *Molecular Pharmacology,* 55:179, 1999). These amino acids include His-377, Asp-387, Glu-425, Asp-453 and His-553. Ethylene-diaminetetraacetic acid (EDTA) is a strong chelating agent for $Zn^{2+}$ and other divalent cations, and thus has the potential to remove $Zn^{2+}$ or other coordinate divalent cations from PSMA. We have determined that EDTA treatment causes the PSMA homodimer to dissociate into monomeric subunits. Similar results can be expected for other agents that possess similar chelating properties, such as ethyleneglycol-bis(beta-aminoethyl ether) (EGTA).

The purified rsPSMA protein was incubated with or without 10 mM EDTA for 16 hr at 4° C. and then analyzed by BN-PAGE. Under these conditions, the EDTA-treated protein was monomeric, whereas rsPSMA remained dimeric in the absence of EDTA. Although the dissociation of the PSMA dimer into monomer was essentially complete, any residual dimeric protein can be removed if desired by gel filtration, ultracentrifugation or other size-based separation methods that are well-known to those skilled in the art.

Example 17

Methods for Identifying Promoters of PSMA Dissociation

Compounds are screened for the ability to promote dissociation of PSMA dimers using a method that includes:
(a) contacting a PSMA dimer with a compound under conditions that do not promote dissociation of the PSMA dimer in the absence of the compound;
(b) measuring the amount of PSMA monomer; and
(c) comparing the amount of PSMA monomer measured in the presence of the compound with that observed in the absence of the compound.

An increase in the amount of PSMA monomer measured in the presence of the compound indicates that the compound is capable of promoting dissociation of the PSMA dimer.

In a further embodiment, compounds are screened for the ability to promote dissociation of PSMA dimers using a method that includes:
(a) contacting a PSMA dimer with a compound under conditions that do not promote dissociation of the PSMA dimer in the absence of the compound;
(b) measuring the amount of PSMA dimer; and
(c) comparing the amount of PSMA dimer measured in the presence of the compound with that observed in the absence of the compound.

A decrease in the amount of PSMA dimer measured in the presence of the compound indicates that the compound is capable of promoting dissociation of the PSMA dimer.

In a further embodiment, compounds are screened for the ability to promote dissociation of PSMA dimers using a method that includes:
(a) contacting a PSMA dimer with a compound under conditions that do not promote dissociation of the PSMA dimer in the absence of the compound;
(b) measuring the amounts of PSMA monomer and PSMA dimer;
(c) calculating a ratio of PSMA monomer to PSMA dimer; and
(d) comparing the ratio obtained in (c) with that obtained in the absence of the compound.

An increase in the ratio measured in the presence of the compound indicates that the compound is capable of promoting dissociation of the PSMA dimer.

Example 18

Cell Surface PSMA Binding Studies

Flow Cytometry

Parent 3T3 cells or PSMA-expressing 3T3 cells ($2 \times 10^5$ cells per condition) were washed in PBS and incubated with PBS containing goat serum (10% v/v) for 20 minutes on ice to block non-specific binding sites. Anti-PSMA monoclonal antibodies (unpurified form in supernatants or purified mAbs) were added in serial dilutions to cells in 100 μl PBS and incubated on ice for 30 minutes. Control anti-human IgG (Caltag, Burlingame, Calif.) was used to establish background binding. After two washes in PBS, the cells were incubated with anti-human IgG (BD Pharmingen, San Diego, Calif.) for 30 minutes on ice. Cells were washed twice in PBS, resuspended in 250 μl PBS and analyzed by flow cytometry using a FACScan machine (Becton Dickinson, Franklin Lakes, N.J.) and CellQuest software. Viable cells were gated by forward scatter and side scatter parameters, and binding was quantified using histogram plots of mean fluorescence intensity (MFI) levels.

Figure 26:
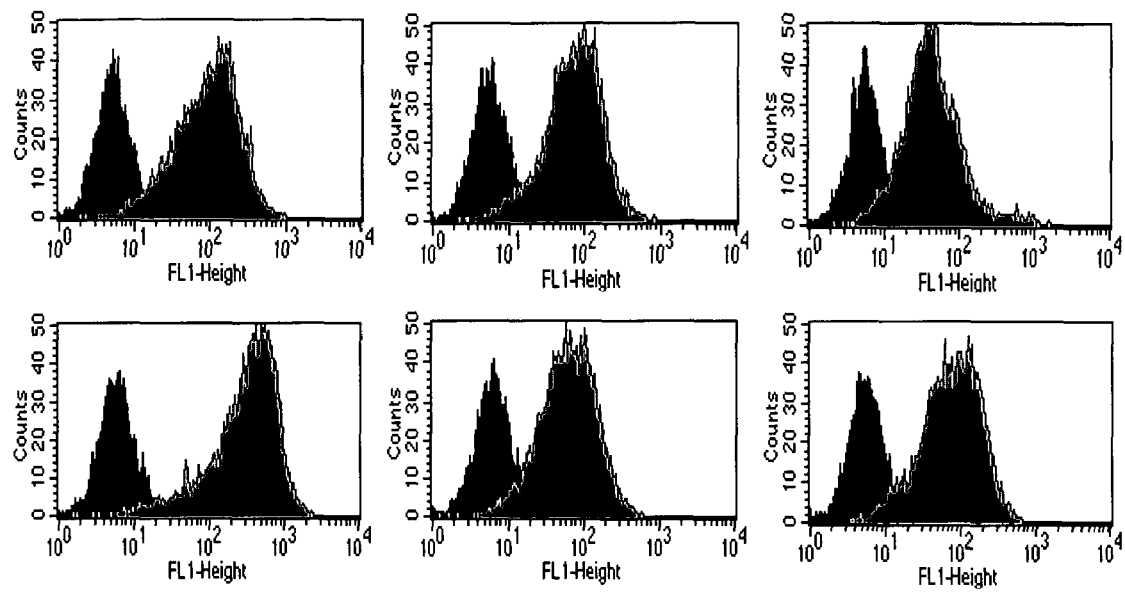
FIG. 26 illustrates the reactivity of anti-PSMA monoclonal antibodies XG-006, XG-051, 4.40.1, 4.49.1, 4.292.1 and 4.304.1 incubated with either parent 3T3 cells (black histogram) or 3T3 cells engineered to express cell-surface human PSMA (red histogram) and analyzed by flow cytometry.

Anti-PSMA mAbs XG-006 (PTA-4403 and PTA-4404, heavy and light chain plasmids), XG-051 (PTA-4407 and PTA-4408), 4.40.1 (PTA-4360; 4.40, 4.40.1 and 4.40.2 are the same antibody that represent different stages of subcloning the hybridoma), 4.49.1, 4.292.1 (PTA-4390) and 4.304.1 were found to avidly bind to cell surface PSMA (FIG. 26).

Maximal Binding

Figure 27A:
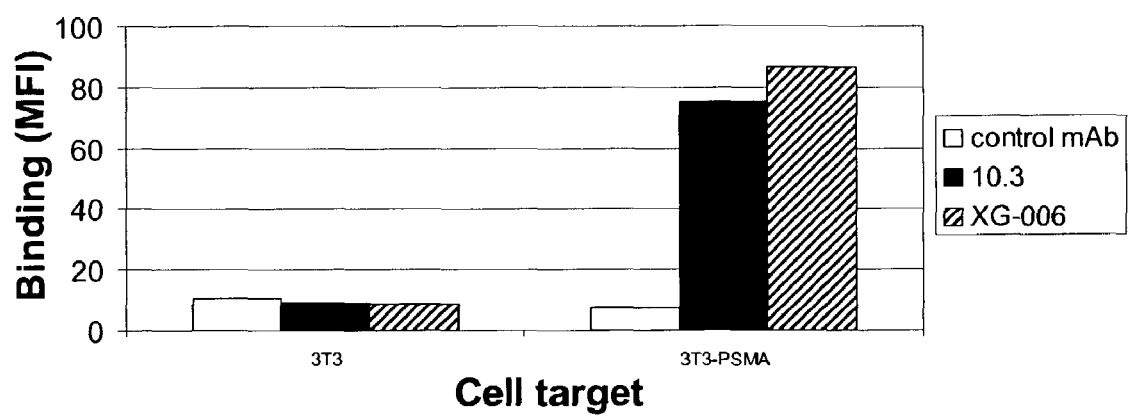
FIG. 27A shows that anti-PSMA mAbs bind to 3T3-PSMA cells and not 3T3 cells. One representative experiment from at least ten determinations is shown.
Figure 27B:
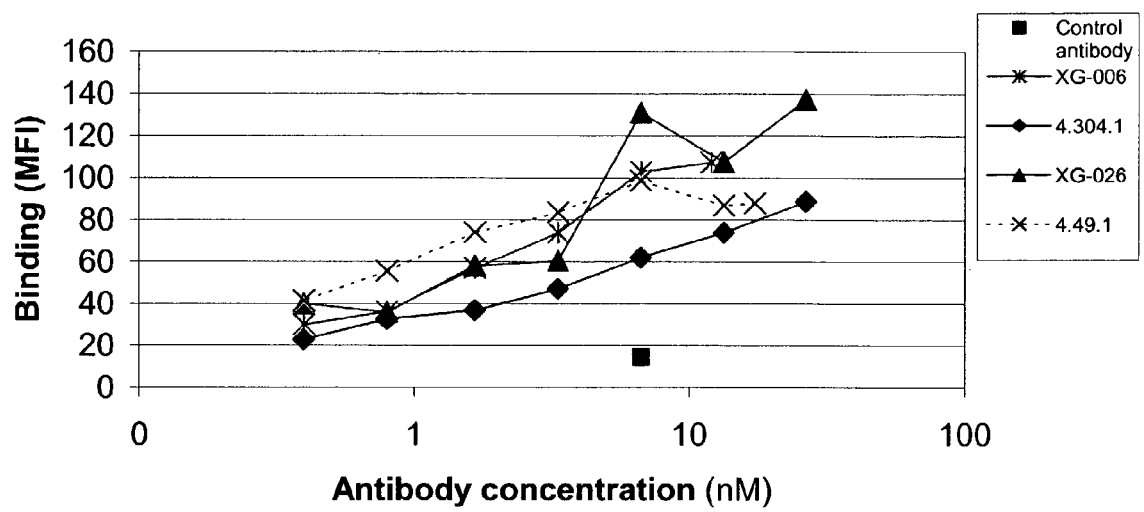
FIG. 27B illustrates that binding to cell-surface PSMA using serial dilutions of anti-PSMA mAb-containing culture supernatants occurred. One representative experiment from five is shown.
Figure 27C:
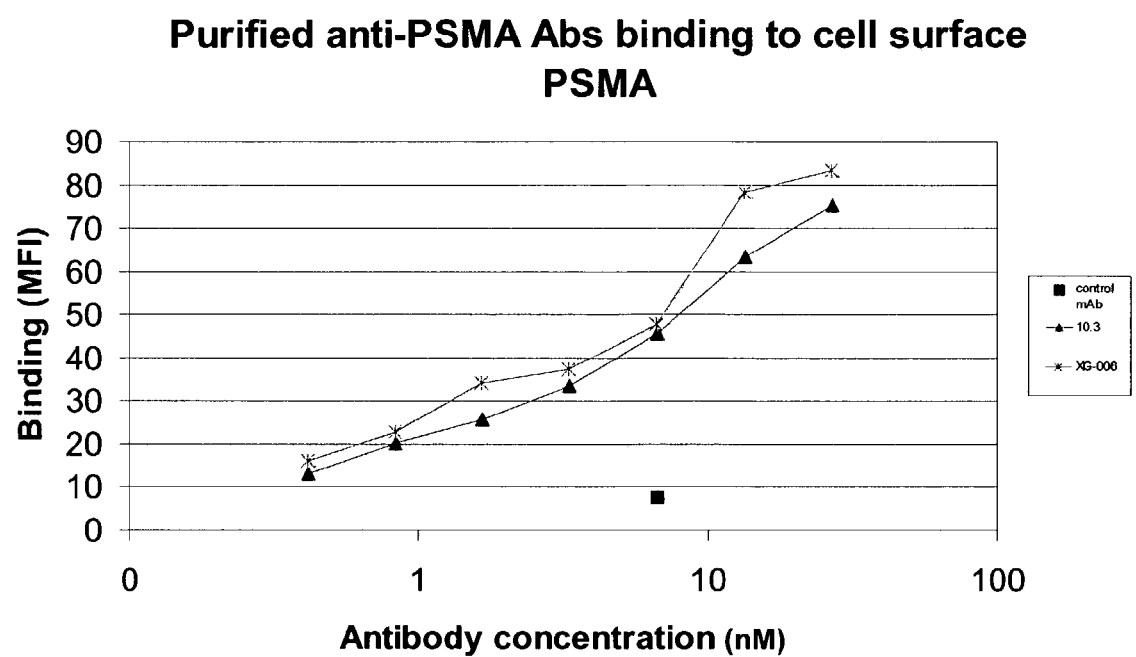
FIG. 27C shows binding to cell-surface PSMA using serial dilutions of purified anti-PSMA mAbs, XG-006 and 10.3 One representative experiment is shown.

Flow cytometry data (mean fluorescence intensity v. antibody concentration) were transposed and plotted using EXCEL software (Microsoft, Redmond, Wash.). Results from representative experiments of at least three determinations are depicted in FIGS. 27A-27C. Binding was compared by calculation of 50% effective concentration (EC50) using the Forecast function in EXCEL. The EC50 value represents the concentration of antibody required for half-maximal binding.

Anti-PSMA mAbs 10.3 (PSMA 10.3) and XG-006 were found to bind to 3T3-PSMA cells and not 3T3 cells (FIG. 27A). Antibody (26 nM) was added to cells, which were analyzed by flow cytometry. Binding to cell-surface PSMA using serial dilutions of anti-PSMA mAb-containing culture supernatants of XG-006, 4.304.1, XG-026 (PTA-4405 and PTA-4406) and 4.49.1 also was demonstrated (FIG. 27B). Binding to cell-surface PSMA using serial dilutions of purified anti-PSMA mAbs XG-006 and 10.3 is represented by FIG. 27C.

Example 19

Cytotoxicity of Toxin-Labeled Antibody

PSMA-3T3, LNCaP, and/or C4-2 cells (and control cell lines 3T3 and PC3 that do not express PSMA) were plated at 2,500 cells/100 μL/well in 96-well microplates (Falcon) and were incubated overnight at 37° C. in the presence of 5% $CO_2$. The media used for PSMA-3T3 (and 3T3) and LNCaP (and C4-2 and PC3) was DMEM or RMPI 1640, respectively, containing 2 mM L-glutamine, 10% FBS, and 1% penicillin-streptomycin. 50 ng (in 50 μL) of Mab-Zap or Hum-ZAP (Advanced Targeting Systems, San Diego, Calif.) in medium was added in each well. Mab-Zap and Hum-Zap are goat anti-mouse IgG antibody or goat anti-human IgG antibody covalently linked to saporin, the most potent of the plant ribosome-inactivating proteins (RIP) from the seeds of the plant *Saponaria officinalis*. Saporin induces cell death by apoptosis (Bergamaschi, G., Perfetti, V., Tonon, L., Novella, A., Lucotti, C., Danova, M., Glennie, M. J., Merlini, G., Cazzola, M. Saporin, a ribosome-inactivating protein used to prepare immunotoxins, induces cell death via apoptosis. *Br J Haematol* 93, 789-94. (1996)). The Mab-Zap did not bind to or internalize in cells in the absence of an appropriate primary antibody.

Murine 3.9, 5.4, mJ591 (ATCC# HB-12126) and human 006, 4.40, 4.304 anti-PSMA antibodies (and control IgG antibodies) were added into plates at different concentrations to bring the total volume to 200 µL in triplicate. The plates were kept cold on ice for at least 30 min to maximize Map-Zap or Hum-Zap binding to PSMA antibodies before internalization. The plates were incubated for 2 days and then the medium was changed and incubated for another 2 days. After 4 days incubation, the medium was withdrawn and fresh medium containing 10% Alamar Blue (20 µL, Bioscience, Camarillo, Calif.) was added into each well and incubated for 2 hrs. A CYTOFLUOR plate reader was used to measure fluorescence in 96-well plates at wavelengths of 530 nm excitation and 590 nm emission. Internalization of toxin was mediated by anti-PSMA antibodies. The cell kill is illustrated in FIG. 28 on C4-2 cells and in FIG. 29 on PSMA-3T3 cells.

Figure 30:
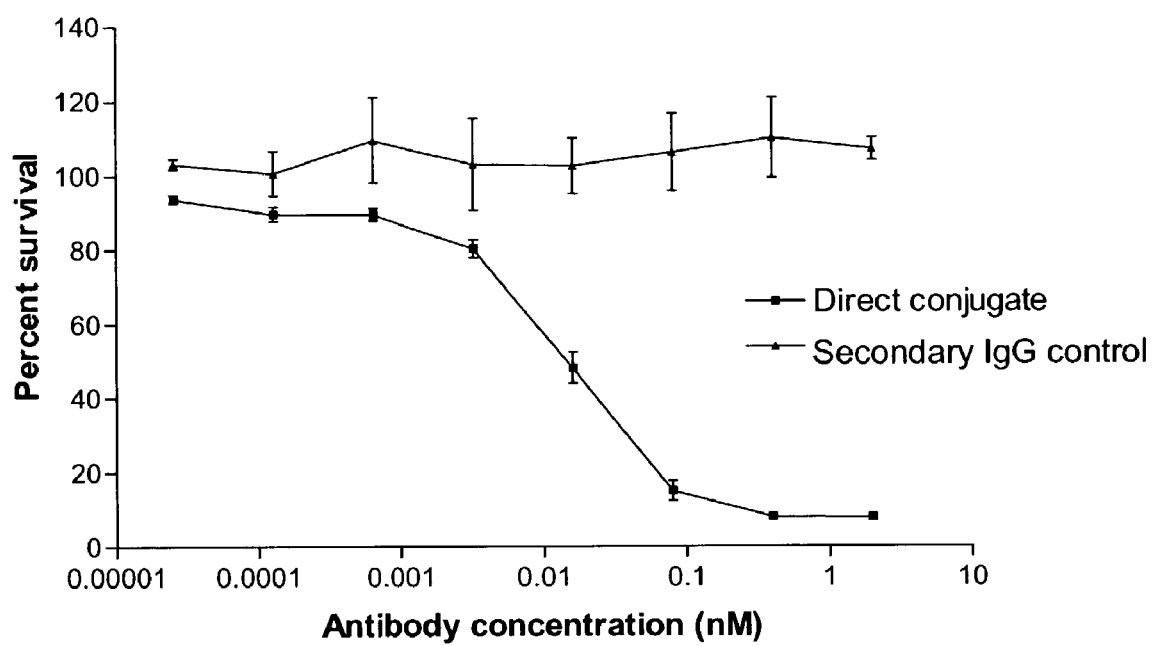
FIG. 30 provides the cytotoxicity of direct conjugated human 4.304 anti-PSMA antibodies with saporin on PSMA-3T3. The LD50 was $1.48 \times 10^{-11}$ M for direct conjugated 4.304 anti-PSMA antibodies with saporin.

Human 4.304 anti-PSMA antibody was directly conjugated with saporin (Wrenn et al., *Brain Res.* 740:175-184, 1996), and its cytotoxicity was demonstrated using a similar protocol as described above (see FIG. 30).

Example 20

Immunoreactivity

PSMA-3T3, LNCaP and C4-2 were used as PSMA expressing cell lines and 3T3 was used as a control cell line not expressing PSMA. The cells were blocked with 10% goat serum on ice to reduce non-specific binding in this assay.

A small amount (1-5 ng) of labeled mAb was added into a cell pellet of 10 million cells and incubated at 0° C. (on ice) with gentle mixing. After a 1 hour incubation, the cells were collected by centrifugation and the supernatant containing unbound mAb was transferred to a fresh cell pellet for an additional 1 hour incubation at 0° C. Both sets of cells were centrifuged and washed twice with cold PBS. The cell pellets, supernatant and wash fractions were counted for radioactivity. Immunoreactivity is defined as the amount of radioactivity in the cell pellets divided by the total radioactivity in the cell pellets, supernatant and wash fractions. These data are shown below in Table 3.

TABLE 3

Immunoreactivity of $^{111}$In Radiolabeled Antibody on PSMA Expressing Cells

| Radiolabeled mAb | Immunoreactivity (%) | Cell line |
|---|---|---|
| $^{111}$In 4.304 | 92.6 (1.4) | PSMA-3T3 (3T3) |
|  | 92.6 | PSMA-3T3 |
|  | 91.4 (1.7) | PSMA-3T3 (3T3) |
|  | 89.1 | LNCaP |
|  | 92.4 | C4-2 |
| Average = | 91.6 ± 1.5 |  |
| $^{111}$In 4.40 | 87.7 (0.5) | PSMA-3T3 (3T3) |
|  | 86.8 | PSMA-3T3 |
|  | 89.4 (1.5) | PSMA-3T3 (3T3) |
| Average = | 88.0 ± 1.3 |  |
| $^{111}$In mJ591 | 58.5 | PSMA-3T3 |
|  | 54.9 (1.1) | PSMA-3T3 (3T3) |
| Average = | 56.7 ± 2.5 |  |
| $^{111}$In3.9 | 88 | LNCaP |
|  | 87 | C4-2 |
|  | 89 (2) | PSMA-3T3 (3T3) |
|  | 95.3 (0.5) | PSMA-3T3 (3T3) |
|  | 88.6 | PSMA-3T3 |
|  | 84.8 | C4-2 |
|  | 89.3 | PSMA-3T3 |
| Average = | 88.6 ± 3.2 |  |

Antibodies 4.40, 4.304 and mJ591 were conjugated to the bifunctional chelate CHX-A"-DTPA and antibody 3.9 was conjugated to C-DOTA.

Immunoreactivity of $^{225}$Ac radiolabeled antibody (026 and 4.40) was also assessed with a methodology similar to that described above for the $^{111}$In labeled antibodies. $^{225}$Ac was chelated with the bifunctional DOTA at 50° C. for 30 minutes. The chelated $^{225}$Ac was then conjugated to antibodies 026 and 4.40 at 35° C. for 30 minutes. Unconjugated $^{225}$Ac was removed by a PD10 column (Amersham Biosciences, Picataway, N.J.). The immunoreactivity of the radiolabeled antibodies was then determined. The data are presented below in Table 4. In addition to the assessment of the immunoreactivity of these antibodies, the yield of the labeling procedure was also assessed, and these data are also provided below in Table 4.

TABLE 4

Yield and Immunoreactivity of $^{225}$Ac Radiolabeled Antibody

| Antibody | Yield | Immunoreactivity |
|---|---|---|
| 026 | 9.3 +/– 0.8 (n = 2) | 61.3 +/– 1.1 (n = 2) |
| 4.40 | 14.3 +/– 0.6 (n = 2) | 78.1 +/– 0.1 (n = 2) |

Example 21

Competitive Binding Assay to Identify Binding Epitopes

To identify whether a given group of mAbs recognize distinct or overlapping epitopes on PSMA, competition binding assays were performed with $^{111}$In radiolabeled antibodies. 2×10$^5$ cells (100 µL) of PSMA-3T3 were plated into 96-well microplates, and antibodies 4.40, 4.304 and mJ591 (100 µL) at different concentrations (series dilution) were added. The cells were incubated at 0° C. for 30 min. 20 µL of In-111 radiolabeled CHX-A"-DTPA antibody constructs were added into each well. After a 2 hour incubation on ice for competition binding, the cells were washed 5 times using cold PBS. The cells containing bound $^{111}$In antibodies were recovered from microplates into test tubes and counted in a gamma counter.

Figure 31:
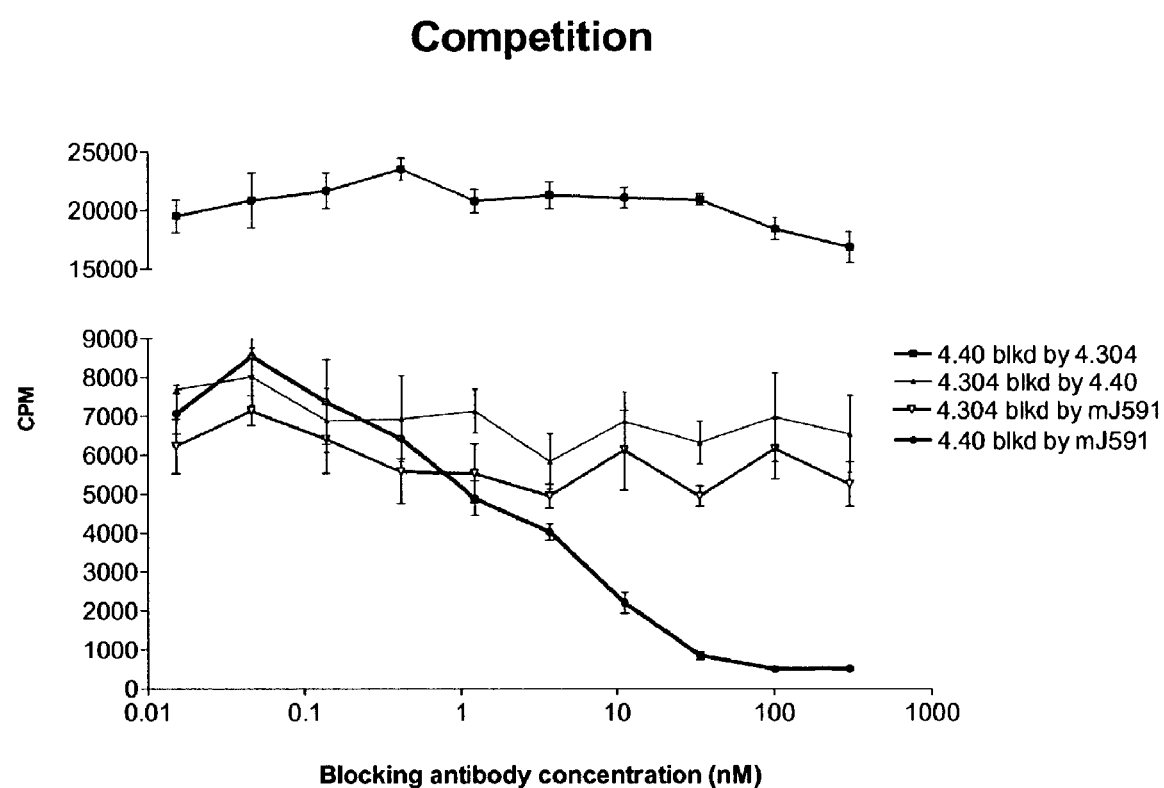
FIG. 31 illustrates the results of the competition assay of unmodified 4.304, 4.40, mJ591 anti-PSMA antibodies used to compete with In-111 radiolabeled 4.40 and 4.304 anti-PSMA antibodies.
Figure 32:
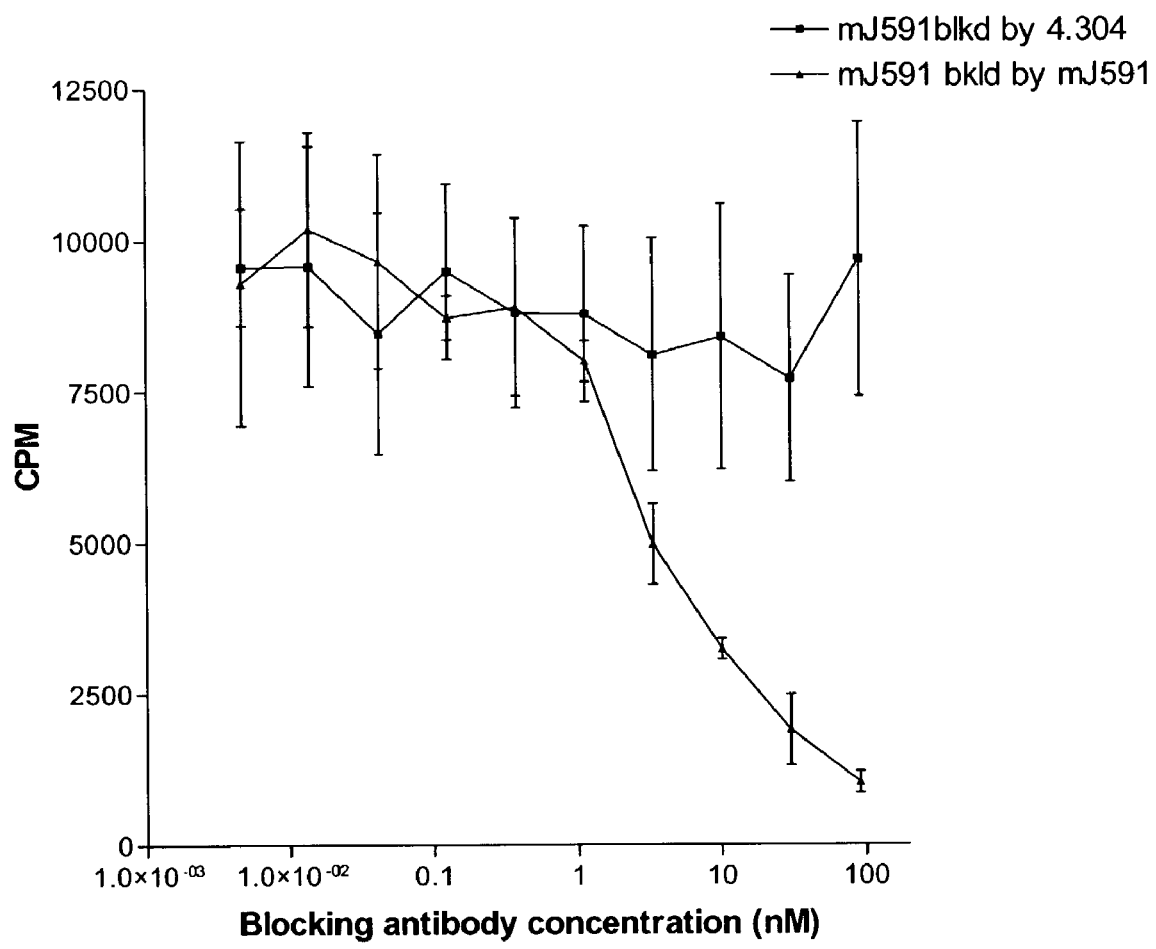
FIG. 32 illustrates the results of the competition assay of unmodified 4.304, mJ591 anti-PSMA antibodies used to compete with In-111 radiolabeled mJ591 anti-PSMA antibodies.

Results detailed in FIGS. 31 show that mJ591 blocked $^{111}$In 4.40 binding to PSMA-3T3 cells and did not block $^{111}$In 4.304. In addition, 4.40 and 4.304 did not block each other. Unmodified antibodies 4.304 and mJ591 were also used to compete with $^{111}$In radiolabeled mJ591. Human 4.304 did not compete with $^{111}$In mJ591 for binding to PSMA-3T3 (FIG. 32).

Example 22

Binding Affinity Using BIACORE 3000

To determine the kinetics and affinity of the antibodies, the antibodies in crude supernatants, in purified form and in bifunctional chelate modified forms were analyzed using a BIACORE 3000 instrument (Biacore Inc., Piscataway, N.J.). BIACORE 3000 is a fully automated surface plasmon resonance (SPR)-based biosensor system that is designed to provide real-time kinetic data from assay formats that require no tags or labeling of compounds for biomolecular interactions. It is ideal for screening crude supernatants.

Figure 33:
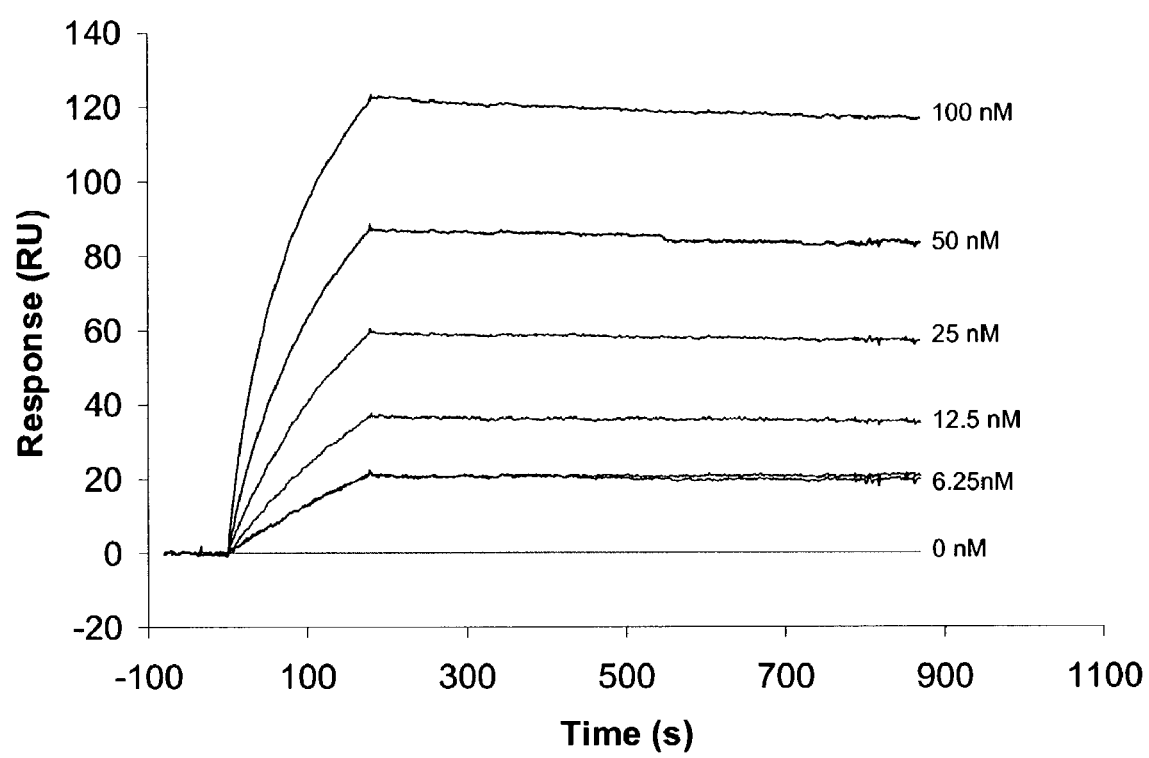
FIG. 33 shows an analysis of antibody PRGX1-XG-006 in association phase and dissociation phase at different concentrations of rsPSMA from 100 nM to 6.25 nM.

The streptavidin-coated sensor chips (SA chips, Biacore, Inc.) were used to capture biotinylated anti-human IgG antibody (Sigma, St. Louis, Mo.). The entire sensor chip surface was conditioned with five injections of conditioning solution (1 M NaCl, 50 mM NaOH) and equilibrated with PBS buffer containing 0.005% polysorbate 20. Two to three thousand resonance units (RU) of biotinylated anti-human IgG antibody (Sigma) were immobilized onto the SA chip followed by an injection of regeneration buffer (glycine-HCl, pH 2.2). Antibodies in supernatants were diluted to 2 µg/mL in PBS buffer and captured onto one anti-human IgG flow cell, while isotype-matched control human antibody (Sigma) was similarly captured on a second flow cell. rsPSMA at different concentrations in PBS buffer was flowed over the cells at 30 µL/min for 3 min in an "association phase" followed by a "dissociation phase" for 10 min. SPR was monitored and displayed as a function of time. For each antibody at one concentration, the chip was regenerated and equilibrated. Examples of the analysis of antibody PRGX1-XG-006 in association phase and dissociation phase at different concentrations of rsPSMA from 100 nM to 6.25 nM are shown in FIG. 33. Thermodynamic and kinetic rate constants of binding were calculated using the BIACORE Evaluation software. For example, the affinity of XG-006 antibodies in a supernatant to rsPSMA was determined to be $4.92 \times 10^{-10}$ M with a $K_a$ of $1.3 \times 10^5$ M$^{-1}$ s$^{-1}$ and a $K_d$ of $6.4 \times 10^{-5}$ s$^{-1}$. Selective data for several human PSMA antibodies in crude supernatant, purified form, and modified with bifunctional chelate is listed in Table 5 for comparison.

Binding activity of $^{III}$In radiolabeled antibodies was determined by Scatchard analysis of binding data obtained using PSMA-expressing cells (LNCaP, C4-2, PSMA-3T3 and parental 3T3 as a control). The experimental procedures and methods of data analysis have been described previously (Scheinberg, D. A. et al. *Leukemia* 3: 440-445 (1991).

TABLE 5

Kinetic Rate Constants of Antibodies in Crude Supernatant, Purified, Bifunctional Chelate Modified Forms along with KD Determined Using $^{111}$In Radiolabeled Scatchard Analysis

| Antibodies | Ka (M$^{-1}$, s$^{-1}$) | Kd (s$^{-1}$) | KD (M$^{-1}$) | Avg KD |
|---|---|---|---|---|
| 006 Supernatant | 1.30E+05 | 6.40E-05 | 4.92E-10 | 4.92E-10 |
| Purified 006-1 | 2.94E+05 | 1.37E-04 | 4.66E-10 | |
| Purified 006-2 | 2.26E+05 | 1.27E-04 | 5.62E-10 | 5.14E-10 |
| 4.40 Supernatant | 2.10E+05 | 1.25E-04 | 5.95E-10 | 5.95E-10 |
| Purified 4.40-1 | 2.54E+05 | 1.52E-04 | 5.98E-10 | |
| Purified 4.40-2 | 2.43E+05 | 2.37E-04 | 9.75E-10 | 7.87E-10 |

TABLE 5-continued

Kinetic Rate Constants of Antibodies in Crude Supernatant, Purified, Bifunctional Chelate Modified Forms along with KD Determined Using $^{111}$In Radiolabeled Scatchard Analysis

| Antibodies | Ka (M$^{-1}$, s$^{-1}$) | Kd (s$^{-1}$) | KD (M$^{-1}$) | Avg KD |
|---|---|---|---|---|
| CHX-4.40-1 | 2.57E+05 | 1.60E-04 | 6.23E-10 | |
| CHX-4.40-2 | 2.47E+05 | 1.55E-04 | 6.28E-10 | 6.25E-10 |
| IN-111CHX-4.40-1 | | | 4.44E-09 | |
| IN-111CHX-4.40-2 | | | 4.95E-09 | 4.70E-09 |
| 4.304 Supernatant | 1.40E+05 | 1.25E-04 | 8.93E-10 | 8.93E-10 |
| Purified 4.304-1 | 8.31E+04 | 1.20E-04 | 1.44E-09 | |
| Purified 4.304-2 | 1.06E+05 | 6.33E-05 | 5.97E-10 | 1.02E-09 |
| CHX-4.304-1 | 6.19E+04 | 1.21E-04 | 1.95E-09 | |
| CHX-4.304-2 | 6.79E+04 | 1.49E-04 | 2.19E-09 | 2.07E-09 |
| IN-111CHX-4.304-1 | | | 9.63E-09 | |
| IN-111CHX-4.304-2 | | | 5.97E-09 | 7.80E-09 |
| 10.3 Supernatant | 1.90E+05 | 3.63E-04 | 1.91E-09 | 1.91E-09 |
| Purified 10.3-1 | 3.28E+05 | 6.32E-05 | 1.93E-10 | |
| Purified 10.3-2 | 2.96E+05 | 6.43E-05 | 2.17E-10 | 2.05E-10 |

Figure 34:
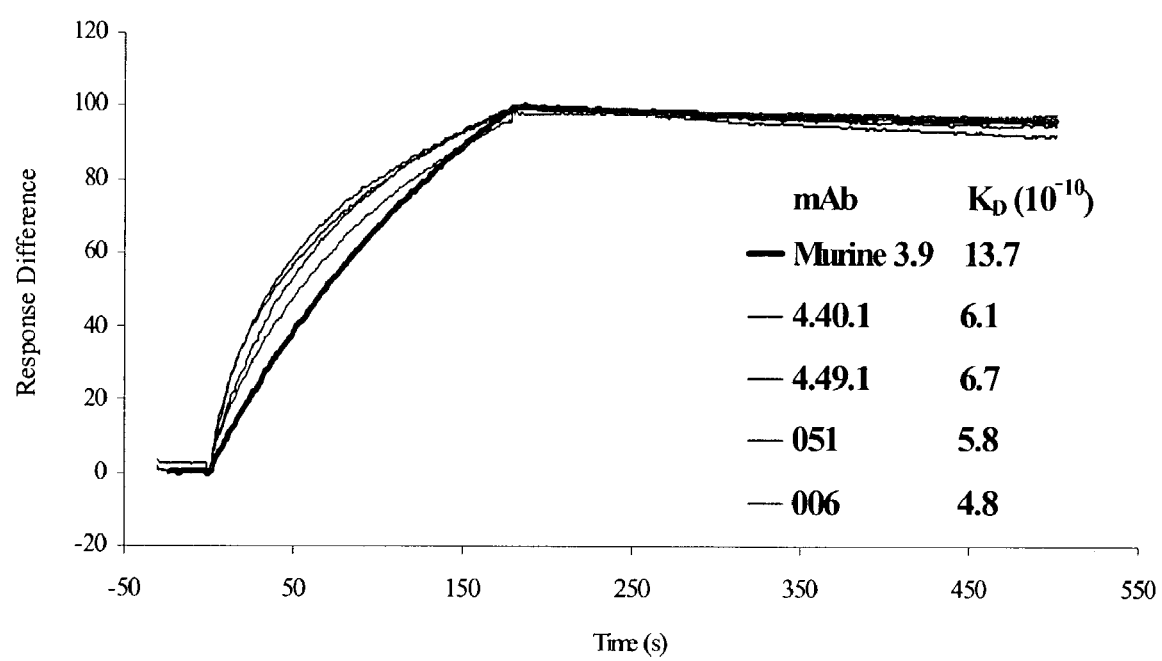
FIG. 34 shows the results of the comparison of the fully human anti-PSMA antibodies 4.40.1, 4.49.1, 051 and 006 and the murine anti-PSMA antibody 3.9 performed using BIACORE analysis.

A comparison of the fully human antibodies 4.40.1, 4.49.1, 051 and 006 and the murine antibody 3.9 was performed by BIACORE. For each antibody for comparison, response was normalized to 100 RU. The graph of time vs. response difference for these antibodies is given in FIG. 34. The binding affinities for these antibodies were determined to be 6.1, 6.7, 5.8, 4.8 and 13.7–10$^{-10}$M, respectively.

Example 23

Characterization of Cell Lines for In Vitro And In Vivo Studies

Figure 35:
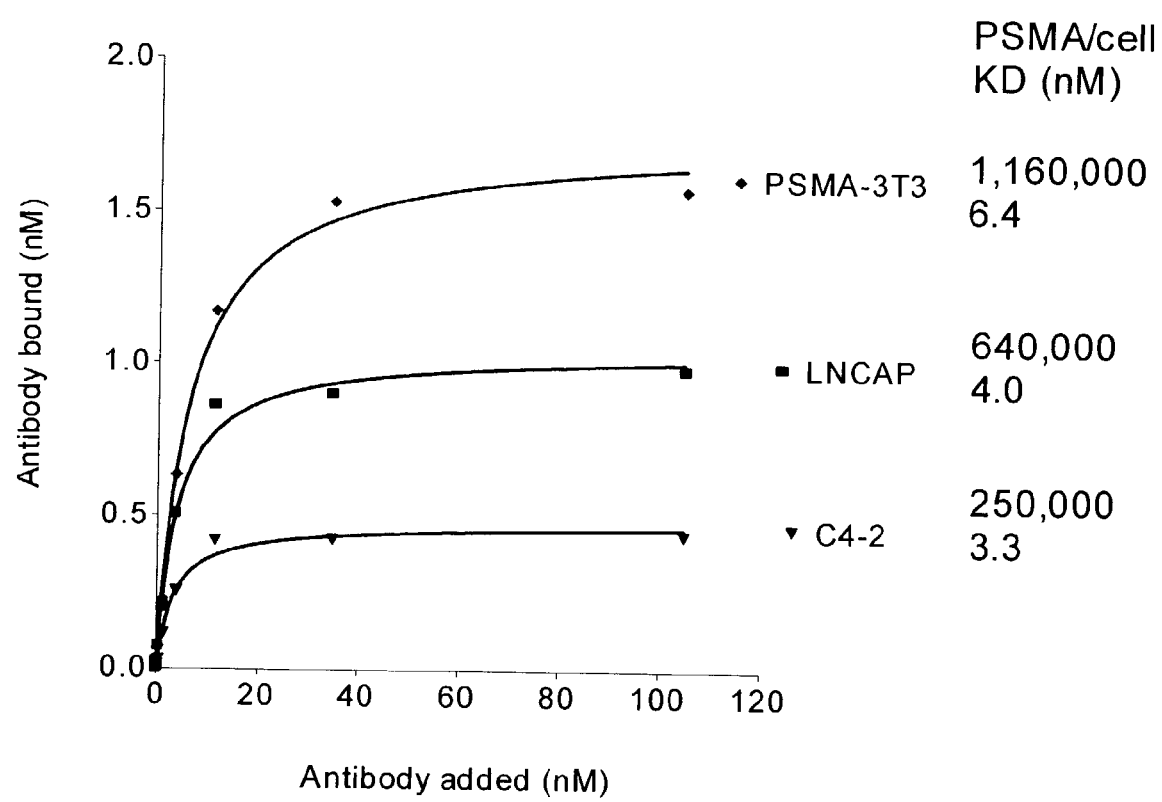
FIG. 35 provides results from the Scatchard analysis using In-111 labeled anti-PSMA antibody 3.9 of the PSMA-3T3, LNCaP and C4-2 cell lines.

Results from a Scatchard analysis using $^{111}$In labeled anti-PSMA antibody 3.9 are represented in FIG. 35. Transfected murine 3T3 cells express >1 million copies of PSMA per cell, LNCAP cells (androgen dependent human prostate cancer cell line) express 0.64 million copies, while C4-2 cells (androgen independent) express 0.25 million copies per cell. The affinity of 3.9 for cell surface PSMA is 6.4 nM for PSMA-3T3, 4.0 nM for LNCAP and 3.3 nM for C4-2 (4.6 nM is the average of these data).

A summary of the analyses of crude supernatants for the human anti-PSMA antibodies is given in Table 6 below.

TABLE 6

Characterization of Anti-PSMA Monoclonal Antibodies

| Supernatant | Ab Conc (µg/mL) PGNX | Lysate EIA | Binding to 3T3-PSMA (FACS) PGNX FACS | Max binding | AVG EC50 | C4.2 FACS | Anti-PSMA Western | Biacore studies KD, M-1 (x 10$^{-10}$) | Ka, M-1s-1 (x 10$^5$) | Kd, s-1 (x 10-5) |
|---|---|---|---|---|---|---|---|---|---|---|
| PRGX1-XG1-026 | 4.7 | ND[1] | ND | 148 | 2.4 | ND | Conf.[2] | 2.0 | 1.5 | 2.9 |
| 4.4.1 | 4.7 | 0.08 | 7 | 8 | ND | 5.2 | Conf. | 4.2 | 2.3 | 9.7 |
| PRGX1-XG1-006 | 1.8 | 0.39 | 114 | 183 | 3.4 | 9.5 | Conf. | 4.8 | 1.3 | 6.4 |
| PRGX1-XG1-051 | 3.5 | 0.48 | 83 | 202 | 2.0 | 9.9 | Conf. | 5.8 | 1.4 | 8.2 |
| 4.40.1 | 4.3 | 0.33 | 53 | 163 | 2.3 | 10.8 | Conf. | 6.1 | 2.1 | 12.5 |
| 4.49.1 | 2.6 | 0.36 | 362 | 162 | 0.9 | 16.2 | Conf. | 6.7 | 3.1 | 20.7 |
| 4292.1 | 2.7 | 0.18 | 75 | 195 | 6.0 | 9.2 | Conf. | 6.8 | 1.2 | 8.5 |
| 4.304.1 | 4.1 | 0.39 | 92 | 184 | 9.1 | 8.4 | Conf. | 8.7 | 1.4 | 12.5 |
| 4.232.1 | 2.4 | 0.49 | 97 | 138 | 2.7 | 6.0 | Linear[3] | 9.4 | 1.5 | 13.8 |

TABLE 6-continued

Characterization of Anti-PSMA Monoclonal Antibodies

| Supernatant | Ab Conc (µg/mL) PGNX | Lysate EIA | Binding to 3T3-PSMA (FACS) | | | C4.2 FACS | Anti-PSMA Western | Biacore studies | | |
| --- | --- | --- | --- | --- | --- | --- | --- | --- | --- | --- |
| | | | PGNX FACS | Max binding | AVG EC50 | | | $K_D$, M-1 (x $10^{-10}$) | Ka, M-1s-1 (x $10^5$) | Kd, s-1 (x $10^{-5}$) |
| 4.153.1 | 5.9 | 0.29 | 279 | 182 | 5.3 | 14.8 | Conf. | 9.5 | 1.2 | 11.8 |
| 4.333.1 | 2.9 | 0.18 | 82 | 168 | 3.1 | 6.6 | Conf. | 11 | 0.7 | 8.5 |
| PRGX1-XG1-077 | 3.9 | 0.45 | 392 | 227 | 6.0 | 12.4 | Conf. | 16 | 0.6 | 10.4 |
| 10.3 | 8.5 | 1.06 | ND | ND | ND | ND | ND | 19 | 1.9 | 36.4 |
| pure 10.3 | | 0.44 | 130 | 181 | 75 | ND | Conf. | ND | | |
| 4.22.1 | 2.8 | 0.08 | 7 | ND | ND | 4.7 | ND | 20 | 1.7 | 33 |
| 4.248.1 | 3.5 | 0.37 | 7 | ND | ND | 4.1 | Conf. | 27 | 1.0 | 28 |
| 4.54.1 | 10 | 0.14 | 267 | 162 | 3.9 | 13.6 | ND | 30 | 1.9 | 56 |
| 4.7.1 | 5 | 0.23 | 156 | 141 | 1.6 | 10.2 | Conf. | 32 | 1.7 | 56 |
| 4.78.1 | 5.3 | 0.00 | 205 | 118 | 1.0 | 7.9 | Conf. | 53 | 2.4 | 125 |
| 4.48.1 | 4.9 | 0.06 | 14 | ND | ND | 7.7 | ND | 62 | 0.9 | 59 |
| 4.209.1 | 3.5 | 0.22 | 60 | ND | ND | 6.7 | ND | 142 | 0.9 | 125 |
| 4.177.1 | 1.1 | 0.15 | 236 | 174 | 2.4 | 10.6 | ND | 155 | 0.6 | 93 |
| 4.152.1 | 3.4 | 0.38 | 81 | 85 | 4.0 | 7.5 | ND | 163 | 0.8 | 126 |
| 4.28.1 | 4.2 | 0.04 | 112 | 155 | 4.2 | 11.3 | ND | 167 | 1.2 | 192 |
| 4.16.1 | 5.3 | 0.00 | 8 | ND | ND | 7.8 | ND | 177 | 1.8 | 313 |
| 4.360.1 | 1.5 | 0.02 | 112 | 130 | 2.2 | 7.9 | ND | 197 | 1.0 | 201 |
| 4.288.1 | 15.4 | 0.02 | 67 | 141 | 4.1 | 6.5 | ND | 198 | 1.3 | 257 |
| 4.219.2 | 0.5 | 0.34 | 69 | ND | ND | 5.9 | ND | ND | | |
| PRGX1-XG1-069 | 6.5 | ND | ND | 71 | 7.9 | ND | ND | No Binding | | |
| Murine 3.9 | | | | | | | | 13.7 | 0.7 | 9.7 |
| Control | | | | | | | | 6.34 | 2.24 | 14.2 |

[1]ND = not determined
[2]conf. = conformational epitope
[3]linear = linear epitope

Example 24

Cytotoxicity of Radiolabeled Antibody

The in vitro cytotoxicity of $^{225}$Ac labeled anti-PSMA antibody (4.40 and 026) was determined using methodology similar to that used in Example 19. Prostate cancer cells (100 µL of C4-2, LNCaP, and PC3 cells at a concentration of 2×10$^4$ cells/mL) were placed into separate wells of a 96 well microplate. For tests with the 026 antibody, C4-2 and PC3 cells were placed into separate wells of a 96 well microplate. After overnight incubation, the cells were treated with $^{225}$Ac labeled human anti-PSMA antibody at different concentrations for over 4 days. Cell cytotoxicity was quantified using Alamar Blue (Biosource International, Camarillo, Calif.).

Figure 36:
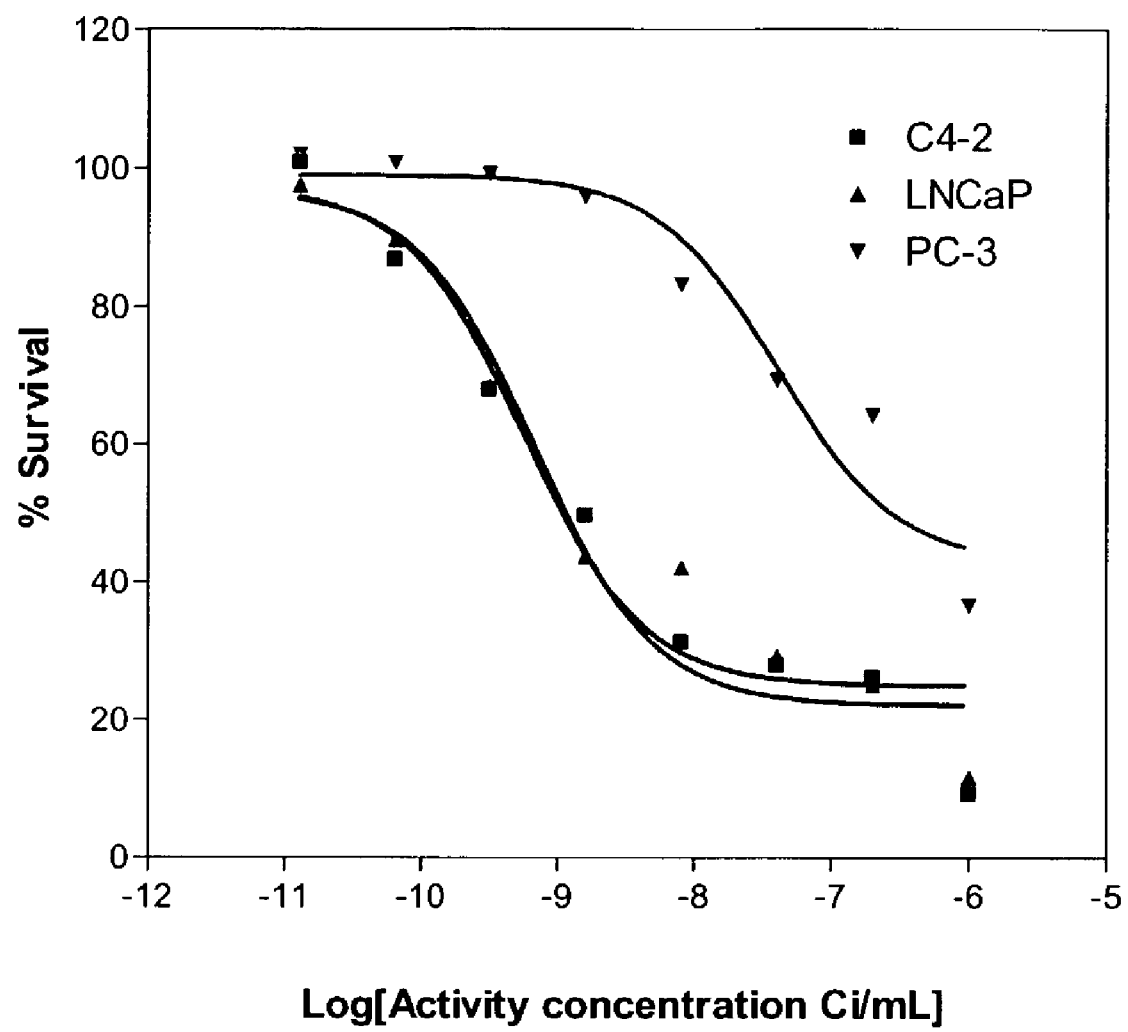
FIG. 36 shows in vitro cytotoxicity of Ac-225 labeled human anti-PSMA antibody 4.40 on prostate cancer cells.

FIG. 36 shows a plot of cell survival vs. $^{225}$Ac activity concentration using $^{225}$Ac labeled 4.40 antibody. The EC50 for PSMA expressing cells (C4-2 and LNCaP) was <2 nCi/mL. However, the EC50 was 420 nCi/mL for PC3 cells, which do not express PSMA on the cell surface. Therefore, the $^{225}$Ac labeled human anti-PSMA 4.40 antibody shows >200-fold selectivity in killing PSMA expressing prostate cancer cells (C4-2 and LNCaP) vs. control cells (PC3).

Figure 37:
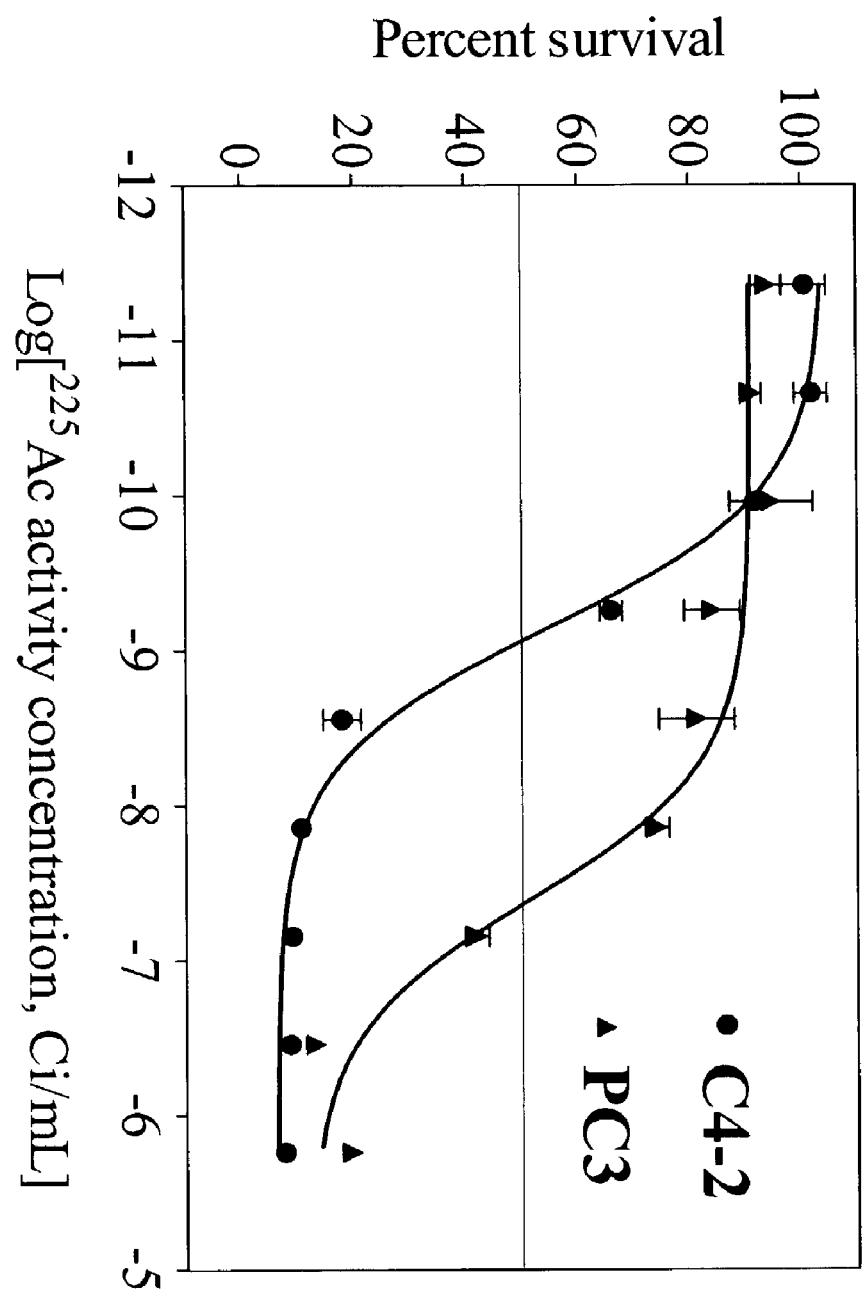
FIG. 37 shows the specific killing of PSMA expressing cells (C4-2) vs. PSMA non-expressing cells (PC-3) treated with $^{225}$Ac labeled mAb 026.

FIG. 37 shows a plot of cell survival vs. $^{225}$Ac activity concentration using $^{225}$Ac labeled 026 antibody. The $^{225}$Ac labeled human anti-PSMA 026 antibody shows >50-fold selectivity in killing PSMA expressing prostate cancer cells (C4-2) vs. control cells (PC3).

Example 25

Cytotoxicity of $^{225}$Ac Labeled Antibody vs. Control Antibody

The in vitro cytotoxicity of $^{225}$Ac labeled anti-PSMA antibody was determined using methodology similar to that used in Example 19 and Example 24 above. Human prostate cancer cells (100 µL of C4-2 and LNCaP cells at a concentration of 2×10$^4$ cells/mL) were placed into, separate wells of a 96 well microplate. After overnight incubation, the cells were treated with $^{225}$Ac labeled human anti-PSMA 026 antibody at different concentrations for 4 days. Cell cytotoxicity was quantified using Alamar Blue (Biosource International, Camarillo, Calif.). Human IgG (HuIgG) was used as a control. The cytotoxicity of an anti-PSMA mAb 026 "2 hour wash" was also determined. A 2 hour wash means that the cells were incubated with $^{225}$Ac labeled antibody for 2 hours. After 2 hours, the media was removed and fresh media was added for the 4 day incubation.

FIG. 38 shows a plot of cell survival vs. the $^{225}$Ac activity concentration for both C4-2 and LNCaP cells using radiolabeled mAb 026, mAb 026 2 hour wash and HuIgG. $^{225}$Ac labeled mAb 026 showed an IC50 of <1 nCi/mL. Therefore, the $^{225}$Ac labeled human anti-PSMA 026 antibody showed >50-fold selectivity in killing the prostate cancer cells vs. the control antibody.

Example 26

Cytotoxicity of $^{225}$Ac Labeled Antibody vs. Control Antibody Evaluated by $^3$H Thymidine Incorporation Human prostate cancer cells (C4-2) in a 96 microplate were treated with $^{225}$Ac labeled mAbs at different concentrations for 4 days. Cell survival was assessed using $^3$H thymidine incorporation (Nikula, T. K, et al. *J. Nucl. Med.* 40: 166-176, 1999).

Figure 39:
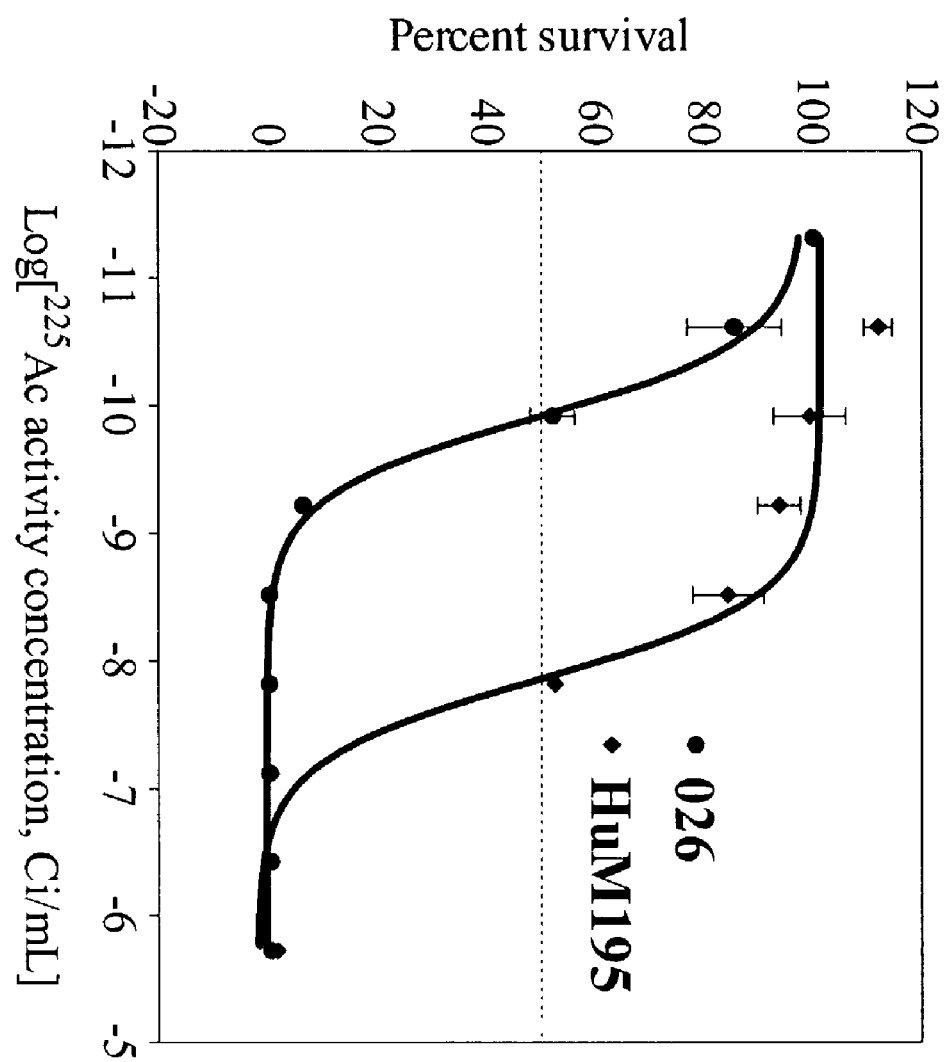
FIG. 39 shows the in vitro cytotoxicity of $^{225}$Ac labeled mAb 026 on human prostate cancer cell line, C4-2, evaluated by $^3$H thymidine incorporation.

FIG. 39 shows a plot of cell survival vs. the $^{225}$Ac activity concentration for C4-2 cells using radiolabeled mAb 026 and control mAb (HuM195). The IC50 was 0.12 nCi/mL using $^{225}$Ac labeled 026 vs. 13 nCi/ml with the control mAb (HuM195). The radiolabeled 026 antibody, therefore, showed >100-fold selectivity in killing the PSMA expressing C4-2 cells vs. the control antibody.

Example 27

In Vivo Radioimmunotherapy with $^{177}$Lu Labeled Antibodies

Figure 40:
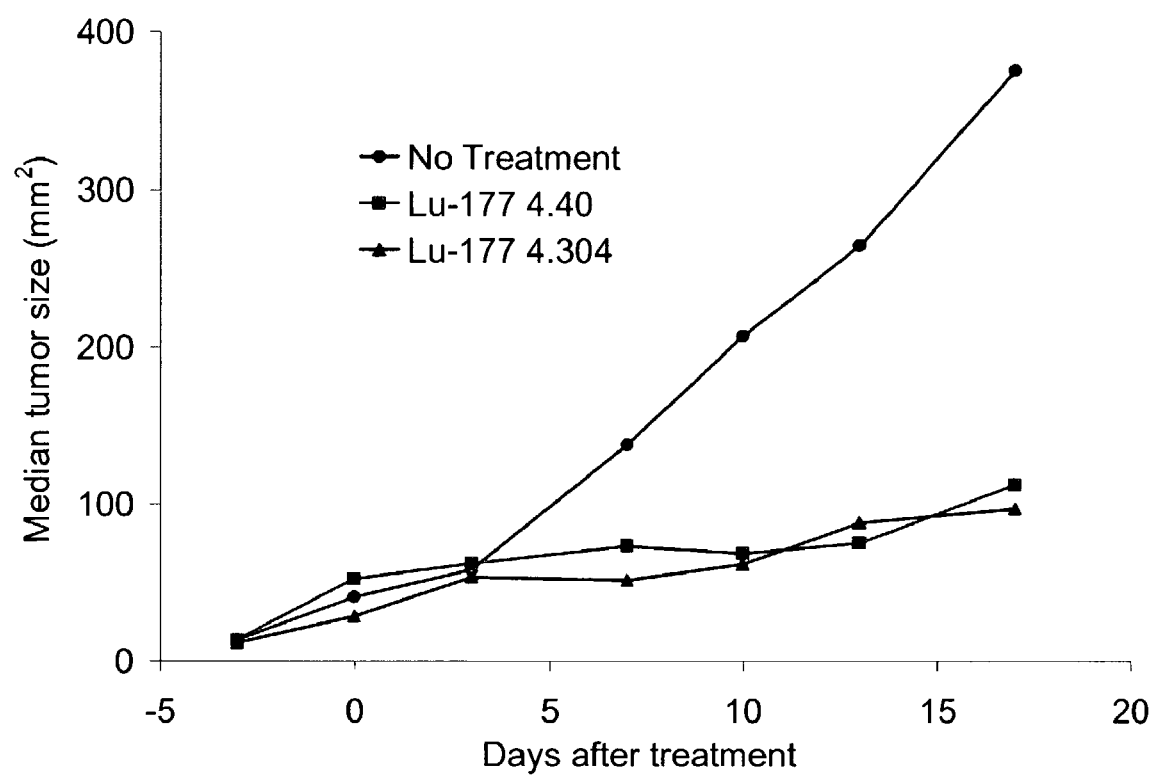
FIG. 40 shows the results of in vivo radioimunotherapy with Lu-177 labeled human anti-PSMA antibodies.

Athymic nude mice from the National Cancer Institute were implanted subcutaneously with 2×10$^6$ PSMA-3T3 cells. After measurable tumors appeared at day 7 post implantation, the mice were treated by injection with either a single 250 μCi dose human anti-PSMA antibody 4.40 or 4.304 labeled with $^{177}$Lu (University of Missouri Research Reactor), or were injected with buffer only as control. The tumor size of individual animals was measured using an electronic caliper. FIG. 40 shows a plot of the median tumor size in each group over time. Tumor growths were substantially reduced in $^{177}$Lu antibody treated groups compared to the control group.

Example 28

In Vivo Biodistribution Study with $^{177}$Lu Labeled Antibodies

Figure 41:
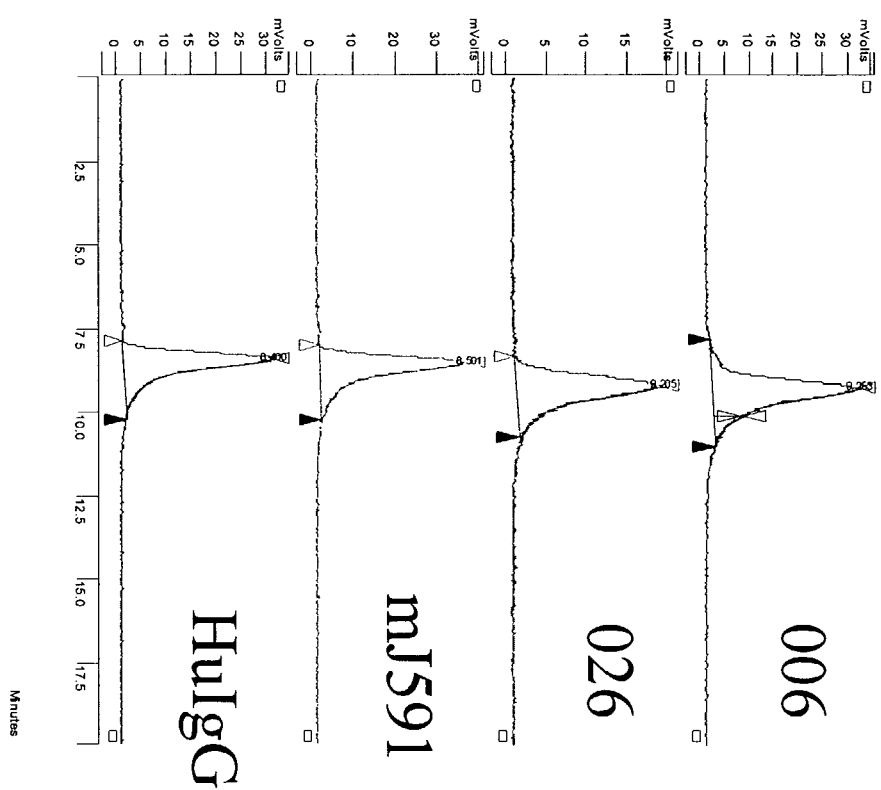
FIG. 41 provides the radio-HPLC profile and cell-based immunoreactivity of $^{177}$Lu labeled antibodies (006, 026, mJ591 and HuIgG (control)).

Athymic nude mice from the National Cancer Institute (male, approximately 6 weeks old) were injected subcutaneously with 4×10$^6$ PSMA-3T3 cells and 2.8×10$^6$ 3T3 cells in 0.2 mL in the right and left flank of each animal, respectively. Anti-PSMA antibodies 006, 026, mJ591 and HuIgG (control) modified with CHX-A"-DTPA were labeled with $^{177}$Lu. FIG. 41 shows the radio-HPLC profile of the radiolabeled antibodies as well as the cell-based immunoreactivity performed as quality control. On day 6 after tumor implantation, $^{177}$Lu labeled antibodies (10 μCi and 1 μg in 0.15 mL) were injected retro-orbitally. The animals were randomized before antibody injection. Mice (30 per antibody, 5 per time point) were sacrificed at different times (days 0.17, 1, 2, 4, 7 and 12). Tumors and individual organs (PSMA+tumor, PSMA−tumor, blood, liver, kidneys, spleen, lungs, heart, bone, muscle, carcass) were taken and weighed. Activity in each organ along with standards prepared from injection solutions were counted using a multi-channel gamma counter.

Figure 42:
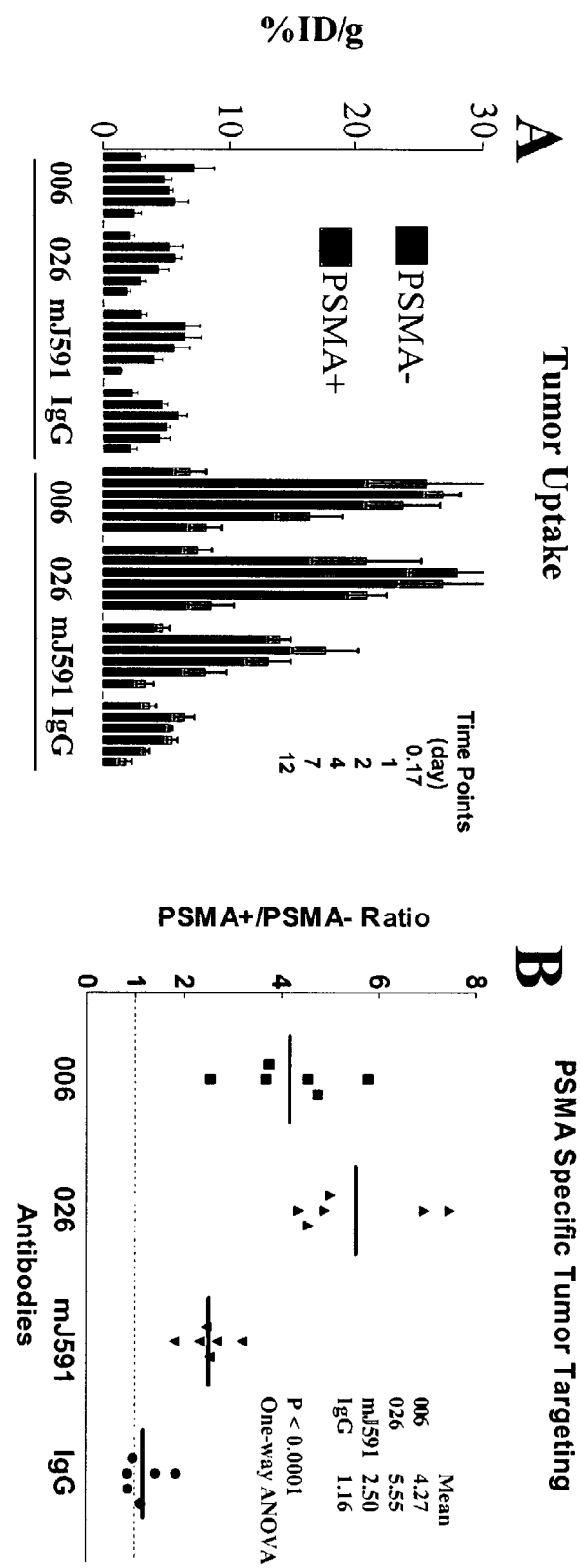
FIG. 42 shows the specific binding of $^{177}$Lu labeled antibodies (006, 026, mJ591 and IgG (control)) to PSMA positive tumors in vivo.

Results of this study show that $^{177}$Lu labeled antibodies specifically bound to tumors expressing PSMA in vivo in the animal model. The percent injected dose per gram of tissue (%ID/g) was calculated and plotted over time for the different antibodies in the PSMA+and PSMA−tumors (FIG. 42A). PSMA specific tumor targeting (ratio of PSMA+/PSMA−tumor uptake) is provided in FIG. 42B.

Figure 43:
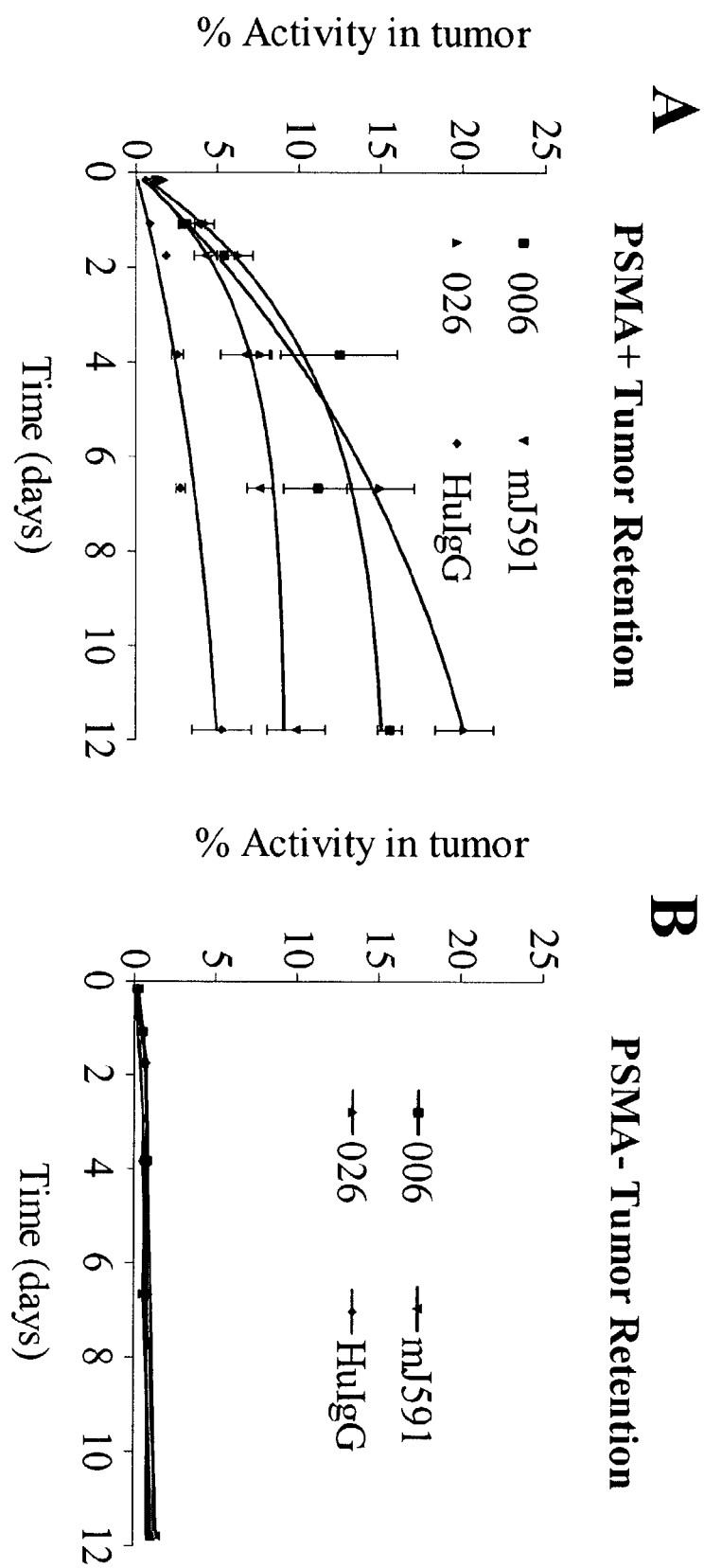
FIG. 43 shows the preferential retention of radiolabeled antibodies (006, 026, mJ591 and HuIgG) in PSMA+tumors vs. PSMA−tumors as assessed by the percent activity in the tumors.
Figure 44:
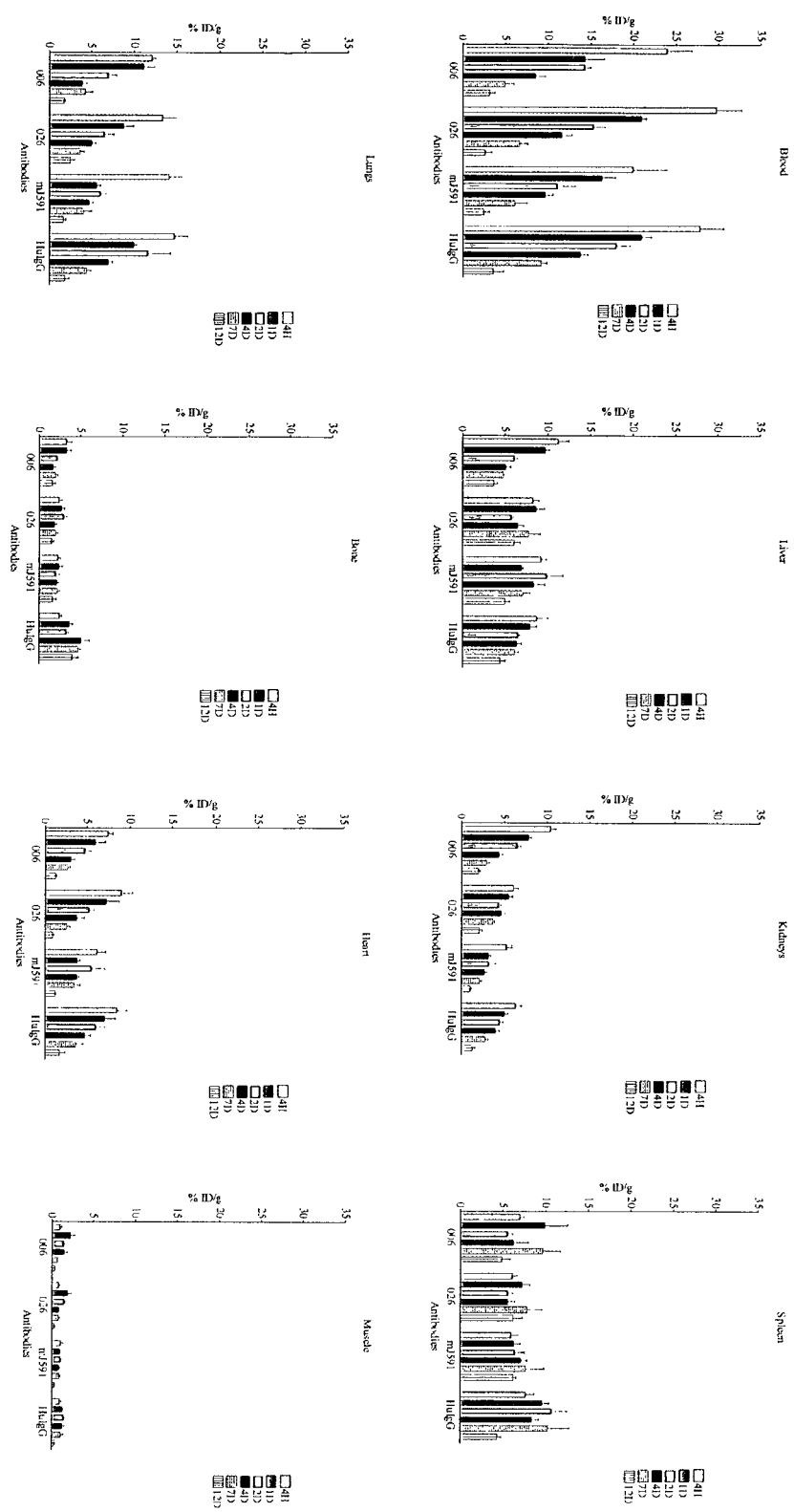
FIG. 44 provides data for normal organ (blood, liver, spleen, lungs, bone, heart and muscle) uptake (injected dose per gram of tissue, %ID/g) for the antibodies (006, 026, mJ591 and HuIgG).

FIG. 43 shows the percent activity in the tumors with the various radiolabeled antibodies (006, 026, mJ591 and HuIgG) over time (% tumor retention vs. total body retention). The data again illustrate the specificity by which the radiolabeled antibodies target the PSMA expressing tumors. FIG. 43A shows the activity over time in the PSMA+tumors while FIG. 43B shows the percent activity over time in the PSMA−tumors for the different antibodies. FIG. 44 shows the data for normal organ (blood, liver, kidneys, spleen, lungs, bone, heart and muscle) uptake (%ID/g) plotted over time.

Example 29

In Vivo Therapeutic Efficacy of $^{177}$Lu Radiolabeled Antibodies

Athymic nude mice from the National Cancer Institute (male, approximately 6 weeks old) were injected subcutaneously with 4×10$^6$ PSMA-3T3 cells and 2.8×10$^6$ 3T3 cells in 0.2 mL in the right and left flank of each animal, respectively. $^{177}$Lu labeled mAb 026 (0 μCi, n=5; 300 μCi and 10 μg, n=9; and 400 μCi and 13.5 μg, n=5) were injected into the mice on day 6 after tumor implantation. Animals were weighed and tumors were measured over time. Tumor size (mm$^3$) was calculated using the formula: length×(width)$^2$/2. Mice were sacrificed if tumor size reached 1000 mm$^3$. Animal survival was also assessed, and the Kaplan-Meier plot was created.

Figure 45:
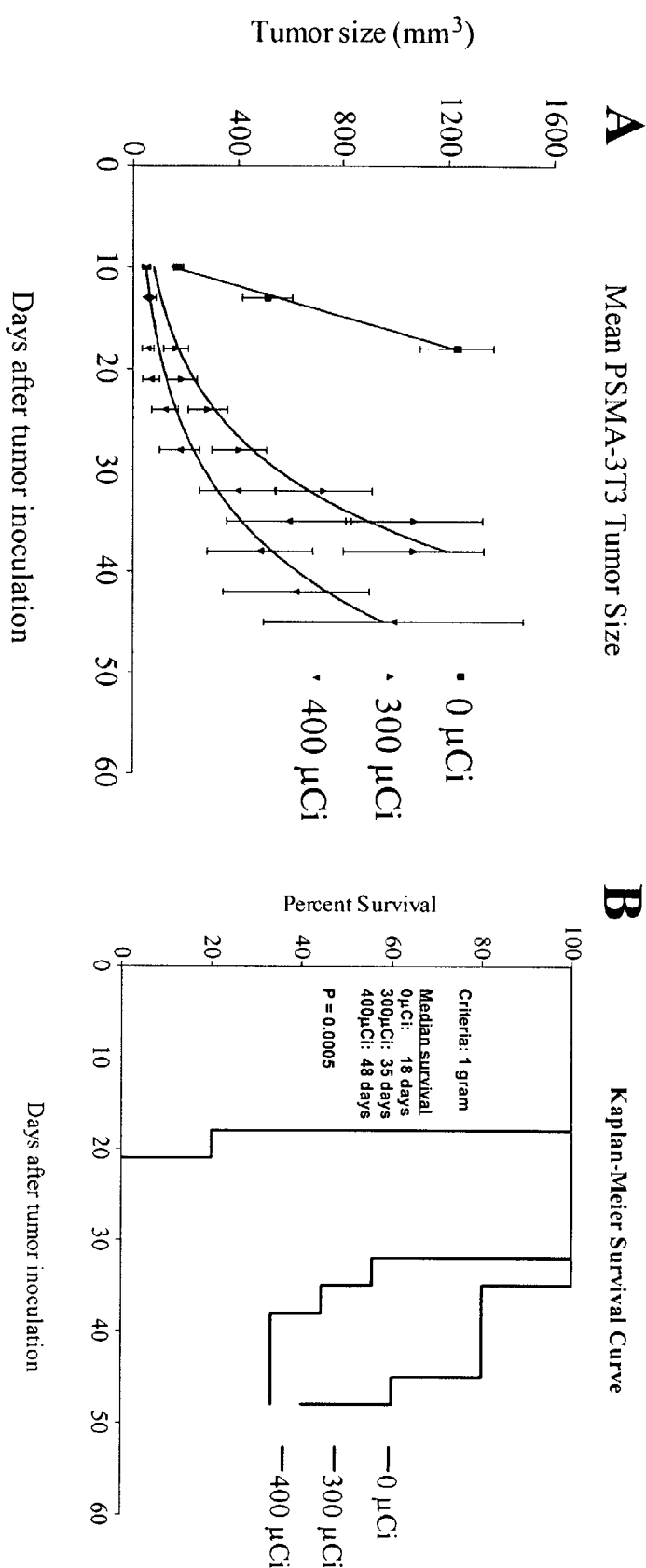
FIG. 45 illustrates the therapeutic efficacy of $^{177}$Lu labeled mAb 026 in PSMA-3T3 and 3T3 tumor-bearing mice.

The results of the study show that treatment decreased tumor size and increased survival in the mice. FIG. 45A shows the tumor size in the mice treated with the radiolabeled antibodies ($^{177}$Lu labeled mAb 026) at all three dose levels. The mice treated with 300 μCi and 400 μCi had consistently smaller tumors than the mice in the control group (0 μCi). FIG. 45B shows that the mice treated with 300 μCi and 400 μCi had increased survival relative to the control mice. Median survival was increased by 2.4-fold in mice treated with 300 μCi and 3.5-fold in mice treated with 400 μCi using time after treatment. Treatment with 400 μCi was found to be non-toxic. Additionally, at the end of the experiment (48 days after tumor implantation), one animal from each treated group remained PSMA-3T3 tumor free but had large 3T3 tumors.

Example 30

Binding of Antibodies to rsPSMA Dimer and Monomer

A BIACORE 3000 instrument was used to monitor, in real time, binding of rsPSMA dimer and monomer to anti-PSMA mAbs. Antibodies were immobilized at approximately 10,000 resonance units to CM5 sensor chips according to the manufacturer's instructions for amine coupling (Biacore, Inc., Piscataway, N.J.). A reference surface of isotype-matched antibody of irrelevant specificity was used as a background control. Binding experiments were performed at 25° C. in PBS buffer with 0.005% [vol/vol] Surfactant P20. Purified rsPSMA dimer (50 nM) or monomer (100 nM) was passed over control and test flow cells at a flow rate of 5 μL/min. The sensor surface was regenerated with two pulses of 20 nM HCl.

Figure 46:
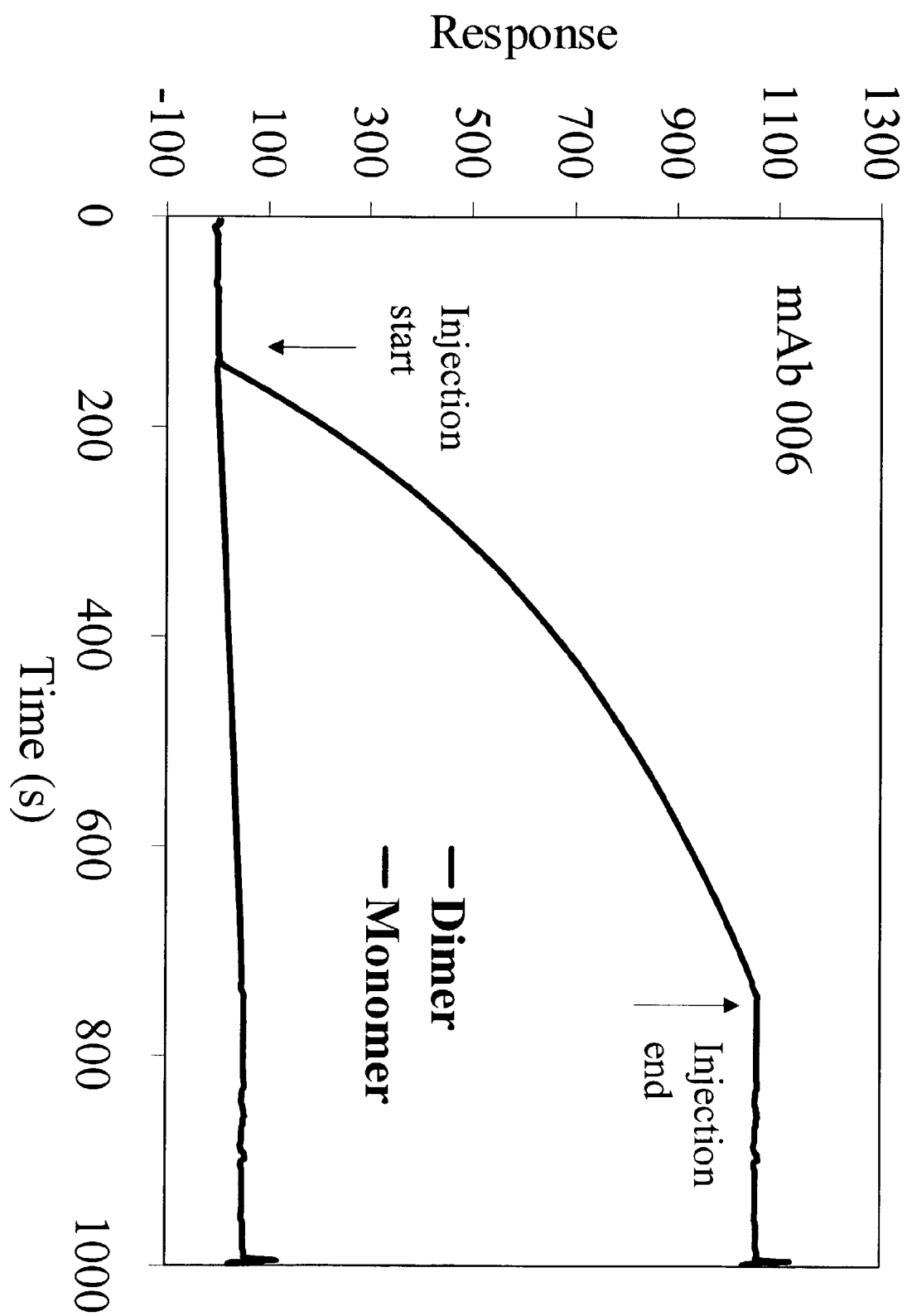
FIG. 46 shows the preferential binding of mAb 006 to rsPSMA dimer.
Figure 47:
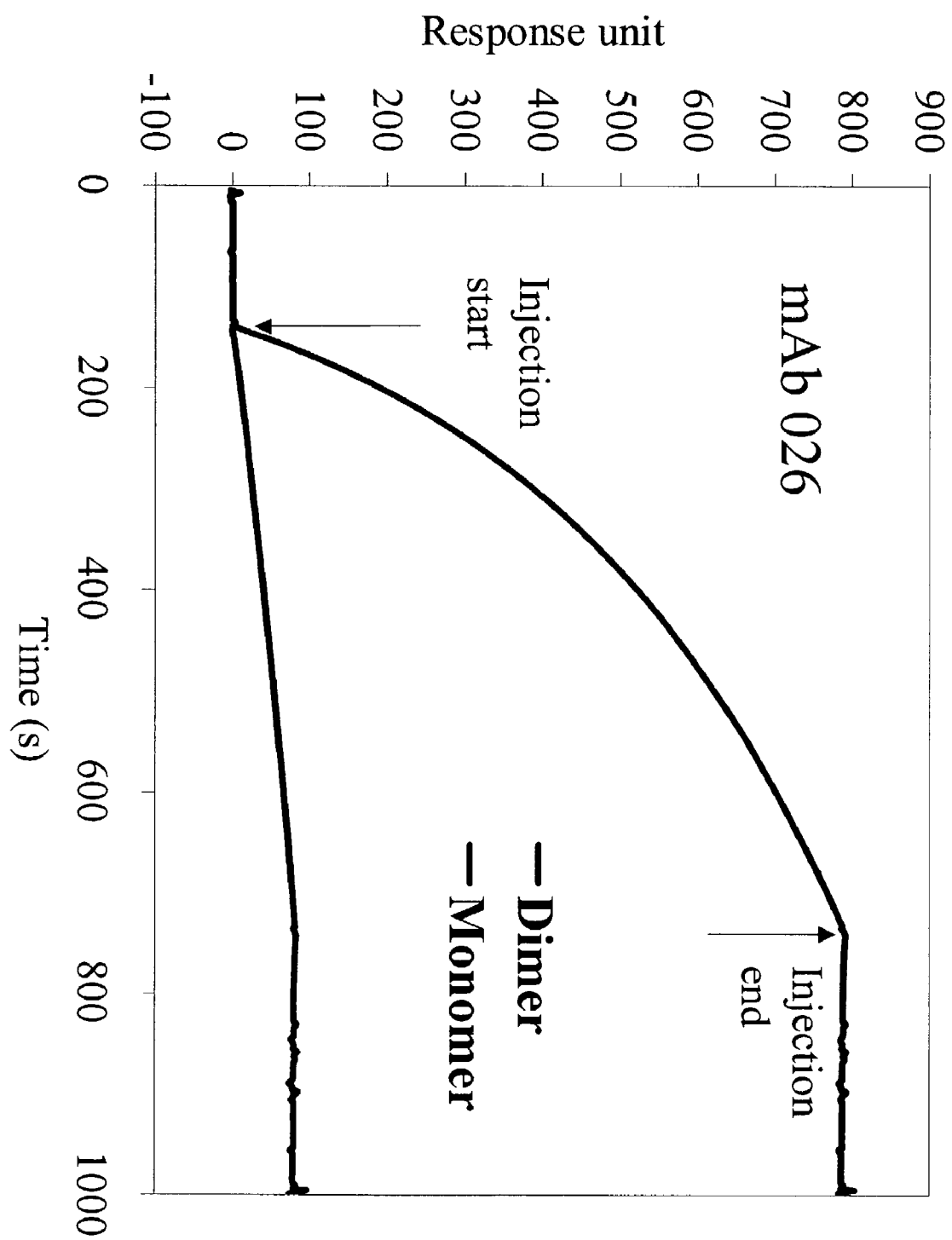
FIG. 47 shows the preferential binding of mAb 026 to rsPSMA dimer.
Figure 48:
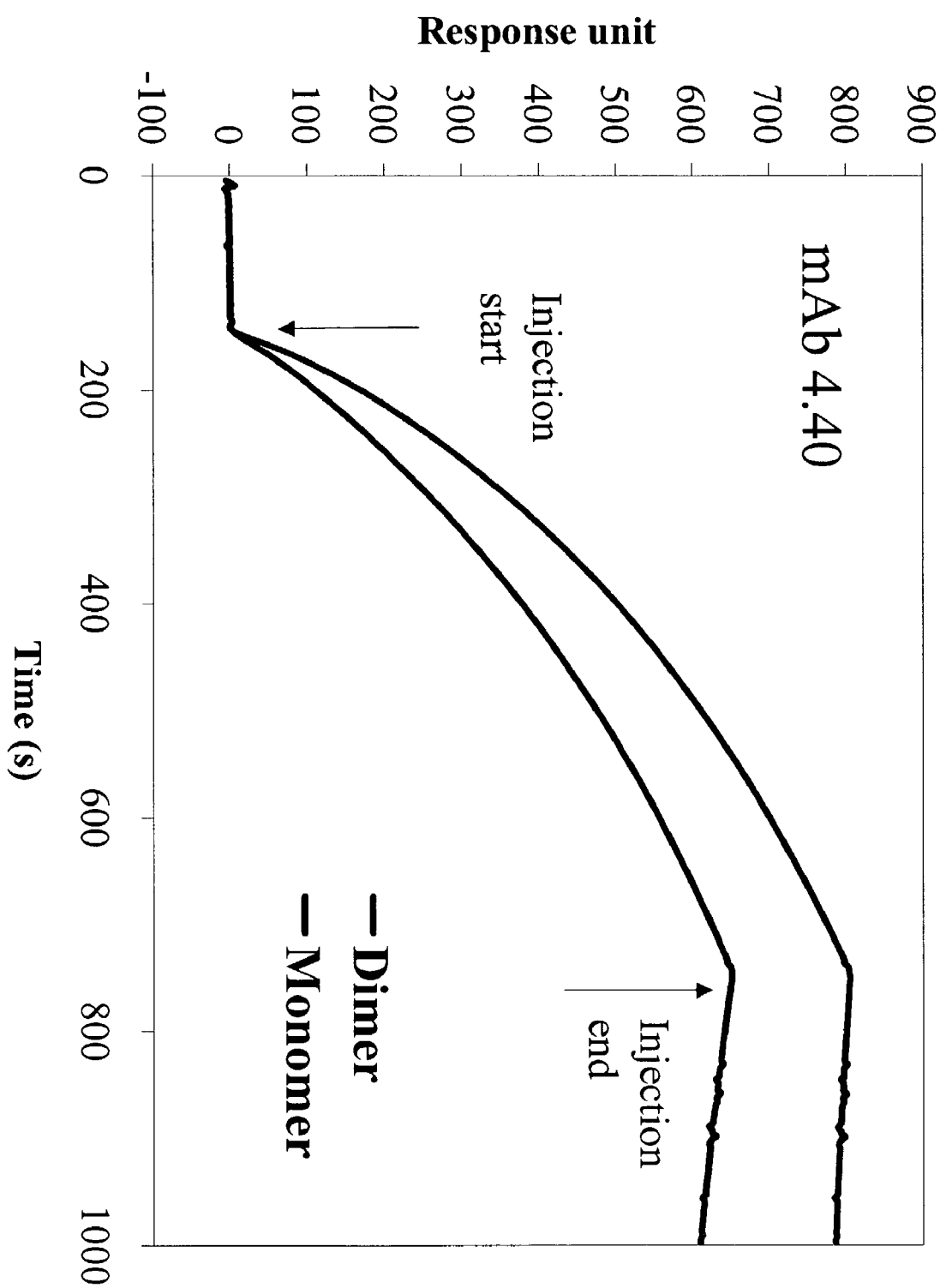
FIG. 48 shows the binding of mAb 4.40 to rsPSMA dimer and monomer.
Figure 49:
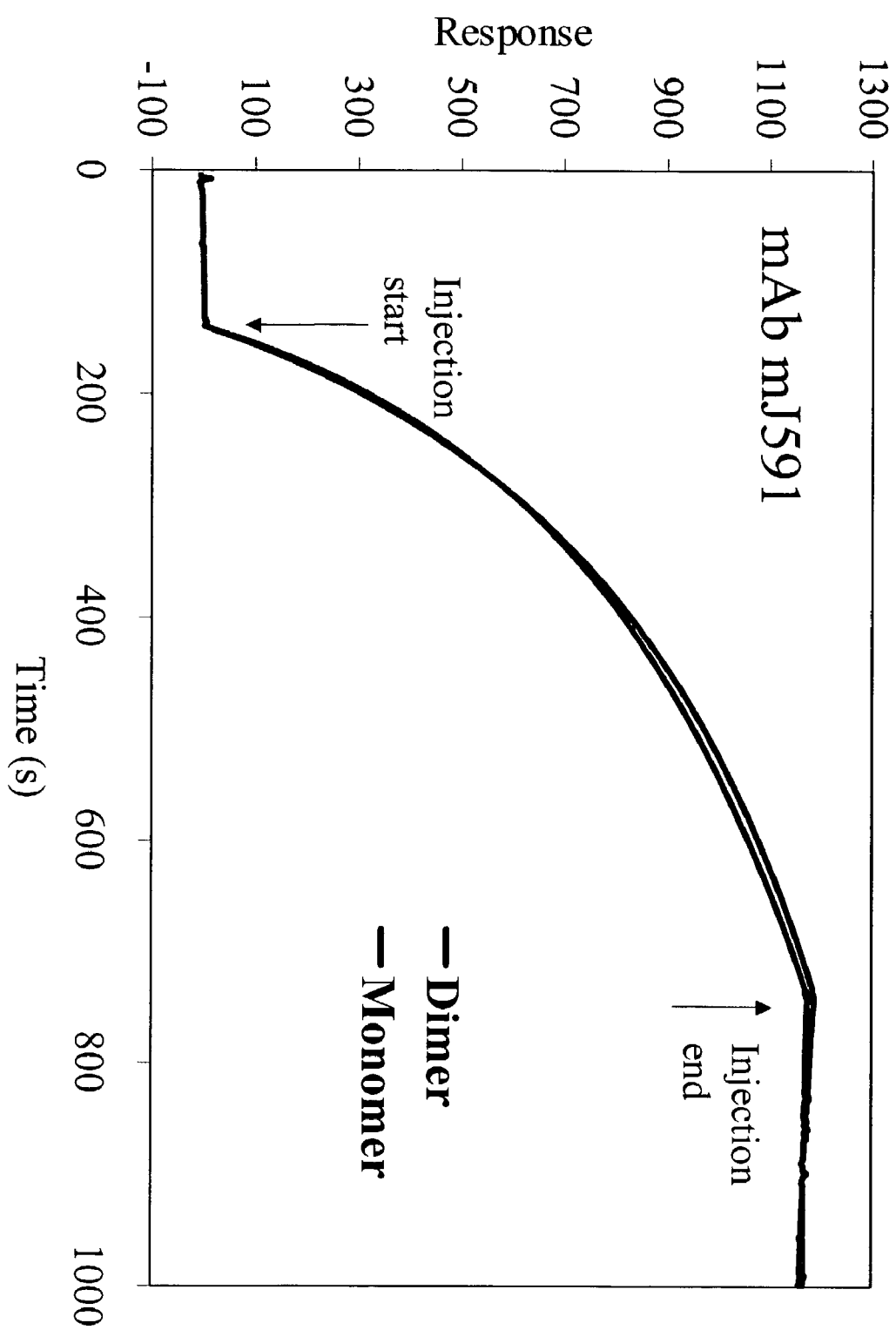
FIG. 49 shows the binding of mAb mJ591 to rsPSMA dimer and monomer.

FIGS. 46 and 47, respectively, show that anti-PSMA mAbs 006 and 026 bind preferentially to the rsPSMA dimer rather than the rsPSMA monomer. Anti-PSMA antibodies 4.40 and mJ591, however, were shown to bind both the rsPSMA dimer and monomer at significant levels (FIGS. 48 and 49, respectively). This study illustrates that anti-PSMA mAbs 006 and 026 are PSMA dimer-specific antibodies and bind dimer-specific epitopes on PSMA.

Example 31

Immunization with rsPSMA Dimer Preparations

Immunization

BALB/c mice were immunized by subcutaneous injection at days 0, 7, 14, and 42 with either 5 µg clinical rsPSMA lot #4019-C0001 (75% dimer/25% monomer) or 5 µg rsPSMA batch # TD045-003 run 1/peak 2 (100% monomer) and adjuvanted with 50 µg ALHYDROGEL per dose. Serum was drawn 10 days after the fourth immunization and analyzed by enzyme-linked immunoassay (EIA) and flow cytometry.

EIA rsPSMA lot # 4019-0001 or rsPSMA batch # TD045-003 run 1/peak 2 was passively adsorbed to 96-well microtiter plates. Remaining binding sites on the plate were blocked with a PBS/Casein/TWEEN 20 buffer. Serially diluted mouse serum or controls were added and bound antibody was detected using a goat anti-mouse IgG antibody conjugated to alkaline phosphatase. The EIA was developed with the substrate pNPP which produces a color change that is directly proportional to the amount of anti-PSMA antibody bound. Absorbance was read at 405 nm with a correction of 620 nm. Antibody titer was defined as the highest dilution of mouse serum yielding a blank corrected absorbance of 0.1. Immune mouse serum with a known anti-PSMA titer or normal mouse serum with no anti-PSMA reactivity was used as controls.

Flow Cytometry Analysis

PSMA-3T3 cells were incubated with 200 µL of immune serum at a dilution of 1/50 in PBS with 0.1% sodium azide on ice for 30 minutes. Immune mouse serum with known anti-PSMA titer or normal mouse serum with no anti-PSMA reactivity was used as controls. The cells were washed twice with PBS with 0.1% sodium azide and incubated for 30 minutes on ice with FITC-conjugated goat anti-mouse IgG. Cells were washed once, resuspended in PBS with 0.1% sodium azide and subjected to flow cytometric analysis on FACScaliber (Becton Dickinson).

Results

5/5 mice immunized with rsPSMA lot # 4019-C001 showed an anti-PSMA antibody response by EIA. Antibody titer was similar for assay plates coated with rsPSMA lot # 4019-C0001 (75% dimer/25% monomer) and assay plates coated with rsPSMA batch # TD045-003 run 1/peak 2 (100% monomer). Median response for the group was 176400.

4/5 mice immunized with rsPSMA batch # TD045-003 run 1/peak 2 showed an anti-PSMA antibody response by EIA. One mouse was negative. Antibody titer was similar for assay plates coated with rsPSMA lot # 4019-C001 (75% dimer/25% monomer) and assay plates coated with rsPSMA batch # TD045-003 run 1/peak 2 (100% monomer). Median response for the group was 1/6400.

The results of the EIA analysis are provided in Table 7.

TABLE 7

Specificity of the Anti-PSMA Antibody Response in Mice Vaccinated 4 Times with rsPSMA 5 µg/dose and 50 µg/dose ALHYDROGEL

| Mouse ID # | Immuno-gen | EIA Titer vs. Lot 4019-C001 | EIA Titer vs. Batch TD045-003 run1/peak2 | Median RFI vs. PSMA-3T3 cells |
|---|---|---|---|---|
| ABIM151 | 4019-C001 Dimer | 1/3200 | 1/3200 | 84 |
| ABIM152 | 4019-C001 Dimer | 1/3200 | 1/3200 | 41 |
| ABIM153 | 4019-C001 Dimer | 1/25600 | 1/25600 | 76 |
| ABIM154 | 4019-C001 Dimer | 1/12800 | 1/12800 | 63 |
| ABIM155 | 4019-C001 Dimer | 1/6400 | 1/6400 | 74 |
| ABIM156 | Monomer | 1/1600 | 1/1600 | 5 |
| ABIM157 | Monomer | 1/6400 | 1/12800 | 8 |
| ABIM158 | Monomer | 0 | 0 | 6 |
| ABIM159 | Monomer | 1/6400 | 1/6400 | 6 |
| ABIM160 | Monomer | 1/6400 | 1/6400 | 12 |

Figure 50:
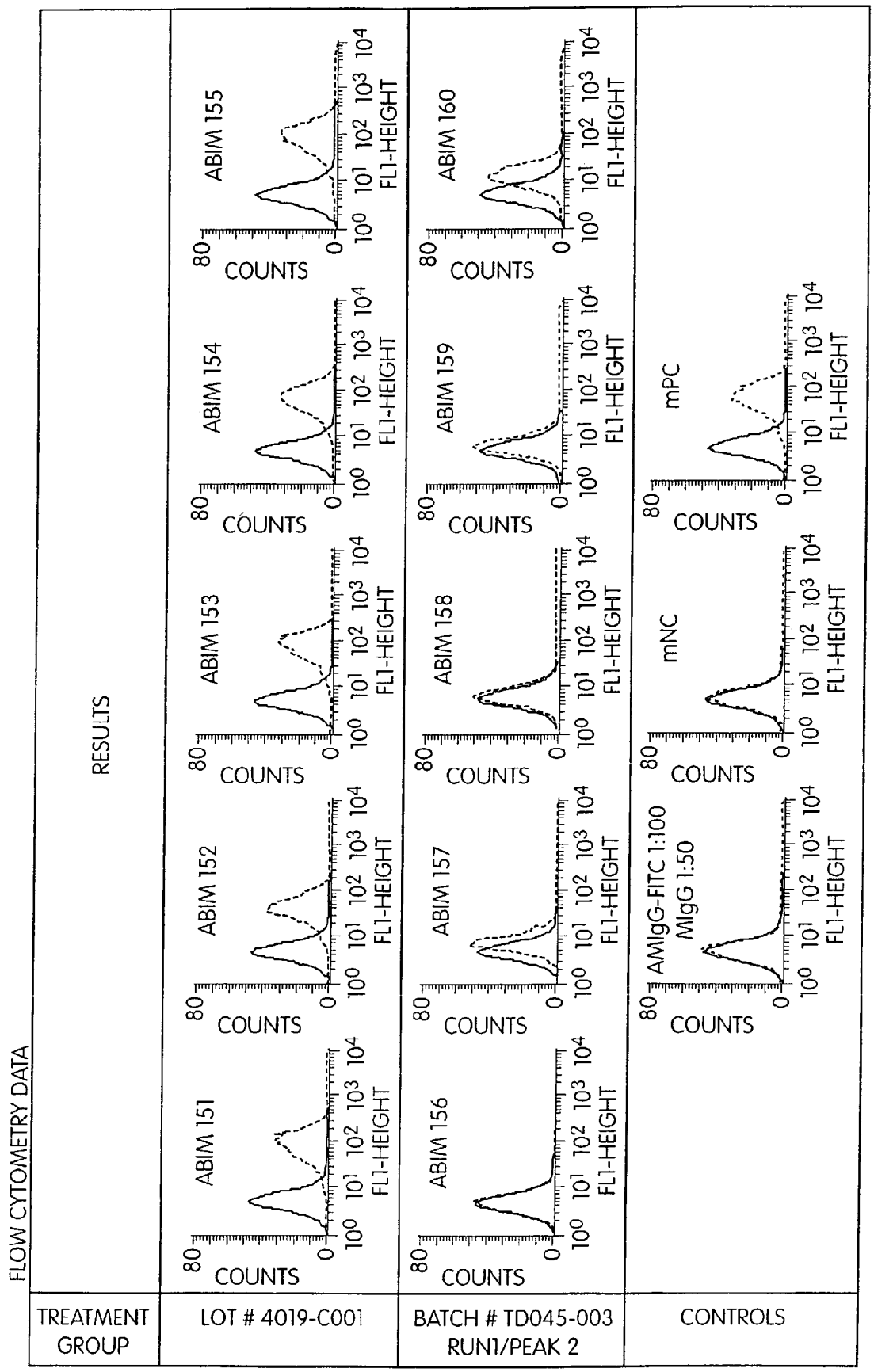
FIG. 50 is a series of graphs that show flow cytometry data for the binding of anti-PSMA antisera to PSMA-3T3 cells. Antisera from mice immunized with a rsPSMA dimer preparation (ABIM151, ABIM152, ABIM153, ABIM154 and ABIM155) exhibited strong binding to PSMA-expressing cells. Antisera from mice immunized with a rsPSMA monomer preparation (ABIM156, ABIM157, ABIM158, ABIM159 and ABIM160) exhibited little or no binding to PSMA-expressing cells.

As shown in FIG. 50, anti-PSMA antibody in the serum of mice immunized with a dimer preparation of rsPSMA (lot # 4019-C001) showed strong binding to PSMA-3T3 cells. Anti-PSMA antibody in the serum of mice immunized with a 100% monomer preparation of rsPSMA (batch # TD045-003 run 1/peak 2) showed no binding to PSMA-3T3 cells.

Although the invention has been described in detail for the purpose of illustration, it is understood that such detail is solely for that purpose and variations can be made by those skilled in the art without departing from the spirit and scope of the invention which is defined by the following claims.

The contents of all references, patents and published patent applications cited throughout this application are incorporated herein by reference.

The invention claimed is:

1. A composition comprising an isolated recombinant soluble PSMA (rsPSMA) protein dimer, wherein each of the rsPSMA proteins of the rsPSMA protein dimer consists of amino acids 44-750 of SEQ ID NO:1.

2. The composition of claim 1, wherein the rsPSMA proteins of the rsPSMA protein dimer are noncovalently associated with each other.

3. The composition of claim 2, wherein the rsPSMA proteins of the rsPSMA protein dimer are noncovalently associated with each other under nondenaturing conditions.

4. The composition of claim 1, wherein the rsPSMA protein dimer mAb 3.9, produced by the hybridoma deposited under ATCC Accession No. PTA-3258 or mAb 10.3, produced by the hybridoma deposited under ATCC Accession No. PTA-3347.

5. The composition of claim 1, wherein the rsPSMA protein dimer is enzymatically active.

6. The composition of claim 5, wherein the enzymatic activity is folate hydrolase activity, NAALADase activity, dipeptidyl dipeptidase IV activity or γ-glutamyl hydrolase activity.

7. The composition of claim 1, further comprising an isolated cytokine.

8. The composition of claim 7, wherein the cytokine is IL-2, IL-12, IL-18 or GM-CSF.

9. The composition of claim 1, further comprising a pharmaceutically acceptable carrier.

10. A method for inducing an immune response comprising administering to a subject an effective amount of the composition of claim 1 to stimulate an immune response against said PSMA protein dimer.

11. The composition of claim 1, further comprising a chemokine.

12. The composition of claim 11, wherein the chemokine is SLC, ELC, MIP3α, MIP3β, IP-10 or MIG.

13. The composition of claim 1, further comprising an adjuvant.

14. A kit comprising the isolated rsPSMA protein dimer of claim 1 and an adjuvant.

15. The kit of claim 14, further comprising a carrier.

16. A composition comprising an isolated recombinant soluble PSMA (rsPSMA) protein dimer, wherein the rsPSMA protein dimer exhibits folate hydrolase activity, NAALADase activity, dipeptidyl dipeptidase IV activity or γ-glutamyl hydrolase activity, wherein each of the rsPSMA proteins of the rsPSMA protein dimer consists of amino acids 44-750 of SEQ ID NO:1, wherein the rsPSMA proteins of the rsPSMA protein dimer are noncovalently associated with each other, and wherein the rsPSMA protein dimer binds mAb 3.9, produced by the hybridoma deposited under ATCC Accession No. PTA-3258 or mAb 10.3, produced by the hybridoma deposited under ATCC Accession No. PTA-3347.

17. An isolated recombinant soluble PSMA (rsPSMA) protein dimer, wherein each of the rsPSMA proteins of the rsPSMA protein dimer consists of amino acids 44-750 of SEQ ID NO:1.

18. The isolated rsPSMA protein dimer of claim 17, wherein the rsPSMA proteins of the rsPSMA protein dimer are noncovalently associated with each other.

19. The isolated rsPSMA protein dimer of claim 18, wherein the rsPSMA proteins of the rsPSMA protein dimer are noncovalently associated with each other under nondenaturing conditions.

20. The isolated rsPSMA protein dimer of claim 17, wherein the rsPSMA protein dimer mAb 3.9, produced by the hybridoma deposited under Accession No. PTA-3258 or mAb 10.3, produced by the hybridoma deposited under ATCC Accession No. PTA-3347.

21. The isolated rsPSMA protein dimer of claim 17, wherein the rsPSMA protein dimer is enzymatically active.

22. The isolated rsPSMA protein dimer of claim 21, wherein the enzymatic activity is folate hydrolase activity, NAALADase activity, dipeptidyl dipeptidase IV activity or γ-glutamyl hydrolase activity.

23. An isolated recombinant soluble PSMA (rsPSMA) protein dimer, wherein the rsPSMA protein dimer exhibits folate hydrolase activity, NAALADase activity, dipeptidyl dipeptidase IV activity or γ-glutamyl hydrolase activity, wherein each of the rsPSMA proteins of the rsPSMA protein dimer consists of amino acids 44-750 of SEQ ID NO:1, wherein the rsPSMA proteins of the rsPSMA protein dimer are noncovalently associated with each other, and wherein the rsPSMA protein dimer binds mAb 3.9, produced by the hybridoma deposited under ATCC Accession No. PTA-3258 or mAb 10.3, produced by the hybridoma deposited under ATCC Accession No. PTA-3347.

24. The composition of claim 13, wherein the adjuvant is alum, alhydrogel, Titermax™ Gold, monophosphoryl lipid A, a saponin, an immunostimulatory oligonucleotide, incomplete Freund's adjuvant, complete Freund's adjuvant, montanide, vitamin E, a water-in-oil emulsion, Quil A, Ribi Detox, CRL-1005 or L-121.

25. The composition of claim 24, wherein the saponin is QS21.

26. The composition of claim 24, wherein the immunostimulatory oligonucleotide is a CpG oligonucleotide.

27. The composition of claim 24, wherein the water-in-oil emulsion is prepared from squalene or tocopherol.

* * * * *